(12) United States Patent
Badiger et al.

(10) Patent No.: US 8,742,106 B2
(45) Date of Patent: Jun. 3, 2014

(54) DISUBSTITUTED HETEROARYL-FUSED PYRIDINES

(75) Inventors: Sangamesh Badiger, Karnataka (IN); Dirk Behnke, Grenzach-Wyhlen (DE); Claudia Betschart, Basel (CH); Vinod Chaudhari, Karnataka (IN); Murali Chebrolu, Andhra Pradesh (IN); Simona Cotesta, Basel (CH); Samuel Hintermann, Basel (CH); Arndt Meyer, Basel (CH); Chetan Pandit, Karnataka (IN)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/517,115

(22) PCT Filed: Dec. 20, 2010

(86) PCT No.: PCT/EP2010/070260
§ 371 (c)(1),
(2), (4) Date: Jun. 29, 2012

(87) PCT Pub. No.: WO2011/076744
PCT Pub. Date: Jun. 30, 2011

(65) Prior Publication Data
US 2012/0258973 A1    Oct. 11, 2012

(30) Foreign Application Priority Data
Dec. 21, 2009 (IN) ............. 2664/DEL/2009

(51) Int. Cl.
*C07D 471/04* (2006.01)
*C07D 498/04* (2006.01)
*C07D 519/00* (2006.01)

(52) U.S. Cl.
USPC ........ 544/319; 544/333; 544/405; 546/116; 546/119

(58) Field of Classification Search
None
See application file for complete search history.

(56) References Cited

U.S. PATENT DOCUMENTS

| | | | |
|---|---|---|---|
| 3,872,133 A | 3/1975 | Fleckenstein et al. | |
| 7,834,028 B2 | 11/2010 | Aissaoui et al. | |
| 2007/0021442 A1 | 1/2007 | Saggar et al. | |
| 2007/0066582 A1 | 3/2007 | Herold et al. | |
| 2009/0022670 A1 | 1/2009 | Alvaro et al. | |

FOREIGN PATENT DOCUMENTS

| | | |
|---|---|---|
| JP | 2007099640 | 4/2007 |
| WO | 01/98301 A1 | 12/2001 |
| WO | 0198301 | 12/2001 |
| WO | 02060900 | 8/2002 |
| WO | 03051366 | 6/2003 |
| WO | 2005014600 | 2/2005 |
| WO | 2006063805 | 6/2006 |
| WO | 2007122591 | 11/2007 |
| WO | 2007144203 | 12/2007 |
| WO | 2007144204 | 12/2007 |
| WO | 2008025947 | 3/2008 |
| WO | 2009003993 | 1/2009 |

OTHER PUBLICATIONS

Cai, Jiaqiang et al., "Antagonist of the Orexin Receptors", Expert Opin. Ther. Patents, 2006, pp. 631-646, vol. 16, Iss. 5.
Minakata, et al., "Functionalization of H-Prrolo[2,3-b]pyridine", Bull. Chem. Soc. Jpn., 1992, pp. 2992-2997, vol. 65, No. 11, The Chemical Society of Japan.
Cai, et al., "Antagonists of the orexin receptors", Expert Opin. Ther. Patents, 2006, pp. 631-646, vol. 16, No. 5, Informa UK Ltd.
Azimov, et al., Azaindole Derivatives. 57.* Dehydrogenation of Substituted 5- and 7-azaindolines with activated manganese dioxide, Khimiya Geterotsiklicheskikh Soedinenii, 1978, pp. 378-378, vol. 3.
CAS Registered Compounds, May 6, 2010-Aug. 23, 2010. 237 pages.

*Primary Examiner* — Janet L Andres
*Assistant Examiner* — Timothy R Rozof
(74) *Attorney, Agent, or Firm* — Laura Madden

(57) ABSTRACT

The invention relates to compound of the formula (I') in which the substituents are as defined in the specification; in free form or in salt form; to its preparation, to its use as medicament and to medicaments comprising it.

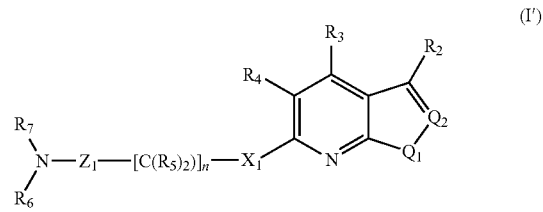

16 Claims, No Drawings

DISUBSTITUTED HETEROARYL-FUSED PYRIDINES

The invention relates to disubstituted heteroaryl-fused pyridines to their preparation, to their use as medicaments and to medicaments comprising them. In particular, the invention relates to 1H-pyrazolo[3,4b]pyridines, 1H-pyrrolo[2,3-b]pyridines, isoxazolo[5,4-b]pyridines and furo[2,3b]pyridines.

Orexins (orexin A/OX-A and orexin B/OX-B), which are also known as hypocretins, are neuropeptides. Orexin A is a 33 amino acid peptide and orexin B is a 28 amino acid peptide (Sakurai T. et al., Cell, 1998, 92, 573-585). Orexins are produced in discrete neurons of the lateral hypothalamus and bind to G-protein-coupled receptors, the orexin receptors (also known as hypocretin receptors): known are the orexin-1 receptor (OX1R) and the orexin-2 receptor (OX2R). The orexin-1 receptor has some selectivity for OX-A, whereas the orexin-2 receptor binds OX-A and OX-B with similar affinity. Orexins regulate states of sleep and wakefulness, opening potentially novel therapeutic approaches for narcolepsy as well as insomnia and other sleep disorders (Chemelli R. M. et al., Cell, 1999, 98, 437-45 1). Furthermore, orexins were found to stimulate food consumption in rats suggesting a physiological role for these peptides as mediators in the central feedback mechanism that regulates feeding behavior (Sakurai T. et al., Cell, 1998, 92, 573-585). Still furthermore, orexins were shown to play a role in brain reward function/motivation suggesting usefulness to treat substance-related disorders (Harris A. C. et al, Nature, 2005, 437, 556-559). Still furthermore, it has been shown that amyloid beta levels inversely correlate with orexin levels in rodents and humans (brain and/or CSF), and that an orexin receptor antagonist reduces both amyloid beta levels and amyloid plaque load in Alzheimer's transgenic mice, thus suggesting usefulness in the treatment of Alzheimers disease (Kang J. E. et al, Science 2009, 326, 1005-1007).

Orexin receptors may have numerous implications in disorders such as i) sleep disorders, e.g. sleep apnea, narcolepsy, insomnia, parasomnia, jet lag syndrome, disturbed biological and circadian rhythms; sleep disturbances associated with diseases such as neurological disorders, neuropathic pain and restless leg syndrome;
ii) eating disorders, e.g. appetite and taste disorders;
iii) substance-related disorders, e.g. substance abuse, substance dependence and substance withdrawal disorders, such as nicotine withdrawal or narcotics withdrawal;
iv) Alzheimers disease;
v) psychiatric, neurological and neurodegenerative disorders, e.g. depression; anxiety; addictions, obsessive compulsive disorder; affective neurosis; depressive neurosis; anxiety neurosis; dysthymic disorder; mood disorder; sexual dysfunction; psychosexual dysfunction; sex disorder; schizophrenia; manic depression; delirium; dementia; severe mental retardation and dyskinesias such as Huntington's disease and Tourette syndrome; Parkinson's disease; ischemic or hemorrhagic stroke; migraine; and neurodegenerative disorders including nosological entities such as disinhibition-dementia-parkinsonism-amyotrophy complex; pallido-ponto-nigral degeneration epilepsy; seizure disorders;
vi) cardiovascular diseases, diabetes; asthma; Cushing's syndrome/disease; basophile adenoma; prolactinoma; hyperprolactinemia; hypopituitarism; hypophysis tumor/adenoma; hypothalamic diseases; Froehlich's syndrome; hypophysis diseases, hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; heart and lung diseases, acute and congestive heart failure; hypotension; hypertension; urinary retention; osteoporosis; angina pectoris; myocardial infarction; subarachnoid hemorrhage; ulcers; allergies; benign prostatic hypertrophy; chronic renal failure; renal disease; impaired glucose tolerance; vomiting and nausea; inflammatory bowel disease; gastric dyskinesia; gastric ulcers; urinary bladder incontinence e.g. urge incontinence; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; conditions associated with visceral pain such as irritable bowel syndrome, migraine and angina; and
vii) other diseases related to general orexin system dysfunction.

Orexin receptor antagonists, are considered to be useful in the treatment of a wide range of disorders, in particular sleep disorders, eating disorders and substance-related disorders.

Therefore, there is a need to provide new orexin receptor antagonists that are good drug candidates. In particular, preferred compounds should bind potently to the orexin receptors (either as OX1R or OX2R subtype selective antagonists or as dual OX1R/OX2R antagonists) whilst showing little affinity for other receptors. They should be well absorbed from the gastrointestinal tract, be sufficiently metabolically stable and possess favorable pharmacokinetic properties. When targeted against receptors in the central nervous system they should cross the blood brain barrier freely and when targeted selectively against receptors in the peripheral nervous system they should not cross the blood brain barrier. They should be non-toxic and demonstrate few side-effects. Furthermore, the ideal drug candidate will be able to exist in a physical form that is stable, non-hygroscopic and easily formulated.

The compounds of formula (I) or (I') are orexin receptor antagonists and are therefore potentially useful in the treatment of a wide range of disorders, particularly sleep disorders, eating disorders, substance-related disorders and Alzheimers disease.

In a first aspect, the invention relates to a compound of the formula I'

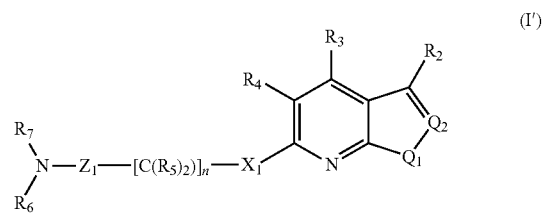

wherein
$Q_1$ is —N($R_1$)—;
wherein $R_1$ is hydrogen; $C_{1-6}$alkyl; $C_{1-6}$halogenalkyl; $C_{2-6}$alkenyl; $C_{2-6}$halogenalkenyl; $C_{2-6}$alkynyl; $C_{2-6}$halogenalkynyl; a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_8$, and wherein a substituent on a nitrogen in a heterocyclic ring system may not be halogen;
and $R_2$ is $C_{2-6}$alkyl; $C_{2-6}$halogenalkyl, $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_9$, and wherein a substituent on a nitrogen in a heterocyclic ring system may not be halogen; or $R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{10}$, and wherein a substituent on a nitrogen in a heterocyclic ring system may not be halogen;

or wherein $R_1$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{11}$, and wherein a substituent on a nitrogen in a heterocyclic ring system may not be halogen;
and $R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{12}$, and wherein a substituent on a nitrogen in a heterocyclic ring system may not be halogen;

each $R_8$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_8$ at the same ring atom together are oxo;

each $R_9$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_9$ at the same ring atom together are oxo;

each $R_{12}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{12}$ at the same ring atom together are oxo;

each $R_{10}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{10}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{13}$, and wherein a substituent on a nitrogen in a heterocyclic ring system may not be halogen; and wherein each $R_{13}$ independently is halogen or $C_{1-6}$alkyl, or two $R_{13}$ at the same ring atom together are oxo;

each $R_{11}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{11}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{14}$, and wherein a substituent on a nitrogen in a heterocyclic ring system may not be halogen; and wherein each $R_{14}$ independently is halogen or $C_{1-6}$alkyl, or two $R_{14}$ at the same ring atom together are oxo;

or $Q_1$ is —O— and $R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{9a}$, and wherein a substituent on a nitrogen in a heterocyclic ring system may not be halogen; or $R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{10a}$, and wherein a substituent on a nitrogen in a heterocyclic ring system may not be halogen;

each $R_{9a}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{9a}$ at the same ring atom together are oxo;

each $R_{10a}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{10a}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{13a}$, and wherein a substituent on a nitrogen in a heterocyclic ring system may not be halogen; and wherein each $R_{13a}$ independently is halogen or $C_{1-6}$alkyl, or two $R_{13a}$ at the same ring atom together are oxo;

$Q_2$ is =N— or =C($R_{1a}$)—;

wherein $R_{1a}$ is hydrogen; $C_{1-6}$alkyl; $C_{1-6}$halogenalkyl; $C_{2-6}$alkenyl; $C_{2-6}$halogenalkenyl; $C_{2-6}$alkynyl; $C_{2-6}$halogenalkynyl;

$R_3$ and $R_4$ are each independently selected from hydrogen, halogen, hydroxyl, $C_{1-6}$alkyl, $C_{1-6}$halogenalkyl, $C_{1-6}$alkoxy, $C_{1-6}$halogenalkoxy, $C_{2-6}$alkenyl, $C_{2-6}$halogenalkenyl, $C_{2-6}$alkinyl, $C_{2-6}$halogenalkinyl, $C_{3-7}$cycloalkyl, $C_{3-7}$cycloalkyl($C_{1-4}$alkyl);

$X_1$ is —O—, —N($R_{15}$)—;

$R_{15}$ is hydrogen or $C_{1-6}$alkyl;

n is 1, 2 or 3;

each $R_5$ independently is selected from hydrogen, halogen, hydroxyl, $C_{1-6}$alkyl, $C_{1-6}$halogenalkyl, $C_{1-6}$alkoxy, $C_{1-6}$halogenalkoxy, $C_{3-7}$cycloalkyl, $C_{3-7}$cycloalkyl($C_{1-4}$alkyl); or two $R_5$ at the same carbon atom together with said carbon atom form $C_{3-7}$cycloalkyl; or two $R_5$ at adjacent carbon atoms together with said carbon atoms form $C_{3-7}$cycloalkyl; or two $R_5$ at carbon atoms separated by one further carbon atom together with said carbon atoms form $C_{4-7}$cycloalkyl;

$Z_1$ is —C(O)—, —S(O)— or —S(O)$_2$—;

$R_6$ is $C_{1-6}$alkyl, $C_{1-6}$halogenalkyl, $C_{2-6}$alkenyl, $C_{2-6}$halogenalkenyl, $C_{2-6}$alkynyl, $C_{2-6}$halogenalkynyl, $C_{3-7}$cycloalkyl, $C_{3-7}$cycloalkyl($C_{1-4}$alkyl) or a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system is attached to the nitrogen atom via a $C_{1-4}$alkylene group, and wherein the ring system may be substituted once or more than once by $R_{16}$, and wherein a substituent on a nitrogen in a heterocyclic ring system may not be halogen;

each $R_{16}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

or two $R_{16}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{17}$, and wherein a substituent on a nitrogen in a heterocyclic ring system may not be halogen; and wherein each $R_{17}$ independently is halogen or $C_{1-6}$alkyl, or two $R_{17}$ at the same ring atom together are oxo;

or $R_6$ is a group A

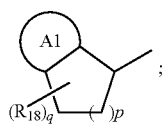

wherein p is 1 or 2;

q is 0, 1, 2, 3 or 4;

each $R_{18}$ independently is halogen or $C_{1-6}$alkyl;

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by $R_{19}$, and wherein a substituent on a nitrogen in a heterocyclic ring system may not be halogen;

each $R_{19}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

and $R_7$ is hydrogen, $C_{1-6}$alkyl, $C_{1-6}$halogenalkyl, $C_{2-6}$alkenyl, $C_{2-6}$halogenalkenyl, $C_{2-6}$alkinyl, $C_{2-6}$halogenalkinyl, $C_{3-7}$cycloalkyl, $C_{3-7}$cycloalkyl($C_{1-4}$alkyl);

in free form or in salt form for use as a medicament.

In a second aspect, the invention relates to a compound of formula I'

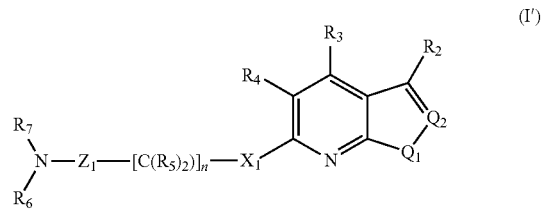

wherein $Q_1$ is —N($R_1$)—;

wherein $R_1$ is hydrogen; $C_{1-6}$alkyl; $C_{1-6}$halogenalkyl; $C_{2-6}$alkenyl; $C_{2-6}$halogenalkenyl; $C_{2-6}$alkynyl; $C_{2-6}$halogenalkynyl; a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$ alkylene group, and wherein the ring system may be substituted once or more than once by $R_8$, and wherein a substituent on a nitrogen in a heterocyclic ring system may not be halogen;

and $R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_9$, and wherein a substituent on a nitrogen in a heterocyclic ring system may not be halogen; or $R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{10}$, and wherein a substituent on a nitrogen in a heterocyclic ring system may not be halogen;

or wherein $R_1$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{11}$, and wherein a substituent on a nitrogen in a heterocyclic ring system may not be halogen;

and $R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{12}$, and wherein a substituent on a nitrogen in a heterocyclic ring system may not be halogen;

each $R_8$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_8$ at the same ring atom together are oxo;

each $R_9$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_9$ at the same ring atom together are oxo;

each $R_{12}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{12}$ at the same ring atom together are oxo;

each $R_{10}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{10}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{13}$, and wherein a substituent on a nitrogen in a heterocyclic ring system may not be halogen; and wherein each $R_{13}$ independently is halogen or $C_{1-6}$alkyl, or two $R_{13}$ at the same ring atom together are oxo;

each $R_{11}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{11}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{14}$, and wherein a substituent on a nitrogen in a heterocyclic ring system may not be halogen; and wherein each $R_{14}$ independently is halogen or $C_{1-6}$alkyl, or two $R_{14}$ at the same ring atom together are oxo;

or $Q_1$ is —O— and $R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{9a}$, and wherein a substituent on a nitrogen in a heterocyclic ring system may not be halogen; or $R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{10a}$, and wherein a substituent on a nitrogen in a heterocyclic ring system may not be halogen;

each $R_{9a}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{9a}$ at the same ring atom together are oxo;

each $R_{10a}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{10a}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{13a}$, and wherein a substituent on a nitrogen in a heterocyclic ring system may not be halogen; and wherein each $R_{13a}$ independently is halogen or $C_{1-6}$alkyl, or two $R_{13a}$ at the same ring atom together are oxo;

$Q_2$ is =N— or =C($R_{1a}$)—;

wherein $R_{1a}$ is hydrogen; $C_{1-6}$alkyl; $C_{1-6}$halogenalkyl; $C_{2-6}$alkenyl; $C_{2-6}$halogenalkenyl; $C_{2-6}$alkynyl; $C_{2-6}$halogenalkynyl;

$R_3$ and $R_4$ are each independently selected from hydrogen, halogen, hydroxyl, $C_{1-6}$alkyl, $C_{1-6}$halogenalkyl, $C_{1-6}$alkoxy, $C_{1-6}$halogenalkoxy, $C_{2-6}$alkenyl, $C_{2-6}$halogenalkenyl, $C_{2-6}$alkinyl, $C_{2-6}$halogenalkinyl, $C_{3-7}$cycloalkyl, $C_{3-7}$cycloalkyl($C_{1-4}$alkyl);

$X_1$ is —O—, —N($R_{15}$)—;

$R_{15}$ is hydrogen or $C_{1-6}$alkyl;

n is 1, 2 or 3;

each $R_5$ independently is selected from hydrogen, halogen, hydroxyl, $C_{1-6}$alkyl, $C_{1-6}$halogenalkyl, $C_{1-6}$alkoxy, $C_{1-6}$halogenalkoxy, $C_{3-7}$cycloalkyl, $C_{3-7}$cycloalkyl($C_{1-4}$alkyl); or two $R_5$ at the same carbon atom together with said carbon atom form $C_{3-7}$cycloalkyl; or two $R_5$ at adjacent carbon atoms together with said carbon atoms form $C_{3-7}$cycloalkyl; or two $R_5$ at carbon atoms separated by one further carbon atom together with said carbon atoms form $C_{4-7}$cycloalkyl;

$Z_1$ is —C(O)—, —S(O)— or —S(O)$_2$—;

$R_6$ is $C_{1-6}$alkyl, $C_{1-6}$halogenalkyl, $C_{2-6}$alkenyl, $C_{2-6}$halogenalkenyl, $C_{2-6}$alkynyl, $C_{2-6}$halogenalkynyl, $C_{3-7}$cycloalkyl, $C_{3-7}$cycloalkyl($C_{1-4}$alkyl) or a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system is attached to the nitrogen atom via a $C_{1-4}$alkylene group, and wherein the ring system may be substituted once or more than once by $R_{16}$, and wherein a substituent on a nitrogen in a heterocyclic ring system may not be halogen;

each $R_{16}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{16}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{17}$, and wherein a substituent on a nitrogen in a heterocyclic ring system may not be halogen; and wherein each $R_{17}$ independently is halogen or $C_{1-6}$alkyl, or two $R_{17}$ at the same ring atom together are oxo;
or
$R_6$ is a group A

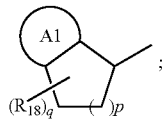

wherein
p is 1 or 2;
q is 0, 1, 2, 3 or 4;
each $R_{18}$ independently is halogen or $C_{1-6}$alkyl;
A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by $R_{19}$, and wherein a substituent on a nitrogen in a heterocyclic ring system may not be halogen; each $R_{19}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;
and $R_7$ is hydrogen, $C_{1-6}$alkyl, $C_{1-6}$halogenalkyl, $C_{2-6}$alkenyl, $C_{2-6}$halogenalkenyl, $C_{2-6}$alkinyl, $C_{2-6}$halogenalkinyl, $C_{3-7}$cycloalkyl, $C_{3-4}$cycloalkyl($C_{1-4}$alkyl);
and provided that the compounds
N-(2-methoxybenzyl)-2-(1-methyl-3-phenyl-4-(trifluoromethyl)-1H-pyrazolo[3,4-b]pyridin-6-yloxy)acetamide;
2-(1-methyl-3-phenyl-4-(trifluoromethyl)-1H-pyrazolo[3,4-b]pyridin-6-yloxy)-N-(2-methylbenzyl)acetamide;
N-(2-ethoxybenzyl)-2-(1-methyl-3-phenyl-4-(trifluoromethyl)-1H-pyrazolo[3,4-b]pyridin-6-yloxy)acetamide;
N-(3-fluorobenzyl)-2-(1-methyl-3-phenyl-4-(trifluoromethyl)-1H-pyrazolo[3,4-b]pyridin-6-yloxy)acetamide;
2-(1-methyl-3-phenyl-4-(trifluoromethyl)-1H-pyrazolo[3,4-b]pyridin-6-yloxy)-N-(4-phenylbutan-2-yl)acetamide;
N-cyclohexyl-2-(1-methyl-3-phenyl-4-(trifluoromethyl)-1H-pyrazolo[3,4-b]pyridin-6-yloxy)acetamide;
N-(4-fluorobenzyl)-2-(1-methyl-3-phenyl-4-(trifluoromethyl)-1H-pyrazolo[3,4-b]pyridin-6-yloxy)acetamide;
2-(1-methyl-3-phenyl-4-(trifluoromethyl)-1H-pyrazolo[3,4-b]pyridin-6-yloxy)-N-(1-phenylethyl)acetamide;
N-(benzo[d][1,3]dioxol-5-ylmethyl)-2-(1-methyl-3-phenyl-4-(trifluoromethyl)-1H-pyrazolo[3,4-b]pyridin-6-yloxy)acetamide;
N-cyclopentyl-2-(1-methyl-3-phenyl-4-(trifluoromethyl)-1H-pyrazolo[3,4-b]pyridin-6-yloxy)acetamide;
N-(4-chlorobenzyl)-2-(1-methyl-3-phenyl-4-(trifluoromethyl)-1H-pyrazolo[3,4-b]pyridin-6-yloxy)acetamide;
N-(2-chlorobenzyl)-2-(1-methyl-3-phenyl-4-(trifluoromethyl)-1H-pyrazolo[3,4-b]pyridin-6-yloxy)acetamide; and
N-benzyl-2-(1-methyl-3-phenyl-4-(trifluoromethyl)-1H-pyrazolo[3,4-b]pyridin-6-yloxy)acetamide
are excluded;
in free form or in salt form.
In a third aspect, the invention relates to a compound of the formula I

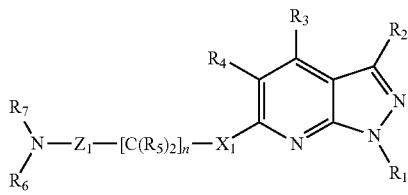

wherein
$R_1$ is hydrogen; $C_{1-6}$alkyl; $C_{1-6}$halogenalkyl; $C_{2-6}$alkenyl; $C_{2-6}$halogenalkenyl; $C_{2-6}$alkinyl; $C_{2-6}$halogenalkinyl; or $R_1$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the nitrogen atom of the 1H-pyrazolo[3,4b]pyridine or via a $C_{1-4}$alkylene group, and wherein the ring system may be substituted once or more than once by $R_8$, and wherein a substituent on a nitrogen in a heterocyclic ring system may not be halogen;
and
$R_2$ is $C_{2-6}$alkyl, $C_{2-6}$halogenalkyl; $C_{2-6}$alkenyl; $C_{2-6}$halogenalkenyl; $C_{2-6}$alkinyl; $C_{2-6}$halogenalkinyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a $C_{1-4}$alkylene group, and wherein the ring system may be substituted once or more than once by $R_s$, and wherein a substituent on a nitrogen in a heterocyclic ring system may not be halogen; or $R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a $C_{1-4}$alkylene group, and wherein the ring system may be substituted once or more than once by $R_{10}$, and wherein a substituent on a nitrogen in a heterocyclic ring system may not be halogen;
or
$R_1$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the nitrogen atom of the 1H-pyrazolo[3,4b]pyridine or via a $C_{1-4}$alkylene group, and wherein the ring system may be substituted once or more than once by $R_{11}$, and wherein a substituent on a nitrogen in a heterocyclic ring system may not be halogen;
and
$R_2$ is $C_{2-6}$alkyl; $C_{2-6}$halogenalkyl; $C_{2-6}$alkenyl; $C_{2-6}$halogenalkenyl; $C_{2-6}$alkinyl; $C_{2-6}$halogenalkinyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a $C_{1-4}$alkylene group, and wherein the ring system may be substituted once or more than once by $R_{12}$, and wherein a substituent on a nitrogen in a heterocyclic ring system may not be halogen;

each $R_8$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_8$ at the same ring atom together are oxo;

each $R_9$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_9$ at the same ring atom together are oxo;

each $R_{12}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{12}$ at the same ring atom together are oxo;

each $R_{10}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{10}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{13}$, and wherein a substituent on a nitrogen in a heterocyclic ring system may not be halogen; and wherein each $R_{13}$ independently is halogen or $C_{1-6}$alkyl, or two $R_{13}$ at the same ring atom together are oxo;

each $R_{11}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{11}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{14}$, and wherein a substituent on a nitrogen in a heterocyclic ring system may not be halogen; and wherein each $R_{14}$ independently is halogen or $C_{1-6}$alkyl, or two $R_{14}$ at the same ring atom together are oxo;

$R_3$ and $R_4$ are each independently selected from hydrogen, halogen, hydroxyl, $C_{1-6}$alkyl, $C_{1-6}$halogenalkyl, $C_{1-6}$alkoxy, $C_{1-6}$halogenalkoxy, $C_{2-6}$alkenyl, $C_{2-6}$halogenalkenyl, $C_{2-6}$alkinyl, $C_{2-6}$halogenalkinyl, $C_{3-7}$cycloalkyl, $C_{3-7}$cycloalkyl($C_{1-4}$alkyl);

$X_1$ is —O—, —N($R_{15}$)—;

$R_{15}$ is hydrogen or $C_{1-6}$alkyl;

n is 1, 2 or 3;

each $R_5$ independently is selected from hydrogen, halogen, hydroxyl, $C_{1-6}$alkyl, $C_{1-6}$halogenalkyl, $C_{1-6}$alkoxy, $C_{1-6}$halogenalkoxy, $C_{3-7}$cycloalkyl, $C_{3-7}$cycloalkyl($C_{1-4}$alkyl); or two $R_5$ at the same carbon atom together with said carbon atom form $C_{3-7}$cycloalkyl; or two $R_5$ at adjacent carbon atoms together with said carbon atoms form $C_{3-7}$cycloalkyl; or two $R_5$ at carbon atoms separated by one further carbon atom together with said carbon atoms form $C_{4-7}$cycloalkyl;

$Z_1$ is —C(O)—, —S(O)— or —S(O)$_2$—;

$R_6$ is $C_{1-6}$alkyl, $C_{1-6}$halogenalkyl, $C_{2-6}$alkenyl, $C_{2-6}$halogenalkenyl, $C_{2-6}$alkinyl, $C_{2-6}$halogenalkinyl, $C_{3-7}$cycloalkyl, $C_{3-7}$cycloalkyl($C_{1-4}$alkyl) or a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system is attached to the nitrogen atom via a $C_{1-4}$alkylene group, and wherein the ring system may be substituted once or more than once by $R_{16}$, and wherein a substituent on a nitrogen in a heterocyclic ring system may not be halogen;

each $R_{16}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

or two $R_{16}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{17}$, and wherein a substituent on a nitrogen in a heterocyclic ring system may not be halogen; and wherein each $R_{17}$ independently is halogen or $C_{1-6}$alkyl, or two $R_{17}$ at the same ring atom together are oxo;

or $R_6$ is a group A

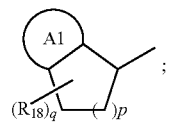

wherein p is 1 or 2;

q is 0, 1, 2, 3 or 4;

each $R_{18}$ independently is halogen or $C_{1-6}$alkyl;

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by $R_{19}$, and wherein a substituent on a nitrogen in a heterocyclic ring system may not be halogen;

each $R_{19}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

and $R_7$ is hydrogen, $C_{1-6}$alkyl, $C_{1-6}$halogenalkyl, $C_{2-6}$alkenyl, $C_{2-6}$halogenalkenyl, $C_{2-6}$alkinyl, $C_{2-6}$halogenalkinyl, $C_{3-7}$cycloalkyl, $C_{3-7}$cycloalkyl($C_{1-4}$alkyl);

in free form or in salt form for use as a medicament.

In a fourth aspect, the invention relates to a compound of the formula I

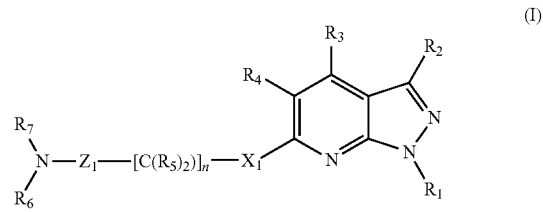

wherein $R_1$ is hydrogen; $C_{1-6}$alkyl; $C_{1-6}$halogenalkyl; $C_{2-6}$alkenyl; $C_{2-6}$halogenalkenyl; $C_{2-6}$alkinyl; $C_{2-6}$halogenalkinyl; or $R_1$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the nitrogen atom of the 1H-pyrazolo[3,4b]pyridine or via a $C_{1-4}$alkylene group, and wherein the ring system may be substituted once or more than once by $R_g$, and wherein a substituent on a nitrogen in a heterocyclic ring system may not be halogen;
and
$R_2$ is $C_{2-6}$alkyl; $C_{2-6}$halogenalkyl; $C_{2-6}$alkenyl; $C_{2-6}$halogenalkenyl; $C_{2-6}$alkinyl; $C_{2-6}$halogenalkinyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a $C_{1-4}$alkylene group, and wherein the ring system may be substituted once or more than once by $R_g$, and wherein a substituent on a nitrogen in a heterocyclic ring system may not be halogen; or $R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a $C_{1-4}$alkylene group, and wherein the ring system may be substituted once or more than once by $R_{10}$, and wherein a substituent on a nitrogen in a heterocyclic ring system may not be halogen;
or
$R_1$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the nitrogen atom of the 1H-pyrazolo[3,4b]pyridine or via a $C_{1-4}$alkylene group, and wherein the ring system may be substituted once or more than once by $R_{11}$, and wherein a substituent on a nitrogen in a heterocyclic ring system may not be halogen;
and
$R_2$ is $C_{2-6}$alkyl; $C_{2-6}$halogenalkyl; $C_{2-6}$alkenyl; $C_{2-6}$halogenalkenyl; $C_{2-6}$alkinyl; $C_{2-6}$halogenalkinyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a $C_{1-4}$alkylene group, and wherein the ring system may be substituted once or more than once by $R_{12}$, and wherein a substituent on a nitrogen in a heterocyclic ring system may not be halogen;
each $R_8$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_8$ at the same ring atom together are oxo;
each $R_9$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_9$ at the same ring atom together are oxo;
each $R_{12}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{12}$ at the same ring atom together are oxo;

each $R_{10}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{10}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{13}$, and wherein a substituent on a nitrogen in a heterocyclic ring system may not be halogen; and wherein each $R_{13}$ independently is halogen or $C_{1-6}$alkyl, or two $R_{13}$ at the same ring atom together are oxo;
each $R_{11}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{11}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{14}$, and wherein a substituent on a nitrogen in a heterocyclic ring system may not be halogen; and wherein each $R_{14}$ independently is halogen or $C_{1-6}$alkyl, or two $R_{14}$ at the same ring atom together are oxo;
$R_3$ and $R_4$ are each independently selected from hydrogen, halogen, hydroxyl, $C_{1-6}$alkyl, $C_{1-6}$halogenalkyl, $C_{1-6}$alkoxy, $C_{1-6}$halogenalkoxy, $C_{2-6}$alkenyl, $C_{2-6}$halogenalkenyl, $C_{2-6}$alkinyl, $C_{2-6}$halogenalkinyl, $C_{3-7}$cycloalkyl, $C_{3-7}$cycloalkyl($C_{1-4}$alkyl);
$X_1$ is —O—, —N($R_{15}$)—;
$R_{15}$ is hydrogen or $C_{1-6}$alkyl;
n is 1, 2 or 3;
each $R_5$ independently is selected from hydrogen, halogen, hydroxyl, $C_{1-6}$alkyl, $C_{1-6}$halogenalkyl, $C_{1-6}$alkoxy, $C_{1-6}$halogenalkoxy, $C_{3-7}$cycloalkyl, $C_{3-7}$cycloalkyl($C_{1-4}$alkyl); or two $R_5$ at the same carbon atom together with said carbon atom form $C_{3-7}$cycloalkyl; or two $R_5$ at adjacent carbon atoms together with said carbon atoms form $C_{3-7}$cycloalkyl; or two $R_5$ at carbon atoms separated by one further carbon atom together with said carbon atoms form $C_{4-7}$cycloalkyl;
$Z_1$ is —C(O)—, —S(O)— or —S(O)$_2$—;
$R_6$ is $C_{1-6}$alkyl, $C_{1-6}$halogenalkyl, $C_{2-6}$alkenyl, $C_{2-6}$halogenalkenyl, $C_{2-6}$alkinyl, $C_{2-6}$halogenalkinyl, $C_{3-7}$cycloalkyl, $C_{3-7}$cycloalkyl($C_{1-4}$alkyl) or a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system is attached to the nitrogen atom via a $C_{1-4}$alkylene group, and wherein the ring system may be substituted once or more than once by $R_{16}$, and wherein a substituent on a nitrogen in a heterocyclic ring system may not be halogen;
each $R_{16}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;
or two $R_{16}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{17}$, and wherein a substituent on a nitrogen in a heterocyclic ring system may not be halogen; and wherein each $R_{17}$ independently is halogen or $C_{1-6}$alkyl, or two $R_{17}$ at the same ring atom together are oxo;

or $R_6$ is a group A

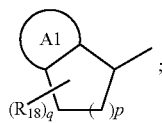

wherein
p is 1 or 2;
q is 0, 1, 2, 3 or 4;
each $R_{18}$ independently is halogen or $C_{1-6}$alkyl;
A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by $R_{19}$, and wherein a substituent on a nitrogen in a heterocyclic ring system may not be halogen;
each $R_{19}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;
and $R_7$ is hydrogen, $C_{1-6}$alkyl, $C_{1-6}$halogenalkyl, $C_{2-6}$alkenyl, $C_{2-6}$halogenalkenyl, $C_{2-6}$alkinyl, $C_{2-6}$halogenalkinyl, $C_{3-7}$cycloalkyl, $C_{3-7}$cycloalkyl($C_{1-4}$alkyl);
in free form or in salt form
and provided that the compounds
N-(2-methoxybenzyl)-2-(1-methyl-3-phenyl-4-(trifluoromethyl)-1H-pyrazolo[3,4-b]pyridin-6-yloxy)acetamide;
2-(1-methyl-3-phenyl-4-(trifluoromethyl)-1H-pyrazolo[3,4-b]pyridin-6-yloxy)-N-(2-methylbenzyl)acetamide;
N-(2-ethoxybenzyl)-2-(1-methyl-3-phenyl-4-(trifluoromethyl)-1H-pyrazolo[3,4-b]pyridin-6-yloxy)acetamide;
N-(3-fluorobenzyl)-2-(1-methyl-3-phenyl-4-(trifluoromethyl)-1H-pyrazolo[3,4-b]pyridin-6-yloxy)acetamide;
2-(1-methyl-3-phenyl-4-(trifluoromethyl)-1H-pyrazolo[3,4-b]pyridin-6-yloxy)-N-(4-phenylbutan-2-yl)acetamide;
N-cyclohexyl-2-(1-methyl-3-phenyl-4-(trifluoromethyl)-1H-pyrazolo[3,4-b]pyridin-6-yloxy)acetamide;
N-(4-fluorobenzyl)-2-(1-methyl-3-phenyl-4-(trifluoromethyl)-1H-pyrazolo[3,4-b]pyridin-6-yloxy)acetamide;
2-(1-methyl-3-phenyl-4-(trifluoromethyl)-1H-pyrazolo[3,4-b]pyridin-6-yloxy)-N-(1-phenylethyl)acetamide;
N-(benzo[d][1,3]dioxol-5-ylmethyl)-2-(1-methyl-3-phenyl-4-(trifluoromethyl)-1H-pyrazolo[3,4-b]pyridin-6-yloxy)acetamide;
N-cyclopentyl-2-(1-methyl-3-phenyl-4-(trifluoromethyl)-1H-pyrazolo[3,4-b]pyridin-6-yloxy)acetamide;
N-(4-chlorobenzyl)-2-(1-methyl-3-phenyl-4-(trifluoromethyl)-1H-pyrazolo[3,4-b]pyridin-6-yloxy)acetamide;
N-(2-chlorobenzyl)-2-(1-methyl-3-phenyl-4-(trifluoromethyl)-1H-pyrazolo[3,4-b]pyridin-6-yloxy)acetamide; and
N-benzyl-2-(1-methyl-3-phenyl-4-(trifluoromethyl)-1H-pyrazolo[3,4-b]pyridin-6-yloxy)acetamide
are excluded;
in free form or in salt form.

Unless indicated otherwise, the expressions used in this invention have the following meaning:

"Alkyl" represents a straight-chain or branched-chain alkyl group, for example, methyl, ethyl, n- or iso-propyl, n-, iso-, sec- or tert-butyl, n-pentyl, n-hexyl; $C_{1-6}$alkyl preferably represents a straight-chain or branched-chain $C_{1-4}$alkyl with particular preference given to methyl, ethyl, n-propyl, iso-propyl and tert-butyl. $C_{2-6}$alkyl preferably represents a straight-chain or branched-chain $C_{2-4}$alkyl with particular preference given to ethyl, n-propyl, iso-propyl and tert-butyl.

Each alkyl part of "alkoxy", "halogenalkyl" and so on shall have the same meaning as described in the above-mentioned definition of "alkyl", especially regarding linearity and preferential size.

"$C_{3-7}$cycloalkyl" represents a saturated alicyclic moiety having from three to six carbon atoms. This term refers to groups such as cyclopropyl, cyclobutyl, cyclopentyl and cyclohexyl.

As used herein, the term "alkylene" refers to divalent alkyl group as defined herein, for example methylene, ethylene, n-propylene, iso-propylene, n-butylene, sec-butylene, iso-, butylene, and tert-butylene.

A substituent being substituted "once or more than once", for example as defined for $R_1$, is preferably substituted by one to three substituents.

Halogen is generally fluorine, chlorine, bromine or iodine; preferably fluorine, chlorine or bromine. Halogenalkyl groups preferably have a chain length of 1 to 4 carbon atoms and are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,2-trichloroethyl, 1,1,2,2-tetrafluoroethyl, 2,2,3,3-tetrafluoropropyl, 2,2,3,3-pentafluoropropyl or 2,2,3,4,4,4-hexafluorobutyl; preferably —$CF_3$, —$CHF_2$, —$CH_2F$, —CHF—$CH_3$, —$CF_2CH_3$, or —$CH_2CF_3$.

In the context of the invention, the definition of $R_1$, $R_2$ and/or A1 as a "five- to six-membered monocyclic aromatic ring system which may contain from 1 to 4 heteroatoms" encompasses a $C_6$-aromatic hydrocarbon group or a five- to six-membered heterocyclic aromatic ring system.

In the context of the invention, the definition of $R_6$ as a "five- to ten-membered monocyclic or fused polycyclic aromatic ring system which may contain from 1 to 4 heteroatoms" encompasses a $C_6$- or $C_{10}$-aromatic hydrocarbon group or a five- to ten-membered heterocyclic aromatic ring system. "Polycyclic" means preferably bicyclic.

The term "fused polycyclic aromatic ring system" refers to an aromatic substituent which consists of multiple, e.g. two, aromatic rings that are fused together.

In the context of the invention, the definition of $R_1$ and $R_2$ as a "three- to eight-membered monocyclic or bicyclic saturated or unsaturated non-aromatic ring system which may contain from 1 to 4 heteroatoms" encompasses three- to eight membered monocyclic or bicyclic non-aromatic hydrocarbon groups and non-aromatic heterocyclic ring systems of the same sizes.

In the context of the invention, the definition of two $R_{10}$, two $R_{11}$ or two $R_{16}$ as a "fused five- to seven-membered unsaturated non-aromatic ring system" encompasses five- to seven-membered non-aromatic hydrocarbon and heterocyclic groups which comprise at least one double-bond, which is shared with the aromatic ring system they are fused to.

A $C_6$- or $C_{10}$-aromatic hydrocarbon group is typically phenyl or naphthyl, especially phenyl.

Preferably, but also depending on substituent definition, "five- to six-membered heterocyclic aromatic ring systems" consist of 5 to 6 ring atoms of which 1-3 ring atoms are hetero atoms.

Examples of heterocyclic ring systems are: pyrrole, pyrazole, imidazole, triazole, tetrazole, furane, furazane (oxadiazole), thiophene, oxazole, isoxazole, thiazole, isothiazole, thiadiazole, pyridine, pyrimidine, pyridazine, pyrazine and triazine. Further examples of heterocycles are: oxazole, isoxazole, thiazole, isothiazole, triazole, pyrrole, furane, pyridine, pyrimidine, imidazole or pyrazole.

The compounds of formula (I) or (I') may exist in optically active form or in form of mixtures of optical isomers, e.g. in form of racemic mixtures or diastereomeric mixtures. In particular, asymmetrical carbon atom(s) may be present in the compounds of formula (I) or (I') and their salts. Unless specified otherwise, all optical isomers and their mixtures, including the racemic mixtures, are embraced by the invention.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of formula (I) or (I') and includes geometric isomers. It is understood that a substituent may be attached at a chiral center of a carbon atom. Therefore, the invention may include enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. The compounds described herein may contain one or more asymmetric centers and may thus give rise to enantiomers, diastereomers, and other stereoisomeric forms that may be defined, in terms of absolute stereochemistry, as (R)- or (S)-. Unless otherwise specified, the invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any asymmetric atom (e.g. carbon or the like) of the compound(s) of formula (I) or (I') can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of formula (I) or (I') can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of formula (I) or (I') into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Depending on substituent definition, compounds of the present invention may occur in various tautomeric forms. All tautomeric forms of the compounds of formula (I) or (I') are embraced by the invention.

Compounds of formula (I) or (I') may exist in free form or as a salt. In this specification, unless otherwise indicated, language such as "compound of formula (I) or (I')" is to be understood as embracing the compounds in any form, for example free or acid addition salt form. Salts which are unsuitable for pharmaceutical uses but which can be employed, for example, for the isolation or purification of free compounds of formula (I) or (I'), such as picrates or perchlorates, are also included. For therapeutic use, only pharmaceutically acceptable salts or free compounds are employed (where applicable in the form of pharmaceutical preparations), and are therefore preferred. Salts are preferably physiologically acceptable salts, formed by the addition of an acid.

As used herein, the term "pharmaceutically acceptable salts" refers to salts that retain the biological effectiveness and properties of the compounds of this invention and, which typically are not biologically or otherwise undesirable. The compounds of formula (I) or (I') may be capable of forming acid salts by virtue of the presence of suitable groups, such as amino groups.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulformate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

The pharmaceutically acceptable salts of the invention can be synthesized from a parent compound by conventional chemical methods. Generally, such salts can be prepared by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

The invention includes all pharmaceutically acceptable isotopically-labeled compounds of formula (I) or (I'), wherein (1) one or more atoms are replaced by atoms having the same atomic number, but an atomic mass or mass number different from the atomic mass or mass number usually found in nature, and/or (2) the isotopic ratio of one or more atoms is different from the naturally occurring ratio.

Examples of isotopes suitable for inclusion in the compounds of formula (I) or (I') comprises isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Certain isotopically-labeled compounds of formula (I) or (I'), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Tomography (PET) studies for examining substrate receptor occupancy.

Isotopically-labeled compounds of formula (I) or (I') can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of formula (I) or (I') that contain groups capable of acting as donors and/or acceptors for hydrogen bonds may be capable of forming co-crystals with suitable co-crystal formers. These co-crystals may be prepared from compounds of formula (I) or (I') by known co-crystal forming procedures. Such procedures include grinding, heating, co-subliming, co-melting, or contacting in solution compounds of formula (I) or (I') with the co-crystal former under crystallization conditions and isolating co-crystals thereby formed. Suitable co-crystal formers include those described in WO 2004/078163. Hence the invention further provides co-crystals comprising a compound of formula (I) or (I').

Compounds of formula (I) or (I') are either obtained in the free form, as a salt thereof, or as prodrug derivatives thereof.

The invention also provides pro-drugs of the compounds of formula (I) or (I') that converts in vivo to the compounds of formula (I) or (I'). A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids (e.g., a carboxylic acid having at least one lipophilic moiety).

Exemplary prodrugs are, e.g., O-acyl derivatives of alcohols. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of formula (I) or (I'), including their salts, can also be obtained in the form of their hydrates, or include other solvents used for their crystallization.

Preferred substituents, preferred ranges of numerical values or preferred ranges of the radicals present in compounds of the formula I', I, I'-a, I-a, I'-1, I-1, I'-2, I-2, I'-3, I-3, I'-4 and I-4 and the corresponding intermediate compounds are defined below. The definition of the substituents applies to the end-products as well as to the corresponding intermediates. The definitions of the substituents may be combined at will, e.g. preferred substituents $R_1$ and preferred substituents $R_2$.

In especially preferred embodiments, the invention relates to one or more than one of the compounds of the formula I' mentioned in the Examples hereinafter, in free form or in salt form.

In one class of compounds of the invention, $Q_1$ is —$N(R_1)$— and $Q_2$ is =N—.

In one class of compounds of the invention, $Q_1$ is —$N(R_1)$— and $Q_2$ =$C(R_{1a})$—.

In one class of compounds of the invention, $Q_1$ is —O— and $Q_2$ is =N—.

In one class of compounds of the invention, $R_1$ is hydrogen, $C_{1-6}$alkyl, $C_{1-6}$halogenalkyl, $C_{2-6}$alkenyl, $C_{2-6}$halogenalkenyl, $C_{2-6}$alkynyl or $C_{2-6}$halogenalkynyl. In one class of compounds of the invention, $R_1$ is $C_{1-6}$alkyl, especially methyl, ethyl or n-propyl. In one class of compounds of the invention, $R_1$ is methyl. In one class of compounds of the invention, $R_1$ is hydrogen.

In one class of compounds of the invention, $R_{1a}$ is hydrogen, $C_{1-6}$alkyl, $C_{1-6}$halogenalkyl, $C_{2-6}$alkenyl, $C_{2-6}$halogenalkenyl, $C_{2-6}$alkynyl, $C_{2-6}$halogenalkynyl. In one class of compounds of the invention, $R_{1a}$ is $C_{1-6}$alkyl, especially methyl. In one class of compounds of the invention, $R_{1a}$ is hydrogen.

In one class of compounds of the invention, $R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_9$, and wherein a substituent on a nitrogen in a heterocyclic ring system may not be halogen. In one class of compounds of the invention, $R_2$ is $C_{2-6}$alkyl. In one class of compounds of the invention, $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_9$, and wherein a substituent on a nitrogen in a heterocyclic ring system may not be halogen. In one class of compounds of the invention, $R_2$ is cyclopropyl being attached directly.

In one class of compounds of the invention, $R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{10}$, and wherein a substituent on a nitrogen in a heterocyclic ring system may not be halogen. In one class of compounds of the invention, $R_2$ is phenyl being attached directly and wherein said phenyl may be substituted once or more than once by $R_{10}$.

In one class of compounds of the invention, $R_3$ is selected from halogen, hydroxyl, $C_{1-6}$alkyl, $C_{1-6}$halogenalkyl, $C_{1-6}$alkoxy, $C_{1-6}$halogenalkoxy, $C_{2-6}$alkenyl, $C_{2-6}$halogenalkenyl, $C_{2-6}$alkynyl, $C_{2-6}$halogenalkynyl, $C_{3-7}$cycloalkyl, $C_{3-7}$cycloalkyl($C_{1-4}$alkyl). In said class, $R_3$ is especially selected from $C_{1-6}$alkyl and $C_{1-6}$halogenalkyl, for example methyl or trifluoromethyl. In said class, $R_3$ is especially trifluoromethyl.

In one class of compounds of the invention, $R_4$ is selected from hydrogen, halogen, $C_{1-6}$alkyl and $C_{1-6}$halogenalkyl. In said class, $R_4$ is especially hydrogen.

In one class of compounds of the invention, $X_1$ is —O—.

In one class of compounds of the invention, $X_1$ is —$N(R_{15})$—.

In one class of compounds of the invention, n is 1.

In one class of compounds of the invention, n is 2.

In one class of compounds of the invention, n is 3.

In one class of compounds of the invention, each $R_5$ independently is selected from hydrogen, halogen, $C_{1-6}$alkyl and $C_{1-6}$halogenalkyl. In said class, each $R_5$ is especially hydrogen. In one class, one $R_5$ is methyl and the other $R_5$ is hydrogen.

In one class of compounds of the invention, $Z_1$ is —C(O)—.

In one class of compounds of the invention, $Z_1$ is —S(O)—.

In one class of compounds of the invention, $Z_1$ is —$S(O)_2$—.

In one class of compounds of the invention, $R_6$ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system is attached to the nitrogen atom via a $C_{1-4}$alkylene group, and wherein the ring system may be substituted once or more than once by $R_{16}$, and wherein a substituent on a nitrogen in a heterocyclic ring system may not be halogen. In said class, each $R_{16}$ independently is especially halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy. In said class, each $R_{16}$ independently is further especially halogen, $C_{1-6}$alkyl $C_{1-6}$alkoxy or $C_{1-6}$halogenalkyl.

In one class of compounds of the invention, $R_6$ is $C_{1-6}$alkyl, $C_{1-6}$halogenalkyl, $C_{2-6}$alkenyl, $C_{2-6}$halogenalkenyl, $C_{2-6}$alkynyl, $C_{2-6}$halogenalkynyl, $C_{3-7}$cycloalkyl, $C_{3-7}$cycloalkyl($C_{1-4}$alkyl). In one class of compounds of the invention, $R_6$ is $C_{1-6}$alkyl. In one class of compounds of the invention, $R_6$ is $C_{3-7}$cycloalkyl.

In one class of compounds of the invention, $R_6$ is a group A. In said class, especially p is 1; q is 0; A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by $R_{19}$, and wherein a substituent on a nitrogen in a heterocyclic ring system may not be halogen; and each $R_{19}$ independently is halogen, $C_{1-6}$alkyl, $C_{1-6}$alkoxy or $C_{1-6}$halogenalkyl.

In one class of compounds of the invention, $R_7$ is hydrogen.

One class of compounds of the invention are compounds of formula I'-1

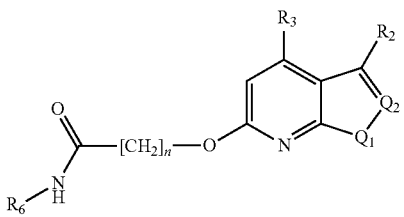

(I'-1)

wherein
Q$_1$ is —N(R$_1$)— or —O—;
Q$_2$ is =N— or =C(R$_{1a}$)—;
especially Q$_1$ is —N(R$_1$)— and Q$_2$ is =N—; or Q$_1$ is —N(R$_1$)— and Q$_2$ is =C(R$_{1a}$)—; or Q$_1$ is —O— and Q$_2$ is =N—;
R$_1$ is hydrogen, C$_{1-6}$alkyl, C$_{1-6}$halogenalkyl, C$_{2-6}$alkenyl, C$_{2-6}$halogenalkenyl, C$_{2-6}$alkynyl or C$_{2-6}$halogenalkynyl; especially R$_1$ is hydrogen or C$_{1-6}$alkyl; further especially methyl; further especially hydrogen;
R$_{1a}$ is hydrogen, C$_{1-6}$alkyl, C$_{1-6}$halogenalkyl, C$_{2-6}$alkenyl, C$_{2-6}$halogenalkenyl, C$_{2-6}$alkynyl or C$_{2-6}$halogenalkynyl; especially R$_1$ is hydrogen or C$_{1-6}$alkyl; further especially methyl; further especially hydrogen;
R$_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a C$_{1-4}$alkylene group, and wherein the ring system may be substituted once or more than once by R$_{10}$, and wherein a substituent on a nitrogen in a heterocyclic ring system may not be halogen; each R$_{10}$ independently is halogen, C$_{1-6}$alkyl, C$_{1-6}$halogenalkyl, C$_{3-7}$cycloalkyl, C$_{3-7}$cycloalkyl(C$_{1-4}$alkyl), C$_{1-6}$alkoxy, or C$_{1-6}$halogenalkoxy;
R$_3$ is selected from C$_{1-6}$alkyl and C$_{1-6}$halogenalkyl; especially R$_3$ is methyl or trifluoromethyl;
n is 1; and
R$_6$ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system is attached to the nitrogen atom via a C$_{1-4}$alkylene group, and wherein the ring system may be substituted once or more than once by R$_{16}$, and wherein a substituent on a nitrogen in a heterocyclic ring system may not be halogen; each R$_{16}$ independently is especially halogen, C$_{1-6}$alkyl, especially C$_{1-4}$alkyl, C$_{1-6}$alkoxy or C$_{1-6}$halogenalkyl.

One class of compounds of the invention, are compounds of formula I'-2,

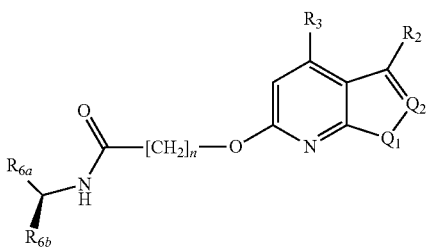

(I'-2)

wherein
Q$_1$ is —N(R$_1$)— or —O—;
Q$_2$ is =N— or =C(R$_{1a}$)—;
especially Q$_1$ is —N(R$_1$)— and Q$_2$ is =N—; or Q$_1$ is —N(R$_1$)— and Q$_2$ is =C(R$_{1a}$)—; or Q$_1$ is —O— and Q$_2$ is =N—;
R$_1$ is hydrogen, C$_{1-6}$alkyl, C$_{1-6}$halogenalkyl, C$_{2-6}$alkenyl, C$_{2-6}$halogenalkenyl, C$_{2-6}$alkynyl or C$_{2-6}$halogenalkynyl; especially R$_1$ is hydrogen or C$_{1-6}$alkyl; further especially methyl; further especially hydrogen;
R$_{1a}$ is hydrogen, C$_{1-6}$alkyl, C$_{1-6}$halogenalkyl, C$_{2-6}$alkenyl, C$_{2-6}$halogenalkenyl, C$_{2-6}$alkynyl or C$_{2-6}$halogenalkynyl; especially R$_1$ is hydrogen or C$_{1-6}$alkyl; further especially methyl; further especially hydrogen;
R$_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a C$_{1-4}$alkylene group, and wherein the ring system may be substituted once or more than once by R$_{10}$, and wherein a substituent on a nitrogen in a heterocyclic ring system may not be halogen; each R$_{10}$ independently is halogen, C$_{1-6}$alkyl, C$_{1-6}$halogenalkyl, C$_{3-7}$cycloalkyl, C$_{3-7}$cycloalkyl(C$_{1-4}$alkyl), C$_{1-6}$alkoxy, or C$_{1-6}$halogenalkoxy;
R$_3$ is selected from C$_{1-6}$alkyl and C$_{1-6}$halogenalkyl; especially R$_3$ is methyl or trifluoromethyl;
n is 1;
R$_{6a}$ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by R$_{16}$, and wherein a substituent on a nitrogen in a heterocyclic ring system may not be halogen; each R$_{16}$ independently is especially halogen, C$_{1-6}$alkyl, especially C$_{1-4}$alkyl, C$_{1-6}$alkoxy or C$_{1-6}$halogenalkyl; and
R$_{6b}$ is C$_{1-3}$alkyl, especially R$_{6b}$ is methyl.

One class of compounds of the invention, are compounds of formula I'-3,

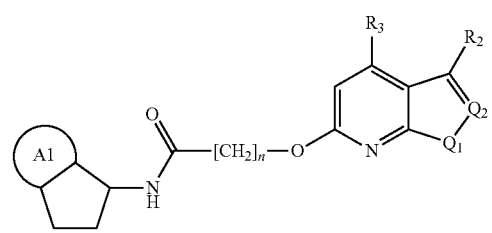

(I'-3)

wherein
Q$_1$ is —N(R$_1$)— or —O—;
Q$_2$ is =N— or =C(R$_{1a}$)—;
especially Q$_1$ is —N(R$_1$)— and Q$_2$ is =N—; or Q$_1$ is —N(R$_1$)— and Q$_2$ is =C(R$_{1a}$)—; or Q$_1$ is —O— and Q$_2$ is =N—;
R$_1$ is hydrogen, C$_{1-6}$alkyl, C$_{1-6}$halogenalkyl, C$_{2-6}$alkenyl, C$_{2-6}$halogenalkenyl, C$_{2-6}$alkynyl or C$_{2-6}$halogenalkynyl; especially R$_1$ is hydrogen or C$_{1-6}$alkyl; further especially methyl; further especially hydrogen;
R$_{1a}$ is hydrogen, C$_{1-6}$alkyl, C$_{1-6}$halogenalkyl, C$_{2-6}$alkenyl, C$_{2-6}$halogenalkenyl, C$_{2-6}$alkynyl or C$_{2-6}$halogenalkynyl;

especially R₁ is hydrogen or C₁₋₆alkyl; further especially methyl; further especially hydrogen;

R₂ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a C₁₋₄alkylene group, and wherein the ring system may be substituted once or more than once by R₁₀, and wherein a substituent on a nitrogen in a heterocyclic ring system may not be halogen; each R₁₀ independently is halogen, C₁₋₆alkyl, C₁₋₆halogenalkyl, C₃₋₇cycloalkyl, C₃₋₇cycloalkyl(C₁₋₄alkyl), C₁₋₆alkoxy, or C₁₋₆halogenalkoxy;

R₃ is selected from C₁₋₆alkyl and C₁₋₆halogenalkyl; especially R₃ is methyl or trifluoromethyl;

n is 1;

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by R₁₉, and wherein a substituent on a nitrogen in a heterocyclic ring system may not be halogen; and each R₁₉ independently is halogen, C₁₋₆alkyl, C₁₋₆alkoxy or C₁₋₆halogenalkyl.

One class of compounds of the invention, are compounds of formula I'-4,

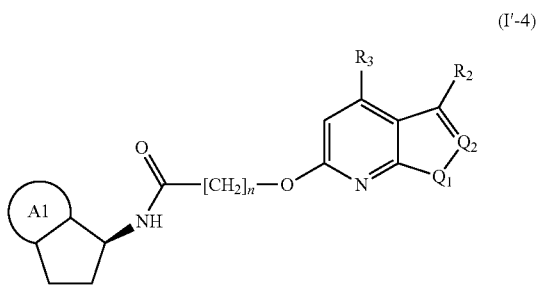

(I'-4)

wherein

Q₁ is —N(R₁)— or —O—;

Q₂ is ═N— or ═C(R₁ₐ)—;

especially Q₁ is —N(R₁)— and Q₂ is ═N—; or Q₁ is —N(R₁)— and Q₂ is ═C(R₁ₐ)—; or Q₁ is —O— and Q₂ is ═N—;

R₁ is hydrogen, C₁₋₆alkyl, C₁₋₆halogenalkyl, C₂₋₆alkenyl, C₂₋₆halogenalkenyl, C₂₋₆alkynyl or C₂₋₆halogenalkynyl; especially R₁ is hydrogen or C₁₋₆alkyl; further especially methyl; further especially hydrogen;

R₁ₐ is hydrogen, C₁₋₆alkyl, C₁₋₆halogenalkyl, C₂₋₆alkenyl, C₂₋₆halogenalkenyl, C₂₋₆alkynyl or C₂₋₆halogenalkynyl; especially R₁ is hydrogen or C₁₋₆alkyl; further especially methyl; further especially hydrogen;

R₂ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a C₁₋₄alkylene group, and wherein the ring system may be substituted once or more than once by R₁₀, and wherein a substituent on a nitrogen in a heterocyclic ring system may not be halogen; each R₁₀ independently is halogen, C₁₋₆alkyl, C₁₋₆halogenalkyl, C₃₋₇cycloalkyl, C₃₋₇cycloalkyl(C₁₋₄alkyl), C₁₋₆alkoxy, or C₁₋₆halogenalkoxy;

R₃ is selected from C₁₋₆alkyl and C₁₋₆halogenalkyl; especially R₃ is methyl or trifluoromethyl;

n is 1;

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by R₁₉, and wherein a substituent on a nitrogen in a heterocyclic ring system may not be halogen; and each R₁₉ independently is halogen, C₁₋₆alkyl, C₁₋₆alkoxy or C₁₋₆halogenalkyl.

One class of compounds of the invention, are compounds of formula I-1,

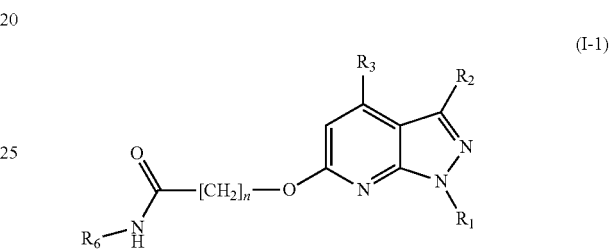

(I-1)

wherein

R₁ is hydrogen, C₁₋₆alkyl, C₁₋₆halogenalkyl, C₂₋₆alkenyl, C₂₋₆halogenalkenyl, C₂₋₆alkynyl or C₂₋₆halogenalkynyl; especially R₁ is hydrogen or C₁₋₆alkyl; further especially methyl; further especially hydrogen;

R₂ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a C₁₋₄alkylene group, and wherein the ring system may be substituted once or more than once by R₁₀, and wherein a substituent on a nitrogen in a heterocyclic ring system may not be halogen; each R₁₀ independently is halogen, C₁₋₆alkyl, C₁₋₆halogenalkyl, C₃₋₇cycloalkyl, C₃₋₇cycloalkyl(C₁₋₄alkyl), C₁₋₆alkoxy, or C₁₋₆halogenalkoxy;

R₃ is selected from C₁₋₆alkyl and C₁₋₆halogenalkyl; especially R₃ is methyl or trifluoromethyl;

n is 1; and

R₆ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system is attached to the nitrogen atom via a C₁₋₄alkylene group, and wherein the ring system may be substituted once or more than once by R₁₆, and wherein a substituent on a nitrogen in a heterocyclic ring system may not be halogen; each R₁₆ independently is especially halogen, C₁₋₆alkyl or C₁₋₆halogenalkyl.

One class of compounds of the invention, are compounds of formula I-2,

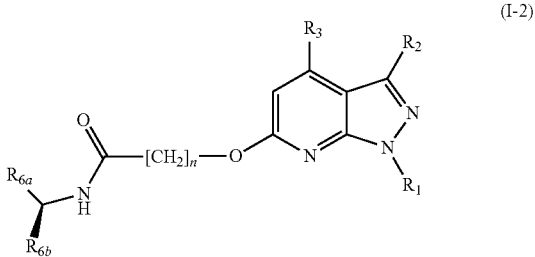

(I-2)

wherein
$R_1$ is hydrogen, $C_{1-6}$alkyl, $C_{1-6}$halogenalkyl, $C_{2-6}$alkenyl, $C_{2-6}$halogenalkenyl, $C_{2-6}$alkynyl or $C_{2-6}$halogenalkynyl; especially $R_1$ is hydrogen or $C_{1-6}$alkyl; further especially methyl; further especially hydrogen;

$R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a $C_{1-4}$alkylene group, and wherein the ring system may be substituted once or more than once by $R_{10}$, and wherein a substituent on a nitrogen in a heterocyclic ring system may not be halogen; each $R_{10}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

$R_3$ is selected from $C_{1-6}$alkyl and $C_{1-6}$halogenalkyl; especially $R_3$ is methyl or trifluoromethyl;

n is 1;

$R_{6a}$ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by $R_{16}$, and wherein a substituent on a nitrogen in a heterocyclic ring system may not be halogen; each $R_{16}$ independently is especially halogen, $C_{1-6}$alkyl or $C_{1-6}$halogenalkyl; and $R_{6b}$ is $C_{1-3}$alkyl, especially $R_{6b}$ is methyl.

One class of compounds of the invention, are compounds of formula I-3,

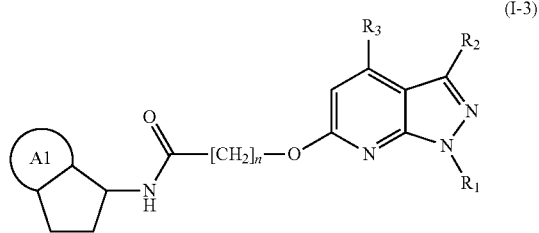

(I-3)

wherein
$R_1$ is hydrogen, $C_{1-6}$alkyl, $C_{1-6}$halogenalkyl, $C_{2-6}$alkenyl, $C_{2-6}$halogenalkenyl, $C_{2-6}$alkynyl or $C_{2-6}$halogenalkynyl; especially $R_1$ is hydrogen or $C_{1-6}$alkyl; further especially methyl; further especially hydrogen;

$R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a $C_{1-4}$alkylene group, and wherein the ring system may be substituted once or more than once by $R_{10}$, and wherein a substituent on a nitrogen in a heterocyclic ring system may not be halogen; each $R_{10}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

$R_3$ is selected from $C_{1-6}$alkyl and $C_{1-6}$halogenalkyl; especially $R_3$ is methyl or trifluoromethyl;

n is 1

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by $R_{19}$, and wherein a substituent on a nitrogen in a heterocyclic ring system may not be halogen; and each $R_{19}$ independently is halogen, $C_{1-6}$alkyl or $C_{1-6}$halogenalkyl.

One class of compounds of the invention, are compounds of formula I-4,

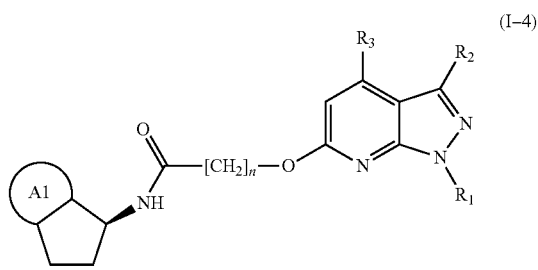

(I-4)

wherein
$R_1$ is hydrogen, $C_{1-6}$alkyl, $C_{1-6}$halogenalkyl, $C_{2-6}$alkenyl, $C_{2-6}$halogenalkenyl, $C_{2-6}$alkynyl or $C_{2-6}$halogenalkynyl; especially $R_1$ is hydrogen or $C_{1-6}$alkyl; further especially methyl; further especially hydrogen;

$R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a $C_{1-4}$alkylene group, and wherein the ring system may be substituted once or more than once by $R_{10}$, and wherein a substituent on a nitrogen in a heterocyclic ring system may not be halogen; each $R_{10}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

$R_3$ is selected from $C_{1-6}$alkyl and $C_{1-6}$halogenalkyl; especially $R_3$ is methyl or trifluoromethyl;

n is 1

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by $R_{19}$, and wherein a substituent on a nitrogen in a heterocyclic ring system may not be halogen; and each $R_{19}$ independently is halogen, $C_{1-6}$alkyl or $C_{1-6}$halogenalkyl.

In one embodiment, the invention provides a compound selected from 2-(3-(2-fluorophenyl)-1-methyl-4-(trifluoromethyl)-1H-pyrazolo[3,4-b]pyridin-6-yloxy)-N-(1-phenylethyl)acetamide;

2-(3-phenyl-4-(trifluoromethyl)-1H-pyrazolo[3,4-b]pyridin-6-yloxy)-N-(1-phenylethyl)acetamide;

N-(2,3-dihydro-1H-inden-1-yl)-2-(1-methyl-3-phenyl-4-(trifluoromethyl)-1H-pyrazolo[3,4-b]pyridin-6-yloxy)acetamide;

N-(1-(4-methoxyphenyl)ethyl)-2-(1-methyl-3-phenyl-4-(trifluoromethyl)-1H-pyrazolo[3,4-b]pyridin-6-yloxy)acetamide;

2-(1-methyl-3-phenyl-4-(trifluoromethyl)-1H-pyrazolo[3,4-b]pyridin-6-yloxy)-N-(2-phenylpropyl)acetamide;

N-(1-(3,5-dimethyl-1H-pyrazol-4-yl)ethyl)-2-(1-methyl-3-phenyl-4-(trifluoromethyl)-1H-pyrazolo[3,4-b]pyridin-6-yloxy)acetamide;

N-(2-ethoxybenzyl)-2-(1-methyl-3-phenyl-4-(trifluoromethyl)-1H-pyrazolo[3,4-b]pyridin-6-yloxy)acetamide;

2-(1,4-dimethyl-3-phenyl-1H-pyrazolo[3,4-b]pyridin-6-yloxy)-N-(1-phenylethyl)acetamide;

N-(2-chlorobenzyl)-2-(1,4-dimethyl-3-phenyl-1H-pyrazolo[3,4-b]pyridin-6-yloxy)acetamide;

N-(benzo[d][1,3]dioxol-5-ylmethyl)-2-(1,4-dimethyl-3-phenyl-1H-pyrazolo[3,4-b]pyridin-6-yloxy)acetamide;

2-(1,4-dimethyl-3-phenyl-1H-pyrazolo[3,4-b]pyridin-6-yloxy)-N-(4-phenylbutan-2-yl)acetamide;

2-(3-(3-methoxyphenyl)-1-methyl-4-(trifluoromethyl)-1H-pyrazolo[3,4-b]pyridin-6-yloxy)-N-(1-phenylethyl)acetamide;

2-(3-(4-methoxyphenyl)-1-methyl-4-(trifluoromethyl)-1H-pyrazolo[3,4-b]pyridin-6-yloxy)-N-(1-phenylethyl)acetamide;

2-(1-methyl-3-(pyridin-2-yl)-4-(trifluoromethyl)-1H-pyrazolo[3,4-b]pyridin-6-yloxy)-N-(1-phenylethyl)acetamide;

2-(3-(3-fluorophenyl)-1-methyl-4-(trifluoromethyl)-1H-pyrazolo[3,4-b]pyridin-6-yloxy)-N-(1-phenylethyl)acetamide;

2-(3-(4-fluorophenyl)-1-methyl-4-(trifluoromethyl)-1H-pyrazolo[3,4-b]pyridin-6-yloxy)-N-(1-phenylethyl)acetamide;

2-(1-methyl-3-m-tolyl-4-(trifluoromethyl)-1H-pyrazolo[3,4-b]pyridin-6-yloxy)-N-(1-phenylethyl)acetamide;

2-(1-methyl-3-(pyridin-4-yl)-4-(trifluoromethyl)-1H-pyrazolo[3,4-b]pyridin-6-yloxy)-N-(1-phenylethyl)acetamide;

2-(1-methyl-3-o-tolyl-4-(trifluoromethyl)-1H-pyrazolo[3,4-b]pyridin-6-yloxy)-N-(1-phenylethyl)acetamide;

2-(1-methyl-3-phenyl-4-(trifluoromethyl)-1H-pyrazolo[3,4-b]pyridin-6-yloxy)-N-(1-(5-methylfuran-2-yl)ethyl)acetamide;

2-(1-methyl-3-phenyl-4-(trifluoromethyl)-1H-pyrazolo[3,4-b]pyridin-6-yloxy)-N-(1-(pyridin-2-yl)ethyl)acetamide;

2-(1-methyl-3-phenyl-4-(trifluoromethyl)-1H-pyrazolo[3,4-b]pyridin-6-yloxy)-N-(1-(pyridin-3-yl)ethyl)acetamide;

2-(1-methyl-3-phenyl-4-(trifluoromethyl)-1H-pyrazolo[3,4-b]pyridin-6-yloxy)-N-(1-(pyridin-4-yl)ethyl)acetamide;

2-(1-methyl-3-phenyl-4-(trifluoromethyl)-1H-pyrazolo[3,4-b]pyridin-6-yloxy)-N-(4-methylbenzyl)acetamide;

N-(3-methoxybenzyl)-2-(1-methyl-3-phenyl-4-(trifluoromethyl)-1H-pyrazolo[3,4-b]pyridin-6-yloxy)acetamide;

2-(1-methyl-3-(pyridin-3-yl)-4-(trifluoromethyl)-1H-pyrazolo[3,4-b]pyridin-6-yloxy)-N-(1-phenylethyl)acetamide;

N-(1-(4-ethyl-4H-1,2,4-triazol-3-yl)ethyl)-2-(1-methyl-3-phenyl-4-(trifluoromethyl)-1H-pyrazolo[3,4-b]pyridin-6-yloxy)acetamide;

N-(1-(3-isopropyl-1,2,4-oxadiazol-5-yl)ethyl)-2-(1-methyl-3-phenyl-4-(trifluoromethyl)-1H-pyrazolo[3,4-b]pyridin-6-yloxy)acetamide;

2-(3-tert-butyl-1-methyl-4-(trifluoromethyl)-1H-pyrazolo[3,4-b]pyridin-6-yloxy)-N-(1-phenylethyl)acetamide;

N-(1-(1-ethyl-1H-pyrazol-5-yl)ethyl)-2-(1-methyl-3-phenyl-4-(trifluoromethyl)-1H-pyrazolo[3,4-b]pyridin-6-yloxy)acetamide;

N-(1-(2,5-dimethylthiazol-4-yl)ethyl)-2-(1-methyl-3-phenyl-4-(trifluoromethyl)-1H-pyrazolo[3,4-b]pyridin-6-yloxy)acetamide;

N-(4-methoxybenzyl)-2-(1-methyl-3-phenyl-4-(trifluoromethyl)-1H-pyrazolo[3,4-b]pyridin-6-yloxy)acetamide;

N-(2-fluorobenzyl)-2-(1-methyl-3-phenyl-4-(trifluoromethyl)-1H-pyrazolo[3,4-b]pyridin-6-yloxy)acetamide;

N-(3-chlorobenzyl)-2-(1-methyl-3-phenyl-4-(trifluoromethyl)-1H-pyrazolo[3,4-b]pyridin-6-yloxy)acetamide;

N-(1-(2-methoxyphenyl)ethyl)-2-(1-methyl-3-phenyl-4-(trifluoromethyl)-1H-pyrazolo[3,4-b]pyridin-6-yloxy)acetamide;

N-(1-(4-methoxyphenyl)ethyl)-2-(1-methyl-3-phenyl-4-(trifluoromethyl)-1H-pyrazolo[3,4-b]pyridin-6-yloxy)acetamide;

N-(1-(3-methoxyphenyl)ethyl)-2-(1-methyl-3-phenyl-4-(trifluoromethyl)-1H-pyrazolo[3,4-b]pyridin-6-yloxy)acetamide;

2-(4-cyclopropyl-1-methyl-3-phenyl-1H-pyrazolo[3,4-b]pyridin-6-yloxy)-N-(1-phenylethyl)acetamide;

2-(1-methyl-3-p-tolyl-4-(trifluoromethyl)-1H-pyrazolo[3,4-b]pyridin-6-yloxy)-N-(1-phenylethyl)acetamide;

2-(3-(2-methoxyphenyl)-1-methyl-4-(trifluoromethyl)-1H-pyrazolo[3,4-b]pyridin-6-yloxy)-N-(1-phenylethyl)acetamide;

2-(3-cyclopropyl-1-methyl-4-(trifluoromethyl)-1H-pyrazolo[3,4-b]pyridin-6-yloxy)-N-(1-phenylethyl)acetamide;

2-(3-cyclohexyl-1-methyl-4-(trifluoromethyl)-1H-pyrazolo[3,4-b]pyridin-6-yloxy)-N-(1-phenylethyl)acetamide;

2-(3-cyclopentyl-1-methyl-4-(trifluoromethyl)-1H-pyrazolo[3,4-b]pyridin-6-yloxy)-N-(1-phenylethyl)acetamide;

N-cyclopropyl-2-(1-methyl-3-phenyl-4-(trifluoromethyl)-1H-pyrazolo[3,4-b]pyridin-6-yloxy)acetamide;

N-cyclobutyl-2-(1-methyl-3-phenyl-4-(trifluoromethyl)-1H-pyrazolo[3,4-b]pyridin-6-yloxy)acetamide;

2-(1-methyl-3-phenyl-4-(trifluoromethyl)-1H-pyrazolo[3,4-b]pyridin-6-yloxy)-N-propylacetamide;

2-(1-methyl-3-phenyl-4-(trifluoromethyl)-1H-pyrazolo[3,4-b]pyridin-6-yloxy)-N-(1,2,3,4-tetrahydronaphthalen-1-yl)acetamide;

2-(3-(3-chlorophenyl)-1-methyl-4-(trifluoromethyl)-1H-pyrazolo[3,4-b]pyridin-6-yloxy)-N-(1-phenylethyl)acetamide;

2-(3-(3-bromophenyl)-1-methyl-4-(trifluoromethyl)-1H-pyrazolo[3,4-b]pyridin-6-yloxy)-N-(1-phenylethyl)acetamide;

N-(1-(4-methoxyphenyl)ethyl)-2-(1-methyl-3-phenyl-4-(trifluoromethyl)-1H-pyrazolo[3,4-b]pyridin-6-yloxy)acetamide;

N-(2,3-dihydro-1H-inden-1-yl)-2-(3-(2-fluorophenyl)-1-methyl-4-(trifluoromethyl)-1H-pyrazolo[3,4-b]pyridin-6-yloxy)acetamide;

N-(2,3-dihydro-1H-inden-1-yl)-2-(3-(3-fluorophenyl)-1-methyl-4-(trifluoromethyl)-1H-pyrazolo[3,4-b]pyridin-6-yloxy)acetamide;

2-(1-methyl-3-phenyl-1H-pyrazolo[3,4-b]pyridin-6-yloxy)-N-(1-phenylethyl)acetamide;

2-(1-methyl-3-phenyl-4-(trifluoromethyl)-1H-pyrazolo[3,4-b]pyridin-6-ylamino)-N-(1-phenylethyl)acetamide;

2-(1,4-dimethyl-3-phenyl-1H-pyrazolo[3,4-b]pyridin-6-yloxy)-N-(1-(pyridin-4-yl)ethyl)acetamide;

2-(1,4-dimethyl-3-phenyl-1H-pyrazolo[3,4-b]pyridin-6-yloxy)-N-(1-(pyridin-3-yl)ethyl)acetamide;

2-(1,4-dimethyl-3-phenyl-1H-pyrazolo[3,4-b]pyridin-6-yloxy)-N-(1-(pyridin-2-yl)ethyl)acetamide;

2-(1-methyl-3-phenyl-4-(trifluoromethyl)-1H-pyrazolo[3,4-b]pyridin-6-yloxy)-N-(3-methyl benzyl)acetamide;

N-(1-(6-methoxypyridin-3-yl)ethyl)-2-(1-methyl-3-phenyl-4-(trifluoromethyl)-1H-pyrazolo[3,4-b]pyridin-6-yloxy)acetamide;

N-isopentyl-2-(1-methyl-3-phenyl-4-(trifluoromethyl)-1H-pyrazolo[3,4-b]pyridin-6-yloxy)acetamide;

2-(3-cyclopropyl-1,4-dimethyl-1H-pyrazolo[3,4-b]pyridin-6-yloxy)-N-(1-phenylethyl)acetamide;

2-(1-methyl-3-phenyl-4-(trifluoromethyl)-1H-pyrazolo[3,4-b]pyridin-6-yloxy)-N-(1-(1,3,5-trimethyl-1H-pyrazol-4-yl)ethyl)acetamide;

2-(3-cyclopropyl-1,4-dimethyl-1H-pyrazolo[3,4-b]pyridin-6-yloxy)-N-(1-(4-methoxyphenyl)ethyl)acetamide;

2-(3-cyclopropyl-1,4-dimethyl-1H-pyrazolo[3,4-b]pyridin-6-yloxy)-N-(1-(1,3,5-trimethyl-1H-pyrazol-4-yl)ethyl)acetamide;

2-(1-methyl-3-phenyl-4-(trifluoromethyl)-1H-pyrazolo[3,4-b]pyridin-6-yloxy)-N-(1-phenylethyl)propanamide;

2-(3-cyclopropyl-1,4-dimethyl-1H-pyrazolo[3,4-b]pyridin-6-yloxy)-N-(2,3-dihydro-1H-inden-1-yl)acetamide;

2-(3-cyclopropyl-1,4-dimethyl-1H-pyrazolo[3,4-b]pyridin-6-yloxy)-N-(1-(3,5-dimethyl-1H-pyrazol-4-yl)ethyl)acetamide;

2-(1-methyl-3-phenyl-4-(trifluoromethyl)-1H-pyrazolo[3,4-b]pyridin-6-yloxy)-N-(1-(6-methylpyridin-3-yl)ethyl)acetamide;

2-(3-(3-fluoropyridin-2-yl)-1,4-dimethyl-1H-pyrazolo[3,4-b]pyridin-6-yloxy)-N-(1-p-tolylethyl)acetamide;

2-(1,4-dimethyl-3-(1-methyl-1H-pyrazol-5-yl)-1H-pyrazolo[3,4-b]pyridin-6-yloxy)-N-(1-p-tolylethyl)acetamide;

2-(3-(1,2-dimethyl-1H-imidazol-5-yl)-1,4-dimethyl-1H-pyrazolo[3,4-b]pyridin-6-yloxy)-N-(1-p-tolylethyl)acetamide;

2-(3-(1,3-dimethyl-1H-pyrazol-5-yl)-1,4-dimethyl-1H-pyrazolo[3,4-b]pyridin-6-yloxy)-N-(1-p-tolylethyl)acetamide;

2-(1,4-dimethyl-3-(1-methyl-1H-pyrazol-4-yl)-1H-pyrazolo[3,4-b]pyridin-6-yloxy)-N-(1-p-tolylethyl)acetamide;

2-(1,4-dimethyl-3-(pyrimidin-2-yl)-1H-pyrazolo[3,4-b]pyridin-6-yloxy)-N-(1-p-tolylethyl)acetamide;

2-(1,4-dimethyl-3-(pyrazin-2-yl)-1H-pyrazolo[3,4-b]pyridin-6-yloxy)-N-(1-p-tolylethyl)acetamide;

2-(1,4-dimethyl-3-(5-methylpyridin-2-yl)-1H-pyrazolo[3,4-b]pyridin-6-yloxy)-N-(1-p-tolylethyl)acetamide;

2-(1,4-dimethyl-3-(thiazol-4-yl)-1H-pyrazolo[3,4-b]pyridin-6-yloxy)-N-(1-p-tolylethyl)acetamide;

2-(1,4-dimethyl-3-(1-methyl-1H-imidazol-5-yl)-1H-pyrazolo[3,4-b]pyridin-6-yloxy)-N-(1-p-tolylethyl)acetamide;

2-(3-(6-methoxypyrazin-2-yl)-1,4-dimethyl-1H-pyrazolo[3,4-b]pyridin-6-yloxy)-N-(1-p-tolylethyl)acetamide;

2-(1,4-dimethyl-3-(1-methyl-1H-imidazol-4-yl)-1H-pyrazolo[3,4-b]pyridin-6-yloxy)-N-(1-p-tolylethyl)acetamide;

2-(1,4-dimethyl-3-(oxazol-2-yl)-1H-pyrazolo[3,4-b]pyridin-6-yloxy)-N-(1-p-tolylethyl)acetamide;

2-(1,4-dimethyl-3-(4-methylthiazol-2-yl)-1H-pyrazolo[3,4-b]pyridin-6-yloxy)-N-(1-p-tolylethyl)acetamide;

2-(1,4-dimethyl-3-(thiazol-2-yl)-1H-pyrazolo[3,4-b]pyridin-6-yloxy)-N-(1-p-tolylethyl)acetamide;

2-(3-(4-methoxypyrimidin-2-yl)-1,4-dimethyl-1H-pyrazolo[3,4-b]pyridin-6-yloxy)-N-(1-p-tolylethyl)acetamide;

2-(1,4-dimethyl-3-(thiazol-5-yl)-1H-pyrazolo[3,4-b]pyridin-6-yloxy)-N-(1-p-tolylethyl)acetamide;

2-(3-(2-methoxythiazol-4-yl)-1,4-dimethyl-1H-pyrazolo[3,4-b]pyridin-6-yloxy)-N-(1-p-tolylethyl)acetamide;

2-(1,4-dimethyl-3-(5-methylthiazol-2-yl)-1H-pyrazolo[3,4-b]pyridin-6-yloxy)-N-(1-p-tolylethyl)acetamide;

2-(1,4-dimethyl-3-(6-methylpyridin-2-yl)-1H-pyrazolo[3,4-b]pyridin-6-yloxy)-N-(1-p-tolylethyl)acetamide;

2-(3-(3,5-dimethoxyphenyl)-1,4-dimethyl-1H-pyrazolo[3,4-b]pyridin-6-yloxy)-N-(1-p-tolylethyl)acetamide;

2-(3-cyclopropyl-4-(difluoromethyl)-1-methyl-1H-pyrazolo[3,4-b]pyridin-6-yloxy)-N-(2-methyl-6,7-dihydro-5H-cyclopenta[b]pyridin-5-yl)acetamide;

2-(3-cyclopropyl-1,4-dimethyl-1H-pyrazolo[3,4-b]pyridin-6-yloxy)-N-(5-methoxy-2,3-dihydro-1H-inden-1-yl)acetamide;

2-(3-cyclopropyl-1,4-dimethyl-1H-pyrazolo[3,4-b]pyridin-6-yloxy)-N-(2-p-tolylpropan-2-yl)acetamide;

2-(3-cyclopropyl-4-(difluoromethyl)-1-methyl-1H-pyrazolo[3,4-b]pyridin-6-yloxy)-N-(1-(4-methoxyphenyl)ethyl)acetamide;

2-(3-cyclopropyl-4-(difluoromethyl)-1-methyl-1H-pyrazolo[3,4-b]pyridin-6-yloxy)-N-(1-p-tolylethyl)acetamide;

2-(3-cyclopropyl-4-(difluoromethyl)-1-methyl-1H-pyrazolo[3,4-b]pyridin-6-yloxy)-N-(1-(1,3,5-trimethyl-1H-pyrazol-4-yl)ethyl)acetamide;

2-(3-cyclopropyl-4-(difluoromethyl)-1-methyl-1H-pyrazolo[3,4-b]pyridin-6-yloxy)-N-(1-(6-methoxypyridin-3-yl)ethyl)acetamide;

2-(3-cyclopropyl-4-isopropyl-1-methyl-1H-pyrazolo[3,4-b]pyridin-6-yloxy)-N-(1-p-tolylethyl)acetamide;

2-(3-cyclopropyl-1-methyl-4-(trifluoromethyl)-1H-pyrazolo[3,4-b]pyridin-6-yloxy)-N-(1-(1,3,5-trimethyl-1H-pyrazol-4-yl)ethyl)acetamide;

2-(3-cyclopropyl-1-methyl-4-(trifluoromethyl)-1H-pyrazolo[3,4-b]pyridin-6-yloxy)-N-(1-p-tolylethyl)acetamide;

2-(3-cyclopropyl-1-methyl-4-(trifluoromethyl)-1H-pyrazolo[3,4-b]pyridin-6-yloxy)-N-(1-(6-methoxypyridin-3-yl)ethyl)acetamide;

2-(3-cyclopropyl-1-methyl-4-(trifluoromethyl)-1H-pyrazolo[3,4-b]pyridin-6-yloxy)-N-(1-(4-methoxyphenyl)ethyl)acetamide;

2-(3-cyclopropyl-1-methyl-4-(trifluoromethyl)-1H-pyrazolo[3,4-b]pyridin-6-yloxy)-N-(1-(6-methylpyridin-3-yl)ethyl)acetamide;

2-(4-(difluoromethyl)-1-methyl-3-phenyl-1H-pyrazolo[3,4-b]pyridin-6-yloxy)-N-(1-(4-methoxyphenyl)ethyl)acetamide;

2-(4-(difluoromethyl)-1-methyl-3-phenyl-1H-pyrazolo[3,4-b]pyridin-6-yloxy)-N-(1-(6-methylpyridin-3-yl)ethyl)acetamide;

2-(3-cyclopropyl-4-(difluoromethyl)-1-methyl-1H-pyrazolo[3,4-b]pyridin-6-yloxy)-N-(1-(6-methylpyridin-3-yl)ethyl)acetamide;

2-(4-(difluoromethyl)-1-methyl-3-phenyl-1H-pyrazolo[3,4-b]pyridin-6-yloxy)-N-(1-(1,3,5-trimethyl-1H-pyrazol-4-yl)ethyl)acetamide;

2-(4-(difluoromethyl)-1-methyl-3-phenyl-1H-pyrazolo[3,4-b]pyridin-6-yloxy)-N-(1-p-tolylethyl)acetamide;

2-(4-(difluoromethyl)-1-methyl-3-phenyl-1H-pyrazolo[3,4-b]pyridin-6-yloxy)-N-(1-(6-methoxypyridin-3-yl)ethyl)acetamide;

2-(3-cyclopropyl-1-methyl-1H-pyrazolo[3,4-b]pyridin-6-yloxy)-N-(1-p-tolylethyl)acetamide;

2-(3-(2-methoxyphenyl)-1-methyl-1H-pyrazolo[3,4-b]pyridin-6-yloxy)-N-(1-p-tolylethyl)acetamide;

2-(3-tert-butyl-1-methyl-1H-pyrazolo[3,4-b]pyridin-6-yloxy)-N-(1-p-tolylethyl)acetamide;

2-(3-isopropyl-1,4-dimethyl-1H-pyrazolo[3,4-b]pyridin-6-yloxy)-N-(1-p-tolylethyl)acetamide;

2-(3-isopropyl-1,4-dimethyl-1H-pyrazolo[3,4-b]pyridin-6-yloxy)-N-(1-(4-methoxyphenyl)ethyl)acetamide;

2-(3-isopropyl-1,4-dimethyl-1H-pyrazolo[3,4-b]pyridin-6-yloxy)-N-(1-(6-methoxypyridin-3-yl)ethyl)acetamide;

2-(3-isopropyl-1,4-dimethyl-1H-pyrazolo[3,4-b]pyridin-6-yloxy)-N-(1-(1,3,5-trimethyl-1H-pyrazol-4-yl)ethyl)acetamide;

2-(3-(2,5-dimethylfuran-3-yl)-1,4-dimethyl-1H-pyrazolo[3,4-b]pyridin-6-yloxy)-N-(1-p-tolylethyl)acetamide;

2-(3-(2,5-dimethylfuran-3-yl)-1,4-dimethyl-1H-pyrazolo[3,4-b]pyridin-6-yloxy)-N-(1-(4-methoxyphenyl)ethyl)acetamide;

2-(3-(2,5-dimethylfuran-3-yl)-1,4-dimethyl-1H-pyrazolo[3,4-b]pyridin-6-yloxy)-N-(1-(6-methoxypyridin-3-yl)ethyl)acetamide;

2-(3-(2,5-dimethylfuran-3-yl)-1,4-dimethyl-1H-pyrazolo[3,4-b]pyridin-6-yloxy)-N-(1-(1,3,5-trimethyl-1H-pyrazol-4-yl)ethyl)acetamide;

2-(1,4-dimethyl-3-(2-methylfuran-3-yl)-1H-pyrazolo[3,4-b]pyridin-6-yloxy)-N-(1-(4-methoxyphenyl)ethyl)acetamide;

2-(1-methyl-3-o-tolyl-1H-pyrazolo[3,4-b]pyridin-6-yloxy)-N-(1-p-tolylethyl)acetamide;

2-(3-(3,5-dimethoxyphenyl)-1,4-dimethyl-1H-pyrazolo[3,4-b]pyridin-6-yloxy)-N-(1-(4-methoxyphenyl)ethyl)acetamide;

2-(3-(4-methoxypyridin-2-yl)-1,4-dimethyl-1H-pyrazolo[3,4-b]pyridin-6-yloxy)-N-(1-p-tolylethyl)acetamide;

2-(3-cyclopropyl-1,4-dimethyl-1H-pyrazolo[3,4-b]pyridin-6-yloxy)-N-(5-fluoro-2,3-dihydro-1H-inden-1-yl)acetamide;

2-(3-cyclopropyl-4-(difluoromethyl)-1-methyl-1H-pyrazolo[3,4-b]pyridin-6-yloxy)-N-(5-methoxy-2,3-dihydro-1H-inden-1-yl)acetamide;

2-(3-cyclopropyl-1-methyl-4-(trifluoromethyl)-1H-pyrazolo[3,4-b]pyridin-6-yloxy)-N-(5-methoxy-2,3-dihydro-1H-inden-1-yl)acetamide;

2-(3-cyclopropyl-1,4-dimethyl-1H-pyrazolo[3,4-b]pyridin-6-yloxy)-N-(5-methyl-2,3-dihydro-1H-inden-1-yl)acetamide;

2-(3-cyclopropyl-1,4-dimethyl-1H-pyrazolo[3,4-b]pyridin-6-yloxy)-N-isobutylacetamide;

N-cyclopentyl-2-(3-cyclopropyl-1,4-dimethyl-1H-pyrazolo[3,4-b]pyridin-6-yloxy)acetamide;

2-(3-cyclopropyl-1,4-dimethyl-1H-pyrazolo[3,4-b]pyridin-6-yloxy)-N-(1-(6-methoxypyridin-3-yl)ethyl)acetamide;

2-(3-cyclopropyl-1,4-dimethyl-1H-pyrazolo[3,4-b]pyridin-6-yloxy)-N-(1-(5-neopentylisoxazol-3-yl)ethyl)acetamide;

2-(3-cyclopropyl-1,4-dimethyl-1H-pyrazolo[3,4-b]pyridin-6-yloxy)-N-phenethylacetamide;

2-(3-cyclopropyl-1,4-dimethyl-1H-pyrazolo[3,4-b]pyridin-6-yloxy)-N-(3-phenylpropyl)acetamide;

2-(3-cyclopropyl-1,4-dimethyl-1H-pyrazolo[3,4-b]pyridin-6-yloxy)-N-(1-(4-methoxyphenyl)ethyl)-N-methylacetamide;

2-(3-cyclopropyl-1,4-dimethyl-1H-pyrazolo[3,4-b]pyridin-6-yloxy)-N-methylacetamide;

2-(3-cyclopropyl-1,4-dimethyl-1H-pyrazolo[3,4-b]pyridin-6-yloxy)-N-(1-cyclopropylethyl)acetamide;

2-(3-cyclopropyl-1,4-dimethyl-1H-pyrazolo[3,4-b]pyridin-6-yloxy)-N-(1-(1-ethyl-1H-pyrazol-3-yl)ethyl)acetamide;

2-(3-cyclopropyl-1,4-dimethyl-1H-pyrazolo[3,4-b]pyridin-6-yloxy)-N-(1-(6-methylpyridin-3-yl)ethyl)acetamide;

N-(1-cyclopentylethyl)-2-(3-cyclopropyl-1,4-dimethyl-1H-pyrazolo[3,4-b]pyridin-6-yloxy)acetamide;

N-(1-(1H-pyrrolo[2,3-b]pyridin-5-yl)ethyl)-2-(3-cyclopropyl-1,4-dimethyl-1H-pyrazolo[3,4-b]pyridin-6-yloxy)acetamide;

2-(3-cyclopropyl-1,4-dimethyl-1H-pyrazolo[3,4-b]pyridin-6-yloxy)-N-(1-(1-methyl-1H-benzo[d]imidazol-5-yl)ethyl)acetamide;

2-(3-cyclopropyl-1,4-dimethyl-1H-pyrazolo[3,4-b]pyridin-6-yloxy)-N-(1-(1-methyl-1H-indol-5-yl)ethyl)acetamide;

2-(3-cyclopropyl-1,5-dimethyl-1H-pyrazolo[3,4-b]pyridin-6-yloxy)-N-(1-p-tolylethyl)acetamide;

2-(3-cyclopropyl-1,4-dimethyl-1H-pyrazolo[3,4-b]pyridin-6-yloxy)-N-(2-(4-methoxyphenyl)propan-2-yl)acetamide;

2-(3-cyclopropyl-1,4-dimethyl-1H-pyrazolo[3,4-b]pyridin-6-yloxy)-N-(2-methyl-6,7-dihydro-5H-cyclopenta[b]pyridin-5-yl)acetamide;

2-(3-cyclopropyl-1,4-dimethyl-1H-pyrazolo[3,4-b]pyridin-6-yloxy)-N-(3-methyl-6,7-dihydro-5H-cyclopenta[c]pyridin-7-yl)acetamide;

2-(3-cyclopropyl-1,4-dimethyl-1H-pyrazolo[3,4-b]pyridin-6-yloxy)-N-(4-methylbenzyl)acetamide;

2-(3-cyclopropyl-1,4-dimethyl-1H-pyrazolo[3,4-b]pyridin-6-yloxy)-N-(4-methoxybenzyl)acetamide;

2-(3-cyclopropyl-1,4-dimethyl-1H-pyrazolo[3,4-b]pyridin-6-yloxy)-N-(5-ethoxy-2,3-dihydro-1H-inden-1-yl)acetamide;

2-(3-cyclopropyl-1,4-dimethyl-1H-pyrazolo[3,4-b]pyridin-6-yloxy)-N-(5-isopropoxy-2,3-dihydro-1H-inden-1-yl)acetamide;

2-(3-cyclopropyl-1,4-dimethyl-1H-pyrazolo[3,4-b]pyridin-6-yloxy)-N-(5-methoxy-2,3-dihydro-1H-inden-1-yl)propanamide;

2-(3-cyclopropyl-1,4-dimethyl-1H-pyrazolo[3,4-b]pyridin-6-yloxy)-N-(1-(4-methoxyphenyl)ethyl)propanamide;

2-(3-cyclopropyl-1,4,5-trimethyl-1H-pyrazolo[3,4-b]pyridin-6-yloxy)-N-(1-(4-methoxyphenyl)ethyl)acetamide;

2-(3-cyclopropyl-1,4,5-trimethyl-1H-pyrazolo[3,4-b]pyridin-6-yloxy)-N-(1-p-tolylethyl)acetamide;

2-(3-cyclopropyl-1,5-dimethyl-1H-pyrazolo[3,4-b]pyridin-6-yloxy)-N-(1-(4-methoxyphenyl)ethyl)acetamide;

2-(1-methyl-3-phenyl-4-(trifluoromethyl)-1H-pyrrolo[2,3-b]pyridin-6-yloxy)-N-(1-phenylethyl)acetamide;

2-(3-phenyl-4-(trifluoromethyl)isoxazolo[5,4-b]pyridin-6-yloxy)-N-(1-phenylethyl)acetamide;

2-(3-(2,5-dimethylfuran-3-yl)-1-methyl-4-(trifluoromethyl)-1H-pyrazolo[3,4-b]pyridin-6-yloxy)-N-(2-methyl-6,7-dihydro-5H-cyclopenta[b]pyridin-5-yl)acetamide;

2-(3-(2,5-dimethylfuran-3-yl)-1-methyl-4-(trifluoromethyl)-1H-pyrazolo[3,4-b]pyridin-6-yloxy)-N-(1-(4-methoxyphenyl)ethyl)acetamide;

2-(4-(difluoromethyl)-3-(2,5-dimethylfuran-3-yl)-1-methyl-1H-pyrazolo[3,4-b]pyridin-6-yloxy)-N-(2-methyl-6,7-dihydro-5H-cyclopenta[b]pyridin-5-yl)acetamide;

2-(4-(difluoromethyl)-3-(2,5-dimethylfuran-3-yl)-1-methyl-1H-pyrazolo[3,4-b]pyridin-6-yloxy)-N-(1-(4-methoxyphenyl)ethyl)acetamide;

2-(3-cyclopropyl-1,4-dimethyl-1H-pyrazolo[3,4-b]pyridin-6-yloxy)-N-(5,6-dimethoxy-2,3-dihydro-1H-inden-1-yl)acetamide;

2-(3-cyclopropyl-1,4-dimethyl-1H-pyrazolo[3,4-b]pyridin-6-yloxy)-N-((5-methylpyrazin-2-yl)methyl)acetamide;

N-(3-(1H-imidazol-1-yl)propyl)-2-(3-cyclopropyl-1,4-dimethyl-1H-pyrazolo[3,4-b]pyridin-6-yloxy)acetamide;

2-(3-cyclopropyl-1,4-dimethyl-1H-pyrazolo[3,4-b]pyridin-6-yloxy)-N-((2,3-dihydrobenzofuran-5-yl)methyl)acetamide;

N-(2-(1H-indol-3-yl)ethyl)-2-(3-cyclopropyl-1,4-dimethyl-1H-pyrazolo[3,4-b]pyridin-6-yloxy)acetamide;

N-(cyclohexylmethyl)-2-(3-cyclopropyl-1,4-dimethyl-1H-pyrazolo[3,4-b]pyridin-6-yloxy)acetamide;

2-(3-cyclopropyl-1,4-dimethyl-1H-pyrazolo[3,4-b]pyridin-6-yloxy)-N-(1-(6-methylpyridin-2-yl)ethyl)acetamide;
2-(3-cyclopropyl-1,4-dimethyl-1H-pyrazolo[3,4-b]pyridin-6-yloxy)-N-(5,6,7,8-tetrahydroquinolin-5-yl)acetamide;
2-(3-cyclopropyl-1,4-dimethyl-1H-pyrazolo[3,4-b]pyridin-6-yloxy)-N-(6-methoxy-2,3-dihydro-1H-inden-1-yl)acetamide;
2-(3-cyclopropyl-1,4-dimethyl-1H-pyrazolo[3,4-b]pyridin-6-yloxy)-N-(1-p-tolylethyl)acetamide;
2-(3-cyclopropyl-1,4-dimethyl-1H-pyrazolo[3,4-b]pyridin-6-yloxy)-N-(1-(3-methoxyphenyl)ethyl)acetamide;
2-(3-cyclopropyl-1,4-dimethyl-1H-pyrazolo[3,4-b]pyridin-6-yloxy)-N-(1-(2-methoxyphenyl)ethyl)acetamide;
N-((6-chloropyridin-3-yl)methyl)-2-(3-cyclopropyl-1,4-dimethyl-1H-pyrazolo[3,4-b]pyridin-6-yloxy)acetamide;
N-(3-chloro-4-methoxybenzyl)-2-(3-cyclopropyl-1,4-dimethyl-1H-pyrazolo[3,4-b]pyridin-6-yloxy)acetamide;
N-(1-(1H-indol-5-yl)ethyl)-2-(3-cyclopropyl-1,4-dimethyl-1H-pyrazolo[3,4-b]pyridin-6-yloxy)acetamide;
2-(3-cyclopropyl-1,4-dimethyl-1H-pyrazolo[3,4-b]pyridin-6-yloxy)-N-((3-methylpyridin-2-yl)methyl)acetamide;
2-(3-cyclopropyl-1,4-dimethyl-1H-pyrazolo[3,4-b]pyridin-6-yloxy)-N-(1-(3-fluoro-4-methoxyphenyl)ethyl)acetamide;
2-(3-cyclopropyl-1,4-dimethyl-1H-pyrazolo[3,4-b]pyridin-6-yloxy)-N-(1-(1-methyl-1H-pyrazol-4-yl)ethyl)acetamide;
2-(3-cyclopropyl-1,4-dimethyl-1H-pyrazolo[3,4-b]pyridin-6-yloxy)-N-(1-(4-methylpyridin-2-yl)ethyl)acetamide;
2-(3-cyclopropyl-1,4-dimethyl-1H-pyrazolo[3,4-b]pyridin-6-yloxy)-N-(1-(4-methylthiazol-2-yl)ethyl)acetamide;
N-(1-(benzo[d]thiazol-2-yl)ethyl)-2-(3-cyclopropyl-1,4-dimethyl-1H-pyrazolo[3,4-b]pyridin-6-yloxy)acetamide;
2-(3-cyclopropyl-1,4-dimethyl-1H-pyrazolo[3,4-b]pyridin-6-yloxy)-N-(1-methyl-4,5,6,7-tetrahydro-1H-indazol-4-yl)acetamide;
2-(3-cyclopropyl-1,4-dimethyl-1H-pyrazolo[3,4-b]pyridin-6-yloxy)-N-(1-(imidazo[2,1-b]thiazol-6-yl)ethyl)acetamide;
2-(3-cyclopropyl-1,4-dimethyl-1H-pyrazolo[3,4-b]pyridin-6-yloxy)-N-(4-phenylbutan-2-yl)acetamide;
2-(3-cyclopropyl-1,4-dimethyl-1H-pyrazolo[3,4-b]pyridin-6-yloxy)-N-(2,4-dimethoxybenzyl)acetamide;
2-(3-cyclopropyl-1,4-dimethyl-1H-pyrazolo[3,4-b]pyridin-6-yloxy)-N-(1-m-tolylethyl)acetamide;
2-(3-cyclopropyl-1,4-dimethyl-1H-pyrazolo[3,4-b]pyridin-6-yloxy)-N-((1,5-dimethyl-1H-indazol-4-yl)methyl)acetamide;
2-(3-cyclopropyl-1,4-dimethyl-1H-pyrazolo[3,4-b]pyridin-6-yloxy)-N-(5-methoxy-1,2,3,4-tetrahydronaphthalen-1-yl)acetamide;
2-(3-cyclopropyl-1,4-dimethyl-1H-pyrazolo[3,4-b]pyridin-6-yloxy)-N-(4-ethoxybenzyl)acetamide;
2-(3-cyclopropyl-1,4-dimethyl-1H-pyrazolo[3,4-b]pyridin-6-yloxy)-N-((1-methyl-1H-indazol-7-yl)methyl)acetamide;
N-((1H-indazol-4-yl)methyl)-2-(3-cyclopropyl-1,4-dimethyl-1H-pyrazolo[3,4-b]pyridin-6-yloxy)acetamide;
2-(3-cyclopropyl-1,4-dimethyl-1H-pyrazolo[3,4-b]pyridin-6-yloxy)-N-(6-methyl-2,3-dihydro-1H-inden-1-yl)acetamide;
N-(1-(6-chlorobenzo[d]thiazol-2-yl)ethyl)-2-(3-cyclopropyl-1,4-dimethyl-1H-pyrazolo[3,4-b]pyridin-6-yloxy)acetamide;
2-(3-cyclopropyl-1,4-dimethyl-1H-pyrazolo[3,4-b]pyridin-6-yloxy)-N-(1-(1-methyl-1H-pyrrolo[2,3-b]pyridin-5-yl)ethyl)acetamide;
2-(3-cyclopropyl-1,4-dimethyl-1H-pyrazolo[3,4-b]pyridin-6-yloxy)-N-(-5-methoxy-2,3-dihydro-1H-inden-1-yl)propanamide; and
2-(3-cyclopropyl-1,4-dimethyl-1H-pyrazolo[3,4-b]pyridin-6-yloxy)-N-(-1-(4-methoxyphenyl)ethyl)propanamide.

In a further aspect, the invention also provides a process for the production of compounds of the formula I'a. Compounds of the formula I' are obtainable according to the following process as described in scheme 1:

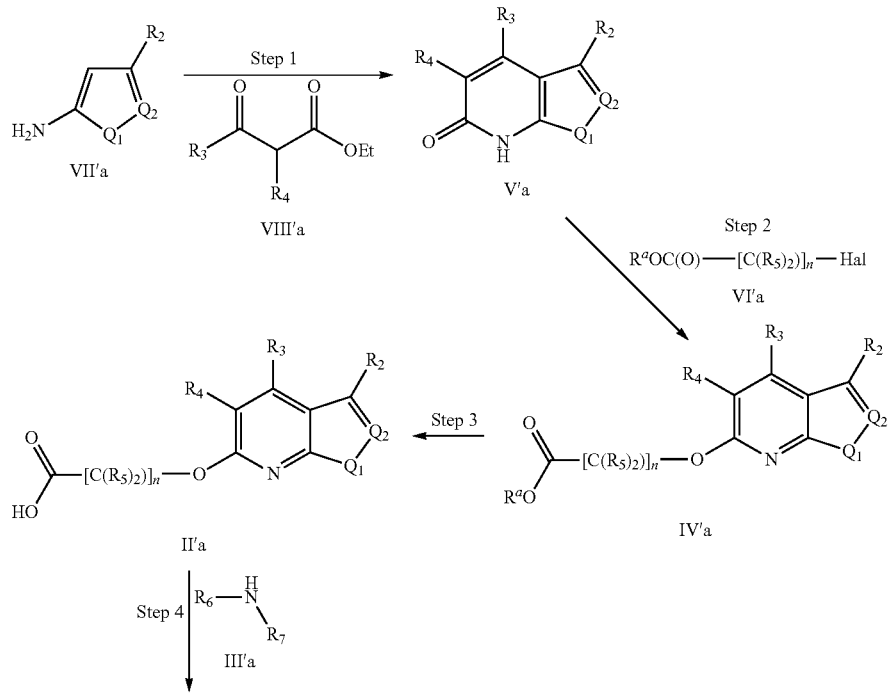

Scheme 1:

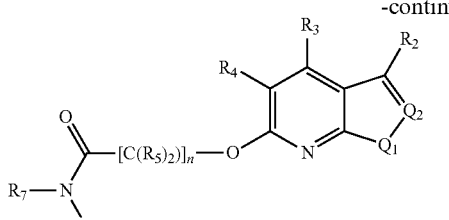

I'a

The process steps are described in more detail below:

Step 1: A compound of formula V'a, in which $Q_1$, $Q_2$, $R_1$, $R_{1a}$, $R_2$, $R_3$ and $R_4$ are as defined under formula I', may be obtained by reacting the compound of formula VII'a with a compound of formula VII'a, in which $R_3$ and $R_4$ are as defined under formula I', in the presence of an acid, e.g. acetic acid, optionally in the presence of a suitable solvent.

Step 2: An ester of formula IV'a, in which $Q_1$, $Q_2$, $R_1$, $R_{1a}$, $R_2$, $R_3$, $R_4$, $R_5$ and n are as defined under formula I', and $R^a$ is $C_{1-6}$alkyl, e.g. ethyl, may be obtained by reacting the compound of formula V'a with a halogenide of formula VI'a, in which $R_5$ and n are as defined under formula I' and $R^a$ is as defined under formula IV'a, with a base, e.g. NaH, in the presence of a suitable solvent, e.g. dimethylformamide.

Step 3: An acid of formula II'a, in which $Q_1$, $Q_2$, $R_1$, $R_{1a}$, $R_2$, $R_3$, $R_a$, $R_5$ and n are as defined under formula I', is produced from the ester of formula IV'a by addition of a base, e.g. LiOH, and water, optionally in the presence of a suitable solvent, e.g. tetrahydrofurane.

Step 4: A compound of formula I'a, in which $Q_1$, $Q_2$, $R_1$, $R_{1a}$, $R_2$, $R_3$, $R_4$, $R_5$, $R_6$, $R_7$ and n are as defined under formula I', may be obtained by reacting the compound of formula II'a with an amine of formula III'a, in which $R_6$ and $R_7$ are as defined under formula I', in the presence of dicyclohexylcarbodiimide, 1-hydroxybenzotriazole trihydrate and dimethylformamide.

In a further aspect, the invention also provides a process for the production of compounds of the formula I'a

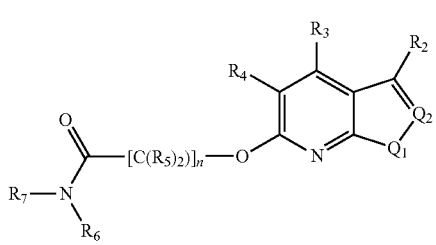

I'a in which $Q_1$, $Q_2$, $R_1$, $R_{1a}$, $R_2$, $R_3$, $R_4$, $R_5$, $R_6$, $R_7$ and n are as defined under formula I', which comprises reacting a compound of the formula II'a

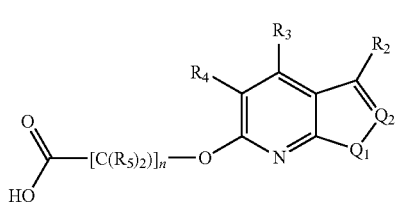

II'a in which $Q_1$, $Q_2$, $R_1$, $R_{1a}$, $R_2$, $R_3$, $R_4$, $R_5$ and n are as defined under formula I', with a compound of the formula III'a

III'a in which in which $R_6$ and $R_7$ are as defined under formula I', in the presence of dicyclohexylcarbodiimide, 1-hydroxybenzotriazole trihydrate and dimethylformamide.

The starting materials of the formulae II'a and III'a may be known or may be prepared according to conventional procedures starting from known compounds, for example as described in the Examples.

In a further aspect, the invention also provides a process for the production of compounds of formula II''a

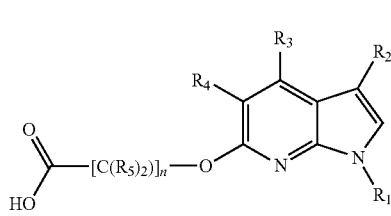

II''a in which $R_1$, $R_2$, $R_3$, $R_4$, $R_5$ and n are as defined under formula I'. The process is described in scheme 2.

Scheme 2:

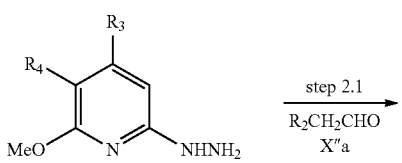

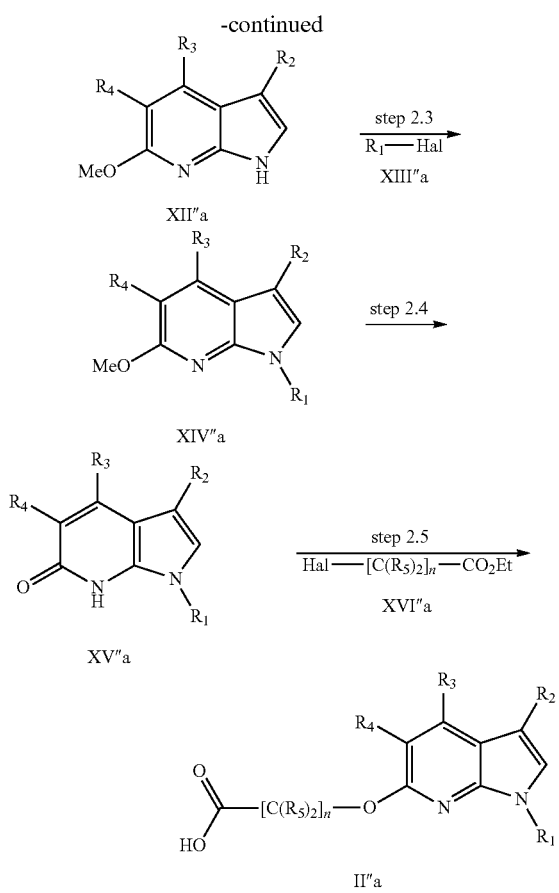

The process steps are described in more detail below:

Step 2.1: A compound of formula XI"a, in which $R_2$, $R_3$ and $R_4$ are as defined under formula I', may be obtained by reacting the compound of formula IX"a in which $R_3$ and $R_4$ are as defined under formula I' with a compound of formula X"a, in which $R_2$ is as defined under formula I' in the presence of a suitable solvent, e.g. toluene.

Step 2.2: A compound of formula XII"a, in which $R_2$, $R_3$ and $R_4$ are as defined under formula I', may be obtained by heating the compound of formula XI"a in the presence of a suitable solvent, e.g. diethyleneglycol.

Step 2.3: A compound of formula XIV"a, in which $R_1$, $R_2$, $R_3$ and $R_4$ are as defined under formula I', may be produced by reacting a compound of formula XII"a with a compound of formula XIII"a in which R1 is as defined under formula I' and Hal is a halogen in the presence of a suitable base and in the presence of a suitable solvent, e.g. dimethylformamide.

Step 2.4: A compound of formula XV"a, in which $R_1$, $R_2$, $R_3$, and $R_4$ are as defined under formula I', may be obtained by heating the compound of formula XIV" in the presence of a suitable solvent, TMSI and DMAP.

Step 2.5: A compound of formula II"a, in which $R_1$, $R_2$, $R_3$, $R_4$, $R_5$ and n are as defined under formula I', may be obtained by reacting compound XV"a with a compound of formula XVI"a wherein $R_5$ and n are as defined under formula I' and Hal is a halogen in the presence of a suitable base and a suitable solvent, followed by treatment with water.

In a further aspect, the invention also provides a process for the production of compounds of the formula Ia. Compounds of the formula Ia are obtainable according to the following process as described in scheme 3:

Scheme 3:

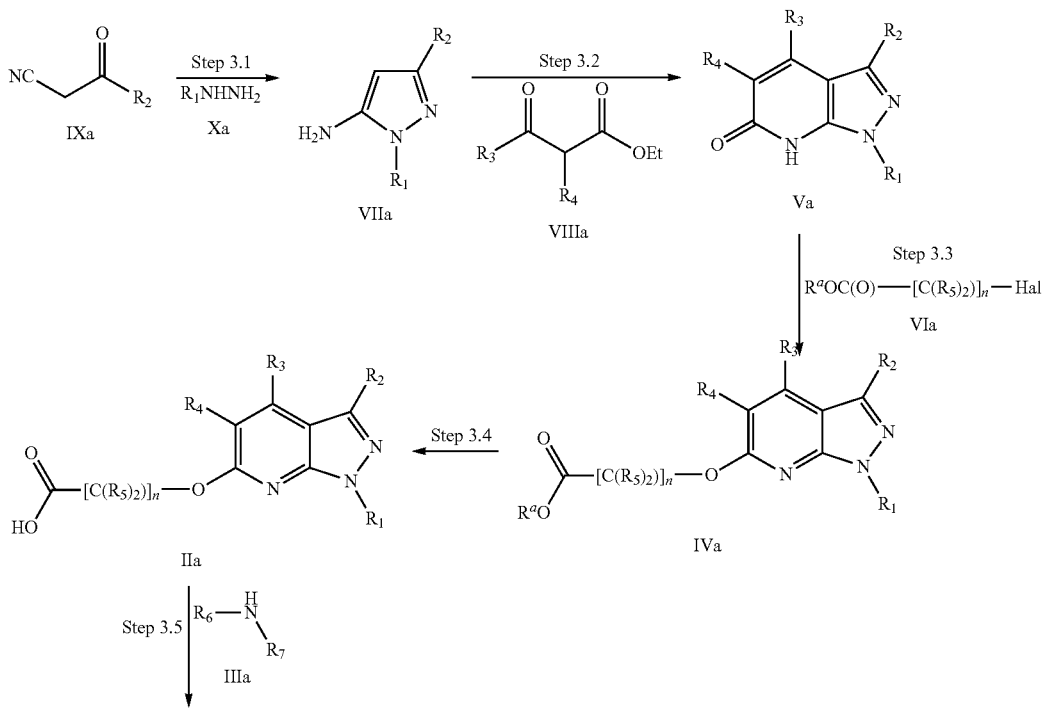

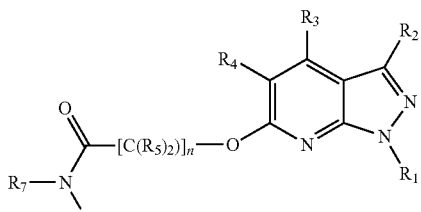

Ia

The process steps are described in more detail below:

Step 3.1: A compound of formula VIIa, in which $R_1$ and $R_2$ are as defined under formula I, may be obtained by reacting a compound of formula IXa, in which $R_2$ is as defined under formula I, with a hydrazine of formula Xa, in which $R_1$ is defined under formula I, in the presence of a suitable solvent, e.g. methanol.

Step 3.2: A compound of formula Va, in which $R_1$, $R_2$, $R_3$ and $R_4$ are as defined under formula I, may be obtained by reacting the compound of formula VIIIa with a compound of formula VIIIa, in which $R_3$ and $R_4$ are as defined under formula I, in the presence of an acid, e.g. acetic acid, optionally in the presence of a suitable solvent.

Step 3.3: An ester of formula IVa, in which $R_1$, $R_2$, $R_3$, $R_4$, $R_5$ and n are as defined under formula I, and $R^a$ is $C_{1-6}$alkyl, e.g. ethyl, may be obtained by reacting the compound of formula Va with a halogenide of formula Via, in which $R_5$ and n are as defined under formula I and $R^a$ is as defined under formula IVa, with a base, e.g. NaH, in the presence of a suitable solvent, e.g. dimethylformamide.

Step 3.4: An acid of formula IIa, in which $R_1$, $R_2$, $R_3$, $R_4$, $R_5$ and n are as defined under formula I, is produced from the ester of formula IVa by addition of a base, e.g. LION, and water, optionally in the presence of a suitable solvent, e.g. tetrahydrofurane.

Step 3.5: A compound of formula Ia, in which $R_1$, $R_2$, $R_3$, $R_4$, $R_5$, $R_6$, $R_7$ and n are as defined under formula I, may be obtained by reacting the compound of formula IIa with an amine of formula IIIa, in which $R_6$ and $R_7$ are as defined under formula I, in the presence of dicyclohexylcarbodiimide, 1-hydroxybenzotriazole trihydrate and dimethylformamide.

Further compounds of formula I' or I may be obtainable from compounds of formula I'a or Ia—prepared as described according to schemes 1 or 3—by reduction, oxidation and/or other functionalization of resulting compounds and/or by cleavage of any protecting group(s) optionally present, and of recovering the so obtainable compound of the formula I or I'.

The reactions can be effected according to conventional methods, for example as described in the Examples.

The work-up of the reaction mixtures and the purification of the compounds thus obtainable may be carried out in accordance with known procedures.

Acid addition salts may be produced from the free bases in known manner, and vice-versa.

Compounds of formula (I) or (I') can also be prepared by further conventional processes, e.g. as described in the Examples, which processes are further aspects of the invention.

The starting materials, e.g. of the formulae IIIa, IVa, VIIIa, IXa and Xa, are known or may be prepared according to conventional procedures starting from known compounds, for example as described in the Examples. In some cases, an intermediate of schemes 1, 2 or 3 may be known. In such a situation, said intermediate could be used as an alternative starting point for the process according to schemes 1, 2 or 3.

In a further aspect, the invention also provides a process for the production of compounds of the formula Ia

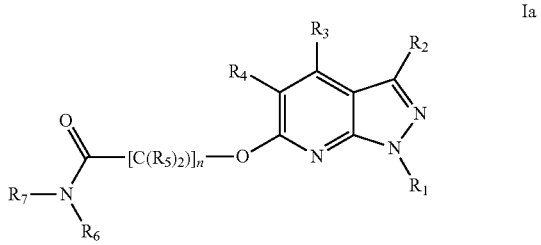

Ia in which $R_1$, $R_2$, $R_3$, $R_4$, $R_5$, $R_6$, $R_7$ and n are as defined under formula I, which comprises reacting a compound of the formula IIa

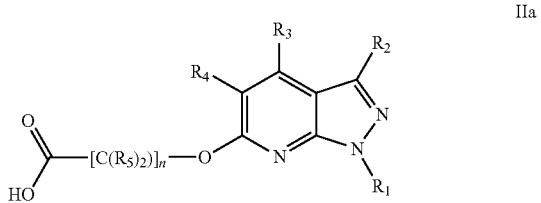

IIa in which $R_1$, $R_2$, $R_3$, $R_4$, $R_5$ and n are as defined under formula I, with a compound of the formula IIIa

IIIa in which in which $R_6$ and $R_7$ are as defined under formula I, in the presence of dicyclohexylcarbodiimide, 1-hydroxybenzotriazole trihydrate and dimethylformamide.

In another aspect, the invention provides a pharmaceutical composition comprising a compound of formula (I) or (I') and a pharmaceutically acceptable carrier. The pharmaceutical composition can be formulated for particular routes of administration such as oral administration, parenteral administration, and rectal administration, etc. In addition, the pharmaceutical compositions of formula (I) or (I') can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers etc.

Typically, the pharmaceutical compositions are tablets and gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of formula (I) or (I') in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of formula (I) or (I') with carrier. Carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The invention further provides anhydrous pharmaceutical compositions and dosage forms comprising the compounds of formula (I) or (I') as active ingredients, since water may facilitate the degradation of certain compounds.

Anhydrous pharmaceutical compositions and dosage forms of formula (I) or (I') can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the invention as an active ingredient will decompose. Such agents, which are referred to herein as "stabilizers," include, but are not limited to, antioxidants such as ascorbic acid, pH buffers, or salt buffers, etc.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The compounds of formula (I) or (I') in free form or in pharmaceutically acceptable salt form, exhibit valuable pharmacological properties, e.g. orexin receptor modulating properties, e.g. as indicated in in-vitro and in-vivo tests as provided in the next sections and are therefore indicated for therapy.

Preferred compounds of the invention show an inhibition of calcium accumulation in recombinant cells expressing at least one of hOx1R or hOx2R at 10 µM of test compound of at least 10%. In one embodiment of the invention, compounds of the invention, which are described in Table 6 as showing an inhibition of calcium accumulation in recombinant cells expressing at least one of hOx1R or hOx2R at 10 µM of test compound of lower than 10%, are excluded.

Further preferred compounds of the invention show a Ki value for said calcium accumulation in recombinant cells expressing at least one of hOx1R or hOx2R of at least 1 µM.

Further preferred compounds of the invention show a Ki value for said calcium accumulation in recombinant cells expressing at least one of hOx1R or hOx2R of at least 500 nM.

Further preferred compounds of the invention show a Ki value for said calcium accumulation in recombinant cells expressing at least one of hOx1R or hOx2R of at least 100 nM.

Further preferred compounds of the invention show a Ki value for said calcium accumulation in recombinant cells expressing at least one of hOx1R or hOx2R of at least 50 nM.

Compounds of the invention may be useful in the treatment of an indication selected from:
i) sleep disorders;
ii) eating disorders;
iii) substance-related disorders;
iv) Alzheimers disease;
v) psychiatric, neurological and neurodegenerative disorders, such as depression; anxiety; addictions, obsessive compulsive disorder; affective neurosis; depressive neurosis; anxiety neurosis; dysthymic disorder; mood disorder; sexual dysfunction; psychosexual dysfunction; sex disorder; schizophrenia; manic depression; delirium; dementia; severe mental retardation and dyskinesias such as Huntington's disease and Tourette syndrome; Parkinson's disease; ischemic or haemorrhagic stroke; migraine; and neurodegenerative disorder including nosological entities such as disinhibition-dementia-parkinsonism-amyotrophy complex; pallido-ponto-nigral degeneration epilepsy; seizure disorders;
vi) cardiovascular diseases, diabetes; asthma; Cushing's syndrome/disease; basophil adenoma; prolactinoma; hyperprolactinemia; hypopituitarism; hypophysis tumour/adenoma; hypothalamic diseases; Froehlich's syndrome; hypophysis diseases, hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; heart and lung diseases, acute and congestive heart failure; hypotension; hypertension; urinary retention; osteoporosis; angina pectoris; myocardial infarction; subarachnoid haemorrhage; ulcers; allergies; benign prostatic hypertrophy; chronic renal failure; renal disease; impaired glucose tolerance; vomiting and nausea; inflammatory bowel disease; gastric dyskinesia; gastric ulcers; urinary bladder incontinence e.g. urge incontinence; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; conditions associated with visceral pain such as irritable bowel syndrome, migraine and angina; and
vii) other diseases related to general orexin system dysfunction.

Compounds of the invention may be especially useful in the treatment of an indication selected from: sleep disorders, eating disorders, substance-related disorders and Alzheimers disease.

"Eating disorders" may be defined as comprising metabolic dysfunction; dysregulated appetite control; compulsive obesities; emeto-bulimia or anorexia nervosa. This pathologically modified food intake may result from disturbed appetite (attraction or aversion for food); altered energy balance (intake vs expenditure); disturbed perception of food quality (high fat or carbohydrates, high palatability); disturbed food availability (unrestricted diet or deprivation) or disrupted water balance.

"Sleep disorders" include insomnias, narcolepsy and other disorders of excessive sleepiness, sleep-related dystonias; restless leg syndrome; sleep apneas; jet-lag syndrome; shift-work syndrome, delayed or advanced sleep phase syndrome. Insomnias are defined as comprising sleep disorders associated with aging; intermittent treatment of chronic insomnia; situational transient insomnia (new environment, noise) or short-term insomnia due to stress; grief; pain or illness.

"Substance-related disorders" include substance abuse, substance dependence and substance withdrawal disorders, e.g. nicotine withdrawal or narcotics withdrawal.

Thus, as a further embodiment, the invention provides the use of a compound of formula (I) or (I') in free form or in pharmaceutically acceptable salt form as a medicament.

As a further embodiment, the invention provides the use of a compound of formula (I) or (I') in free form or in pharmaceutically acceptable salt form in therapy.

In another embodiment, the invention relates to the use of a compound according to the invention, for the treatment of a disorder or disease in a subject mediated by orexin receptors.

In another embodiment, the invention relates to the use of a compound according to the invention, for the treatment of a disorder or disease in a subject characterized by an abnormal activity of orexin receptors.

In a further embodiment, the therapy is selected from a disease which is ameliorated by modulation, preferably antagonism, of orexin receptors. In another embodiment, the disease is selected from the afore-mentioned list, suitably sleep disorders, eating disorders, substance-related disorders or Alzheimers disease.

In another embodiment, the invention provides a method of treating a disease which is ameliorated by modulation, preferably antagonism, of orexin receptors comprising administration of a therapeutically acceptable amount of a compound of formula (I) or (I') in free form or in pharmaceutically acceptable salt form. In a further embodiment, the disease is selected from the afore-mentioned list, suitably sleep disorders, eating disorders or Alzheimers disease.

In another embodiment, the invention provides a method of inhibiting orexin receptor activity in a subject, wherein the method comprises administering to the subject a therapeutically effective amount of the compound of formula (I) or (I').

In another embodiment, the invention relates to a combination comprising a therapeutically effective amount of the compound according to the invention and one or more therapeutically active agents.

The term "a therapeutically effective amount" of a compound of the invention refers to an amount of the compound of the invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the invention that, when administered to a subject, is effective to (1) at least partially alleviating, inhibiting, preventing and/or ameliorating a condition, or a disorder or a disease (i) mediated by orexin receptors, or (ii) associated with orexin receptor activity, or (iii) characterized by abnormal activity of orexin receptors; or (2) reducing or inhibiting the activity of orexin receptors; or (3) reducing or inhibiting the expression of orexin receptors. In another non-limiting embodiment, the term "a therapeutically effective amount" refers to the amount of the compound of the invention that, when administered to a cell, or a tissue, or a non-cellular biological material, or a medium, is effective to at least partially reducing or inhibiting the activity of orexin receptors; or at least partially reducing or inhibiting the expression of orexin receptors.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

The pharmaceutical composition or combination of the invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the invention can be assessed by in vitro & in vivo methods described herein.

The compound of the invention may be administered either simultaneously with, or before or after, at least one other therapeutic agent. The compound of the invention may be administered separately, by the same or different route of administration, or together in the same pharmaceutical composition.

The following Examples illustrate the invention, but do not limit it.

| Abbreviations: | |
|---|---|
| AcOH | acetic acid |
| BINAP | 2,2'-bis(diphenylphosphino)-1,1'-binaphthyl |
| d | day(s) |
| DABCO | 1,4-diazabicyclo[2.2.2]octane |
| DCM | dichloromethane |
| DIC | dicyclohexylcarbodiimide |
| DIPEA | N,N-Diisopropylethylamine (Hünig's base) |
| DMF | dimethylformamide |
| DMSO | dimethylsulfoxide |
| EDC | 1-(3-dimethylaminopropyl)-3-ethylcarbodiimide |
| ESIMS | electrospray ionization mass spectrometry |
| EtOAc | ethyl acetate |
| Et$_2$O | diethyl ether |
| h | hour(s) |
| HATU | O-(7-Azabenzotriazol-1-yl)-N,N,N',N'-tetramethyluronium hexafluorophosphate |
| Hex | hexane |
| HOBt | 1-Hydroxybenzotriazole trihydrate |
| HPLC | high pressure liquid chromatography |
| LCMS | liquid chromatography mass spectroscopy |
| min | minute(s) |
| NMR | nuclear magnetic resonance spectrometry |
| quant. | quantitative |
| Rt | retention time |
| rt | room temperature |
| SCF | supercritical fluid chromatography |
| THF | tetrahydrofuran |
| TFA | trifluoroacetic acid |
| UPLC | ultra performance liquid chromatography |

HPLC Conditions: (%=Percent by Volume)

Method A: ($Rt_A$=Retention Time A)

Agilent 1100 &1200 series; Column—Zorbax XDB—C18 5μ, 150×4.6 mm; gradient: A—0.01% TFA in water/B—acetonitrile:methanol (1:1); 0-1 min 70A-30B; 1-6 min 30A-100B; 6-10 min 0A-30B; 10-12 min 70A-30B; column temperature 40° C.

Method B: ($Rt_B$=Retention Time B).

Agilent 1100 &1200 series; Column—Zorbax XDB—C18 5μ, 150×4.6 mm; gradient: A—0.01% TFA in water/B—acetonitrile:methanol (1:1); 0-1 min 95A-05B; 1-6 min 95A-100B; 6-10 min 0A-05B; 10-12 min 95A-05B; flow 1.0 ml/min; column temperature 40° C.

Method C: $Rt_C$=Retention Time C)

Agilent 1100 &1200 series; Column—Zorbax XDB—C18 5μ, 150×4.6 mm; gradient: A—5 mM Ammonium acetate in water/B—acetonitrile; 0-1 min 70A-30B; 1-6 min 30A-100B; 6-10 min 0A-30B; 10-12 min 70A-30B; flow 1.0 ml/min; column temperature 40° C.

Method D: ($Rt_D$=Retention Time D)

Agilent 1100 &1200 series; Column—Zorbax XDB—C18 5μ, 150×4.6 mm; gradient: A—5 mM Ammonium acetate in water/B—acetonitrile; 0-1 min 95A-05B; 1-6 min 95A-100B; 6-10 min 0A-05B; 10-12 min 95A-05B; flow 1.0 ml/min; column temperature 40° C.

Method E: ($Rt_E$=Retention Time E)

Agilent 1100 series; Column—Chiralpak AD-H 5μ, 250×4.6 mm; isocratic: A—n-Heptane/B—Ethanol, 80:20; Flow 0.8 ml/min; column temperature 40° C.

LCMS/HPLC-MS Conditions:

Method A: ($Rt_A$=Retention Time A)
Agilent 1100 series; LC-MSD; column Mercury MS Synergi 2µ, 20×4.0 mm; gradient: A—0.1% formic acid in water/B—acetonitrile; 0-0.5 min 70A-30B; 1.5-2.4 min 5A-95B; 2.5-3.0 min 70A-30B; flow 2.0 ml/min; column temperature 30° C.

Method B: ($Rt_B$=Retention Time B)
Agilent 1100 series; LC-MSD; column Mercury MS Synergi 2µ, 20×4.0 mm; gradient: A—0.1% formic acid in water/B—acetonitrile; 0-0.5 min 30A-70B; 1.5-2.4 min 100B-0A; 2.5-3.0 min 30A-70B; flow 2.0 ml/min; column temperature 30° C.

Method C: ($Rt_C$=Retention Time C)
Agilent 1100 series; LC-MSD; column Mercury MS Synergi 2µ, 20×4.0 mm; gradient: A—0.1% formic acid in water/B—acetonitrile; 0-0.5 min 30A-70B; 1.5-2.4 min 10A-90B; 2.5-3.0 min 30A-70B; flow 2.0 ml/min; column temperature 30° C.

Method D: ($Rt_D$=Retention Time D)
Agilent 1100 series; LC-MSD; column Atlantis C18 5µ, 50×4.6 mm; gradient: A—0.1% formic acid in water/B—0.1% formic acid in 9:1 acetonitrile: water; 0-1.0 min 30A-70B; 1.5-2.5 min 05A-95B; 2.5-3.0 min 05A-70B; 3.0-5.0 min 30A-70B flow 0.8-1.0 ml/min; column temperature 30° C.

Method E: ($Rt_E$=Retention Time E)
Agilent 1100 series; LC-MSD; column Mercury MS Synergi 2µ, 20×4.0 mm; gradient: A—0.1% formic acid in water/B—acetonitrile; 0-0.5 min 95A-05B; 1.5-2.4 min 10A-90B; 2.5-3.0 min 05A-95B; flow 2.0 ml/min; column temperature 30° C.

Method F ($Rt_F$=Retention Time F)
Waters 2795 Alliance HT; LC-MS; column SunFire C18 20×4.6 mm, 3.5 µm, reverse phase; Eluent A: water/Eluent B: acetonitrile, both containing 0.1% trifluoroacetic acid; gradient 05-100% B, in 4.0 min; Flow 3.0 ml/min; column temperature 45° C.

Method G ($Et_G$=Retention Time G)
Waters UPLC Acquity-SQD: column Acquity UPLC BEH C18 1.7µ, 30×2.1 mm; A—0.05% formic acid in water/B—0.04% formic acid in methanol; 0 min 98A-2B; 0-0.15 min 90A-10B; 0.15-0.60 min 2A-98B; 0.60-1.10 min 2A-98B; 1.10-1.15 98A-2B; flow 1.3 ml/min; column temperature 60° C.

Method H: ($Rt_H$=Retention Time H)
Agilent 1100 series; LC-MSD; Zorbax SB-C18 1.8 µm; 3×30 mm; gradient: A water+0.05% TFA/B acetonitrile+0.05% TFA; 0-3.25 min 70A:30B-0A:100B; 3.25-4.0 min 0A:100B; 4.0-4.25 min 0A:100B-70A:30 B; flow 0.7 ml/min; column temperature 35° C.

Method I: ($Rt_I$=Retention Time I)
Agilent 1100 series; LC-MSD; Zorbax SB-C18 1.8 µm; 3×30 mm; gradient: A water+0.05% TFA/B acetonitrile+0.05% TFA; 0-3.25 min 100A:0B-0A:100B; 3.25-4.0 min 100B; 4.0-4.25 min 0A:100B-100A:0B; flow 0.7 ml/min; column temperature 35° C.

Method J ($Rt_J$=Retention Time J)
Waters UPLC Acquity-SQD: column Acquity HSS T3 1.8 µm 2.1×50 mm; A 0.05% formic acid+0.05% ammonium acetate in water/B 0.04% formic acid in acetonitrile; 0-1.40 min 98A:2B-2A:98B, 1.40-2.15 min 2A:98B, 2.15-2.20 min 98A:2B; flow 1.2 ml/min; column temperature 50° C.

Method K: ($Rt_K$=Retention Time K)
Agilent 1100 series; LC-MSD; Zorbax SB-C18 1.8 µm; 3×30 mm; gradient: A water+0.05% TFA/B acetonitrile+0.05% TFA; 0-3.25 min 60A:40B-0A:100B; 3.25-4.0 min 100B; 4.0-4.25 min 0A:100B-60A:40B; flow 0.7 ml/min; column temperature 35° C.

Method L: ($Rt_L$=Retention Time L)
Agilent 1100 series; LC-MSD; Zorbax SB-C18 1.8 µm; 3×30 mm; gradient: A water+0.05% TFA/B acetonitrile+0.05% TFA; 0-3.25 min 90A:10B-0A:100B; 3.25-4.0 min 100B; 4.0-4.25 min 0A:100B-90A:10B; flow 0.7 ml/min; column temperature 35° C.

Method M: ($Rt_M$=Retention Time M)
Agilent 1100 series; LC-MSD; Zorbax SB-C18 1.8 µm; 3×30 mm; gradient: A water+0.05% TFA/B acetonitrile+0.05% TFA; 0-3.25 min 50A:50B-0A:100B; 3.25-4.0 min 100B; 4.0-4.25 min 0A:100B-50A:50B; flow 0.7 ml/min; column temperature 35° C.

Method N ($Rt_N$=Retention Time N)
Agilent 1100 Bin; ZMD2000; Ascentis Express FusedCore 2.1×30 mm 2.7 µm C18; A: water+0.05% TFA/B: acetonitrile+0.04% TFA; 2% B to 98% B in 1.4 min, 0.75 min at 98% B, 98% B to 2% B in 0.04 min; flow 1.2 ml/min; column temperature 50° C.

1H-NMR Instruments: Varian Mercury (300 MHz), Bruker BioSpin (600 MHz), Bruker (400 MHz), Varian (400 MHz), Bruker Advance (600 MHz), Bruker BioSpin (360 MHz).

METHOD A

Example 1.1

(S)-2-(3-(2-fluorophenyl)-1-methyl-4-(trifluoromethyl)-1H-pyrazolo[3,4-b]pyridin-6-yloxy)-N-(1-phenylethyl)acetamide

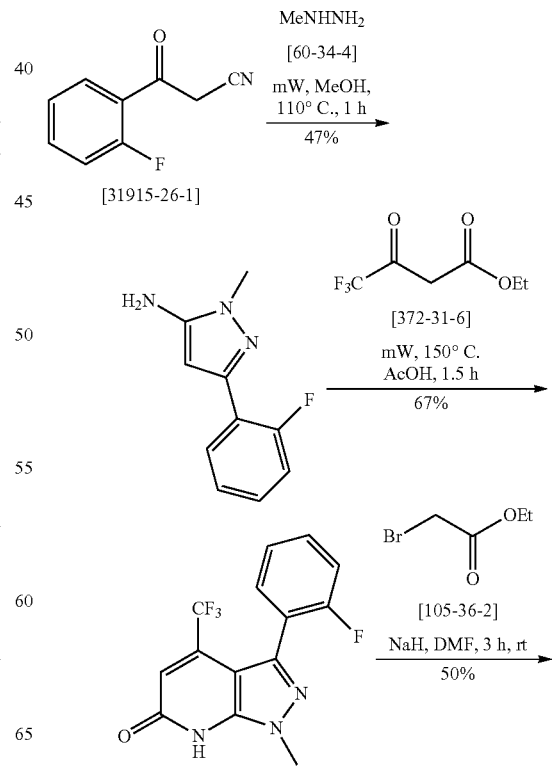

51
-continued

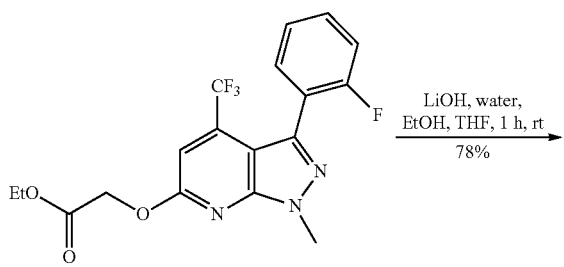

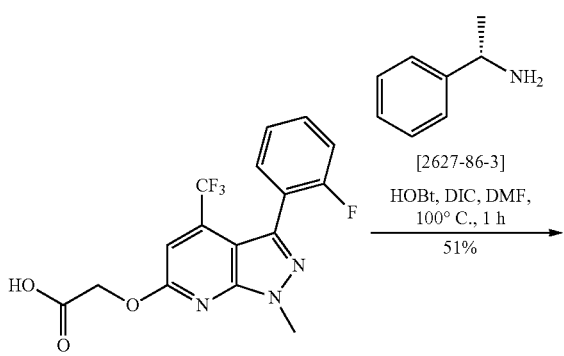

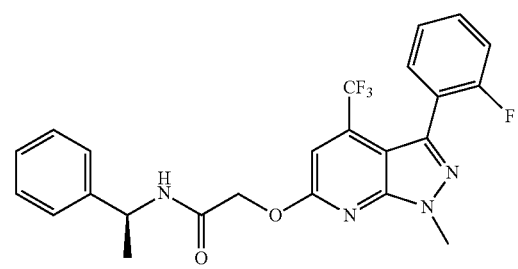

a) 3-(2-fluorophenyl)-1-methyl-1H-pyrazol-5-amine

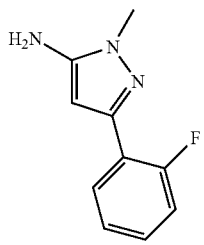

A solution of 2-fluorobenzoylacetonitrile (1.5 g, 9.19 mmol) and methyl hydrazine (0.42 g, 9.19 mmol) in MeOH (15 ml) was heated in a sealed tube at 120° C. for 7 h. The solution was evaporated under reduced pressure and the resulting crude product was purified by column chromatography (eluent: 5% EtOAc in hexane) to yield 830 mg (47%) of the title compound.

[$^1$H-NMR (CDCl$_3$, 300 MHz) 7.95 (t, 1H), 7.35-7.0 (m, 4H), 6.05 (d, 1H), 3.9-3.4 (m, 4H); LCMS Rt$_A$=0.921 min; [M+H]$^+$=192.1]

b) 3-(2-fluorophenyl)-1-methyl-4-(trifluoromethyl)-1H-pyrazolo-[3,4-b]pyridin-6(7H)-one

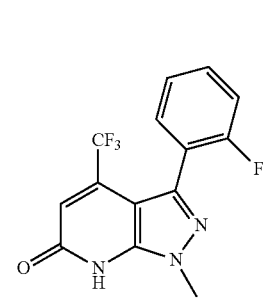 [SMILES: Cn1nc(-c2ccccc2F)c2c(C(F)(F)F)cc(=O)[nH]c21]

A solution of 3-(2-fluorophenyl)-1-methyl-1H-pyrazol-5-amine (830 mg, 4.34 mmol) and 4,4,4-Trifluoro-3-oxo-butyric acid ethyl ester (960 mg, 5.21 mmol) in acetic acid (5 ml) was irradiated using a microwave at 150° C. for 1.5 h. After completion of the reaction, ice-cold water was added and the reaction mixture was stirred for 10 min. The precipitate was filtered, washed twice with pentane and dried under vacuum to yield 900 mg (67%) of the title compound. [$^1$H-NMR (CDCl$_3$, 300 MHz): δ 13.6 (s, 1H), 7.51-7.05 (m, 4H), 6.75 (s, 1H), 4.21 (s, 3H); LCMS Rt$_A$=1.459 min; [M+H]$^+$=312.1]

c) ethyl 2-(3-(2-fluorophenyl)-1-methyl-4-(trifluoromethyl)-1H-pyrazolo[3,4-b]pyridin-6-yloxy)acetate

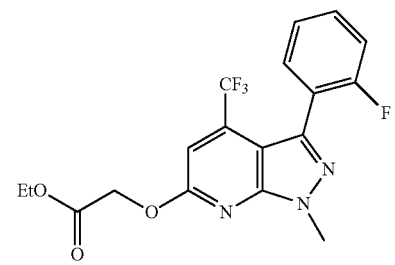 [SMILES: CCOC(=O)COc1cc(C(F)(F)F)c2c(-c3ccccc3F)nn(C)c2n1]

To a solution of 3-(2-fluorophenyl)-1-methyl-4-(trifluoromethyl)-1H-pyrazolo[3,4-b]pyridin-6(7H)-one (280 mg, 0.89 mmol) in DMF (2 ml) was added bromo EtOAc (180.3 mg, 1.08 mmol) and the mixture was stirred for 15 min. Then, sodium hydride (86.4 mg, 3.60 mmol) was added at rt under argon and the reaction mixture was stirred at rt for 3 h. Ice cold water was added dropwise and the reaction mixture was extracted with diethyl ether. The organic layer was separated and dried over Na$_2$SO$_4$, filtered and concentrated under reduced pressure. The resulting crude product was purified by flash chromatography (EtOAc:Hex 5:95) to yield 180 mg (50%) of the title compound. [$^1$H-NMR (CDCl$_3$, 300 MHz) δ 7.55-7.04 (m, 5H), 5.02 (s, 2H), 4.33 (q, 2H), 4.02 (s, 3H), 1.32 (t, 3H); LCMS Rt$_C$=3.63 min; [M+H]$^+$=398.0]

d) 2-(3-(2-fluorophenyl)-1-methyl-4-(trifluoromethyl)-1H-pyrazolo[3,4-b]pyridin-6-yloxy)acetic acid

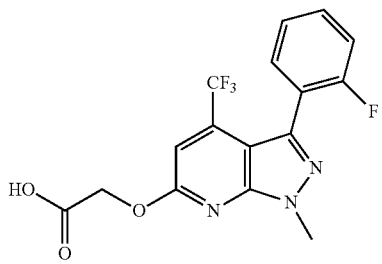 [SMILES: Cn1nc(-c2ccccc2F)c2c(C(F)(F)F)cc(OCC(=O)O)nc21]

To a solution of ethyl 2-(3-(2-fluorophenyl)-1-methyl-4-(trifluoromethyl)-1H-pyrazolo[3,4-b]pyridin-6-yloxy)acetate (180 mg, 0.45 mmol) in a mixture of EtOH, THF and water (2 ml/1 ml/0.5 ml) was added LiOH.H$_2$O (76.1 mg, 1.81 mmol). The reaction mixture was stirred for 1 h at rt. Aqueous HCl was then added to adjust the reaction mixture to pH ~2. The resulting precipitate was filtered off and washed twice with pentane (2×10 mL). The obtained solid was dried under vacuum to furnish 130 mg (78%) of the title compound. [$^1$H-NMR (CDCl$_3$, 300 MHz) δ 7.58-6.95 (m, 5H), 5.25 (s, 2H), 4.15 (s, 3H); LCMS Rt$_A$=1.681 min; [M+H]$^+$=370.1]

e) (S)-2-(3-(2-fluorophenyl)-1-methyl-4-(trifluoromethyl)-1H-pyrazolo[3,4-b]pyridin-6-yloxy)-N-(1-phenylethyl)acetamide

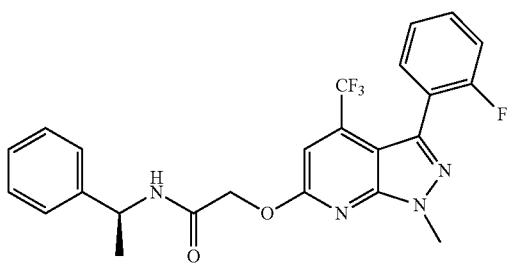 [SMILES: C[C@H](NC(=O)COc1cc(C(F)(F)F)c2c(-c3ccccc3F)nn(C)c2n1)c1ccccc1]

A solution of 2-(3-(2-fluorophenyl)-1-methyl-4-(trifluoromethyl)-1H-pyrazolo[3,4-b]pyridin-6-yloxy)acetic acid (70 mg, 0.189 mmol), DIC (31.1 mg, 0.246 mmol) and HOBt (38.4 mg, 0.285 mmol) in DMF (3 ml) was stirred at rt for 15 min. (S)-(−)-α-methyl benzyl amine (25.3 mg, 0.208 mmol) was added dropwise to the reaction mixture at rt and then the mixture was heated at 100° C. for 1 h. After completion of the reaction, ice-cold water was added and the reaction mixture was stirred for 10 min. The resulting precipitate was collected by filtration. The crude product was re-crystallized from diethyl ether to yield 46 mg (51%) of the title compound. [$^1$H-NMR (CDCl$_3$, 300 MHz) δ 7.55-7.05 (m, 9H), 7.01 (s, 1H), 6.55 (d, 1H), 5.23 (m, 1H), 5.01 (s, 2H), 4.03 (s, 3H), 1.60 (d, 3H); HPLC Rt$_A$=5.384 min (98%); LCMS Rt$_D$=3.055; [M+H]$^+$=473.1].

Examples 1.2 to 1.77 were synthesized according to method A using the corresponding intermediates.

Example 1.2

(S)-2-(3-phenyl-4-(trifluoromethyl)-1H-pyrazolo[3,4-b]pyridin-6-yloxy)-N-(1-phenylethyl)acetamide

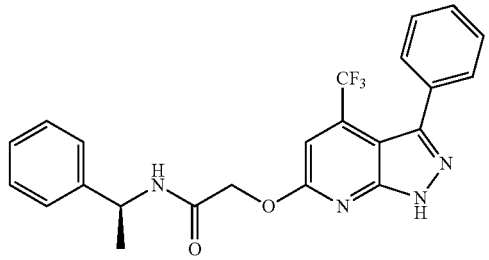 [SMILES: C[C@H](NC(=O)COc1cc(C(F)(F)F)c2c(-c3ccccc3)n[nH]c2n1)c1ccccc1]

A solution of Phenyl-4-trifluoromethyl-1H-pyrazolo[3,4-b]pyridin-6-yloxy)-acetic acid (80 mg, 0.24 mmol), DIC (45 mg, 0.36 mmol) and HOBt (43 mg, 0.32 mmol) in DMF (5 ml) was stirred at rt for 15 min. (S)-(−)-α-methyl benzyl amine (25.3 mg, 0.208 mmol) was added dropwise to the reaction mixture at rt and stirring was continued overnight. After completion of the reaction, ice-cold water (10 mL) was added to the reaction mixture and the mixture was extracted with diethyl ether. The organic layer was dried over Na$_2$SO$_4$, filtered and concentrated under reduced pressure. The crude product was purified by preparative HPLC using acetonitrile/water as mobile phase to yield the title compound as a white solid (35 mg, 34%). [$^1$H-NMR (CDCl$_3$, 300 MHz) δ 7.55-7.42 (m, 5H), 7.33-7.25 (m, 5H), 7.05 (s, 1H), 6.68 (d, 1H), 5.35-5.20 (m, 1H), 4.99 (dd, 2H), 1.62 (d, 3H); HPLC Rt$_A$=5.688 (99%) min; LCMS Rt$_D$=2.303; [M+H]$^+$=441.1]

Example 1.3

(S)—N-(2,3-dihydro-1H-inden-1-yl)-2-(1-methyl-3-phenyl-4-(trifluoromethyl)-1H-pyrazolo[3,4-b]pyridin-6-yloxy)acetamide

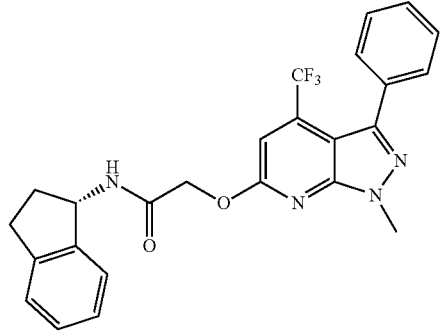 [SMILES: Cn1nc(-c2ccccc2)c2c(C(F)(F)F)cc(OCC(=O)N[C@H]3CCc4ccccc43)nc21]

A solution of (1-Methyl-3-phenyl-4-trifluoromethyl-1H-pyrazolo[3,4-b]pyridin-6-yloxy)-acetic acid (100 mg, 0.285 mmol), DIC (54 mg, 0.427 mmol) and HOBt (50 mg, 0.37 mmol) in DMF (4 ml) was stirred at rt for 10 min. S-(+)-1-amino indane (42 mg, 0.313 mmol) was added to the reaction mixture at rt and stirring was continued for 12 h at rt. After completion of the reaction, the reaction mixture was poured into rapidly stirred ice-cold water to obtain the crude product as a solid. The solid was collected by filtration and dried under vacuum. The product was triturated in a mixture of diethyl ether (3 mL) and pentane (10 mL), filtered and dried to yield the pure title compound as a white solid (102 mg, 82%). [$^1$H-NMR (CDCl$_3$, 300 MHz) δ 7.55-7.48 (m, 5H), 7.40-7.22 (m, 4H), 6.99 (s, 1H), 6.61 (d, 1H), 5.56 (q, 1H), 5.08 (dd, 2H), 4.12 (s, 3H) 3.15-2.86 (m, 2H), 2.63-2.75 (m, 1H), 1.75-1.92 (m, 1H); HPLC Rt$_A$=6.067 (98%) min; LCMS Rt$_E$=2.029, [M+H]$^+$=467.1; Mp=203-205.2° C.]

Example 1.4

(S)—N-(1-(4-methoxyphenyl)ethyl)-2-(1-methyl-3-phenyl-4-(trifluoromethyl)-1H-pyrazolo[3,4-b]pyridin-6-yloxy)acetamide

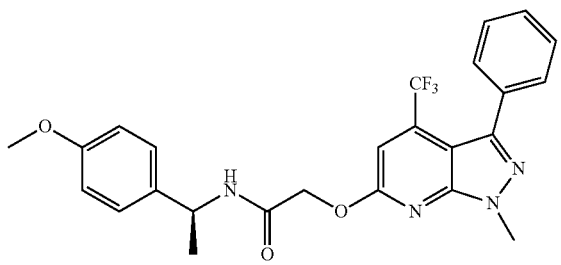 [SMILES: COc1ccc([C@H](C)NC(=O)COc2cc(C(F)(F)F)c3c(-c4ccccc4)nn(C)c3n2)cc1]

A solution of (1-Methyl-3-phenyl-4-trifluoromethyl-1H-pyrazolo[3,4-b]pyridin-6-yloxy)-acetic acid (350 mg, 0.996 mmol), DIC (189 mg, 1.494 mmol) and HOBt (175 mg, 1.295 mmol) in DMF (10 ml) was stirred at rt for 10 min. (S)-(−)-4-methoxy-α-methyl benzyl amine (166 mg, 1.096 mmol) was added to the reaction mixture at rt and stirring was continued for 12 h at rt. After completion of the reaction, the reaction mixture was poured into rapidly stirred ice-cold water to obtain the crude product as a solid. The solid was collected by filtration and dried under vacuum. The product was further purified by flash column chromatography [(eluent: EtOAc/hexane (1:3)] to yield the title compound as a white solid (305 mg, 63%). [$^1$H-NMR (CDCl$_3$, 300 MHz) δ 7.58-7.39 (m, 5H), 7.32-7.21 (m, 2H), 6.99 (s, 1H), 6.85 (d, 2H), 6.51 (d, 1H), 5.31-5.22 (m, 1H), 5.0 (s, 2H), 4.05 (s, 3H), 3.8 (s, 3H), 1.52 (d, 3H); HPLC Rt$_A$=5.933 min. (98%); LCMS Rt$_A$=1.785, [M+H]$^+$=485.1; Mp=172-174° C.]

Example 1.5

(S)-2-(1-methyl-3-phenyl-4-(trifluoromethyl)-1H-pyrazolo[3,4-b]pyridin-6-yloxy)-N-(2-phenylpropyl)acetamide

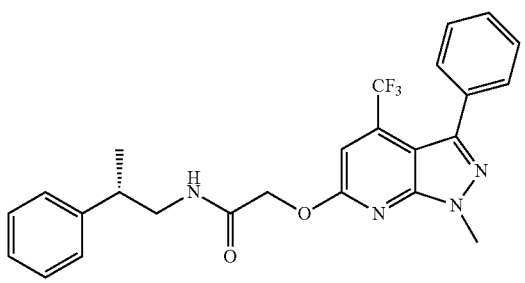 [SMILES: C[C@H](CNC(=O)COc1cc(C(F)(F)F)c2c(-c3ccccc3)nn(C)c2n1)c1ccccc1]

A solution of (1-Methyl-3-phenyl-4-trifluoromethyl-1H-pyrazolo[3,4-b]pyridin-6-yloxy)-acetic acid (100 mg, 0.28 mmol), DIC (53 mg, 0.42 mmol) and HOBt (49 mg, 0.36 mmol) in DMF (5 ml) was stirred at rt for 10 min. (S)-(+)-2-Phenyl-propylamine (42 mg, 0.31 mmol) was added to the reaction mixture at rt and stirring was continued overnight at rt. After completion of the reaction, ice-cold water (10 mL) was added to the reaction mixture and the mixture was stirred for 20 min. The reaction mixture was extracted with diethyl ether, dried over sodium sulfate and concentrated under reduced pressure. The solid was triturated with pentane (20 ml×3) followed by hexane (15 ml) to yield the title compound as white solid. (100 mg, 75%). Mp=91-93° C. [$^1$H-NMR (CDCl$_3$, 300 MHz) δ 7.63-7.42 (m, 5H), 7.20-6.92 (m, 5H), 6.80 (s, 1H), 6.18-6.12 (m, 1H), 4.92 (dd, 2H), 4.1 (s, 3H), 3.81-3.68 (m, 1H), 3.40-3.33 (m, 1H), 2.98-2.90 (m, 1H), 1.41 (d, 3H); HPLC Rt$_A$=6.325 min. (98%); LCMS Rt$_A$=1.835, [M+H]$^+$=469.1]

Example 1.6

(S)—N-(1-(3,5-dimethyl-1H-pyrazol-4-yl)ethyl)-2-(1-methyl-3-phenyl-4-(trifluoromethyl)-1H-pyrazolo[3,4-b]pyridin-6-yloxy)acetamide

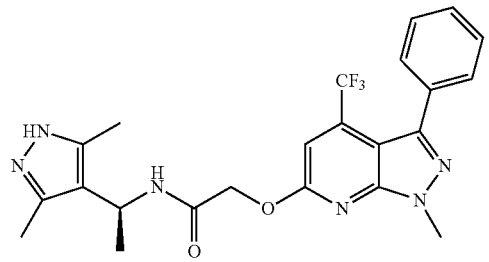 [SMILES: Cc1n[nH]c(C)c1[C@H](C)NC(=O)COc1cc(C(F)(F)F)c2c(-c3ccccc3)nn(C)c2n1]

A solution of (1-Methyl-3-phenyl-4-trifluoromethyl-1H-pyrazolo[3,4-b]pyridin-6-yloxy)-acetic acid (1.35 g, 3.843 mmol), DIC (727 mg, 5.769 mmol) and HOBt (674 mg, 4.996 mmol) in DMF (15 ml) was stirred at rt for 15 min. 1-(3,5-dimethyl-1H-pyrazole-4-yl)ethanamine (642 mg, 4.612 mmol) was added to the solution at rt and stirring was continued overnight at rt. After completion of the reaction, ice-cold water was added to the reaction mixture and the mixture was stirred for 10 min. The precipitate was collected by filtration and dried under vacuum. The racemic mixture was subjected to chiral preparative chromatographic separation to yield the enantiomeric pure title compound (165 mg) and the R enantiomer (165 mg, see example 1.62). [$^1$H-NMR (CDCl$_3$, 300 MHz) δ 7.62-7.48 (m, 5H), 6.99 (s, 1H), 6.55 (d, 1H), 5.33-4.92 (m, 3H), 4.1 (s, 3H), 2.25 (s, 6H), 1.55 (d, 3H); HPLC Rt$_E$=6.194 min. (98%); LCMS Rt$_A$=1.382, [M+H]$^+$=473.1; Mp=145-147° C.]

TABLE 1

| Compounds Number 1.7 to 1.77: | | | | |
|---|---|---|---|---|
| Number | Structure | IUPAC Name | LCMS Rt [min] (method) | [M + H]+ |
| 1.7 | | N-(2-ethoxybenzyl)-2-(1-methyl-3-phenyl-4-(trifluoromethyl)-1H-pyrazolo[3,4-b]pyridin-6-yloxy)acetamide | 0.696 (G) | 485.2 |
| 1.8 | | N-(3-fluorobenzyl)-2-(1-methyl-3-phenyl-4-(trifluoromethyl)-1H-pyrazolo[3,4-b]pyridin-6-yloxy)acetamide | 0.675 (G) | 459.1 |
| 1.9 | | N-cyclohexyl-2-(1-methyl-3-phenyl-4-(trifluoromethyl)-1H-pyrazolo[3,4-b]pyridin-6-yloxy)acetamide | 0.693 (G) | 433.2 |
| 1.10 | | N-cyclopentyl-2-(1-methyl-3-phenyl-4-(trirfluoromethyl)-1H-pyrazolo[3,4-b]pyridin-6-yloxy)acetamide | 0.680 (G) | 419.2 |
| 1.11 | | N-(4-chlorobenzyl)-2-(1-methyl-3-phenyl-4-(trifluoromethyl)-1H-pyrazolo[3,4-b]pyridin-6-yloxy)acetamide | 0.689 (G) | 475.1 |

TABLE 1-continued

Compounds Number 1.7 to 1.77:

| Number | Structure | IUPAC Name | LCMS Rt [min] (method) | [M + H]+ |
|---|---|---|---|---|
| 1.12 | 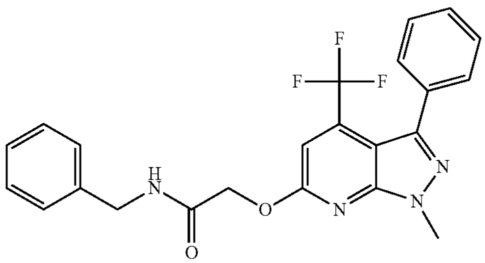 [SMILES: Cn1nc(-c2ccccc2)c2c(C(F)(F)F)cc(OCC(=O)NCc3ccccc3)nc21] | N-benzyl-2-(1-methyl-3-phenyl-4-(trifluoromethyl)-1H-pyrazolo[3,4-b]pyridin-6-yloxy)acetamide | 0.674 (G) | 441.2 |
| 1.13 | 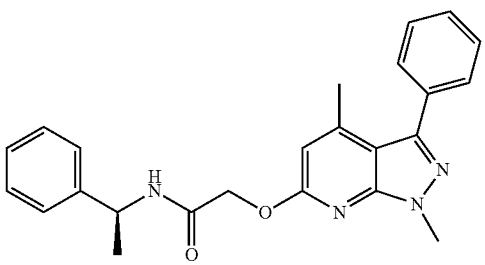 [SMILES: Cc1cc(OCC(=O)N[C@@H](C)c2ccccc2)nc2c1c(-c1ccccc1)nn2C] | (S)-2-(1,4-dimethyl-3-phenyl-1H-pyrazolo[3,4-b]pyridin-6-yloxy)-N-(1-phenylethyl)acetamide | 2.42 (F) | 401.5 |
| 1.14 | 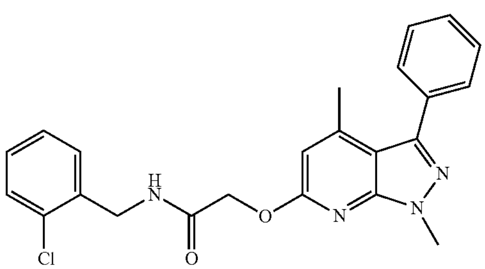 [SMILES: Cc1cc(OCC(=O)NCc2ccccc2Cl)nc2c1c(-c1ccccc1)nn2C] | N-(2-chlorobenzyl)-2-(1,4-dimethyl-3-phenyl-1H-pyrazolo[3,4-b]pyridin-6-yloxy)acetamide | 2.51 (F) | 421.4 |
| 1.15 | 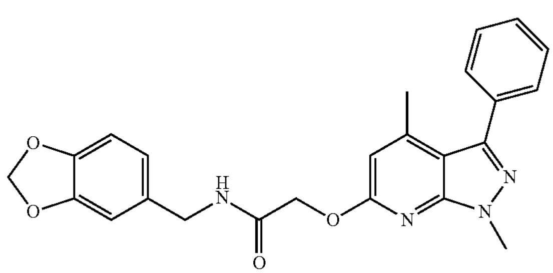 [SMILES: Cc1cc(OCC(=O)NCc2ccc3c(c2)OCO3)nc2c1c(-c1ccccc1)nn2C] | N-(benzo[d][1,3]dioxol-5-ylmethyl)-2-(1,4-dimethyl-3-phenyl-1H-pyrazolo[3,4-b]pyridin-6-yloxy)acetamide | 2.28 (F) | 431.6 |
| 1.16 | 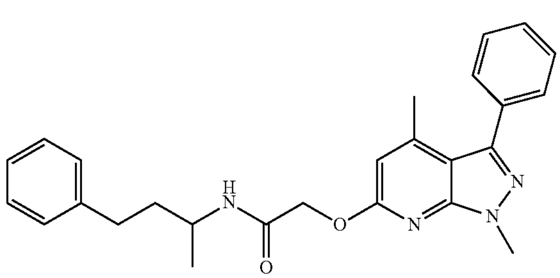 [SMILES: Cc1cc(OCC(=O)NC(C)CCc2ccccc2)nc2c1c(-c1ccccc1)nn2C] | 2-(1,4-dimethyl-3-phenyl-1H-pyrazolo[3,4-b]pyridin-6-yloxy)-N-(4-phenylbutan-2-yl)acetamide | 2.63 (F) | 429.6 |

TABLE 1-continued

Compounds Number 1.7 to 1.77:

| Number | Structure | IUPAC Name | LCMS Rt [min] (method) | [M + H]+ |
|---|---|---|---|---|
| 1.17 | 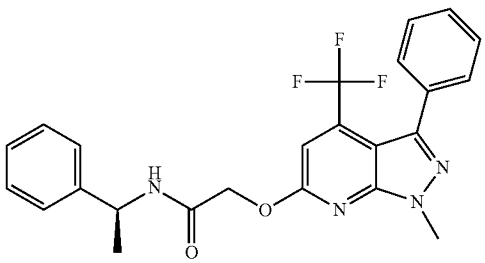 | (S)-2-(1-methyl-3-phenyl-4-(trifluoromethyl)-1H-pyrazolo[3,4-b]pyridin-6-yloxy)-N-(1-phenylethyl)acetamide | 1.16 (D) | 455.0 |
| 1.18 | 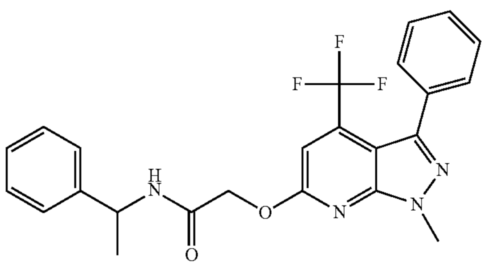 [SMILES: CC(NC(=O)COc1cc(C(F)(F)F)c2c(-c3ccccc3)nn(C)c2n1)c1ccccc1] | 2-(1-methyl-3-phenyl-4-(trifluoromethyl)-1H-pyrazolo[3,4-b]pyridin-6-yloxy)-N-(1-phenylethyl)acetamide | 3.12 (D) | 455.1 |
| 1.19 | 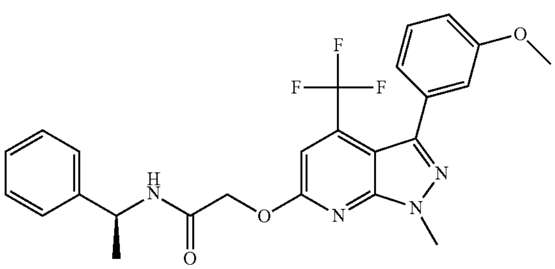 [SMILES: COc1cccc(-c2nn(C)c3nc(OCC(=O)N[C@@H](C)c4ccccc4)cc(C(F)(F)F)c23)c1] | (S)-2-(3-(3-methoxyphenyl)-1-methyl-4-(trifluoromethyl)-1H-pyrazolo[3,4-b]pyridin-6-yloxy)-N-(1-phenylethyl)acetamide | 2.77 (D) | 485.1 |
| 1.20 | 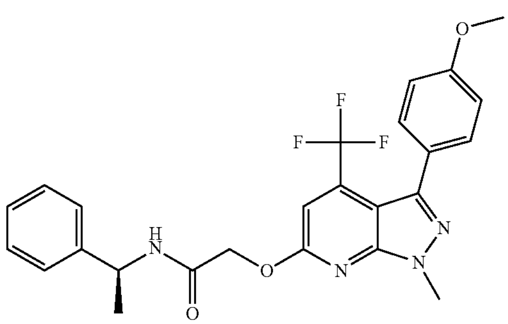 [SMILES: COc1ccc(-c2nn(C)c3nc(OCC(=O)N[C@@H](C)c4ccccc4)cc(C(F)(F)F)c23)cc1] | (S)-2-(3-(4-methoxyphenyl)-1-methyl-4-(trifluoromethyl)-1H-pyrazolo[3,4-b]pyridin-6-yloxy)-N-(1-phenylethyl)acetamide | 2.74 (D) | 484.9 |
| 1.21 | 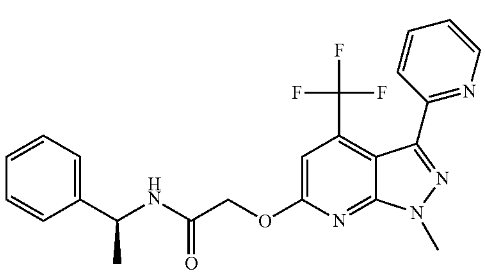 [SMILES: C[C@H](NC(=O)COc1cc(C(F)(F)F)c2c(-c3ccccn3)nn(C)c2n1)c1ccccc1] | (S)-2-(1-methyl-3-(pyridin-2-yl)-4-(trifluoromethyl)-1H-pyrazolo[3,4-b]pyridin-6-yloxy)-N-(1-phenylethyl)acetamide | 1.72 (D) | 455.8 |

TABLE 1-continued

Compounds Number 1.7 to 1.77:

| Number | Structure | IUPAC Name | LCMS Rt [min] (method) | [M + H]+ |
|---|---|---|---|---|
| 1.22 | 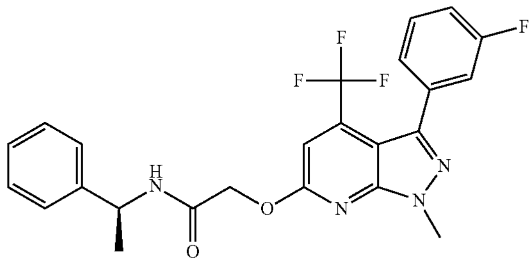 [SMILES: C[C@H](NC(=O)COc1cc(C(F)(F)F)c2c(-c3cccc(F)c3)nn(C)c2n1)c1ccccc1] | (S)-2-(3-(3-fluorophenyl)-1-methyl-4-(trifluoromethyl)-1H-pyrazolo[3,4-b]pyridin-6-yloxy)-N-(1-phenylethyl)acetamide | 3.28 (D) | 473.1 |
| 1.23 | 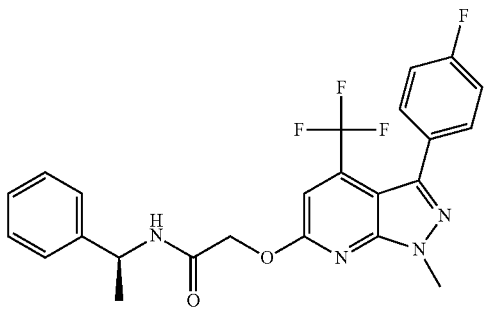 [SMILES: C[C@H](NC(=O)COc1cc(C(F)(F)F)c2c(-c3ccc(F)cc3)nn(C)c2n1)c1ccccc1] | (S)-2-(3-(4-fluorophenyl)-1-methyl-4-(trifluoromethyl)-1H-pyrazolo[3,4-b]pyridin-6-yloxy)-N-(1-phenylethyl)acetamide | 3.25 (D) | 473.1 |
| 1.24 | 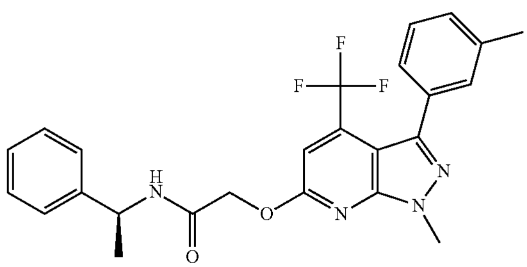 [SMILES: Cc1cccc(-c2nn(C)c3nc(OCC(=O)N[C@@H](C)c4ccccc4)cc(C(F)(F)F)c23)c1] | (S)-2-(1-methyl-3-m-tolyl-4-(trifluoromethyl)-1H-pyrazolo[3,4-b]pyridin-6-yloxy)-N-(1-phenylethyl)acetamide | 0.59 (C) | 469.1 |
| 1.25 | 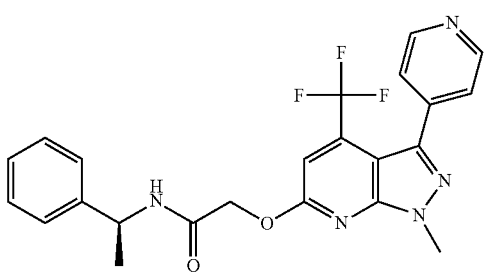 [SMILES: C[C@H](NC(=O)COc1cc(C(F)(F)F)c2c(-c3ccncc3)nn(C)c2n1)c1ccccc1] | (S)-2-(1-methyl-3-(pyridin-4-yl)-4-(trifluoromethyl)-1H-pyrazolo[3,4-b]pyridin-6-yloxy)-N-(1-phenylethyl)acetamide | 1.24 (C) | 456.1 |
| 1.26 | 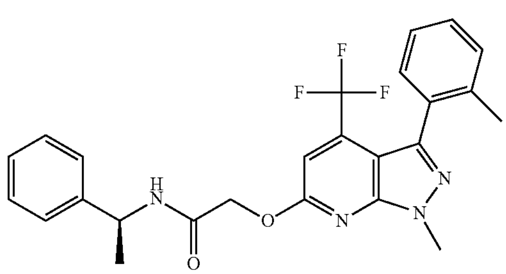 [SMILES: Cc1ccccc1-c1nn(C)c2nc(OCC(=O)N[C@@H](C)c3ccccc3)cc(C(F)(F)F)c12] | (S)-2-(1-methyl-3-o-tolyl-4-(trifluoromethyl)-1H-pyrazolo[3,4-b]pyridin-6-yloxy)-N-(1-phenylethyl)acetamide | 3.34 (D) | 469.1 |

TABLE 1-continued

Compounds Number 1.7 to 1.77:

| Number | Structure | IUPAC Name | LCMS Rt [min] (method) | [M + H]+ |
|---|---|---|---|---|
| 1.27 | 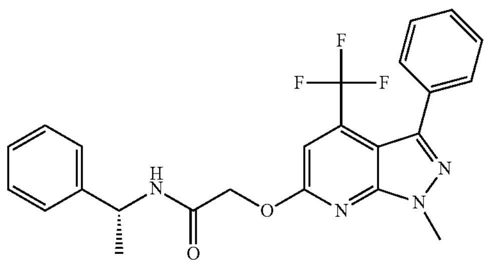 | (R)-2-(1-methyl-3-phenyl-4-(trifluoromethyl)-1H-pyrazolo[3,4-b]pyridin-6-yloxy)-N-(1-phenylethyl)acetamide | 3.19 (D) | 455.1 |
| 1.28 | 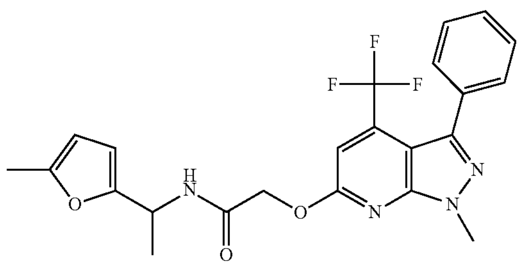 [SMILES: Cc1ccc(C(C)NC(=O)COc2cc(C(F)(F)F)c3c(-c4ccccc4)nn(C)c3n2)o1] | 2-(1-methyl-3-phenyl-4-(trifluoromethyl)-1H-pyrazolo[3,4-b]pyridin-6-yloxy)-N-(1-(5-methylfuran-2-yl)ethyl)acetamide | 3.21 (D) | 459.1 |
| 1.29 | 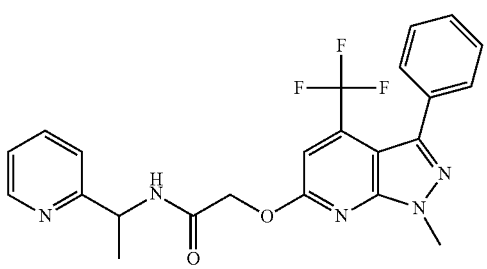 [SMILES: CC(NC(=O)COc1cc(C(F)(F)F)c2c(-c3ccccc3)nn(C)c2n1)c1ccccn1] | 2-(1-methyl-3-phenyl-4-(trifluoromethyl)-1H-pyrazolo[3,4-b]pyridin-6-yloxy)-N-(1-(pyridin-2-yl)ethyl)acetamide | 1.65 (D) | 456.1 |
| 1.30 | 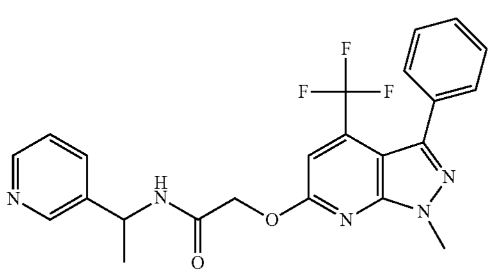 [SMILES: CC(NC(=O)COc1cc(C(F)(F)F)c2c(-c3ccccc3)nn(C)c2n1)c1cccnc1] | 2-(1-methyl-3-phenyl-4-(trifluoromethyl)-1H-pyrazolo[3,4-b]pyridin-6-yloxy)-N-(1-(pyridin-3-yl)ethyl)acetamide | 1.07 (D) | 456.1 |
| 1.31 | 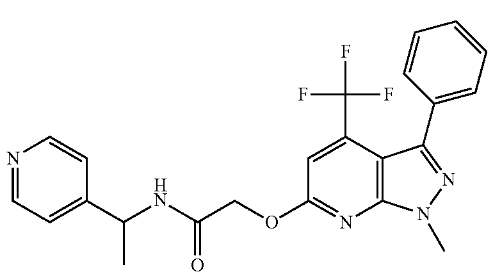 [SMILES: CC(NC(=O)COc1cc(C(F)(F)F)c2c(-c3ccccc3)nn(C)c2n1)c1ccncc1] | 2-(1-methyl-3-phenyl-4-(trifluoromethyl)-1H-pyrazolo[3,4-b]pyridin-6-yloxy)-N-(1-(pyridin-4-yl)ethyl)acetamide | 0.35 (C) | 455.9 |

TABLE 1-continued

Compounds Number 1.7 to 1.77:

| Number | Structure | IUPAC Name | LCMS Rt [min] (method) | [M + H]+ |
|---|---|---|---|---|
| 1.32 | 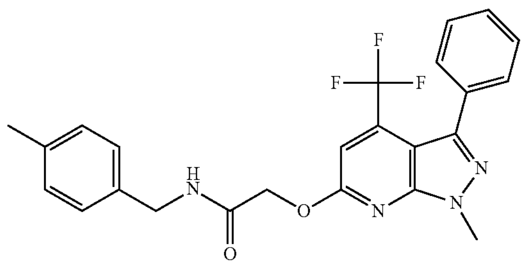 [SMILES: Cc1ccc(CNC(=O)COc2cc(C(F)(F)F)c3c(-c4ccccc4)nn(C)c3n2)cc1] | 2-(1-methyl-3-phenyl-4-(trifluoromethyl)-1H-pyrazolo[3,4-b]pyridin-6-yloxy)-N-(4-methylbenzyl)acetamide | 3.27 (D) | 455.1 |
| 1.33 | 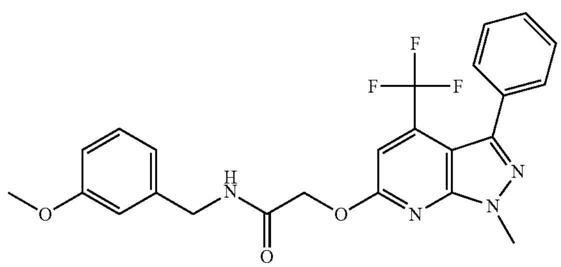 [SMILES: COc1cccc(CNC(=O)COc2cc(C(F)(F)F)c3c(-c4ccccc4)nn(C)c3n2)c1] | N-(3-methoxybenzyl)-2-(1-methyl-3-phenyl-4-(trifluoromethyl)-1H-pyrazolo[3,4-b]pyridin-6-yloxy)acetamide | 2.83 (D) | 471.1 |
| 1.34 | 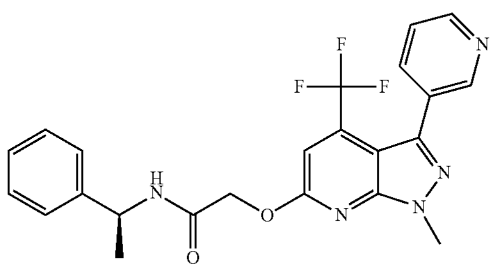 [SMILES: C[C@H](NC(=O)COc1cc(C(F)(F)F)c2c(-c3cccnc3)nn(C)c2n1)c1ccccc1] | (S)-2-(1-methyl-3-(pyridin-3-yl)-4-(trifluoromethyl)-1H-pyrazolo[3,4-b]pyridin-6-yloxy)-N-(1-phenylethyl)acetamide | 1.74 (A) | 456.1 |
| 1.35 | 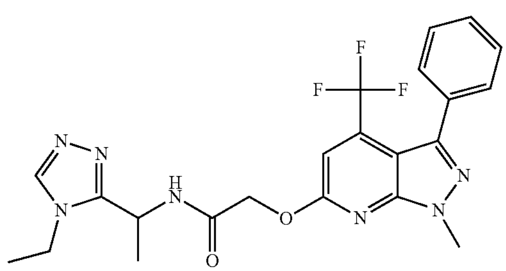 [SMILES: CCn1cnnc1C(C)NC(=O)COc1cc(C(F)(F)F)c2c(-c3ccccc3)nn(C)c2n1] | N-(1-(4-ethyl-4H-1,2,4-triazol-3-yl)ethyl)-2-(1-methyl-3-phenyl-4-(trifluoromethyl)-1H-pyrazolo[3,4-b]pyridin-6-yloxy)acetamide | 0.38 (C) | 474.0 |
| 1.36 | 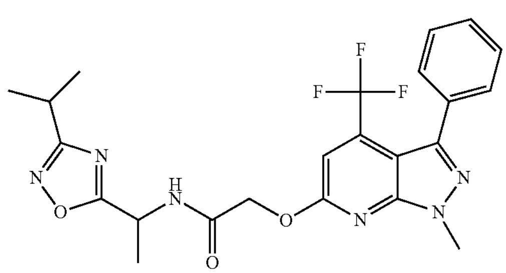 [SMILES: CC(C)c1noc(C(C)NC(=O)COc2cc(C(F)(F)F)c3c(-c4ccccc4)nn(C)c3n2)n1] | N-(1-(3-isopropyl-1,2,4-oxadiazol-5-yl)ethyl)-2-(1-methyl-3-phenyl-4-(trifluoromethyl)-1H-pyrazolo[3,4-b]pyridin-6-yloxy)acetamide | 0.5 (C) | 489.0 |

TABLE 1-continued

Compounds Number 1.7 to 1.77:

| Number | Structure | IUPAC Name | LCMS Rt [min] (method) | [M + H]+ |
|---|---|---|---|---|
| 1.37 | 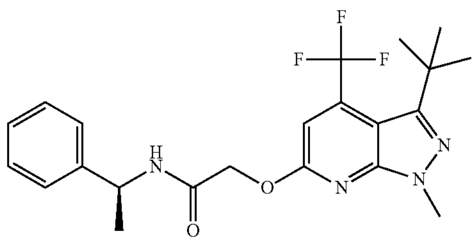 [SMILES: C[C@H](NC(=O)COc1cc(C(F)(F)F)c2c(C(C)(C)C)nn(C)c2n1)c1ccccc1] | (S)-2-(3-tert-butyl-1-methyl-4-(trifluoromethyl)-1H-pyrazolo[3,4-b]pyridin-6-yloxy)-N-(1-phenylethyl)acetamide | 2.13 (E) | 435.1 |
| 1.38 | 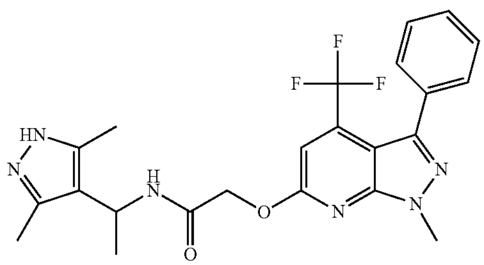 [SMILES: Cc1n[nH]c(C)c1C(C)NC(=O)COc1cc(C(F)(F)F)c2c(-c3ccccc3)nn(C)c2n1] | N-(1-(3,5-dimethyl-1H-pyrazol-4-yl)ethyl)-2-(1-methyl-3-phenyl-4-(trifluoromethyl)-1H-pyrazolo[3,4-b]pyridin-6-yloxy)acetamide | 0.38 (C) | 473.1 |
| 1.39 | 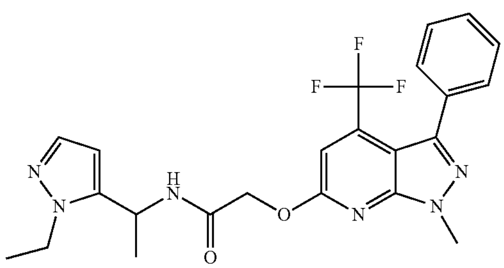 [SMILES: CCn1nccc1C(C)NC(=O)COc1cc(C(F)(F)F)c2c(-c3ccccc3)nn(C)c2n1] | N-(1-(1-ethyl-1H-pyrazol-5-yl)ethyl)-2-(1-methyl-3-phenyl-4-(trifluoromethyl)-1H-pyrazolo[3,4-b]pyridin-6-yloxy)acetamide | 1.87 (E) | 473.1 |
| 1.40 | 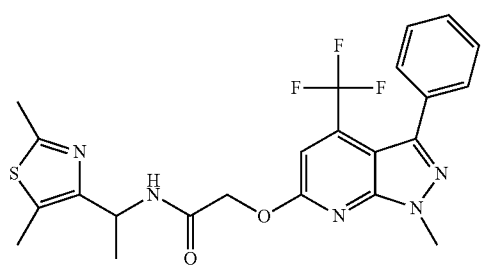 [SMILES: Cc1nc(C(C)NC(=O)COc2cc(C(F)(F)F)c3c(-c4ccccc4)nn(C)c3n2)c(C)s1] | N-(1-(2,5-dimethylthiazol-4-yl)ethyl)-2-(1-methyl-3-phenyl-4-(trifluoromethyl)-1H-pyrazolo[3,4-b]pyridin-6-yloxy)acetamide | 0.5 (C) | 490.0 |
| 1.41 | 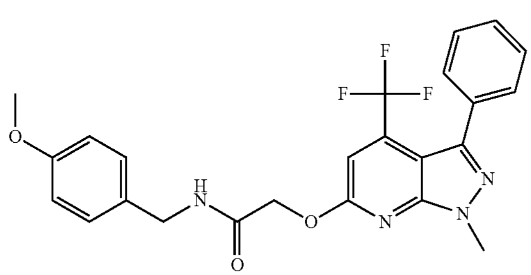 [SMILES: COc1ccc(CNC(=O)COc2cc(C(F)(F)F)c3c(-c4ccccc4)nn(C)c3n2)cc1] | N-(4-methoxybenzyl)-2-(1-methyl-3-phenyl-4-(trifluoromethyl)-1H-pyrazolo[3,4-b]pyridin-6-yloxy)acetamide | 0.48 (C) | 471.1 |

TABLE 1-continued

Compounds Number 1.7 to 1.77:

| Number | Structure | IUPAC Name | LCMS Rt [min] (method) | [M + H]+ |
|---|---|---|---|---|
| 1.42 | 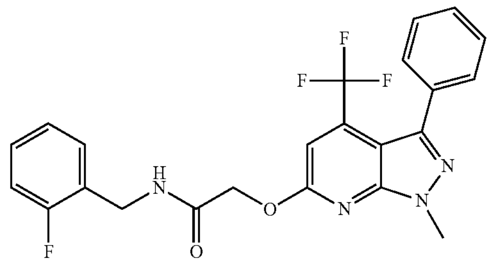 [SMILES: Cn1nc(-c2ccccc2)c2c(C(F)(F)F)cc(OCC(=O)NCc3ccccc3F)nc21] | N-(2-fluorobenzyl)-2-(1-methyl-3-phenyl-4-(trifluoromethyl)-1H-pyrazolo[3,4-b]pyridin-6-yloxy)acetamide | 1.97 (E) | 459.0 |
| 1.43 | 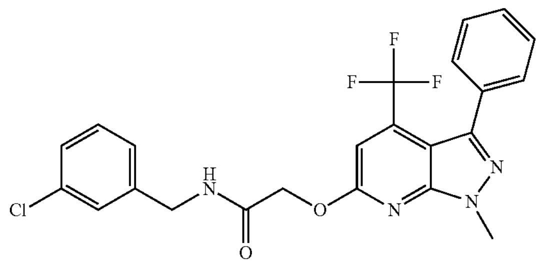 [SMILES: Cn1nc(-c2ccccc2)c2c(C(F)(F)F)cc(OCC(=O)NCc3cccc(Cl)c3)nc21] | N-(3-chlorobenzyl)-2-(1-methyl-3-phenyl-4-(trifluoromethyl)-1H-pyrazolo[3,4-b]pyridin-6-yloxy)acetamide | 0.53 (C) | 474.9 |
| 1.44 | 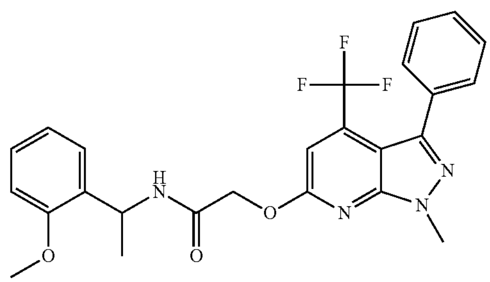 [SMILES: COc1ccccc1C(C)NC(=O)COc1cc(C(F)(F)F)c2c(-c3ccccc3)nn(C)c2n1] | N-(1-(2-methoxyphenyl)ethyl)-2-(1-methyl-3-phenyl-4-(trifluoromethyl)-1H-pyrazolo[3,4-b]pyridin-6-yloxy)acetamide | 0.55 (C) | 485.0 |
| 1.45 | 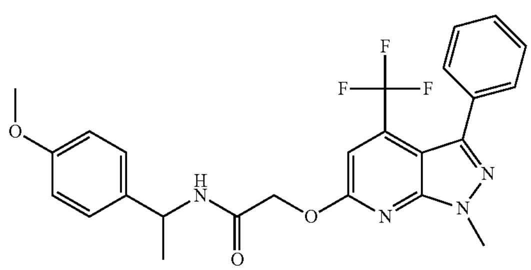 [SMILES: COc1ccc(C(C)NC(=O)COc2cc(C(F)(F)F)c3c(-c4ccccc4)nn(C)c3n2)cc1] | N-(1-(4-methoxyphenyl)ethyl)-2-(1-methyl-3-phenyl-4-(trifluoromethyl)-1H-pyrazolo[3,4-b]pyridin-6-yloxy)acetamide | 1.98 (E) | 485.1 |
| 1.46 | 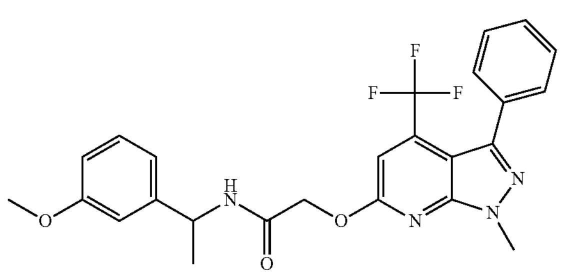 [SMILES: COc1cccc(C(C)NC(=O)COc2cc(C(F)(F)F)c3c(-c4ccccc4)nn(C)c3n2)c1] | N-(1-(3-methoxyphenyl)ethyl)-2-(1-methyl-3-phenyl-4-(trifluoromethyl)-1H-pyrazolo[3,4-b]pyridin-6-yloxy)acetamide | 1.98 (E) | 485.0 |

TABLE 1-continued

Compounds Number 1.7 to 1.77:

| Number | Structure | IUPAC Name | LCMS Rt [min] (method) | [M + H]+ |
|---|---|---|---|---|
| 1.47 | 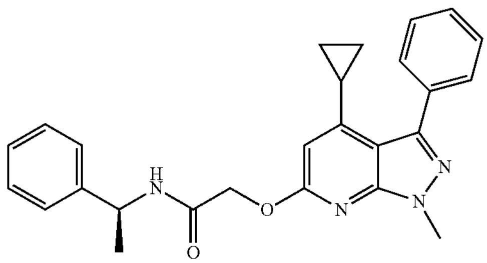 [SMILES: C[C@H](NC(=O)COc1cc(C2CC2)c2c(-c3ccccc3)nn(C)c2n1)c1ccccc1] | (S)-2-(4-cyclopropyl-1-methyl-3-phenyl-1H-pyrazolo[3,4-b]pyridin-6-yloxy)-N-(1-phenylethyl)acetamide | 3.11 (D) | 427.1 |
| 1.48 | 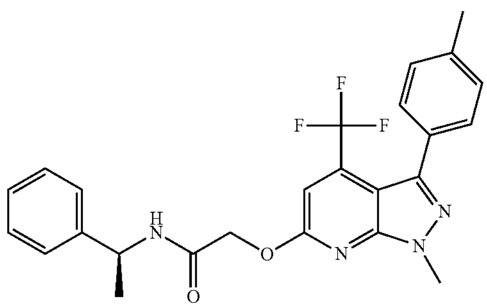 [SMILES: Cc1ccc(-c2nn(C)c3nc(OCC(=O)N[C@@H](C)c4ccccc4)cc(C(F)(F)F)c23)cc1] | (S)-2-(1-methyl-3-p-tolyl-4-(trifluoromethyl)-1H-pyrazolo[3,4-b]pyridin-6-yloxy)-N-(1-phenylethyl)acetamide | 3.47 (D) | 469.1 |
| 1.49 | 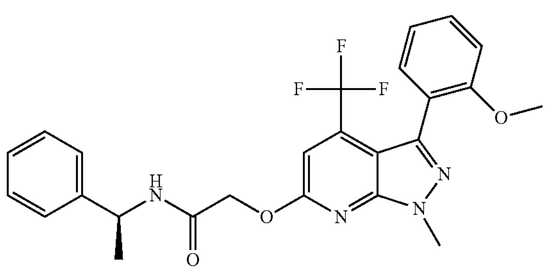 [SMILES: COc1ccccc1-c1nn(C)c2nc(OCC(=O)N[C@@H](C)c3ccccc3)cc(C(F)(F)F)c12] | (S)-2-(3-(2-methoxyphenyl)-1-methyl-4-(trifluoromethyl)-1H-pyrazolo[3,4-b]pyridin-6-yloxy)-N-(1-phenylethyl)acetamide | 0.48 (C) | 485.0 |
| 1.50 | 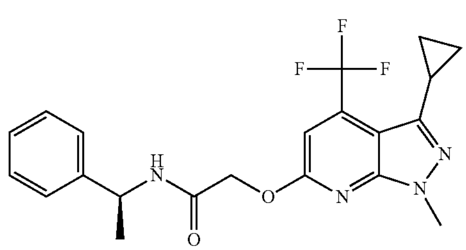 [SMILES: C[C@H](NC(=O)COc1cc(C(F)(F)F)c2c(C3CC3)nn(C)c2n1)c1ccccc1] | (S)-2-(3-cyclopropyl-1-methyl-4-(trifluoromethyl)-1H-pyrazolo[3,4-b]pyridin-6-yloxy)-N-(1-phenylethyl)acetamide | 2.0 (E) | 419.1 |
| 1.51 | 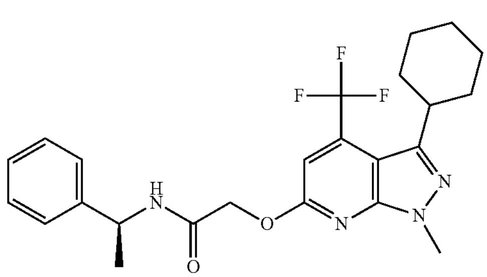 [SMILES: C[C@H](NC(=O)COc1cc(C(F)(F)F)c2c(C3CCCCC3)nn(C)c2n1)c1ccccc1] | (S)-2-(3-cyclohexyl-1-methyl-4-(trifluoromethyl)-1H-pyrazolo[3,4-b]pyridin-6-yloxy)-N-(1-phenylethyl)acetamide | 2.17 (E) | 461.1 |

TABLE 1-continued

Compounds Number 1.7 to 1.77:

| Number | Structure | IUPAC Name | LCMS Rt [min] (method) | [M + H]+ |
|---|---|---|---|---|
| 1.52 | 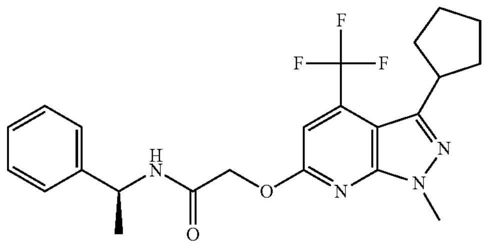 [SMILES: C[C@H](NC(=O)COc1cc(C(F)(F)F)c2c(C3CCCC3)nn(C)c2n1)c1ccccc1] | (S)-2-(3-cyclopentyl-1-methyl-4-(trifluoromethyl)-1H-pyrazolo[3,4-b]pyridin-6-yloxy)-N-(1-phenylethyl)acetamide | 0.78 (C) | 446.8 |
| 1.53 | 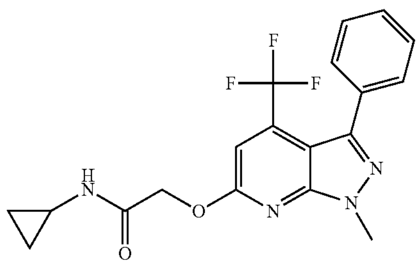 [SMILES: Cn1nc(-c2ccccc2)c2c(C(F)(F)F)cc(OCC(=O)NC3CC3)nc21] | N-cyclopropyl-2-(1-methyl-3-phenyl-4-(trifluoromethyl)-1H-pyrazolo[3,4-b]pyridin-6-yloxy)acetamide | 0.43 (C) | 390.9 |
| 1.54 | 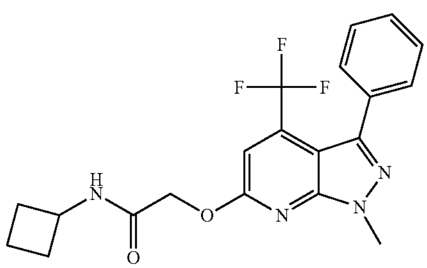 [SMILES: Cn1nc(-c2ccccc2)c2c(C(F)(F)F)cc(OCC(=O)NC3CCC3)nc21] | N-cyclobutyl-2-(1-methyl-3-phenyl-4-(trifluoromethyl)-1H-pyrazolo[3,4-b]pyridin-6-yloxy)acetamide | 1.72 (C) | 405.1 |
| 1.55 | 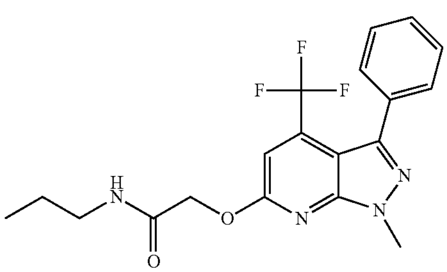 [SMILES: CCCNC(=O)COc1cc(C(F)(F)F)c2c(-c3ccccc3)nn(C)c2n1] | 2-(1-methyl-3-phenyl-4-(trifluoromethyl)-1H-pyrazolo[3,4-b]pyridin-6-yloxy)-N-propylacetamide | 1.68 (A) | 393.1 |
| 1.56 | 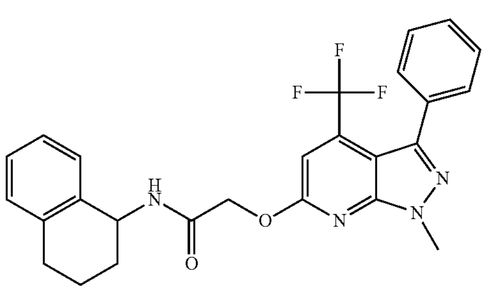 [SMILES: Cn1nc(-c2ccccc2)c2c(C(F)(F)F)cc(OCC(=O)NC3CCCc4ccccc43)nc21] | 2-(1-methyl-3-phenyl-4-(trifluoromethyl)-1H-pyrazolo[3,4-b]pyridin-6-yloxy)-N-(1,2,3,4-tetrahydronaphthalen-1-yl)acetamide | 0.63 (C) | 480.8 |

TABLE 1-continued

Compounds Number 1.7 to 1.77:

| Number | Structure | IUPAC Name | LCMS Rt [min] (method) | [M + H]+ |
|---|---|---|---|---|
| 1.57 | 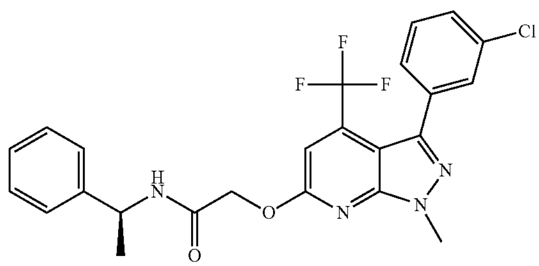 [SMILES: C[C@H](NC(=O)COc1cc(C(F)(F)F)c2c(-c3cccc(Cl)c3)nn(C)c2n1)c1ccccc1] | (S)-2-(3-(3-chlorophenyl)-1-methyl-4-(trifluoromethyl)-1H-pyrazolo[3,4-b]pyridin-6-yloxy)-N-(1-phenylethyl)acetamide | 1.89 (A) | 498.0 |
| 1.58 | 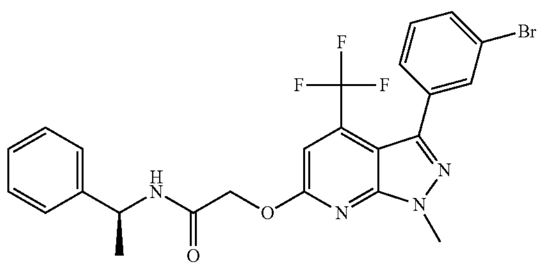 [SMILES: C[C@H](NC(=O)COc1cc(C(F)(F)F)c2c(-c3cccc(Br)c3)nn(C)c2n1)c1ccccc1] | (S)-2-(3-(3-bromophenyl)-1-methyl-4-(trifluoromethyl)-1H-pyrazolo[3,4-b]pyridin-6-yloxy)-N-(1-phenylethyl)acetamide | 1.91 (A) | 533.0 |
| 1.59 | 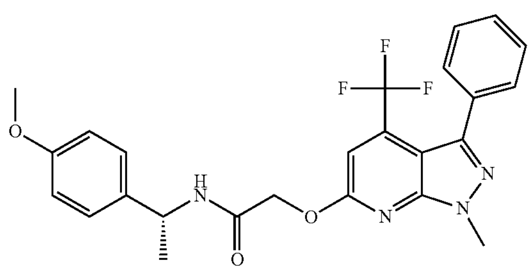 | (R)-N-(1-(4-methoxyphenyl)ethyl)-2-(1-methyl-3-phenyl-4-(trifluoromethyl)-1H-pyrazolo[3,4-b]pyridin-6-yloxy)acetamide | 0.5 (C) | 485.2 |
| 1.60 | 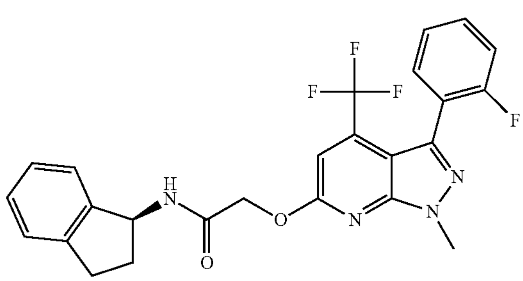 [SMILES: Cn1nc(-c2ccccc2F)c2c(C(F)(F)F)cc(OCC(=O)N[C@H]3CCc4ccccc43)nc21] | (S)-N-(2,3-dihydro-1H-inden-1-yl)-2-(3-(2-fluorophenyl)-1-methyl-4-(trifluoromethyl)-1H-pyrazolo[3,4-b]pyridin-6-yloxy)acetamide | 0.56 (C) | 485.3 |
| 1.61 | 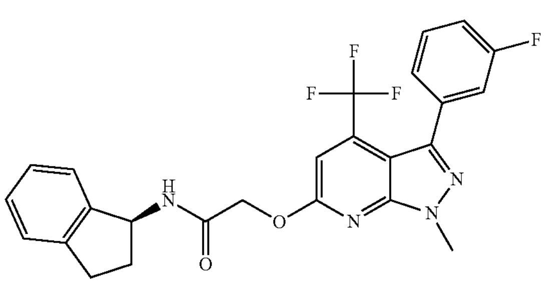 [SMILES: Cn1nc(-c2cccc(F)c2)c2c(C(F)(F)F)cc(OCC(=O)N[C@H]3CCc4ccccc43)nc21] | (S)-N-(2,3-dihydro-1H-inden-1-yl)-2-(3-(3-fluorophenyl)-1-methyl-4-(trifluoromethyl)-1H-pyrazolo[3,4-b]pyridin-6-yloxy)acetamide | 0.41 (C) | 485.0 |

TABLE 1-continued

Compounds Number 1.7 to 1.77:

| Number | Structure | IUPAC Name | LCMS Rt [min] (method) | [M + H]+ |
|---|---|---|---|---|
| 1.62 | 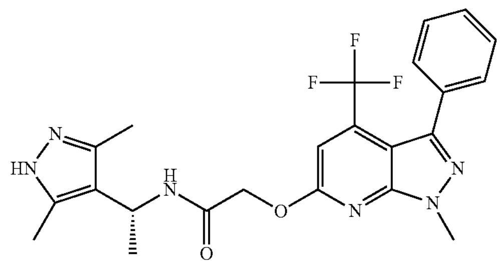 [SMILES: Cc1n[nH]c(C)c1[C@@H](C)NC(=O)COc1cc(C(F)(F)F)c2c(-c3ccccc3)nn(C)c2n1] | (R)-N-(1-(3,5-dimethyl-1H-pyrazol-4-yl)ethyl)-2-(1-methyl-3-phenyl-4-(trifluoromethyl)-1H-pyrazolo[3,4-b]pyridin-6-yloxy)acetamide | 1.38 (A) | 473.1 |
| 1.63 | 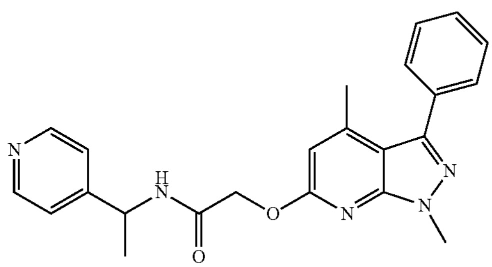 [SMILES: Cc1cc(OCC(=O)NC(C)c2ccncc2)nc2c1c(-c1ccccc1)nn2C] | 2-(1,4-dimethyl-3-phenyl-1H-pyrazolo[3,4-b]pyridin-6-yloxy)-N-(1-(pyridin-4-yl)ethyl)acetamide | 1.51 (F) | 402.4 |
| 1.64 | 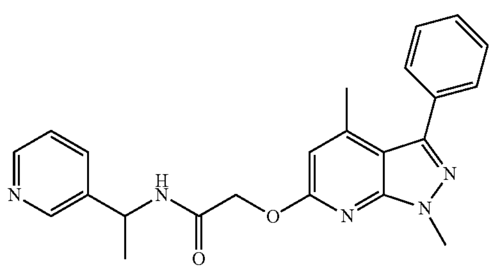 [SMILES: Cc1cc(OCC(=O)NC(C)c2cccnc2)nc2c1c(-c1ccccc1)nn2C] | 2-(1,4-dimethyl-3-phenyl-1H-pyrazolo[3,4-b]pyridin-6-yloxy)-N-(1-(pyridin-3-yl)ethyl)acetamide | 1.47 (F) | 402.4 |
| 1.65 | 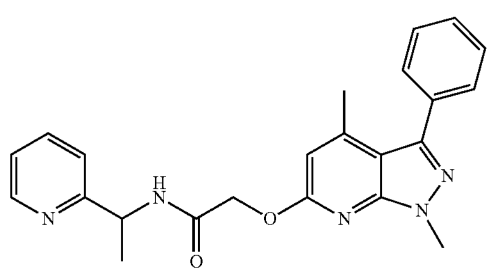 [SMILES: Cc1cc(OCC(=O)NC(C)c2ccccn2)nc2c1c(-c1ccccc1)nn2C] | 2-(1,4-dimethyl-3-phenyl-1H-pyrazolo[3,4-b]pyridin-6-yloxy)-N-(1-(pyridin-2-yl)ethyl)acetamide | 1.51 (F) | 402.5 |
| 1.66 | 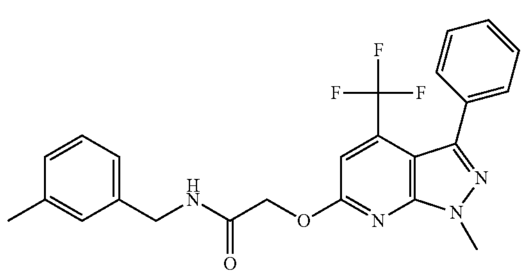 [SMILES: Cc1cccc(CNC(=O)COc2cc(C(F)(F)F)c3c(-c4ccccc4)nn(C)c3n2)c1] | 2-(1-methyl-3-phenyl-4-(trifluoromethyl)-1H-pyrazolo[3,4-b]pyridin-6-yloxy)-N-(3-methyl benzyl)acetamide | 3.27 (D) | 455.1 |

TABLE 1-continued

Compounds Number 1.7 to 1.77:

| Number | Structure | IUPAC Name | LCMS Rt [min] (method) | [M + H]+ |
|---|---|---|---|---|
| 1.67 | 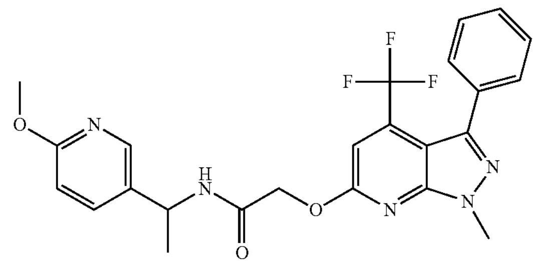 [SMILES: COc1ccc(C(C)NC(=O)COc2cc(C(F)(F)F)c3c(-c4ccccc4)nn(C)c3n2)cn1] | N-(1-(6-methoxypyridin-3-yl)ethyl)-2-(1-methyl-3-phenyl-4-(trifluoromethyl)-1H-pyrazolo[3,4-b]pyridin-6-yloxy)acetamide | 1.67 (A) | 486.1 |
| 1.68 | 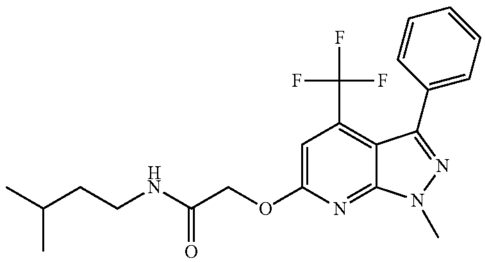 [SMILES: CC(C)CCNC(=O)COc1cc(C(F)(F)F)c2c(-c3ccccc3)nn(C)c2n1] | N-isopentyl-2-(1-methyl-3-phenyl-4-(trifluoromethyl)-1H-pyrazolo[3,4-b]pyridin-6-yloxy)acetamide | 0.56 (C) | 421.1 |
| 1.69 | 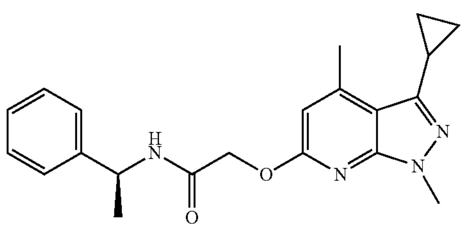 [SMILES: Cc1cc(OCC(=O)N[C@@H](C)c2ccccc2)nc2c1c(C1CC1)nn2C] | (S)-2-(3-cyclopropyl-1,4-dimethyl-1H-pyrazolo[3,4-b]pyridin-6-yloxy)-N-(1-phenylethyl)acetamide | 1.72 (C) | 364.9 |
| 1.70 | 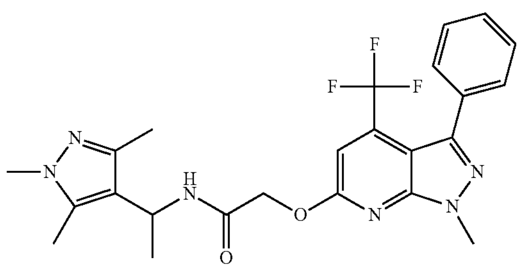 [SMILES: Cc1nn(C)c(C)c1C(C)NC(=O)COc1cc(C(F)(F)F)c2c(-c3ccccc3)nn(C)c2n1] | 2-(1-methyl-3-phenyl-4-(trifluoromethyl)-1H-pyrazolo[3,4-b]pyridin-6-yloxy)-N-(1-(1,3,5-trimethyl-1H-pyrazol-4-yl)ethyl)acetamide | 1.64 (C) | 487.1 |
| 1.71 | 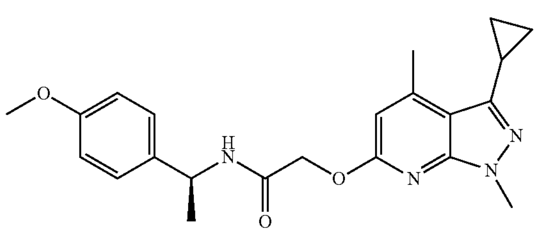 [SMILES: COc1ccc([C@H](C)NC(=O)COc2cc(C)c3c(C4CC4)nn(C)c3n2)cc1] | (S)-2-(3-cyclopropyl-1,4-dimethyl-1H-pyrazolo[3,4-b]pyridin-6-yloxy)-N-(1-(4-methoxyphenyl)ethyl)acetamide | 1.69 (C) | 395.0 |
| 1.72 | 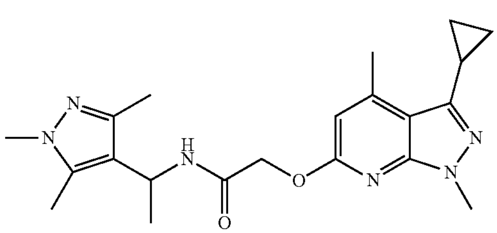 [SMILES: Cc1nn(C)c(C)c1C(C)NC(=O)COc1cc(C)c2c(C3CC3)nn(C)c2n1] | 2-(3-cyclopropyl-1,4-dimethyl-1H-pyrazolo[3,4-b]pyridin-6-yloxy)-N-(1-(1,3,5-trimethyl-1H-pyrazol-4-yl)ethyl)acetamide | 0.92 (C) | 397.2 |

TABLE 1-continued

Compounds Number 1.7 to 1.77:

| Number | Structure | IUPAC Name | LCMS Rt [min] (method) | [M + H]+ |
|---|---|---|---|---|
| 1.73 | 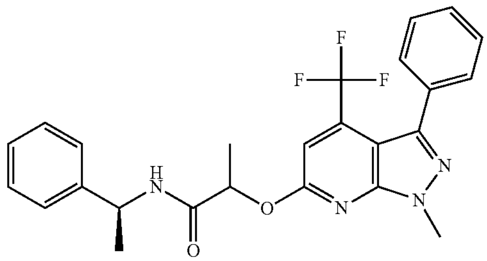 [SMILES: CC(Oc1cc(C(F)(F)F)c2c(-c3ccccc3)nn(C)c2n1)C(=O)N[C@@H](C)c1ccccc1] | 2-(1-methyl-3-phenyl-4-(trifluoromethyl)-1H-pyrazolo[3,4-b]pyridin-6-yloxy)-N-((S)-1-phenylethyl)propanamide (diastereoisomer 1) | 0.53 (C) | 469.0 |
| 1.74 | 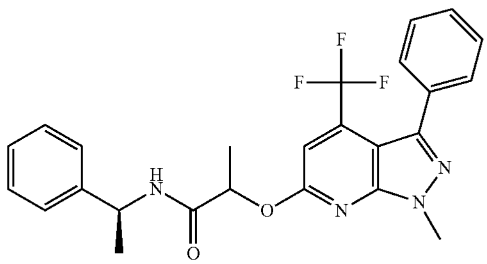 [SMILES: CC(Oc1cc(C(F)(F)F)c2c(-c3ccccc3)nn(C)c2n1)C(=O)N[C@@H](C)c1ccccc1] | 2-(1-methyl-3-phenyl-4-(trifluoromethyl)-1H-pyrazolo[3,4-b]pyridin-6-yloxy)-N-((S)-1-phenylethyl)propanamide (diastereoisomer 2) | 0.59 (C) | 469.2 |
| 1.75 | 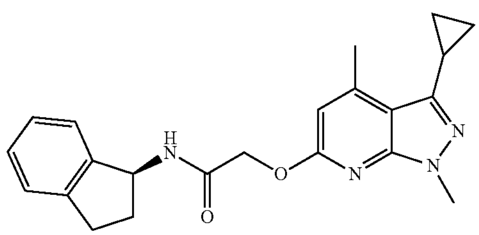 [SMILES: Cc1cc(OCC(=O)N[C@H]2CCc3ccccc32)nc2c1c(C1CC1)nn2C] | (S)-2-(3-cyclopropyl-1,4-dimethyl-1H-pyrazolo[3,4-b]pyridin-6-yloxy)-N-(2,3-dihydro-1H-inden-1-yl)acetamide | 1.66 (A) | 377.1 |
| 1.76 | 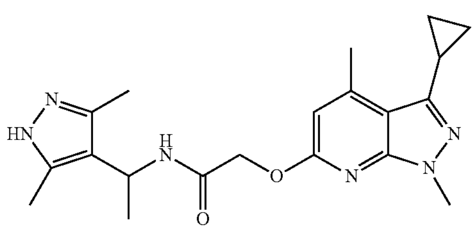 [SMILES: Cc1n[nH]c(C)c1C(C)NC(=O)COc1cc(C)c2c(C3CC3)nn(C)c2n1] | 2-(3-cyclopropyl-1,4-dimethyl-1H-pyrazolo[3,4-b]pyridin-6-yloxy)-N-(1-(3,5-dimethyl-1H-pyrazol-4-yl)ethyl)acetamide | 0.33 (A) | 383.2 |
| 1.77 | 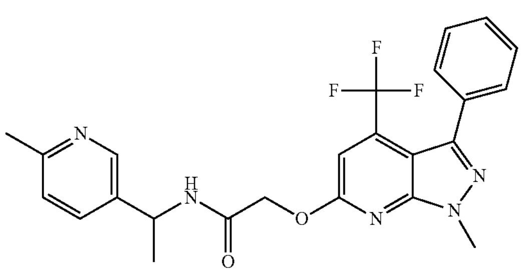 [SMILES: Cc1ccc(C(C)NC(=O)COc2cc(C(F)(F)F)c3c(-c4ccccc4)nn(C)c3n2)cn1] | 2-(1-methyl-3-phenyl-4-(trifluoromethyl)-1H-pyrazolo[3,4-b]pyridin-6-yloxy)-N-(1-(6-methylpyridin-3-yl)ethyl)acetamide | 0.61 (A) | 470.1 |

METHOD B

Example 2.1

(S)-2-(1-methyl-3-phenyl-1H-pyrazolo[3,4-b]pyridin-6-yloxy)-N-(1-phenylethyl)acetamide

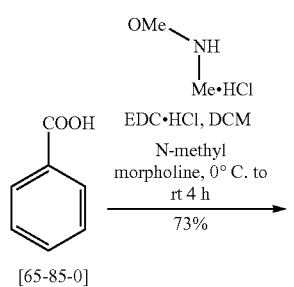

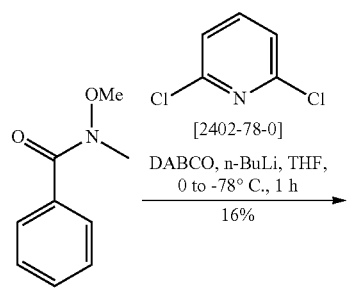

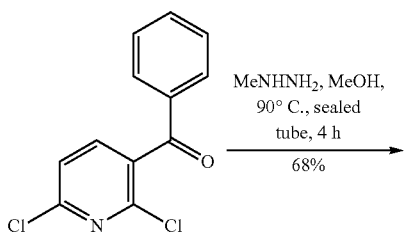

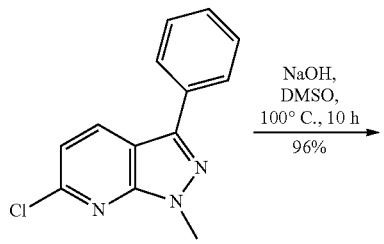

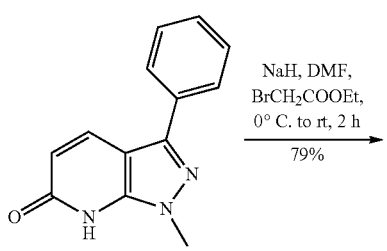

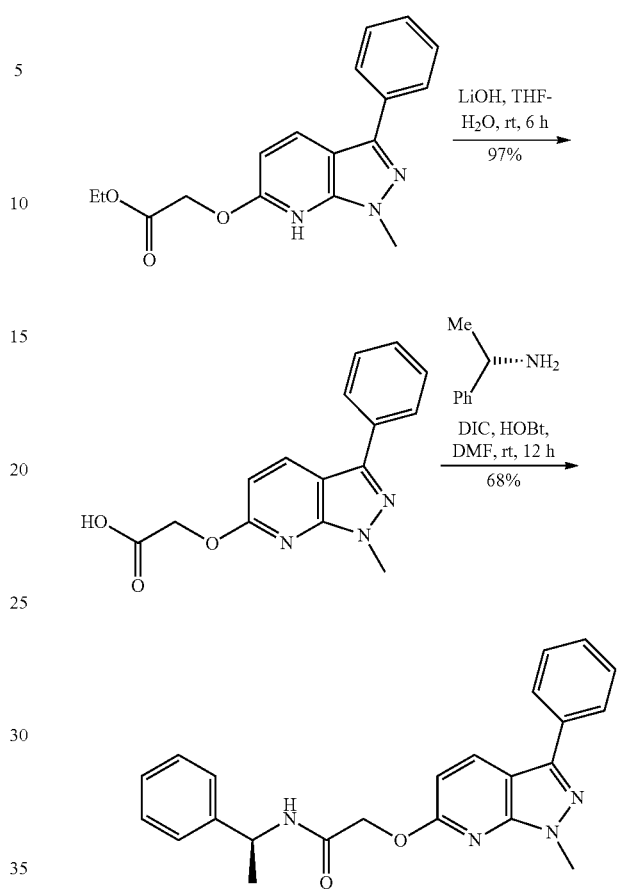

a) N-methoxy-N-methylbenzamide

N,O-dimethyl hydroxyl amine hydrochloride (4.393 g, 45.037 mmol) was added to a stirred solution of benzoic acid (5.0 g, 40.943), EDC.HCl (9.418 g, 49.132) and N-methyl morpholine (4.141 g, 40.943 mmol) in dichloromethane (100 mL). The reaction mixture was stirred at rt for 4 h. After completion of the reaction, the reaction mixture was concentrated. Diethyl ether was added and the mixture was extracted with water and brine. The organic layer was dried over $Na_2SO_4$ and filtrated. Concentration of the organic layer furnished the title compound as a colorless liquid (4.933 g, 73%). [$^1$H-NMR (CDCl$_3$, 300 MHz) δ 7.72-7.64 (m, 2H), 7.52-7.36 (m, 3H), 3.58 (s, 3H), 3.38 (s, 3H); HPLC Rt$_A$=6.281 min. (98%); LCMS Rt$_A$=0.38 min; [M+H]$^+$=166.1]

b) (2,6-dichloropyridin-3-yl)(phenyl)methanone

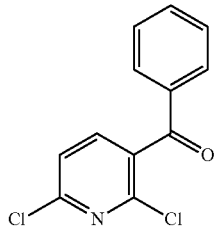 [SMILES: O=C(c1ccccc1)c1ccc(Cl)nc1Cl]

n-BuLi (1.6 M in hexane, 13.94 mL, 22.298 mmol) was added dropwise to a cooled (−78° C.) solution of 1,4-diazabicyclo[2.2.2]octane (2.501 g, 22.298 mmol) in dry THF (40 mL) and stirred for 1 h. 2,6-Dichloropyridine (3.684 g, 20.272 mmol) was added portionwise to the reaction mixture while the color of the reaction mixture turned to pale pink. Stirring was continued for 1 h at −78° C. N-methoxy-N-methylbenzamide (3.0 g, 22.298 mmol) in dry THF (10 mL) was added to the reaction mixture dropwise (color changes to orange then slowly to yellow) and stirring was continued for 1 h. After completion of the reaction, the reaction mixture was concentrated and diluted with diethyl ether. The organic layer was washed with water, followed by brine and dried over Na$_2$SO$_4$. Concentration of the organic layer furnished the crude product as a pale yellow oil. The crude compound was purified by column chromatography (3% EtOAc in hexane) to yield the title compound as a colorless solid (0.736 g, 16.1%). [$^1$H-NMR (CDCl$_3$, 300 MHz) δ 7.84-7.76 (m, 2H), 7.74-7.63 (m, 2H), 7.58-7.48 (m, 2H), 7.422 (d, 1H); HPLC$_A$ Rt=4.851 min. (94%); LCMS Rt$_A$=0.471 min; [M+H]$^+$=251.9]

c) 6-chloro-1-methyl-3-phenyl-1H-pyrazolo[3,4-b]pyridine

A mixture of (2,6-dichloropyridin-3-yl)(phenyl)methanone (0.7 g, 2.776 mmol) and methyl hydrazine (0.256 g, 5.553) in methanol (7 mL) was heated at 90° C. in a sealed tube for 4 h. The reaction mixture was concentrated under reduced pressure and diethyl ether was added. The organic layer was washed with an excess of water, followed by brine and dried over Na$_2$SO$_4$. Concentration of the organic layer furnished the crude product as a pale yellow solid. The product was purified by column chromatography (5% EtOAc in hexane) to yield the title compound (0.455 g, 68%) as a white solid. [$^1$H-NMR (CDCl$_3$, 300 MHz) δ 8.26 (d, 2H), 7.91 (m, 2H), 7.56-7.39 (m, 3H), 7.18 (d, 1H), 4.18 (s, 3H); HPLC Rt$_A$=5.880 min. (97%); LCMS Rt$_C$=1.990 min; [M+H]$^+$=244.0; Mp=94-96° C.]

d) 1-methyl-3-phenyl-1H-pyrazolo[3,4-b]pyridin-6(7H)-one

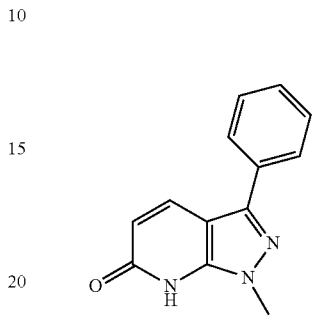

A mixture of aqueous NaOH (0.64 g, 16.00 mmol in 2.0 mL H$_2$O) and 6-chloro-1-methyl-3-phenyl-1H-pyrazolo[3,4-b]pyridine (0.39 g, 1.6 mmol) in DMSO (2.0 mL) was heated at 100° C. for 10 h. The reaction mixture was cooled to rt and neutralized with diluted HCl. A white solid was obtained. The solid was collected by filtration, washed with diethyl ether and dried under vacuum to yield the title compound as white solid (0.345 g, 96%). [$^1$H-NMR (DMSO-d6, 300 MHz) δ 8.27 (d, 1H), 7.92 (m, 2H), 7.55-7.35 (m, 3H), 6.46 (d, 1H), 3.9 (s, 3H); HPLC Rt$_A$=6.802 min (99.7%); LCMS Rt$_A$=0.360 min; [M+H]$^+$=226.0]

e) Ethyl 2-(1-methyl-3-phenyl-1H-pyrazolo[3,4-b]pyridin-6-yloxy)acetate

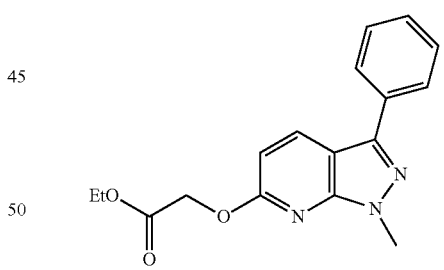

NaH (0.115 g, 2.886 mmol) was added to an ice cold solution of 1-methyl-3-phenyl-1H-pyrazolo[3,4-b]pyridin-6(7H)-one (0.325 g, 1.443 mmol) in DMF (5.0 mL) and stirred at ambient temperature for 30 min. Ethyl bromoacetate (0.482 g, 2.886 mmol) was added to the reaction mixture dropwise and stirring was continued for 2 h. After completion of the reaction, the excess of NaH was quenched by the addition of ice cold water. Diethyl ether was added and the mixture was extracted with water and brine. The organic layer was dried over Na$_2$SO$_4$ and filtered. Concentration of the organic layer furnished the title compound as a white solid (0.353 g, 79%). [$^1$H-NMR (CDCl$_3$, 300 MHz) δ 8.2 (d, 1H), 7.94-7.87 (m, 2H), 7.54-7.36 (m, 3H), 6.79 (d, 1H), 5.0 (s, 2H), 4.29 (q, 2H), 4.05 (s, 3H), 1.30 (t, 3H); HPLC Rt$_A$=5.555 min (95%); LCMS Rt$_C$=1.967 min; [M+H]$^+$=312.1]

f) 2-(1-methyl-3-phenyl-1H-pyrazolo[3,4-b]pyridin-6-yloxy)acetic acid

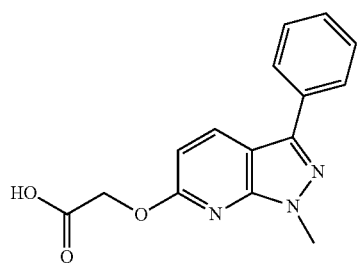 [SMILES: Cn1nc(-c2ccccc2)c2ccc(OCC(=O)O)nc21]

A mixture of Ethyl 2-(1-methyl-3-phenyl-1H-pyrazolo[3,4-b]pyridin-6-yloxy)acetate (0.33 g, 1.059 mmol) and aqueous LiOH (0.446 g, 10.599 mmol in 3.0 mL H$_2$O) in THF (3.0 mL) was stirred at rt for 6 h. The reaction mixture was neutralized with diluted HCl and diluted with diethyl ether. The organic layer was extracted with water and brine and dried over anhydrous Na$_2$SO$_4$. Concentration of the organic layer furnished the crude product as a white solid. The crude product was purified by column chromatography (eluent: 75% EtOAc in hexane) to yield the title compound as a white solid (0.291 g, 97%). [$^1$H-NMR (CDCl$_3$, 300 MHz) δ 8.21 (d, 1H), 7.92-7.84 (m, 2H), 7.52-7.35 (m, 3H), 6.77 (d, 1H), 5.05 (s, 2H), 4.02 (s, 3H); HPLC Rt$_A$=4.315 min (97%); LCMS Rt$_C$=0.389 min; [M+H]$^+$=283.9]

g) (S)-2-(1-methyl-3-phenyl-1H-pyrazolo[3,4-b]pyridin-6-yloxy)-N-(1-phenylethyl)acetamide

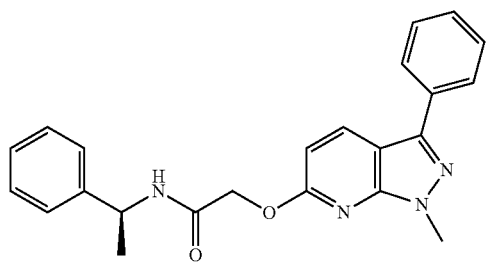 [SMILES: C[C@H](NC(=O)COc1ccc2c(-c3ccccc3)nn(C)c2n1)c1ccccc1]

A solution of 2-(1-methyl-3-phenyl-1H-pyrazolo[3,4-b]pyridin-6-yloxy)acetic acid (0.14 g, 0.494 mmol), DIC (0.094 g, 0.744 mmol) and HOBt (0.087 g mg, 0.644 mmol) in DMF (4.0 ml) was stirred at rt for 15 min. (S)-(−)-α methyl benzyl amine (0.072 g, 0.594 mmol) was added to the reaction mixture at rt and stirring was continued overnight. The reaction mixture was concentrated. Diethyl ether was added and the mixture was washed with water, followed by brine and dried over Na$_2$SO$_4$. Concentration of the organic layer furnished the crude product as an off-white solid. The product was purified by preparative HPLC using acetonitrile/water as mobile phase to yield the title compound as a white solid (0.133 g, 68%). [$^1$H-NMR (CDCl$_3$, 300 MHz) δ 8.22 (d, 1H), 7.96-7.89 (m, 2H), 7.55-7.38 (m, 3H), 7.37-7.21 (m, 5H), 6.73 (d, 1H), 6.61 (d, 1H), 5.35-5.21 (m, 1H), 4.99 (s, 2H), 4.03 (s, 3H), 1.53 (d, 3H); HPLC Rt$_A$=5.273 min (98%) LCMS Rt$_E$=1.921 min; [M+H]$^+$=387.1; Mp=55-56° C.]

METHOD C

Example 3.1

(S)-2-(1-methyl-3-phenyl-4-(trifluoromethyl)-1H-pyrazolo[3,4-b]pyridin-6-ylamino)-N-(1-phenylethyl)acetamide

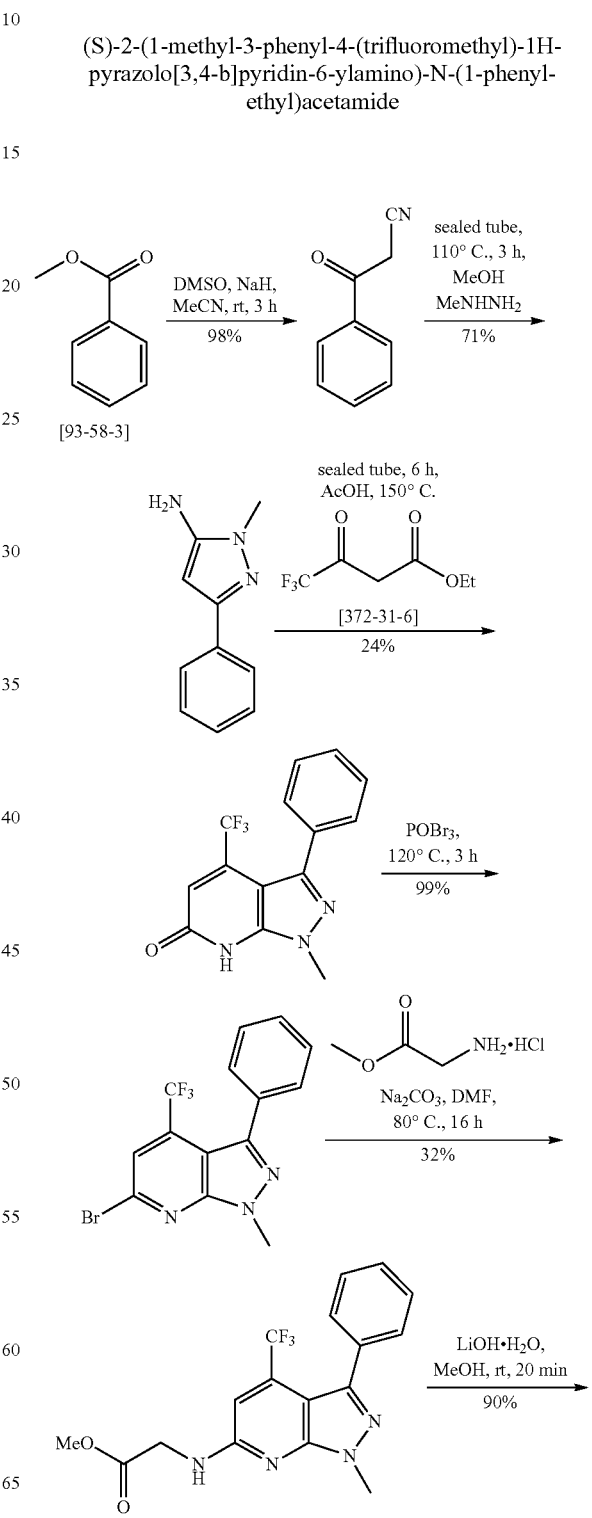

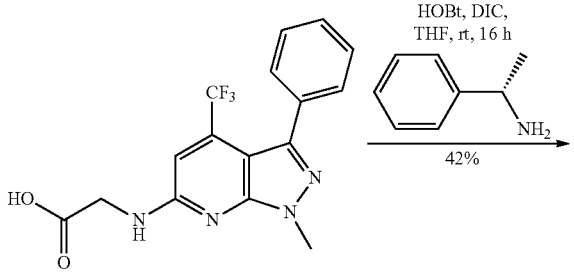

a) 3-oxo-3-phenylpropanenitrile

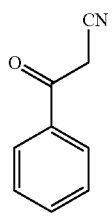

NaH (3.8 g, 95 mmol) was added to an ice cooled solution of acetonitrile (5.6 mL, 1.095 mmol) in DMSO (3.0 mL) and stirred at ambient temperature for 20 min. Methyl benzoate (10.0 g, 73.0 mmol) was added to the reaction mixture and stirring was continued for 2 h. The excess of NaH was quenched by addition of ice-cold water to the reaction mixture. The resulting reaction mixture was treated with diluted HCl (pH ~2) to obtain a white solid which was collected by filtration and dried under vacuum. The solid was triturated with a mixture of hexane and diethyl ether (1:1) to yield a white solid (10.5 g, 98%). [$^1$H-NMR (CDCl$_3$, 300 MHz) δ 7.98-7.88 (m 2H), 7.71-7.45 (m, 3H), 4.12 (s, 2H)]

b) 1-methyl-3-phenyl-1H-pyrazol-5-amine

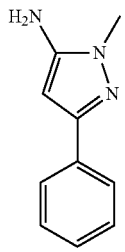

A mixture of benzoyl acetonitrile (2.0 g, 13.778 mmol) and methyl hydrazine (0.698, 15.156 mmol) in methanol (10 mL) was irradiated under microwave conditions at 110° C. for 90 min. The reaction mixture was cooled to rt and poured into rapidly stirred ice cold water. The obtained solid was collected by filtration, dried under vacuum and triturated with a mixture of pentane-hexane (~10 mL) to yield a white solid (1.7 g, 71%). [$^1$H-NMR (CDCl$_3$, 300 MHz) δ 7.82-7.65 (m, 2H), 7.45-7.20 (m, 3H), 5.90 (s, 1H), 3.75 (s, 3H), 3.55 (s, 2H); LCMS Rt$_A$=0.824 min; [M+H]$^+$=174.1]

c) 1-methyl-3-phenyl-4-(trifluoromethyl)-1H-pyrazolo[3,4-b]pyridin-6(7H)-one

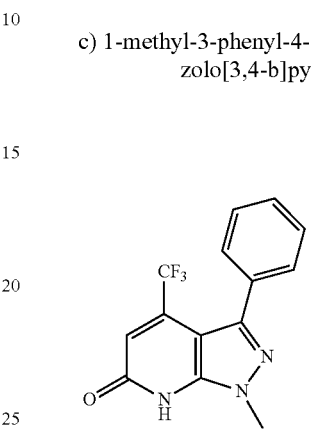

A mixture of 1-methyl-3-phenyl-1H-pyrazol-5-amine (1.7 g, 9.815 mmol) and 4,4,4-Trifluoro-3-oxo-butyric acid ethyl ester (2.168 g, 11.776 mmol) in acetic acid (3.0 mL) was heated at 150° C. for 10 h in a sealed tube under constant stirring. The reaction mixture was cooled to rt and poured into rapidly stirred ice-cold water to obtain the crude product as a solid. The product was collected by filtration and dried under vacuum. The product was purified by flash-chromatography (eluent: 35% EtOAc in hexane) to yield the title compound as a white solid (0.7 g, 24%). [$^1$H-NMR (CDCl$_3$, 300 MHz) δ 13.65 (s, 1H), 7.52-7.37 (m, 5H), 6.78 (s, 1H), 4.20 (s, 3H); LCMS Rt$_C$=1.430 min; [M+H]$^+$=294.0]

d) 6-bromo-1-methyl-3-phenyl-4-(trifluoromethyl)-1H-pyrazolo[3,4-b]pyridine

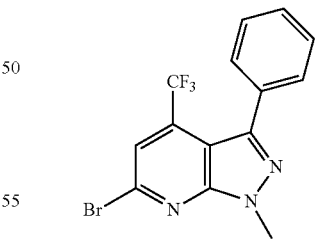

A mixture of 1-methyl-3-phenyl-4-(trifluoromethyl)-1H-pyrazolo[3,4-b]pyridin-6(7H)-one (1.0 g, 3.4 mmol) and POBr$_3$ (0.962 g, 3.4 mmol) was heated at 120° C. for 3 h. The reaction mixture was cooled to it and poured into rapidly stirred ice cold water to obtain a solid product. The product was collected by filtration and dried under vacuum to yield an off-white solid (1.20 g, 99%). [$^1$H-NMR (CDCl$_3$, 300 MHz) δ 7.58 (s, 1H), 7.54-7.41 (m, 5H), 4.22 (s, 3H); LCMS Rt$_A$=1.943 min; [M+H]$^+$=355.9]

e) methyl 2-(1-methyl-3-phenyl-4-(trifluoromethyl)-1H-pyrazolo[3,4-b]pyridin-6-ylamino)acetate

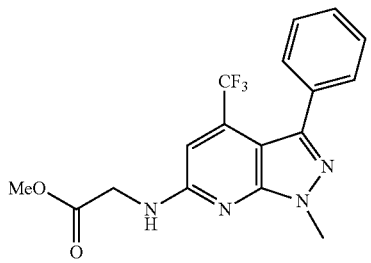 [SMILES: COC(=O)CNc1cc(C(F)(F)F)c2c(-c3ccccc3)nn(C)c2n1]

To a stirred mixture of 6-bromo-1-methyl-3-phenyl-4-(trifluoromethyl)-1H-pyrazolo[3,4-b]pyridine (0.15 g, 0.422 mmol) and Na$_2$CO$_3$ (0.135 g, 1.267 mmol) in dry DMF (6.0 mL), glycine methylester×HCl (0.08 g, 0.633 mmol) was added at it and heated to 100° C. for 6 h. The reaction mixture was cooled to it and poured into rapidly stirred ice cold water. The crude compound was extracted with EtOAc and purified by column chromatography (eluent: 10% EtOAc in hexane) to yield the title compound as a colorless solid (0.05 g, 32%). [$^1$H-NMR (CDCl$_3$, 300 MHz) δ 7.55-7.38 (m, 5H), 6.68 (s, 1H), 5.42 (t, 1H), 4.32 (d, 2H), 4.05 (s, 3H), 3.75 (s, 3H); LCMS Rt$_C$=0.469 min; [M+H]$^+$=364.8]

f) 2-(1-methyl-3-phenyl-4-(trifluoromethyl)-1H-pyrazolo[3,4-b]pyridin-6-ylamino)acetic acid

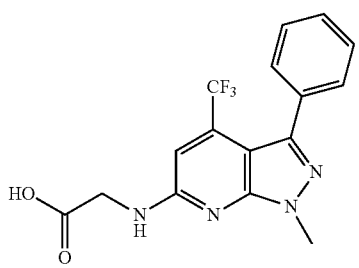 [SMILES: Cn1nc(-c2ccccc2)c2c(C(F)(F)F)cc(NCC(=O)O)nc21]

To a solution of methyl 2-(1-methyl-3-phenyl-4-(trifluoromethyl)-1H-pyrazolo[3,4-b]pyridin-6-ylamino)acetate (0.045 g, 0.123 mmol) in ethanol (2.0 mL), aqueous LiOH×H$_2$O (0.026 g, 0.618 mmol in 0.1 mL) was added and stirred at it for 15 min. The organic solvents were removed under reduced pressure and the reaction mixture was acidified with 10% HCl (pH ~2) to obtain a white solid which was filtered through a funnel and dried under vacuum to yield the title compound as a white solid (0.036 g, 90%). [$^1$H-NMR (DMSO-d$_6$, 300 MHz) δ 7.99 (s, 1H), 7.45-7.38 (m, 5H), 6.85 (s, 1H), 4.15 (d, 2H), 3.92 (s, 3H); LCMS Rt$_C$=0.39 min; [M+H]$^+$=351.1]

g) (S)-2-(1-methyl-3-phenyl-4-(trifluoromethyl)-1H-pyrazolo[3,4-b]pyridin-6-ylamino)-N-(1-phenylethyl)acetamide

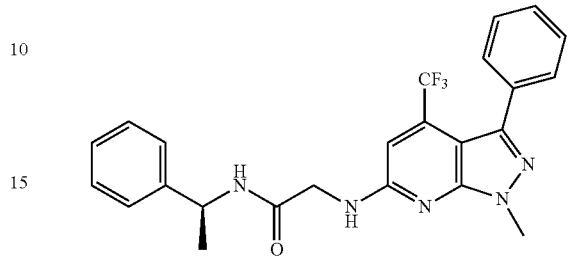

A solution of 2-(1-methyl-3-phenyl-4-(trifluoromethyl)-1H-pyrazolo[3,4-b]pyridin-6-ylamino) acetic acid (0.035 g, 0.095 mmol), DIC (0.018 g, 0.143 mmol) and HOBt (0.020 g, 0.143 mmol) in THF (5 ml) was stirred at rt for 10 min. (S)-(−)-α-methyl benzyl amine (0.013 g, 0.104 mmol) was added to the reaction mixture dropwise at rt and stirring was continued for 16 h. The reaction mixture was poured into ice cold water and the precipitated product was collected by filtration and dried under vacuum. The crude product was purified by preparative HPLC using acetonitrile/water as mobile phase to yield the title compound as a white solid (0.018 g, 42%). [$^1$H-NMR (CDCl$_3$, 300 MHz) δ 7.52-7.38 (m, 4H), 7.32-7.21 (m, 6H), 6.66 (s, 1H), 6.39 (d, 1H), 5.51 (t, 1H), 5.30-5.15 (m, 1H), 4.20 (dd, 2H), 3.95 (s, 3H), 1.52 (d, 3H); HPLC Rt$_A$=5.294 (98%) min; LCMS Rt$_A$=1.682 min; [M+H]$^+$=454.1]

METHOD D

Example 4.1

(S)-2-((3-(3-fluoropyridin-2-yl)-1,4-dimethyl-1H-pyrazolo[3,4-b]pyridin-6-yl)oxy)-N-(1-(p-tolyl)ethyl)acetamide

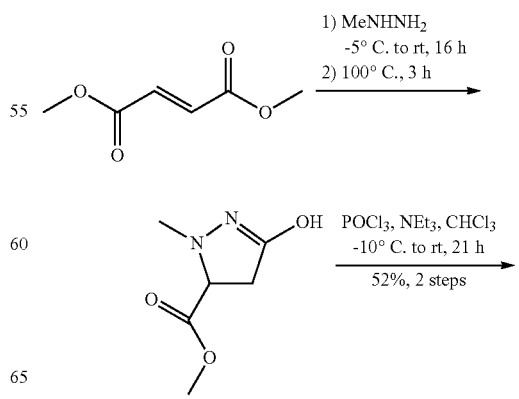

-continued

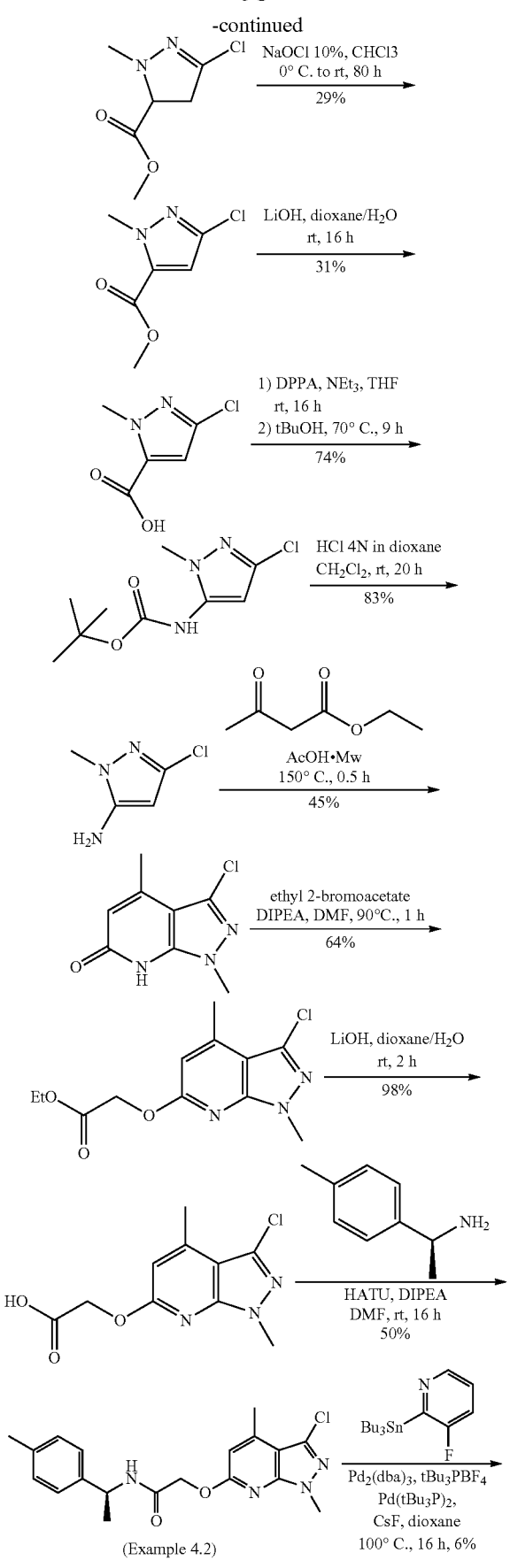

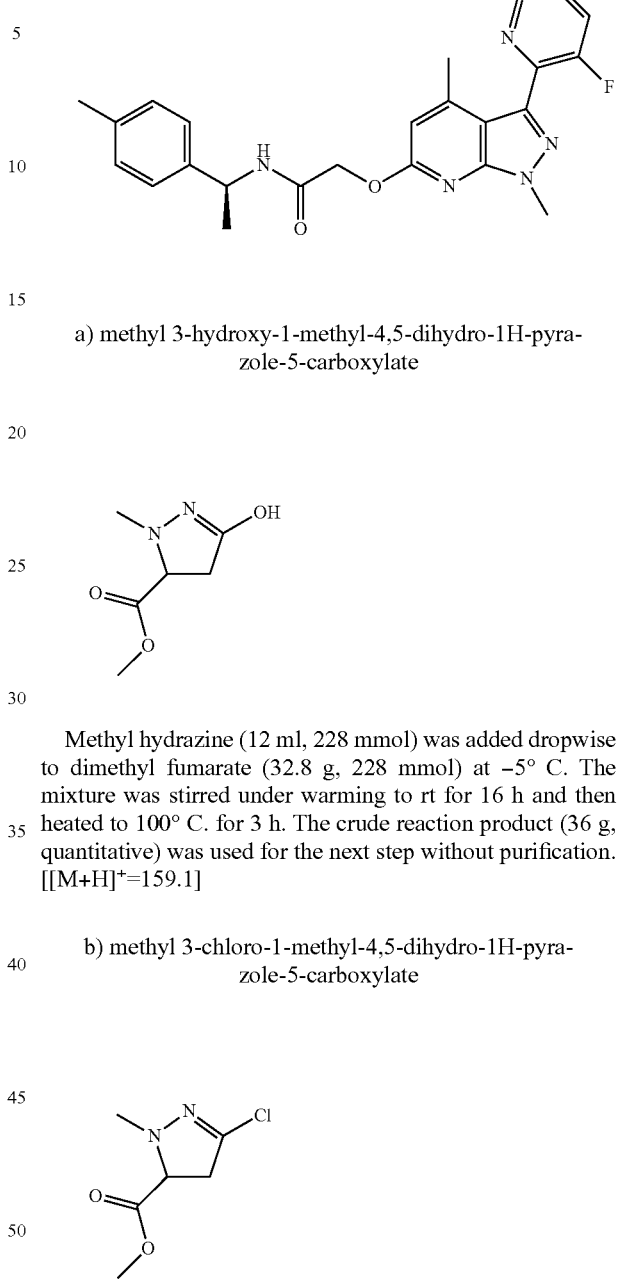

a) methyl 3-hydroxy-1-methyl-4,5-dihydro-1H-pyrazole-5-carboxylate

Methyl hydrazine (12 ml, 228 mmol) was added dropwise to dimethyl fumarate (32.8 g, 228 mmol) at −5° C. The mixture was stirred under warming to rt for 16 h and then heated to 100° C. for 3 h. The crude reaction product (36 g, quantitative) was used for the next step without purification. [[M+H]$^+$=159.1]

b) methyl 3-chloro-1-methyl-4,5-dihydro-1H-pyrazole-5-carboxylate

To a solution of POCl$_3$ (31.8 ml, 341 mmol) and Net$_3$ (47.6 ml, 341 mmol) in CHCl$_3$ (100 ml) at −5° C. was added a solution of methyl 3-hydroxy-1-methyl-4,5-dihydro-1H-pyrazole-5-carboxylate (36 g, 228 mmol) in CHCl$_3$ (100 ml). After 1 h at this temperature, the mixture was stirred for another 20 h under warming to rt. Then, the reaction mixture was poured on ice water and extracted with CHCl$_3$. The combined organics were washed with water, dried over Na$_2$SO$_4$ and evaporated under reduced pressure. This yielded the title compound (21 g, 52%) which was used in the next step without further purification. [LCMS Rt$_f$=0.63 min; [M+H]$^+$=177.0, 179.0]

c) methyl 3-chloro-1-methyl-1H-pyrazole-5-carboxylate

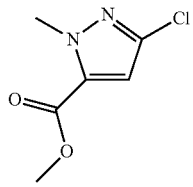

Methyl 3-chloro-1-methyl-4,5-dihydro-1H-pyrazole-5-carboxylate (21 g, 119 mmol) was added drop wise to sodium hypochlorite (95 ml, 155 mmol) under ice cooling. Then, the ice bath was removed and stirring continued for 72 h. The organic phase was separated, washed with $Na_2S_2O_3$ (10% aqueous solution) and water, dried over $Na_2SO_4$ and the solvent removed under reduced pressure. The resulting oil was purified by distillation (bp 35° C., 0.2 mbar) followed by column chromatography (eluent 80% hexane in EtOAc) to yield 6.0 g (29%) of the title compound. [1H-NMR (DMSO-$d_6$, 360 MHz) δ 6.96 (s, 1H), 6.80 (s, 1H), 4.07 (s, 3H), 3.86 (s, 3H)]

d) 3-chloro-1-methyl-1H-pyrazole-5-carboxylic acid

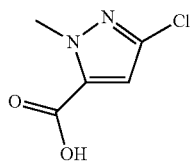

To a solution of methyl 3-chloro-1-methyl-1H-pyrazole-5-carboxylate (6.0 g, 34.4 mmol) in dioxane (10 ml) was added H2O (10 ml) and LiOH (1.65 g, 68.7 mmol). After stirring for 16 h, the reaction mixture was washed with $CH_2Cl_2$ and then the aqueous phase acidified by drop wise addition of conc. HCl. The resulting residue was filtered off, washed with water and dried to yield the title compound (5.0 g, 91%). [1H-NMR (DMSO-$d_6$, 360 MHz) δ 13.77 (br. s, 1H), 6.88 (d, 1H), 4.05 (s, 3H); HPLC-MS $Rt_f$=0.47 min; [M+H]$^+$=160.9, 163.0]

e) tert-butyl (3-chloro-1-methyl-1H-pyrazol-5-yl) carbamate

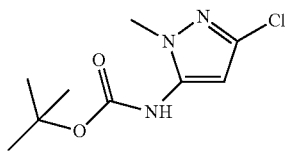

To a solution of 3-chloro-1-methyl-1H-pyrazole-5-carboxylic acid (2.0 g, 12.46 mmol) in THF (20 ml) was added Net_3 (2.60 ml, 18.68 mmol) and diphenyl phosphoryl azide (5.14 g, 18.68 mmol) at 0° C. The mixture was stirred at it for 16 h and then, tert butanol (2.4 ml, 24.9 mmol) was added and the mixture heated at 70° C. for 9 h. Then, the solvents were removed under reduced pressure and the residue purified by column chromatography (eluent 60% hexane in EtOAc) to yield 2.13 g (74%) of the title compound. [1H-NMR (DMSO-$d_6$, 360 MHz) δ 9.55 (br. s, 1H), 6.10 (d, 1H), 3.58 (s, 3H), 1.44 (s, 9H); HPLC-MS $Rt_f$=0.93 min; [M+H]$^+$=232.2, 234.2]

f) 3-chloro-1-methyl-1H-pyrazol-5-amine

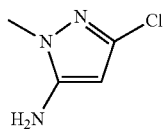

A solution of tert-butyl (3-chloro-1-methyl-1H-pyrazol-5-yl)carbamate (3.1 g, 9.1 mmol) in $CH_2Cl_2$ (10 ml) was treated with HCl (3 ml, 4N in dioxane). After 16 h stirring at rt, more HCl was added (2 ml, 4N in dioxane). After another 4 h, the solvents were removed under reduced pressure and the residue purified by recrystallization from diethyl ether to yield 1.26 g (83%) of the title compound as a white solid as hydrochloride. [1H-NMR (DMSO-$d_6$, 360 MHz) δ 7.60-7.10 (br. s, 3H), 5.27 (d, 1H), 3.10 (s, 3H); HPLC-MS $Rt_f$=0.42 min; [M+H]$^+$=131.9, 133.9]

g) 3-chloro-1,4-dimethyl-1H-pyrazolo[3,4-b]pyridin-6(7H)-one

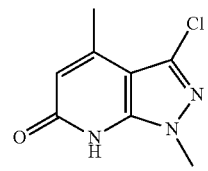

To a solution of 3-chloro-1-methyl-1H-pyrazol-5-amine (1.26 g, 7.50 mmol) in acetic acid (5 ml) was added ethyl 3-oxybutanoate (1.42 ml, 11.25 ml). The suspension was irradiated using a microwave at 150° C. for 0.5 h. Then, the solvent was removed under reduced pressure. Recrystallization from tert-butyl methyl ether yielded the title compound (771 mg, 45%) as white solid. [1H-NMR (DMSO-$d_6$, 400 MHz) δ 6.23 (br. s, 1H), 3.80 (s, 3H), 2.48 (s, 3H); HPLC-MS $Rt_f$=0.65 min; [M+H]$^+$=197.9, 199.9]

h) Ethyl 2-((3-chloro-1,4-dimethyl-1H-pyrazolo[3,4-b]pyridin-6-yl)oxy)acetate

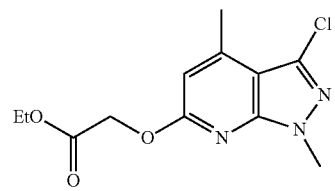 [SMILES: CCOC(=O)COc1cc(C)c2c(Cl)nn(C)c2n1]

3-chloro-1,4-dimethyl-1H-pyrazolo[3,4-b]pyridin-6(7H)-one (720 mg, 3.64 mmol) was dissolved in DMF (5 ml) at rt. Then, DIPEA (1.04 g, 8.0 mmol) and ethyl 2-bromoacetate (0.60 ml, 5.5 mmol) were added and the mixture heated at 90°

C. After 1 h, the mixture was cooled to rt, the solvent removed under reduced pressure and the residue purified by column chromatography (eluent 70% hexane in EtOAc) to yield 664 mg (64%) of the title compound. [1H-NMR (DMSO-d$_6$, 400 MHz) δ 6.67 (s, 1H), 4.98 (s, 2H) 4.17 (q, 2H), 3.84 (s, 3H), 2.62 (s, 3H), 1.19 (t, 3H); HPLC-MS Rt$_f$=1.13 min; [M+H]$^+$=284.0, 286.0 i) 2-((3-chloro-1,4-dimethyl-1H-pyrazolo[3,4-b]pyridin-6-yl)oxy)acetic acid

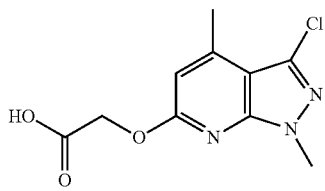 [SMILES: Cc1cc(OCC(=O)O)nc2c1c(Cl)nn2C]

To a solution of Ethyl 2-((3-chloro-1,4-dimethyl-1H-pyrazolo[3,4-b]pyridin-6-yl)oxy)acetate in dioxane (5 ml) were added H2O (2.5 ml) and LiOH (111 mg, 4.65 mmol). After 2 h, more water was added and the mixture extracted with CH$_2$Cl$_2$. Then, the aqueous phase was acidified by drop wise addition of conc. HCl until the product precipitated. The title compound (580 mg, 98%) was filtered off and dried under reduced pressure. [1H-NMR (DMSO-d$_6$, 400 MHz) δ 6.62 (s, 1H), 4.98 (s, 2H) 3.84 (s, 3H), 2.61 (s, 3H); HPLC-MS Rt$_f$=0.81 min; [M+H]$^+$=255.9, 258.0]

j) (S)-2-((3-chloro-1,4-dimethyl-1H-pyrazolo[3,4-b]pyridin-6-yl)oxy)-N-(1-(o-tolyl)ethyl)acetamide

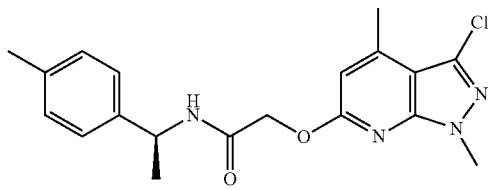 [SMILES: Cc1ccc([C@H](C)NC(=O)COc2cc(C)c3c(Cl)nn(C)c3n2)cc1]

To a solution of 2-((3-chloro-1,4-dimethyl-1H-pyrazolo[3,4-b]pyridin-6-yl)oxy)acetic acid in DMF (5 ml) was added HATU (1.03 g, 2.72 mmol) and DIPEA (1.2 ml, 6.81 mmol). After 20 min at rt, (S)-1-(p-tolylethan)amine (0.43 ml, 2.95 mmol) was added to the mixture. After 16 h, water was added and the mixture extracted with CH$_2$Cl$_2$. The organic phases were dried over Na$_2$SO$_4$ and the solvent removed under reduced pressure. Purification by column chromatography (eluent 60% hexane in EtOAc) yielded 420 mg (50%) of the title compound. [1H-NMR (DMSO-d$_6$, 600 MHz) δ 8.51 (d, 1H), 7.16 (d, 2H), 7.05 (d, 2H), 6.63 (s, 1H), 4.93 (t, 1H), 4.83 (d, 1H), 4.79 (d, 1H), 3.77 (s, 3H), 2.60 (s, 3H), 2.25 (s, 3H), 1.35 (d, 3H); HPLC-MS Rt$_f$=1.15 min; [M+H]$^+$=373.1, 375.1]

k) (S)-2-((3-(3-fluoropyridin-2-yl)-1,4-dimethyl-1H-pyrazolo[3,4-b]pyridin-6-yl)oxy)-N-(1-(p-tolyl)ethyl)acetamide

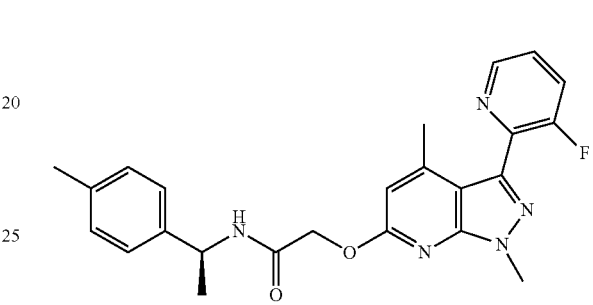

To a sealed tube were added (S)-2-((3-chloro-1,4-dimethyl-1H-pyrazolo[3,4-b]pyridin-6-yl)oxy)-N-(1-(p-tolyl)ethyl)acetamide (50 mg, 0.13 mmol), Pd[P(tBu)$_3$]$_2$ (3.4 mg, 6.7 μmol), CsF (45 mg, 0.30 mmol), [(t-Bu)$_3$PH]BF$_4$ (3.9 mg, 0.013 mmol) and Pd$_2$(dba)$_3$ (6.1 mg, 6.7 μmol). The tube was evacuated and flushed 3 times with argon and then 3-fluoro-2-tributylstannyl-pyridine (104 mg, 0.27 mmol) in dioxane (1 ml) was added and the suspension heated at 100° C. for 16 h. After cooling to rt, CH$_2$Cl$_2$ and NaHCO$_3$ solution were added and the phases separated. The organic layers were washed with water, dried over Na$_2$SO$_4$ and the solvents removed under reduced pressure. Purification using preparative reverse phase chromatography (LC SunFire C18 OBD column) followed by liberation of the free base (SPE cartridge SCX-1, eluent 7M NH$_3$ in methanol) yielded the title compound (3.7 mg, 6%). [1H-NMR (DMSO-d$_6$, 600 MHz) δ 8.59 (d, 1H), 8.54 (d, 1H), 7.91 (t, 1H), 7.62-7.58 (m, 1H), 7.18 (d, 2H), 7.08 (d, 2H), 6.64 (s, 1H), 4.96 (q, 1H), 4.87 (d, 1H), 4.84 (d, 1H), 3.89 (s, 3H), 2.30 (s, 3H), 2.25 (s, 3H), 1.37 (d, 3H); HPLC-MS Rt$_f$=1.08 min; [M+H]$^+$=434.1]

TABLE 2

Compounds Number 4.2 to 4.13

| Number | Structure | IUPAC Name | LCMS Rt [min] (method) | [M + H]$^+$ |
|---|---|---|---|---|
| 4.2 | 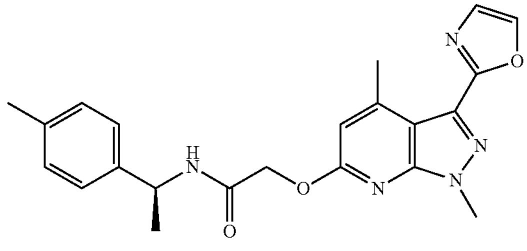 [SMILES: Cc1ccc([C@H](C)NC(=O)COc2cc(C)c3c(-c4ncco4)nn(C)c3n2)cc1] | (S)-2-(1,4-dimethyl-3-(oxazol-2-yl)-1H-pyrazolo[3,4-b]pyridin-6-yloxy)-N-(1-p-tolylethyl)acetamide | 1.07 (J) | 406.2 |

TABLE 2-continued

Compounds Number 4.2 to 4.13

| Number | Structure | IUPAC Name | LCMS Rt [min] (method) | [M + H]+ |
|---|---|---|---|---|
| 4.3 | 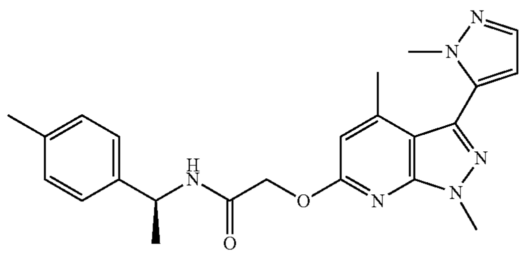 [SMILES: Cc1ccc([C@H](C)NC(=O)COc2cc(C)c3c(-c4ccnn4C)nn(C)c3n2)cc1] | (S)-2-(1,4-dimethyl-3-(1-methyl-1H-pyrazol-5-yl)-1H-pyrazolo[3,4-b]pyridin-6-yloxy)-N-(1-p-tolylethyl)acetamide | 1.03 (J) | 419.4 |
| 4.4 | 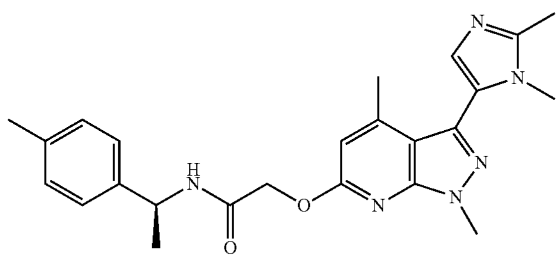 | (S)-2-(3-(1,2-dimethyl-1H-imidazol-5-yl)-1,4-dimethyl-1H-pyrazolo[3,4-b]pyridin-6-yloxy)-N-(1-p-tolylethyl)acetamide | 1.04 (J) | 433.2 |
| 4.5 | 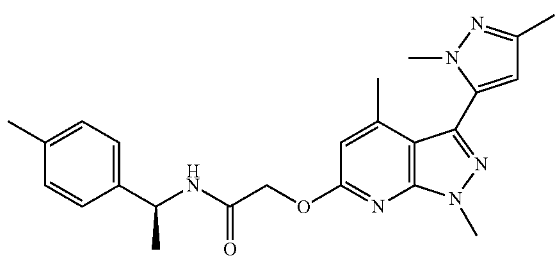 | (S)-2-(3-(1,3-dimethyl-1H-pyrazol-5-yl)-1,4-dimethyl-1H-pyrazolo[3,4-b]pyridin-6-yloxy)-N-(1-p-tolylethyl)acetamide | 1.04 (J) | 433.2 |
| 4.6 | 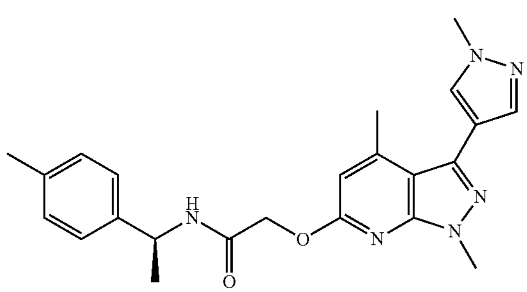 [SMILES: Cc1ccc([C@H](C)NC(=O)COc2cc(C)c3c(-c4cnn(C)c4)nn(C)c3n2)cc1] | (S)-2-(1,4-dimethyl-3-(1-methyl-1H-pyrazol-4-yl)-1H-pyrazolo[3,4-b]pyridin-6-yloxy)-N-(1-p-tolylethyl)acetamide | 0.95 (J) | 419.2 |
| 4.7 | 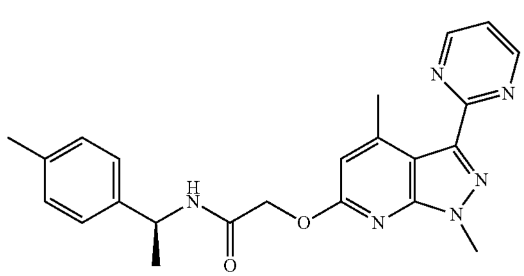 [SMILES: Cc1ccc([C@H](C)NC(=O)COc2cc(C)c3c(-c4ncccn4)nn(C)c3n2)cc1] | (S)-2-(1,4-dimethyl-3-(pyrimidin-2-yl)-1H-pyrazolo[3,4-b]pyridin-6-yloxy)-N-(1-p-tolylethyl)acetamide | 0.97 (J) | 417.2 |

TABLE 2-continued

Compounds Number 4.2 to 4.13

| Number | Structure | IUPAC Name | LCMS Rt [min] (method) | [M + H]⁺ |
|---|---|---|---|---|
| 4.8 | 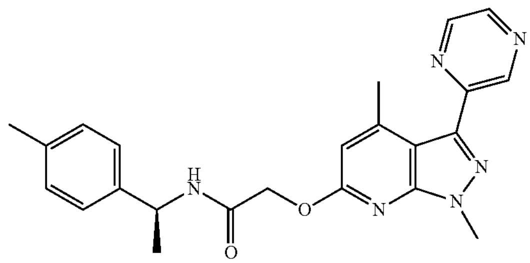 [SMILES: Cc1ccc([C@H](C)NC(=O)COc2cc(C)c3c(-c4cnccn4)nn(C)c3n2)cc1] | (S)-2-(1,4-dimethyl-3-(pyrazin-2-yl)-1H-pyrazolo[3,4-b]pyridin-6-yloxy)-N-(1-p-tolylethyl)acetamide | 1.06 (J) | 417.2 |
| 4.9 | 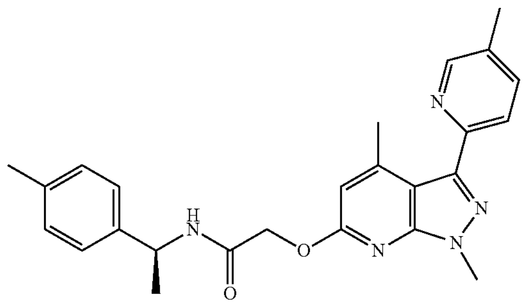 [SMILES: Cc1ccc([C@H](C)NC(=O)COc2cc(C)c3c(-c4ccc(C)cn4)nn(C)c3n2)cc1] | (S)-2-(1,4-dimethyl-3-(5-methylpyridin-2-yl)-1H-pyrazolo[3,4-b]pyridin-6-yloxy)-N-(1-p-tolylethyl)acetamide | 1.18 (J) | 430.2 |
| 4.10 | 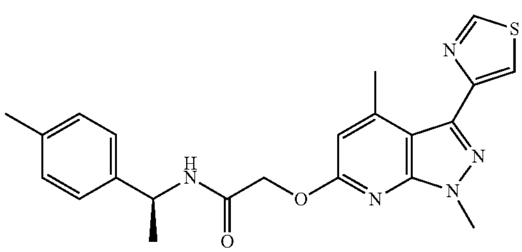 [SMILES: Cc1ccc([C@H](C)NC(=O)COc2cc(C)c3c(-c4cscn4)nn(C)c3n2)cc1] | (S)-2-(1,4-dimethyl-3-(thiazol-4-yl)-1H-pyrazolo[3,4-b]pyridin-6-yloxy)-N-(1-p-tolylethyl)acetamide | 1.08 (J) | 422.2 |
| 4.11 | 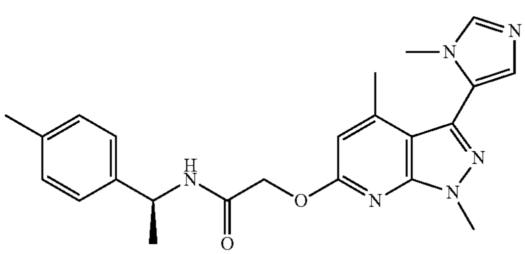 [SMILES: Cc1ccc([C@H](C)NC(=O)COc2cc(C)c3c(-c4cncn4C)nn(C)c3n2)cc1] | (S)-2-(1,4-dimethyl-3-(1-methyl-1H-imidazol-5-yl)-1H-pyrazolo[3,4-b]pyridin-6-yloxy)-N-(1-p-tolylethyl)acetamide | 0.76 (J) | 419.2 |
| 4.12 | 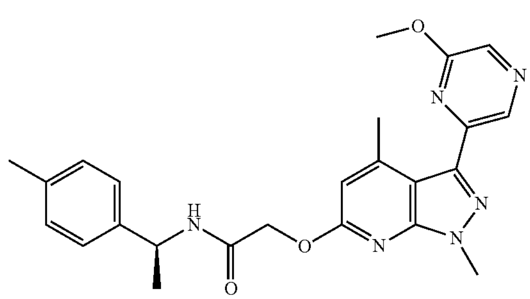 [SMILES: COc1cncc(-c2nn(C)c3nc(OCC(=O)N[C@@H](C)c4ccc(C)cc4)cc(C)c23)n1] | (S)-2-(3-(6-methoxypyrazin-2-yl)-1,4-dimethyl-1H-pyrazolo[3,4-b]pyridin-6-yloxy)-N-(1-p-tolylethyl)acetamide | 1.14 (J) | 447.2 |

TABLE 2-continued

Compounds Number 4.2 to 4.13

| Number | Structure | IUPAC Name | LCMS Rt [min] (method) | [M + H]+ |
|---|---|---|---|---|
| 4.13 | 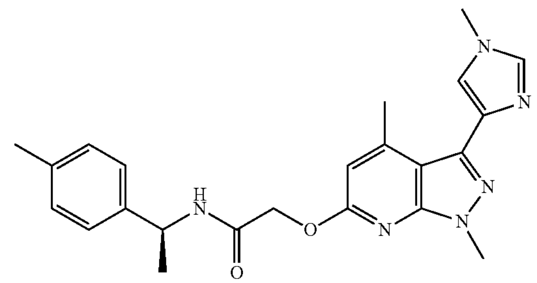 [SMILES: Cc1ccc([C@H](C)NC(=O)COc2cc(C)c3c(-c4cn(C)cn4)nn(C)c3n2)cc1] | (S)-2-(1,4-dimethyl-3-(1-methyl-1H-imidazol-4-yl)-1H-pyrazolo[3,4-b]pyridin-6-yloxy)-N-(1-p-tolylethyl)acetamide | 0.79 (J) | 419.2 |

METHOD E

Example 5.1

(S)-2-((1,4-dimethyl-3-(4-methylthiazol-2-yl)-1H-pyrazolo[3,4-b]pyridin-6-yl)oxy)-N-(1-(p-tolyl)ethyl)acetamide

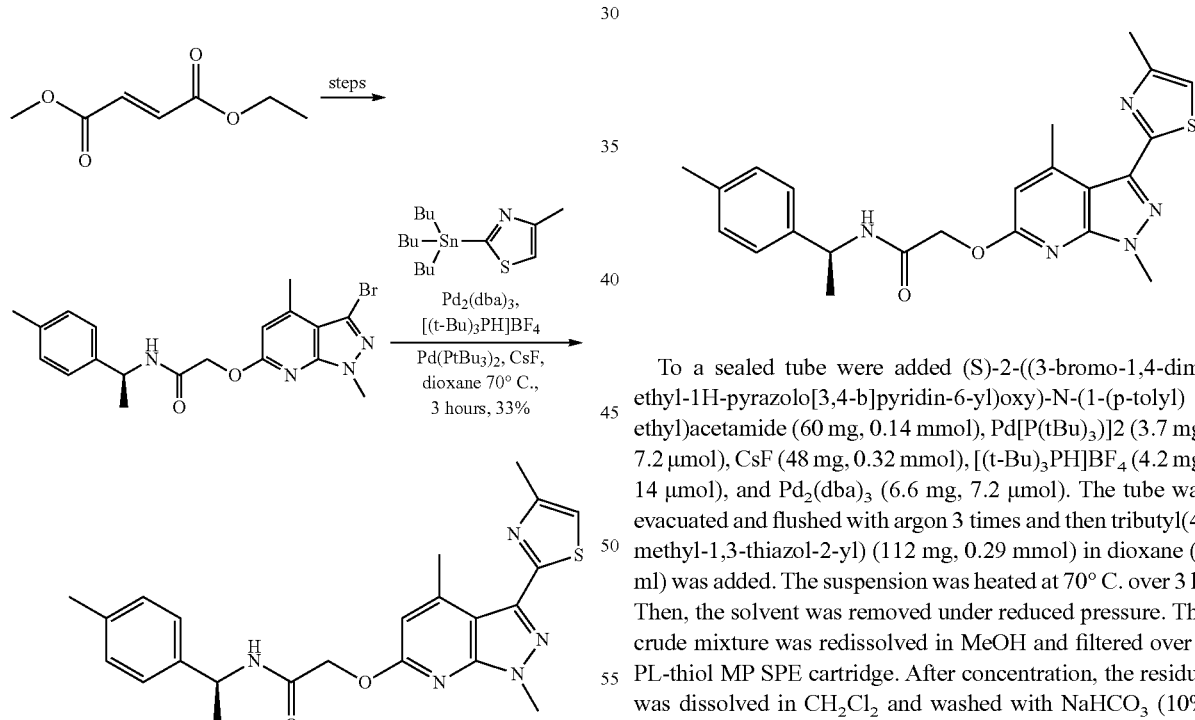

a) (S)-2-((3-bromo-1,4-dimethyl-1H-pyrazolo[3,4-b]pyridin-6-yl)oxy)-N-(1-(p-tolyl)ethyl)acetamide The title compound is prepared in analogy to the example described in example 4.1 but starting from ethyl methyl fumarate and using POBr₃ instead of POCl₃. [1H-NMR (DMSO-d₆, 400 MHz) δ 8.49 (d, 1H), 7.17 (d, 2H), 7.07 (d, 2H), 6.63 (s, 1H), 4.96 (m, 1H), 4.83 (s, 2H), 3.80 (s, 3H), 2.63 (s, 3H), 2.25 (s, 3H), 1.38 (d, 3H); UPLC-MS Rt$_f$=1.18 min; [M+H]+=417.1, 419.1]

b) (S)-2-((1,4-dimethyl-3-(4-methylthiazol-2-yl)-1H-pyrazolo[3,4-b]pyridin-6-yl)oxy)-N-(1-(p-tolyl)ethyl)acetamide To a sealed tube were added (S)-2-((3-bromo-1,4-dimethyl-1H-pyrazolo[3,4-b]pyridin-6-yl)oxy)-N-(1-(p-tolyl)ethyl)acetamide (60 mg, 0.14 mmol), Pd[P(tBu)₃)]2 (3.7 mg, 7.2 μmol), CsF (48 mg, 0.32 mmol), [(t-Bu)₃PH]BF₄ (4.2 mg, 14 μmol), and Pd₂(dba)₃ (6.6 mg, 7.2 μmol). The tube was evacuated and flushed with argon 3 times and then tributyl(4-methyl-1,3-thiazol-2-yl) (112 mg, 0.29 mmol) in dioxane (1 ml) was added. The suspension was heated at 70° C. over 3 h. Then, the solvent was removed under reduced pressure. The crude mixture was redissolved in MeOH and filtered over a PL-thiol MP SPE cartridge. After concentration, the residue was dissolved in CH₂Cl₂ and washed with NaHCO₃ (10% aqueous solution). The organic layer was washed with water, dried over Na₂SO₄, filtered and the solvent was removed under reduced pressure. Purification by preparative reverse phase HPLC (SunFire C18 OBD column) followed by liberation of the free base (SPE cartridge SCX-1, eluent 7M NH3 in methanol) yielded the title compound (21 mg, 33%). [1H-NMR (DMSO-d₆, 400 MHz) δ 8.52 (d, 1H), 7.32 (s, 1H), 7.17 (d, 2H), 7.07 (d, 2H), 6.69 (s, 1H), 5.00-4.88 (m, 1H), 4.85 (s, 2H), 3.88 (s, 3H), 2.87 (s, 3H), 2.46 (s, 3H), 2.25 (s, 3H), 1.37 (d, 3H); UPLC-MS Rt$_f$=1.27 min; [M+H]+=436.1]

TABLE 3

Compounds Number 5.2 to 5.7

| Number | Structure | IUPAC Name | LCMS Rt [min] (method) | [M + H]+ |
|---|---|---|---|---|
| 5.2 | 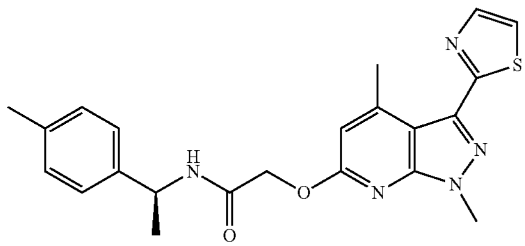 [SMILES: Cc1ccc([C@H](C)NC(=O)COc2cc(C)c3c(-c4nccs4)nn(C)c3n2)cc1] | (S)-2-(1,4-dimethyl-3-(thiazol-2-yl)-1H-pyrazolo[3,4-b]pyridin-6-yloxy)-N-(1-p-tolylethyl)acetamide | 1.21 (J) | 422.1 |
| 5.3 | 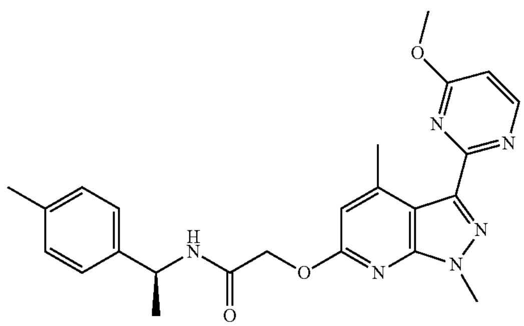 [SMILES: COc1ccnc(-c2nn(C)c3nc(OCC(=O)N[C@@H](C)c4ccc(C)cc4)cc(C)c23)n1] | (S)-2-(3-(4-methoxypyrimidin-2-yl)-1,4-dimethyl-1H-pyrazolo[3,4-b]pyridin-6-yloxy)-N-(1-p-tolylethyl)acetamide | 1.07 (J) | 447.2 |
| 5.4 | 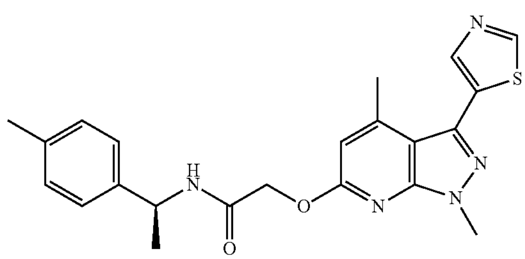 [SMILES: Cc1ccc([C@H](C)NC(=O)COc2cc(C)c3c(-c4cncs4)nn(C)c3n2)cc1] | (S)-2-(1,4-dimethyl-3-(thiazol-5-yl)-1H-pyrazolo[3,4-b]pyridin-6-yloxy)-N-(1-p-tolylethyl)acetamide | 1.03 (J) | 422.1 |
| 5.5 | 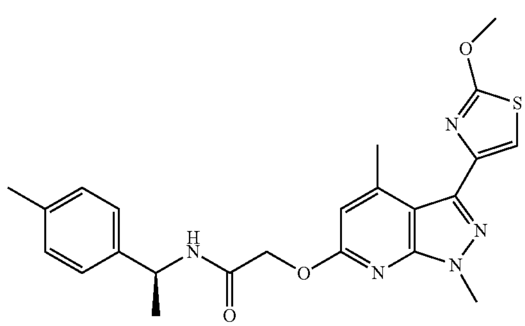 [SMILES: COc1nc(-c2nn(C)c3nc(OCC(=O)N[C@@H](C)c4ccc(C)cc4)cc(C)c23)cs1] | (S)-2-(3-(2-methoxythiazol-4-yl)-1,4-dimethyl-1H-pyrazolo[3,4-b]pyridin-6-yloxy)-N-(1-p-tolylethyl)acetamide | 1.21 (J) | 452.1 |
| 5.6 | 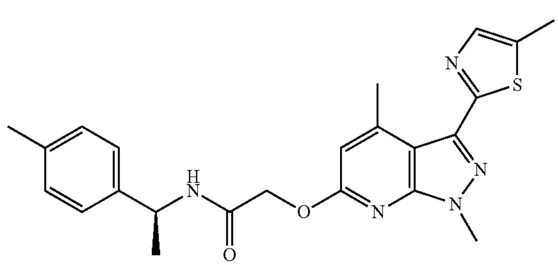 | (S)-2-(1,4-dimethyl-3-(5-methylthiazol-2-yl)-1H-pyrazolo[3,4-b]pyridin-6-yloxy)-N-(1-p-tolylethyl)acetamide | 1.27 (J) | 436.1 |

TABLE 3-continued

Compounds Number 5.2 to 5.7

| Number | Structure | IUPAC Name | LCMS Rt [min] (method) | [M + H]+ |
|---|---|---|---|---|
| 5.7 | 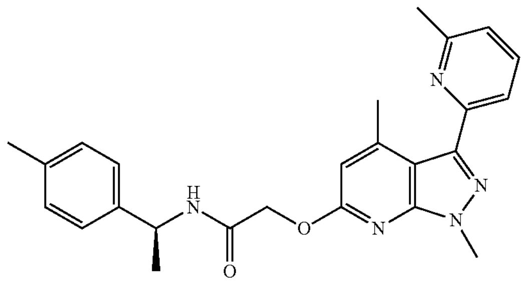 [SMILES: Cc1ccc([C@H](C)NC(=O)COc2cc(C)c3c(-c4cccc(C)n4)nn(C)c3n2)cc1] | (S)-2-(1,4-dimethyl-3-(6-methylpyridin-2-yl)-1H-pyrazolo[3,4-b]pyridin-6-yloxy)-N-(1-p-tolylethyl)acetamide | 1.18 (J) | 430.2 |

METHOD F

General Coupling Procedure

Example 6.1

(S)-2-((3-(3,5-dimethoxyphenyl)-1,4-dimethyl-1H-pyrazolo[3,4-b]pyridin-6-yl)oxy)-N-(1-(4-methoxyphenyl)ethyl)acetamide

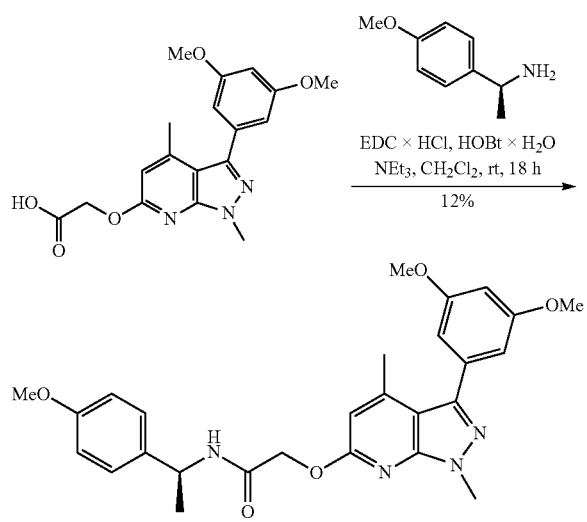

To a solution of [3-(3,5-Dimethoxy-phenyl)-1,4-dimethyl-1H-pyrazolo[3,4-b]pyridin-6-yloxy]-acetic acid (building block A1, 100 mg, 0.28 mmol) in CH$_2$Cl$_2$ were added HOBt× H2O (64 mg, 0.42 mmol), EDC×HCl (80 mg, 0.42 mmol) and NEt3 (0.12 ml, 0.84 mmol). After stirring at rt for 5 min, (S)-1-(4-methoxyphenyl)ethanamine (64 mg, 0.42 mmol) was added and stirring continued for 18 h. Then, water was added and the mixture extracted 3 times with DCM. The organic phases were dried over Na2SO4 and the solvent removed under reduced pressure. Purification by reverse phase HPLC (Sunfire C18 OBD column) followed by liberation of the free base (SPE cartridge SCX-1, eluent 7M NH3 in methanol) yielded the title compound (17 mg, 12%). [1H-NMR (DMSO-d$_6$, 600 MHz) δ 8.48 (d, 1H), 7.21 (d, 2H), 6.82 (d, 2H), 6.70 (s, 1H), 6.58 (s, 1H), 5.00-4.88 (m, 1H), 4.87 (d, 1H), 4.83 (d, 1H), 3.85 (s, 3H), 3.78 (s, 6H), 3.70 (s, 3H), 2.37 (s, 3H), 1.37 (d, 3H); UPLC-MS Rt$_f$=1.14 min; [M+H]+=491.2]

Example 6.2

(S)-2-(3-cyclopropyl-4-(difluoromethyl)-1-methyl-1H-pyrazolo[3,4-b]pyridin-6-yloxy)-N-(2-methyl-6,7-dihydro-5H-cyclopenta[b]pyridin-5-yl)acetamide

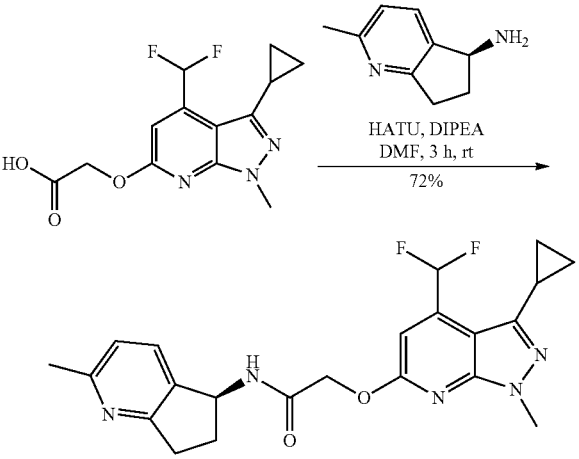

To the solution of (S)-2-methyl-6,7-dihydro-5H-[1]pyrindin-5-ylamine hydrochloride (75 mg, 0.41 mmol) and (3-cyclopropyl-4-difluoromethyl-1-methyl-1H-pyrazolo[3,4-b]pyridin-6-yloxy)-acetic acid (building block A2, 110 mg, 0.37 mmol) in DMF (6 ml) were added DIPEA (0.26 ml, 1.48 mmol) and HATU (169 mg, 0.44 mmol) and the reaction was stirred at it for 3 h. The mixture was diluted with EtOAc, washed with aqueous bicarbonate solution and brine, dried over sodium sulfate, and the solvents were evaporated under reduced pressure. Purification by preparative HPLC (Gilson GX-281, Waters Sunfire C18, 5 µm, 30×100 mm with guard column 19×10 mm, solvent A: water with 0.1% TFA, solvent B: acetonitrile, gradient 10-30% B in 16 min, flow rate 50 ml/min) gave the title compound as off-white solid (115 mg, 72%). [1H-NMR (DMSO-d$_6$, 600 MHz) δ 8.61 (d, 1H), 7.47 (t, 1H), 7.36 (d, 1H), 6.99 (d, 1H), 6.93 (s, 1H), 5.32 (dd, 1H), 4.89 (s, 2H), 3.81 (s, 3H), 3.34 (s, 3H), 2.93-2.89 (m, 1H), 2.86-2.80 (m, 1H), 2.41 (s, 3H), 2.41-2.36 (m, 1H), 2.24-2.19 (m, 1H), 1.92-1.86 (m, 1H), 0.94-0.87 (m, 4H); LCMS Rt$_f$=3.032 min; [M+H]+=428.2]

Example 6.3

2-(3-cyclopropyl-1,4-dimethyl-1H-pyrazolo[3,4-b]pyridin-6-yloxy)-N-(5-methoxy-2,3-dihydro-1H-inden-1-yl)acetamide

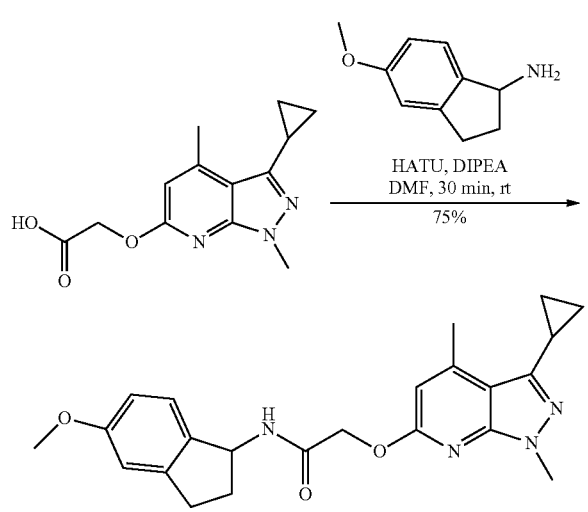

To the solution of 5-methoxy-indan-1-ylamine hydrochloride (92 mg, 0.46 mmol) and (3-cyclopropyl-1,4-dimethyl-1H-pyrazolo[3,4-b]pyridin-6-yloxy)-acetic acid (building block A7, 120 mg, 0.46 mmol) in DMF (6 ml) were added DIPEA (0.24 ml, 1.38 mmol) and HATU (210 mg, 0.55 mmol) and the reaction was stirred at it for 30 min. The mixture was diluted with EtOAc, washed with aqueous bicarbonate solution and brine, dried over sodium sulfate, and the solvents were evaporated under reduced pressure. Purification by preparative HPLC (Gilson GX-281, Waters Sunfire C18, 5 μm, 30×100 mm with guard column 19×10 mm, solvent A: water with 0.1% TFA, solvent B: acetonitrile, gradient 40-60% B in 15 min, flow reate 50 ml/min) gave the title compound as colorless solid (140 mg, 75%). [1H-NMR (DMSO-$d_6$, 600 MHz) δ 8.40 (d, 1H), 7.02 (d, 1H), 6.81 (s, 1H), 6.68 (d, 1H), 6.48 (s, 1H), 5.26 (dd, 1H), 4.80 (s, 2H), 3.76 (s, 3H), 3.71 (s, 3H), 2.91-2.88 (m, 1H), 2.78-2.73 (m, 1H), 2.66 (s, 3H), 2.38-2.33 (m, 1H), 2.28-2.24 (m, 1H), 1.89-1.82 (m, 1H), 0.92-0.85 (m, 4H); LCMS Rt$_H$=3.095 min; [M+H]$^+$=407.2]

EXAMPLES 6.4 AND 6.5

Enantiomers of (2-(3-cyclopropyl-1,4-dimethyl-1H-pyrazolo[3,4-b]pyridin-6-yloxy)-N-(5-methoxy-2,3-dihydro-1H-inden-1-yl)acetamide

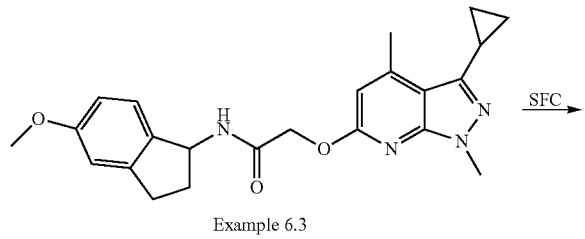

Example 6.3

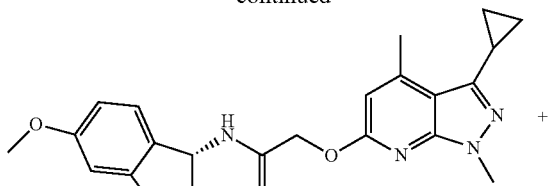

Example 6.4

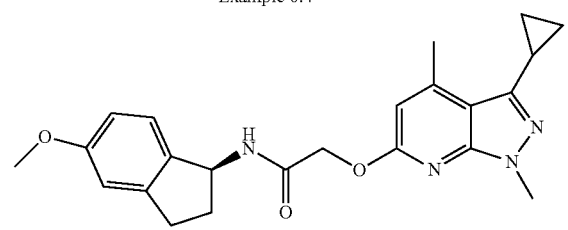

Example 6.5

The enantiomers of example 6.3 were separated by chiral chromatography using a supercritical fluid chromatography system (Waters Thar SFC 100, Chiralpak AS-H, 30×250 mm, CO2/MeOH 75/25 (isocratic), 150 bar, flow rate 80 g/min, injection 990 μl 6.6 mg/l in MeOH, cycle time 8 min). Enantiomeric purity was confirmed on an analytical SFC system (Berger SFC, Chiralpac AS-H 4.6×250 mm, CO2/MeOH/isopropylamine 75/25/1, 150 bar, flow rate 3.0 ml/min, UV detection at 210 nm)

Example 6.4

(R)-2-(3-cyclopropyl-1,4-dimethyl-1H-pyrazolo[3,4-b]pyridin-6-yloxy)-N-(5-methoxy-2,3-dihydro-1H-inden-1-yl)acetamide

[Berger SFC Rt=2.19 min; ee >99%]

Example 6.5

(S)-2-(3-cyclopropyl-1,4-dimethyl-1H-pyrazolo[3,4-b]pyridin-6-yloxy)-N-(5-methoxy-2,3-dihydro-1H-inden-1-yl)acetamide

[Berger SFC Rt=2.81 min; ee 98.2%]

Example 6.6

2-(3-cyclopropyl-1,4-dimethyl-1H-pyrazolo[3,4-b]pyridin-6-yloxy)-N-(2-p-tolylpropan-2-yl)acetamide

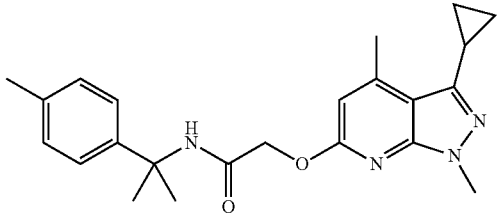 [SMILES: Cc1ccc(C(C)(C)NC(=O)COc2cc(C)c3c(C4CC4)nn(C)c3n2)cc1]

The title compound was obtained in analogy to example 6.2 as colorless solid. [1H-NMR (DMSO-$d_6$, 600 MHz) δ 8.16 (s, 1H), 7.20 (d, 2H), 6.99 (d, 2H), 6.45 (s, 1H), 4.78 (s, 2H), 3.83 (s, 3H), 2.65 (s, 3H), 2.28-2.22 (m, 1H), 2.22 (s, 3H), 1.53 (s, 6H), 0.94-0.85 (m, 4H); LCMS Rt$_K$=3.016 min; [M+H]$^+$=393.2]

TABLE 4

Compounds Number 6.7 to 6.80

| Number | Structure | IUPAC Name | LCMS Rt [min] (method) | [M + H]+ |
|---|---|---|---|---|
| 6.7 | 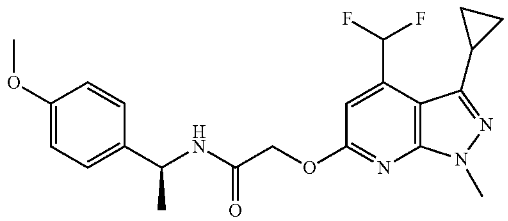 [SMILES: COc1ccc([C@H](C)NC(=O)COc2cc(C(F)F)c3c(C4CC4)nn(C)c3n2)cc1] | (S)-2-(3-cyclopropyl-4-(difluoromethyl)-1-methyl-1H-pyrazolo[3,4-b]pyridin-6-yloxy)-N-(1-(4-methoxyphenyl)ethyl)acetamide | 1.11 (J) | 431.1 |
| 6.8 | 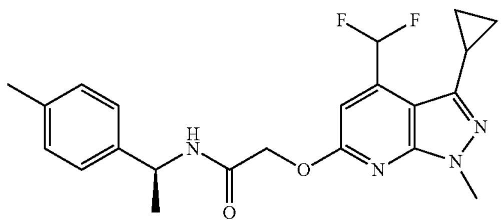 [SMILES: Cc1ccc([C@H](C)NC(=O)COc2cc(C(F)F)c3c(C4CC4)nn(C)c3n2)cc1] | (S)-2-(3-cyclopropyl-4-(difluoromethyl)-1-methyl-1H-pyrazolo[3,4-b]pyridin-6-yloxy)-N-(1-p-tolylethyl)acetamide | 1.19 (J) | 415.1 |
| 6.9 | 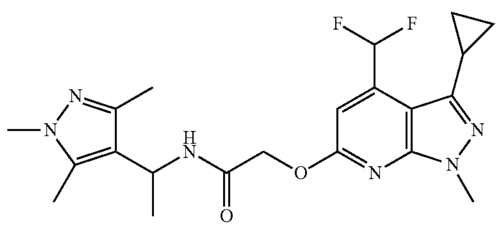 [SMILES: Cc1nn(C)c(C)c1C(C)NC(=O)COc1cc(C(F)F)c2c(C3CC3)nn(C)c2n1] | 2-(3-cyclopropyl-4-(difluoromethyl)-1-methyl-1H-pyrazolo[3,4-b]pyridin-6-yloxy)-N-(1-(1,3,5-trimethyl-1H-pyrazol-4-yl)ethyl)acetamide | 0.93 (J) | 433.1 |
| 6.10 | 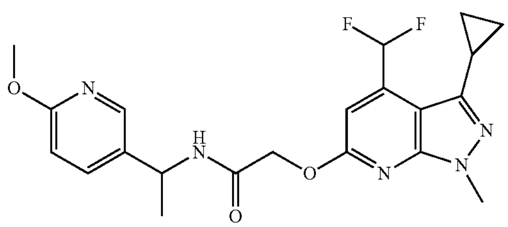 [SMILES: COc1ccc(C(C)NC(=O)COc2cc(C(F)F)c3c(C4CC4)nn(C)c3n2)cn1] | 2-(3-cyclopropyl-4-(difluoromethyl)-1-methyl-1H-pyrazolo[3,4-b]pyridin-6-yloxy)-N-(1-(6-methoxypyridin-3-yl)ethyl)acetamide | 1.03 (J) | 432.3 |
| 6.11 | 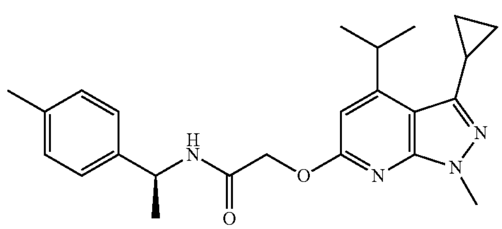 [SMILES: Cc1ccc([C@H](C)NC(=O)COc2cc(C(C)C)c3c(C4CC4)nn(C)c3n2)cc1] | (S)-2-(3-cyclopropyl-4-isopropyl-1-methyl-1H-pyrazolo[3,4-b]pyridin-6-yloxy)-N-(1-p-tolylethyl)acetamide | 1.33 (J) | 407.2 |
| 6.12 | 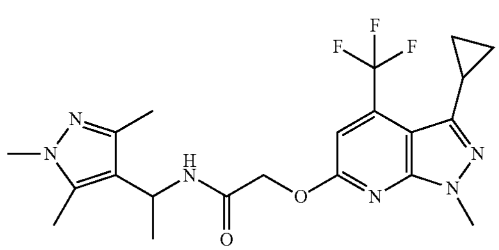 [SMILES: Cc1nn(C)c(C)c1C(C)NC(=O)COc1cc(C(F)(F)F)c2c(C3CC3)nn(C)c2n1] | 2-(3-cyclopropyl-1-methyl-4-(trifluoromethyl)-1H-pyrazolo[3,4-b]pyridin-6-yloxy)-N-(1-(1,3,5-trimethyl-1H-pyrazol-4-yl)ethyl)acetamide | 1.07 (J) | 451.4 |

TABLE 4-continued

Compounds Number 6.7 to 6.80

| Number | Structure | IUPAC Name | LCMS Rt [min] (method) | [M + H]+ |
|---|---|---|---|---|
| 6.13 | 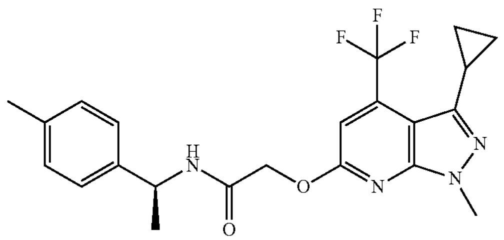 [SMILES: Cc1ccc([C@H](C)NC(=O)COc2cc(C(F)(F)F)c3c(C4CC4)nn(C)c3n2)cc1] | (S)-2-(3-cyclopropyl-1-methyl-4-(trifluoromethyl)-1H-pyrazolo[3,4-b]pyridin-6-yloxy)-N-(1-p-tolylethyl)acetamide | 1.31 (J) | 433.4 |
| 6.14 | 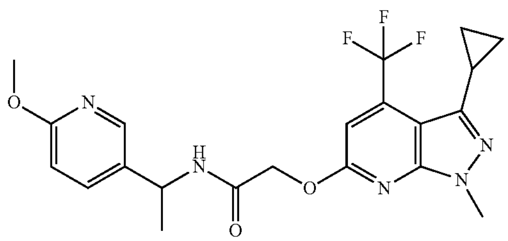 [SMILES: COc1ccc(C(C)NC(=O)COc2cc(C(F)(F)F)c3c(C4CC4)nn(C)c3n2)cn1] | 2-(3-cyclopropyl-1-methyl-4-(trifluoromethyl)-1H-pyrazolo[3,4-b]pyridin-6-yloxy)-N-(1-(6-methoxypyridin-3-yl)ethyl)acetamide | 1.17 (J) | 450.4 |
| 6.15 | 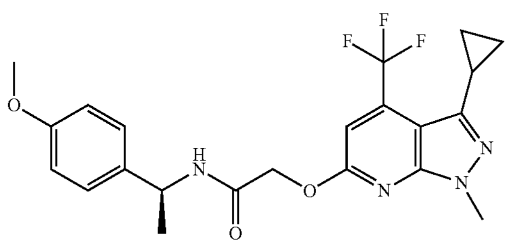 [SMILES: COc1ccc([C@H](C)NC(=O)COc2cc(C(F)(F)F)c3c(C4CC4)nn(C)c3n2)cc1] | (S)-2-(3-cyclopropyl-1-methyl-4-(trifluoromethyl)-1H-pyrazolo[3,4-b]pyridin-6-yloxy)-N-(1-(4-methoxyphenyl)ethyl)acetamide | 1.24 (J) | 449.4 |
| 6.16 | 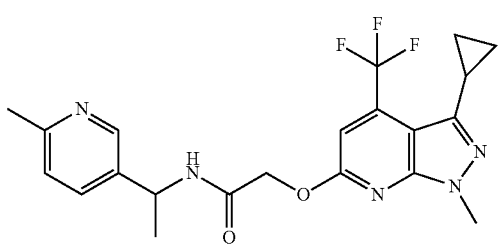 [SMILES: Cc1ccc(C(C)NC(=O)COc2cc(C(F)(F)F)c3c(C4CC4)nn(C)c3n2)cn1] | 2-(3-cyclopropyl-1-methyl-4-(trifluoromethyl)-1H-pyrazolo[3,4-b]pyridin-6-yloxy)-N-(1-(6-methylpyridin-3-yl)ethyl)acetamide | 0.96 (J) | 434.4 |
| 6.17 | 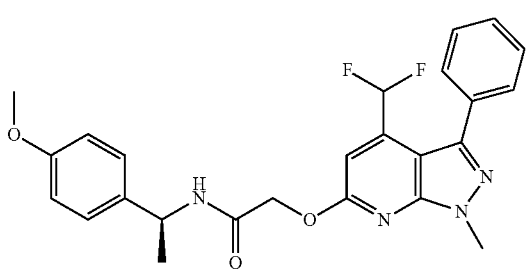 [SMILES: COc1ccc([C@H](C)NC(=O)COc2cc(C(F)F)c3c(-c4ccccc4)nn(C)c3n2)cc1] | (S)-2-(4-(difluoromethyl)-1-methyl-3-phenyl-1H-pyrazolo[3,4-b]pyridin-6-yloxy)-N-(1-(4-methoxyphenyl)ethyl)acetamide | 1.18 (J) | 467.4 |
| 6.18 | 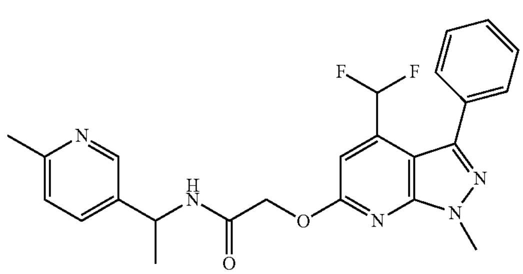 [SMILES: Cc1ccc(C(C)NC(=O)COc2cc(C(F)F)c3c(-c4ccccc4)nn(C)c3n2)cn1] | 2-(4-(difluoromethyl)-1-methyl-3-phenyl-1H-pyrazolo[3,4-b]pyridin-6-yloxy)-N-(1-(6-methylpyridin-3-yl)ethyl)acetamide | 0.92 (J) | 452.4 |

TABLE 4-continued

Compounds Number 6.7 to 6.80

| Number | Structure | IUPAC Name | LCMS Rt [min] (method) | [M + H]+ |
|---|---|---|---|---|
| 6.19 | 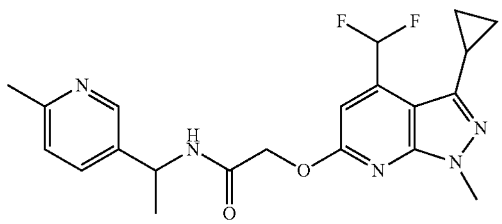 [SMILES: Cc1ccc(C(C)NC(=O)COc2cc(C(F)F)c3c(C4CC4)nn(C)c3n2)cn1] | 2-(3-cyclopropyl-4-(difluoromethyl)-1-methyl-1H-pyrazolo[3,4-b]pyridin-6-yloxy)-N-(1-(6-methylpyridin-3-yl)ethyl)acetamide | 0.82 (J) | 416.3 |
| 6.20 | 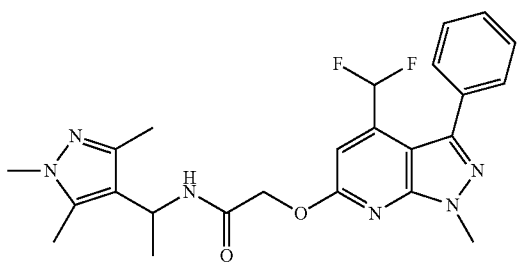 [SMILES: Cc1nn(C)c(C)c1C(C)NC(=O)COc1cc(C(F)F)c2c(-c3ccccc3)nn(C)c2n1] | 2-(4-(difluoromethyl)-1-methyl-3-phenyl-1H-pyrazolo[3,4-b]pyridin-6-yloxy)-N-(1-(1,3,5-trimethyl-1H-pyrazol-4-yl)ethyl)acetamide | 1.02 (J) | 469.4 |
| 6.21 | 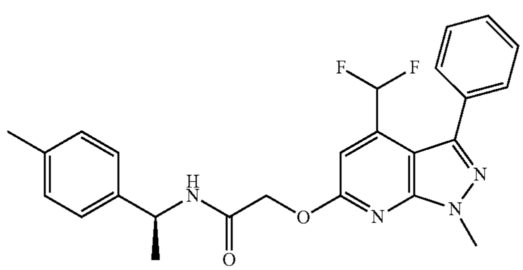 [SMILES: Cc1ccc([C@H](C)NC(=O)COc2cc(C(F)F)c3c(-c4ccccc4)nn(C)c3n2)cc1] | (S)-2-(4-(difluoromethyl)-1-methyl-3-phenyl-1H-pyrazolo[3,4-b]pyridin-6-yloxy)-N-(1-p-tolylethyl)acetamide | 1.24 (J) | 451.4 |
| 6.22 | 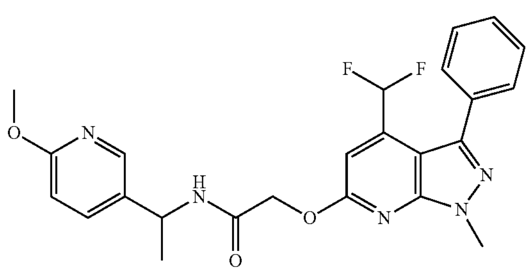 [SMILES: COc1ccc(C(C)NC(=O)COc2cc(C(F)F)c3c(-c4ccccc4)nn(C)c3n2)cn1] | 2-(4-(difluoromethyl)-1-methyl-3-phenyl-1H-pyrazolo[3,4-b]pyridin-6-yloxy)-N-(1-(6-methoxypyridin-3-yl)ethyl)acetamide | 1.11 (J) | 468.4 |
| 6.23 | 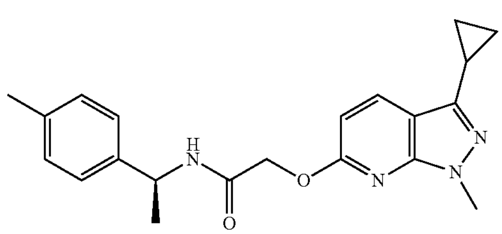 [SMILES: Cc1ccc([C@H](C)NC(=O)COc2ccc3c(C4CC4)nn(C)c3n2)cc1] | (S)-2-(3-cyclopropyl-1-methyl-1H-pyrazolo[3,4-b]pyridin-6-yloxy)-N-(1-p-tolylethyl)acetamide | 1.11 (J) | 365.4 |

TABLE 4-continued

Compounds Number 6.7 to 6.80

| Number | Structure | IUPAC Name | LCMS Rt [min] (method) | [M + H]+ |
|---|---|---|---|---|
| 6.24 | 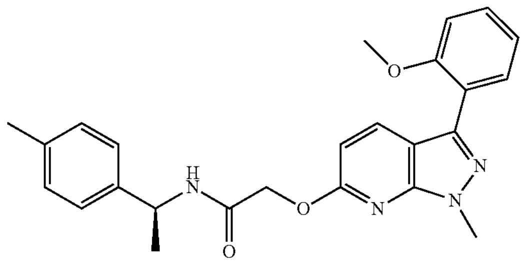 [SMILES: COc1ccccc1-c1nn(C)c2nc(OCC(=O)N[C@@H](C)c3ccc(C)cc3)ccc12] | (S)-2-(3-(2-methoxyphenyl)-1-methyl-1H-pyrazolo[3,4-b]pyridin-6-yloxy)-N-(1-p-tolylethyl)acetamide | 1.20 (J) | 431.4 |
| 6.25 | 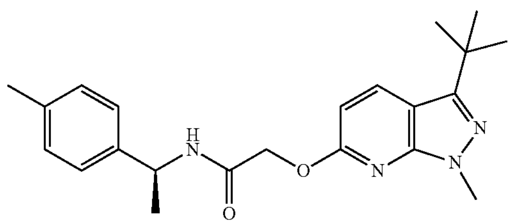 [SMILES: Cc1ccc([C@H](C)NC(=O)COc2ccc3c(C(C)(C)C)nn(C)c3n2)cc1] | (S)-2-(3-tert-butyl-1-methyl-1H-pyrazolo[3,4-b]pyridin-6-yloxy)-N-(1-p-tolylethyl)acetamide | 1.24 (J) | 381.4 |
| 6.26 | 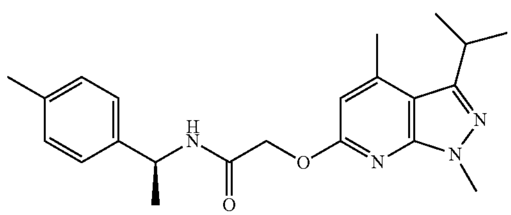 [SMILES: Cc1ccc([C@H](C)NC(=O)COc2cc(C)c3c(C(C)C)nn(C)c3n2)cc1] | (S)-2-(3-isopropyl-1,4-dimethyl-1H-pyrazolo[3,4-b]pyridin-6-yloxy)-N-(1-p-tolylethyl)acetamide | 1.20 (J) | 381.4 |
| 6.27 | 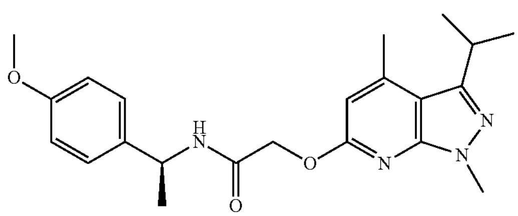 [SMILES: COc1ccc([C@H](C)NC(=O)COc2cc(C)c3c(C(C)C)nn(C)c3n2)cc1] | (S)-2-(3-isopropyl-1,4-dimethyl-1H-pyrazolo[3,4-b]pyridin-6-yloxy)-N-(1-(4-methoxyphenyl)ethyl)acetamide | 1.13 (J) | 379.4 |
| 6.28 | 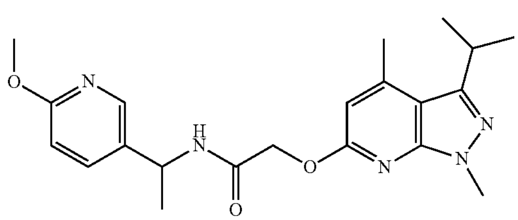 [SMILES: COc1ccc(C(C)NC(=O)COc2cc(C)c3c(C(C)C)nn(C)c3n2)cn1] | 2-(3-isopropyl-1,4-dimethyl-1H-pyrazolo[3,4-b]pyridin-6-yloxy)-N-(1-(6-methoxypyridin-3-yl)ethyl)acetamide | 1.04 (J) | 398.3 |
| 6.29 | 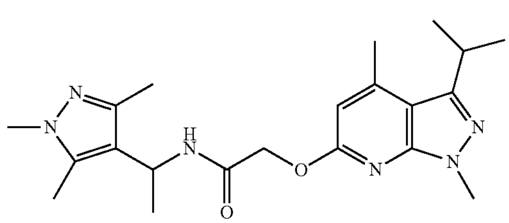 [SMILES: Cc1nn(C)c(C)c1C(C)NC(=O)COc1cc(C)c2c(C(C)C)nn(C)c2n1] | 2-(3-isopropyl-1,4-dimethyl-1H-pyrazolo[3,4-b]pyridin-6-yloxy)-N-(1-(1,3,5-trimethyl-1H-pyrazol-4-yl)ethyl)acetamide | 0.94 (J) | 399.4 |

TABLE 4-continued

Compounds Number 6.7 to 6.80

| Number | Structure | IUPAC Name | LCMS Rt [min] (method) | [M + H]+ |
|---|---|---|---|---|
| 6.30 | 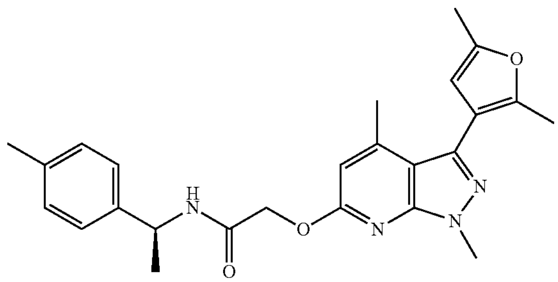 | (S)-2-(3-(2,5-dimethylfuran-3-yl)-1,4-dimethyl-1H-pyrazolo[3,4-b]pyridin-6-yloxy)-N-(1-p-tolylethyl)acetamide | 1.23 (J) | 433.1 |
| 6.31 | 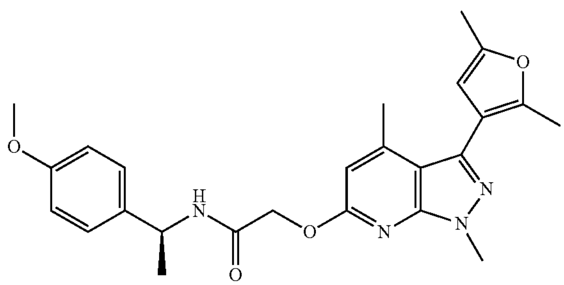 [SMILES: COc1ccc([C@H](C)NC(=O)COc2cc(C)c3c(-c4cc(C)oc4C)nn(C)c3n2)cc1] | (S)-2-(3-(2, 5-dimethylfuran-3-yl)-1,4-dimethyl-1H-pyrazolo[3,4-b]pyridin-6-yloxy)-N-(1-(4-methoxyphenyl)ethyl)acetamide | 1.17 (J) | 449.1 |
| 6.32 | 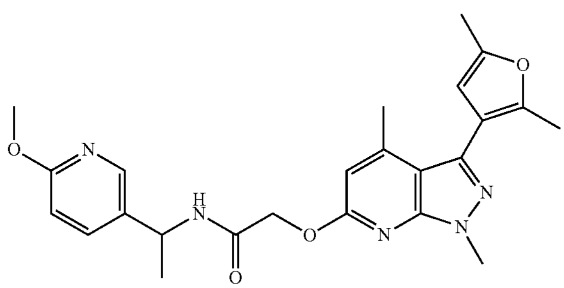 [SMILES: COc1ccc(C(C)NC(=O)COc2cc(C)c3c(-c4cc(C)oc4C)nn(C)c3n2)cn1] | 2-(3-(2,5-dimethylfuran-3-yl)-1,4-dimethyl-1H-pyrazolo[3,4-b]pyridin-6-yloxy)-N-(1-(6-methoxypyridin-3-yl)ethyl)acetamide | 1.09 (J) | 450.1 |
| 6.33 | 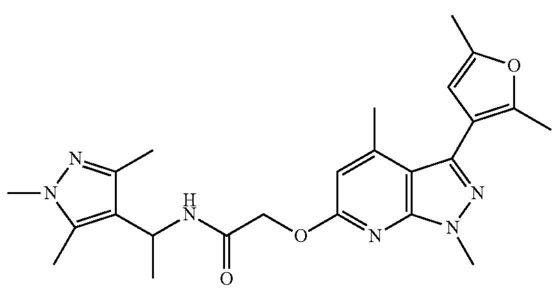 | 2-(3-(2, 5-dimethylfuran-3-yl)-1,4-dimethyl-1H-pyrazolo[3,4-b]pyridin-6-yloxy)-N-(1-(1,3,5-trimethyl-1H-pyrazol-4-yl)ethyl)acetamide | 1.01 (J) | 451.2 |
| 6.34 | 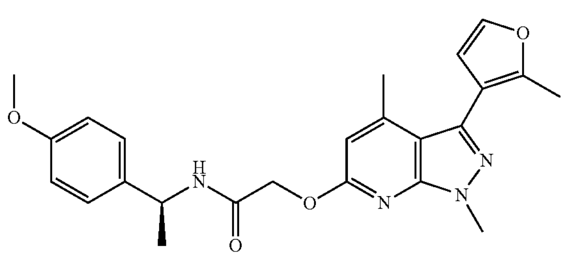 [SMILES: COc1ccc([C@H](C)NC(=O)COc2cc(C)c3c(-c4ccoc4C)nn(C)c3n2)cc1] | (S)-2-(1,4-dimethyl-3-(2-methylfuran-3-yl)-1H-pyrazolo[3,4-b]pyridin-6-yloxy)-N-(1-(4-methoxyphenyl)ethyl)acetamide | 1.12 (J) | 435.4 |

TABLE 4-continued

Compounds Number 6.7 to 6.80

| Number | Structure | IUPAC Name | LCMS Rt [min] (method) | [M + H]+ |
|---|---|---|---|---|
| 6.35 | 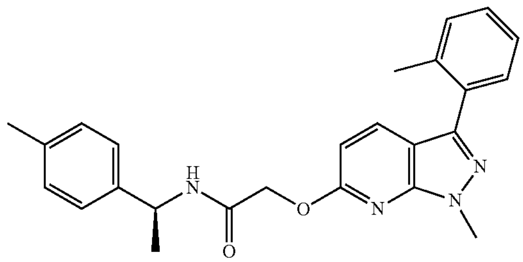 [SMILES: Cc1ccc([C@H](C)NC(=O)COc2ccc3c(-c4ccccc4C)nn(C)c3n2)cc1] | (S)-2-(1-methyl-3-o-tolyl-1H-pyrazolo[3,4-b]pyridin-6-yloxy)-N-(1-p-tolylethyl)acetamide | 1.26 (J) | 415.4 |
| 6.36 | 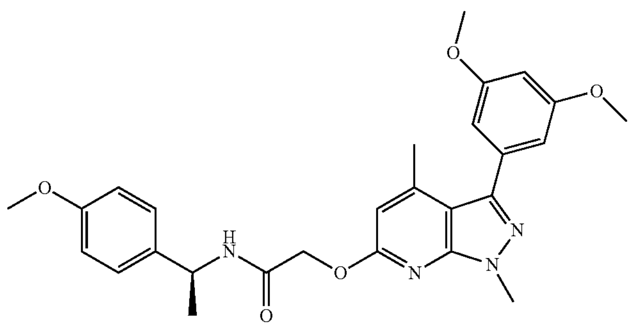 | (S)-2-(3-(3,5-dimethoxyphenyl)-1,4-dimethyl-1H-pyrazolo[3,4-b]pyridin-6-yloxy)-N-(1-(4-methoxyphenyl)ethyl)acetamide | 1.14 (J) | 491.2 |
| 6.37 | 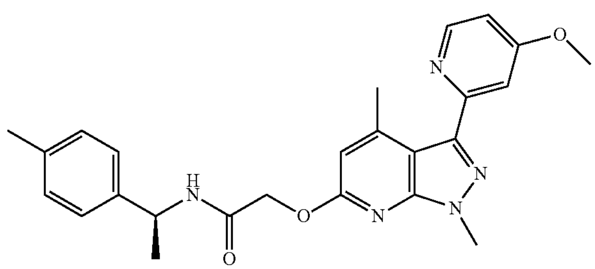 | (S)-2-(3-(4-methoxypyridin-2-yl)-1,4-dimethyl-1H-pyrazolo[3,4-b]pyridin-6-yloxy)-N-(1-p-tolylethyl)acetamide | 1.06 (J) | 446.1 |
| 6.38 | 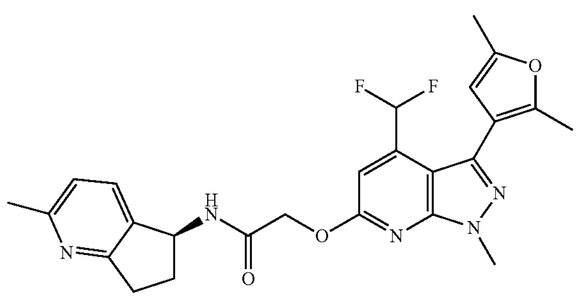 | (S)-2-(4-(difluoromethyl)-3-(2,5-dimethylfuran-3-yl)-1-methyl-1H-pyrazolo[3,4-b]pyridin-6-yloxy)-N-(2-methyl-6,7-dihydro-5H-cyclopenta[b]pyridin-5-yl)acetamide | 2.907 (L) | 482.2 |
| 6.39 | 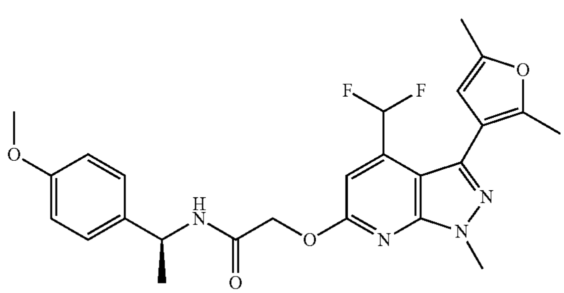 [SMILES: COc1ccc([C@H](C)NC(=O)COc2cc(C(F)F)c3c(-c4cc(C)oc4C)nn(C)c3n2)cc1] | (S)-2-(4-(difluoromethyl)-3-(2,5-dimethylfuran-3-yl)-1-methyl-1H-pyrazolo[3,4-b]pyridin-6-yloxy)-N-(1-(4-methoxyphenyl)ethyl)acetamide | 2.183 (M) | 485.2 |

TABLE 4-continued

Compounds Number 6.7 to 6.80

| Number | Structure | IUPAC Name | LCMS Rt [min] (method) | [M + H]+ |
|---|---|---|---|---|
| 6.40 | 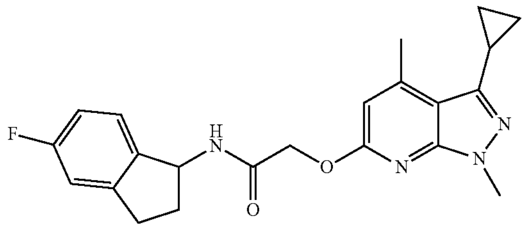 [SMILES: Cc1cc(OCC(=O)NC2CCc3cc(F)ccc32)nc2c1c(C1CC1)nn2C] | 2-(3-cyclopropyl-1,4-dimethyl-1H-pyrazolo[3,4-b]pyridin-6-yloxy)-N-(5-fluoro-2,3-dihydro-1H-inden-1-yl)acetamide | 3.208 (H) | 395.2 |
| 6.41 | 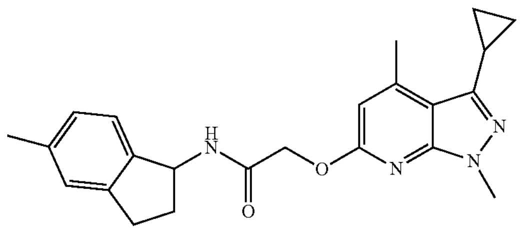 [SMILES: Cc1ccc2c(c1)CCC2NC(=O)COc1cc(C)c2c(C3CC3)nn(C)c2n1] | 2-(3-cyclopropyl-1,4-dimethyl-1H-pyrazolo[3,4-b]pyridin-6-yloxy)-N-(5-methyl-2,3-dihydro-1H-inden-1-yl)acetamide | 3.423 (H) | 391.2 |
| 6.42 | 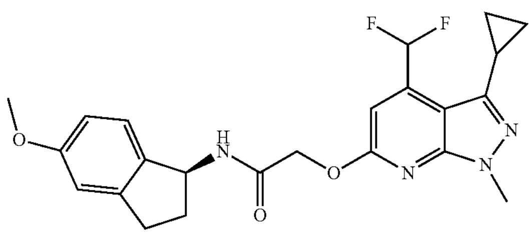 [SMILES: COc1ccc2c(c1)CC[C@@H]2NC(=O)COc1cc(C(F)F)c2c(C3CC3)nn(C)c2n1] | (S)-2-(3-cyclopropyl-4-(difluoromethyl)-1-methyl-1H-pyrazolo[3,4-b]pyridin-6-yloxy)-N-(5-methoxy-2,3-dihydro-1H-inden-1-yl)acetamide | 3.171 (H) | 443.2 |
| 6.43 | 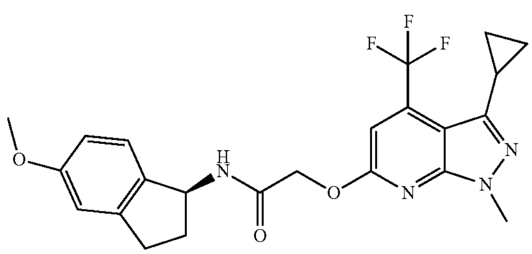 [SMILES: COc1ccc2c(c1)CC[C@@H]2NC(=O)COc1cc(C(F)(F)F)c2c(C3CC3)nn(C)c2n1] | (S)-2-(3-cyclopropyl-1-methyl-4-(trifluoromethyl)-1H-pyrazolo[3,4-b]pyridin-6-yloxy)-N-(5-methoxy-2,3-dihydro-1H-inden-1-yl)acetamide | 3.549 (H) | 461.0 |
| 6.44 | 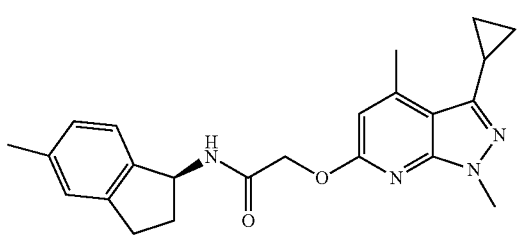 [SMILES: Cc1ccc2c(c1)CC[C@@H]2NC(=O)COc1cc(C)c2c(C3CC3)nn(C)c2n1] | (S)-2-(3-cyclopropyl-1,4-dimethyl-1H-pyrazolo[3,4-b]pyridin-6-yloxy)-N-(5-methyl-2,3-dihydro-1H-inden-1-yl)acetamide | 3.379 (H) | 391.2 |
| 6.45 | 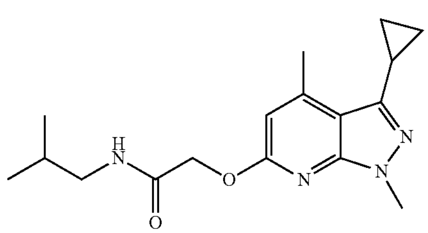 [SMILES: Cc1cc(OCC(=O)NCC(C)C)nc2c1c(C1CC1)nn2C] | 2-(3-cyclopropyl-1,4-dimethyl-1H-pyrazolo[3,4-b]pyridin-6-yloxy)-N-isobutylacetamide | 2.648 (H) | 317.2 |

TABLE 4-continued

Compounds Number 6.7 to 6.80

| Number | Structure | IUPAC Name | LCMS Rt [min] (method) | [M + H]+ |
|---|---|---|---|---|
| 6.46 | 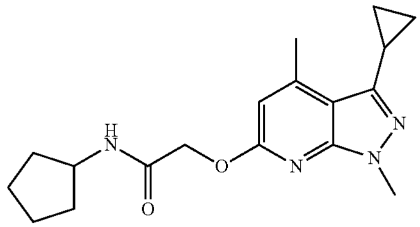 [SMILES: Cc1cc(OCC(=O)NC2CCCC2)nc2c1c(C1CC1)nn2C] | N-cyclopentyl-2-(3-cyclopropyl-1,4-dimethyl-1H-pyrazolo[3,4-b]pyridin-6-yloxy)acetamide | 2.770 (H) | 329.2 |
| 6.47 | 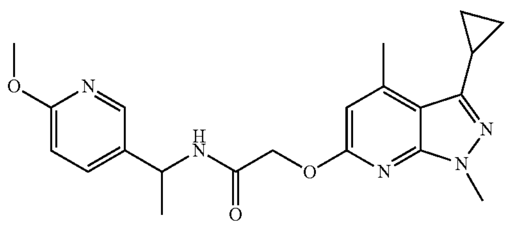 [SMILES: COc1ccc(C(C)NC(=O)COc2cc(C)c3c(C4CC4)nn(C)c3n2)cn1] | 2-(3-cyclopropyl-1,4-dimethyl-1H-pyrazolo[3,4-b]pyridin-6-yloxy)-N-(1-(6-methoxypyridin-3-yl)ethyl)acetamide | 2.127 (H) | 396.2 |
| 6.48 | 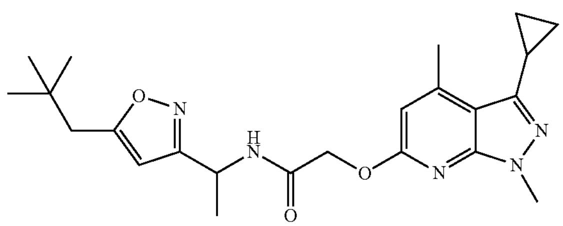 [SMILES: Cc1cc(OCC(=O)NC(C)c2cc(CC(C)(C)C)on2)nc2c1c(C1CC1)nn2C] | 2-(3-cyclopropyl-1,4-dimethyl-1H-pyrazolo[3,4-b]pyridin-6-yloxy)-N-(1-(5-neopentylisoxazol-3-yl)ethyl)acetamide | 2.921 (K) | 426.2 |
| 6.49 | 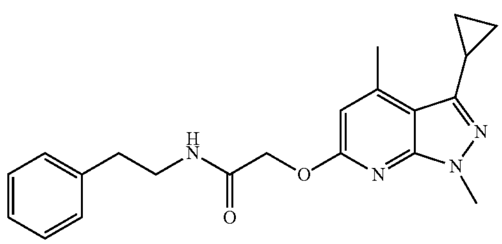 [SMILES: Cc1cc(OCC(=O)NCCc2ccccc2)nc2c1c(C1CC1)nn2C] | 2-(3-cyclopropyl-1,4-dimethyl-1H-pyrazolo[3,4-b]pyridin-6-yloxy)-N-phenethylacetamide | 2.318 (K) | 365.2 |
| 6.50 | 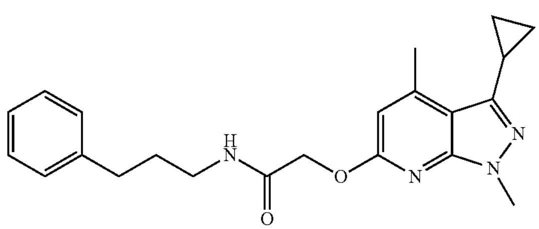 [SMILES: Cc1cc(OCC(=O)NCCCc2ccccc2)nc2c1c(C1CC1)nn2C] | 2-(3-cyclopropyl-1,4-dimethyl-1H-pyrazolo[3,4-b]pyridin-6-yloxy)-N-(3-phenylpropyl)acetamide | 2.553 (K) | 379.2 |
| 6.51 | 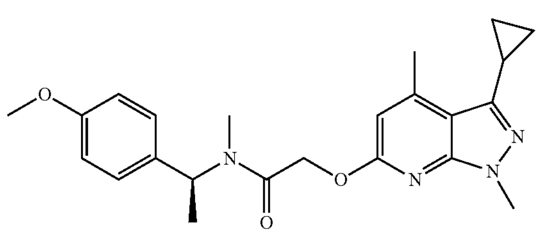 [SMILES: COc1ccc([C@H](C)N(C)C(=O)COc2cc(C)c3c(C4CC4)nn(C)c3n2)cc1] | 2-(3-cyclopropyl-1,4-dimethyl-1H-pyrazolo[3,4-b]pyridin-6-yloxy)-N-(3-phenylpropyl)acetamide | 3.150 (H) | 409.2 |

TABLE 4-continued

Compounds Number 6.7 to 6.80

| Number | Structure | IUPAC Name | LCMS Rt [min] (method) | [M + H]+ |
|---|---|---|---|---|
| 6.52 | 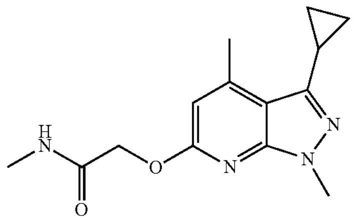 [SMILES: CNC(=O)COc1cc(C)c2c(C3CC3)nn(C)c2n1] | (S)-2-(3-cyclopropyl-1,4-dimethyl-1H-pyrazolo[3,4-b]pyridin-6-yloxy)-N-(1-(4-methoxyphenyl)ethyl)-N-methylacetamide | 2.885 (L) | 275.2 |
| 6.53 | 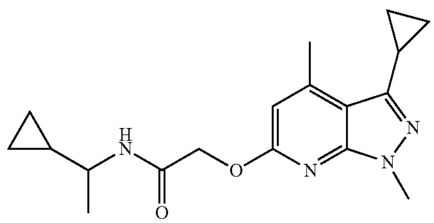 [SMILES: Cc1cc(OCC(=O)NC(C)C2CC2)nc2c1c(C1CC1)nn2C] | 2-(3-cyclopropyl-1,4-dimethyl-1H-pyrazolo[3,4-b]pyridin-6-yloxy)-N-methylacetamide | 2.727 (H) | 329.2 |
| 6.54 | 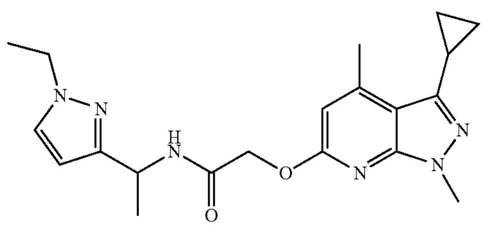 [SMILES: CCn1ccc(C(C)NC(=O)COc2cc(C)c3c(C4CC4)nn(C)c3n2)n1] | 2-(3-cyclopropyl-1,4-dimethyl-1H-pyrazolo[3,4-b]pyridin-6-yloxy)-N-(1-cyclopropylethyl)acetamide | 2.292 (H) | 383.2 |
| 6.55 | 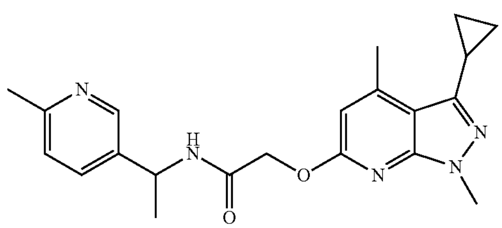 [SMILES: Cc1ccc(C(C)NC(=O)COc2cc(C)c3c(C4CC4)nn(C)c3n2)cn1] | 2-(3-cyclopropyl-1,4-dimethyl-1H-pyrazolo[3,4-b]pyridin-6-yloxy)-N-(1-(1-ethyl-1H-pyrazol-3-yl)ethyl)acetamide | 2.644 (L) | 380.2 |
| 6.56 | 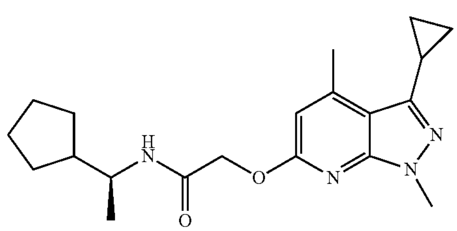 [SMILES: Cc1cc(OCC(=O)N[C@@H](C)C2CCCC2)nc2c1c(C1CC1)nn2C] | (S)-N-(1-cyclopentylethyl)-2-(3-cyclopropyl-1,4-dimethyl-1H-pyrazolo[3,4-b]pyridin-6-yloxy)acetamide | 1.876 (M) | 357.2 |
| 6.57 | 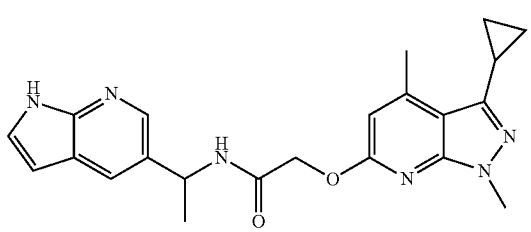 [SMILES: Cc1cc(OCC(=O)NC(C)c2cnc3[nH]ccc3c2)nc2c1c(C1CC1)nn2C] | N-(1-(1H-pyrrolo[2,3-b]pyridin-5-yl)ethyl)-2-(3-cyclopropyl-1,4-dimethyl-1H-pyrazolo[3,4-b]pyridin-6-yloxy)acetamide | 2.762 (L) | 405.2 |

TABLE 4-continued

Compounds Number 6.7 to 6.80

| Number | Structure | IUPAC Name | LCMS Rt [min] (method) | [M + H]+ |
|---|---|---|---|---|
| 6.58 | 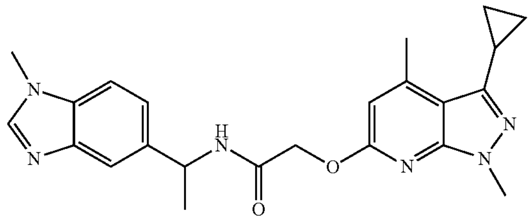 [SMILES: Cc1cc(OCC(=O)NC(C)c2ccc3c(c2)ncn3C)nc2c1c(C1CC1)nn2C] | 2-(3-cyclopropyl-1,4-dimethyl-1H-pyrazolo[3,4-b]pyridin-6-yloxy)-N-(1-(1-methyl-1H-benzo[d]imidazol-5-yl)ethyl)acetamide | 2.661 (L) | 419.2 |
| 6.59 | 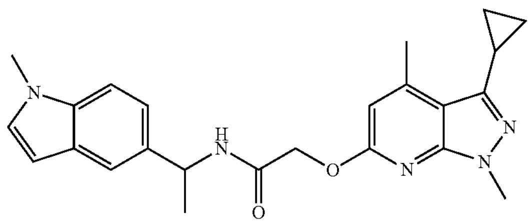 [SMILES: Cc1cc(OCC(=O)NC(C)c2ccc3c(ccn3C)c2)nc2c1c(C1CC1)nn2C] | 2-(3-cyclopropyl-1,4-dimethyl-1H-pyrazolo[3,4-b]pyridin-6-yloxy)-N-(1-(1-methyl-1H-indol-5-yl)ethyl)acetamide | 2.503 (K) | 418.2 |
| 6.60 | 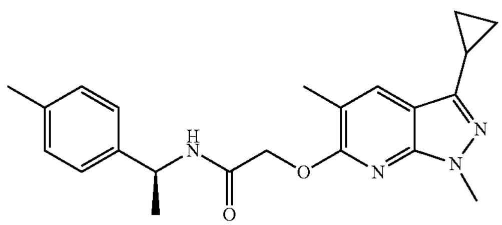 [SMILES: Cc1ccc([C@H](C)NC(=O)COc2nc3c(cc2C)c(C2CC2)nn3C)cc1] | (S)-2-(3-cyclopropyl-1,5-dimethyl-1H-pyrazolo[3,4-b]pyridin-6-yloxy)-N-(1-p-tolylethyl)acetamide | 2.700 (K) | 379.2 |
| 6.61 | 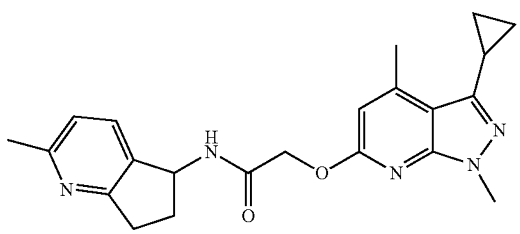 [SMILES: Cc1ccc2c(n1)CCC2NC(=O)COc1cc(C)c2c(C3CC3)nn(C)c2n1] | 2-(3-cyclopropyl-1,4-dimethyl-1H-pyrazolo[3,4-b]pyridin-6-yloxy)-N-(2-methyl-6,7-dihydro-5H-cyclopenta[b]pyridin-5-yl)acetamide | 2.925 (I) | 392.2 |
| 6.62 | 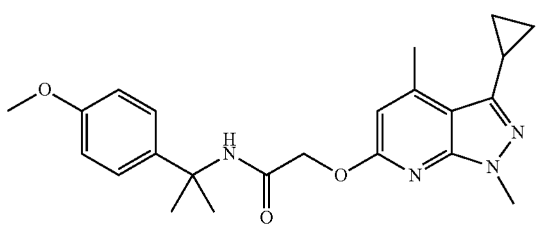 [SMILES: COc1ccc(C(C)(C)NC(=O)COc2cc(C)c3c(C4CC4)nn(C)c3n2)cc1] | 2-(3-cyclopropyl-1,4-dimethyl-1H-pyrazolo[3,4-b]pyridin-6-yloxy)-N-(2-(4-methoxyphenyl)propan-2-yl)acetamide | 2.689 (K) | 409.2 |
| 6.63 | 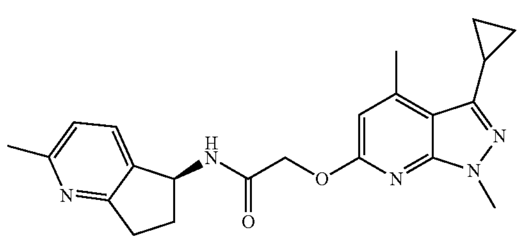 [SMILES: Cc1ccc2c(n1)CC[C@@H]2NC(=O)COc1cc(C)c2c(C3CC3)nn(C)c2n1] | (S)-2-(3-cyclopropyl-1H-dimethyl-1H-pyrazolo[3,4-b]pyridin-6-yloxy)-N-(2-methyl-6,7-dihydro-5H-cyclopenta[b]pyridin-5-yl)acetamide | 2.925 (I) | 392.2 |

TABLE 4-continued

Compounds Number 6.7 to 6.80

| Number | Structure | IUPAC Name | LCMS Rt [min] (method) | [M + H]+ |
|---|---|---|---|---|
| 6.64 | 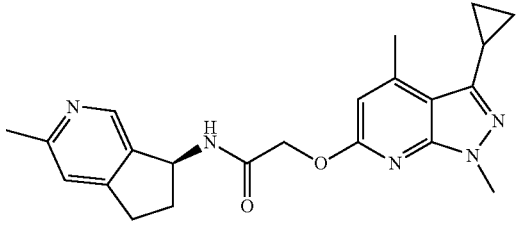 [SMILES: Cc1cc2c(cn1)[C@@H](NC(=O)COc1cc(C)c3c(C4CC4)nn(C)c3n1)CC2] | (S)-2-(3-cyclopropyl-1,4-dimethyl-1H-pyrazolo[3,4-b]pyridin-6-yloxy)-N-(3-methyl-6,7-dihydro-5H-cyclopenta[c]pyridin-7-yl)acetamide | 2.949 (I) | 392.2 |
| 6.65 | 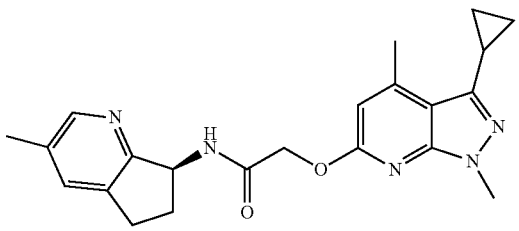 [SMILES: Cc1cnc2c(c1)CC[C@@H]2NC(=O)COc1cc(C)c2c(C3CC3)nn(C)c2n1] | (S)-2-(3-cyclopropyl-1,4-dimethyl-1H-pyrazolo[3,4-b]pyridin-6-yloxy)-N-(3-methyl-6,7-dihydro-5H-cyclopenta[b]pyridin-7-yl)acetamide | 2.727 (L) | 392.2 |
| 6.66 | 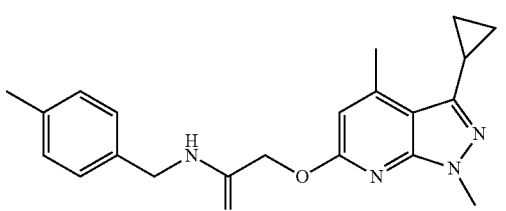 | 2-(3-cyclopropyl-1,4-dimethyl-1H-pyrazolo[3,4-b]pyridin-6-yloxy)-N-(4-methylbenzyl)acetamide | 3.017 (H) | 365.2 |
| 6.67 | 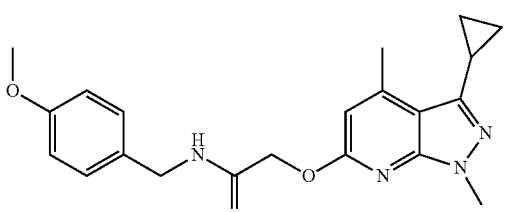 | 2-(3-cyclopropyl-1,4-dimethyl-1H-pyrazolo[3,4-b]pyridin-6-yloxy)-N-(4-methoxybenzyl)acetamide | 2.736 (H) | 381.2 |
| 6.68 | 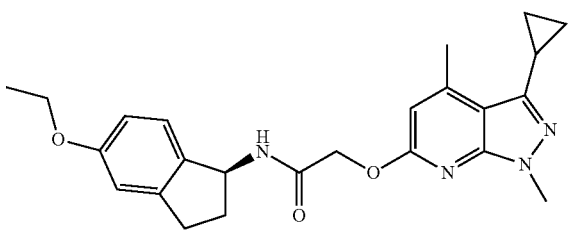 [SMILES: CCOc1ccc2c(c1)CC[C@@H]2NC(=O)COc1cc(C)c2c(C3CC3)nn(C)c2n1] | (S)-2-(3-cyclopropyl-1,4-dimethyl-1H-pyrazolo[3,4-b]pyridin-6-yloxy)-N-(5-ethoxy-2,3-dihydro-1H-inden-1-yl)acetamide | 3.296 (H) | 421.2 |
| 6.69 | 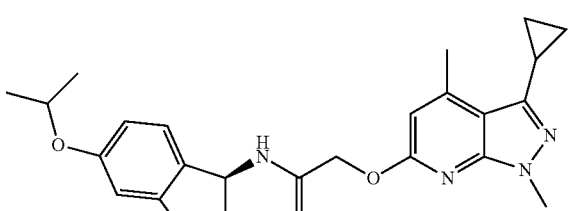 | (S)-2-(3-cyclopropyl-1,4-dimethyl-1H-pyrazolo[3,4-b]pyridin-6-yloxy)-N-(5-isopropoxy-2,3-dihydro-1H-inden-1-yl)acetamide | 3.503 (H) | 435.2 |

TABLE 4-continued

Compounds Number 6.7 to 6.80

| Number | Structure | IUPAC Name | LCMS Rt [min] (method) | [M + H]+ |
|---|---|---|---|---|
| 6.70 | 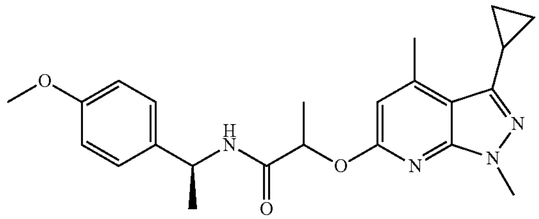 [SMILES: COc1ccc([C@H](C)NC(=O)C(C)Oc2cc(C)c3c(C4CC4)nn(C)c3n2)cc1] | 2-(3-cyclopropyl-1,4-dimethyl-1H-pyrazolo[3,4-b]pyridin-6-yloxy)-N-((S)-1-(4-methoxyphenyl)ethyl)propanamide | 2.94/3.02 (H) | 409.2 |
| 6.71 | diastereomer A | (R or S)-2-(3-cyclopropyl-1,4-dimethyl-1H-pyrazolo[3,4-b]pyridin-6-yloxy)-N-((S)-5-methoxy-2,3-dihydro-1H-inden-1-yl)propanamide | 3.134 (H) | 421.2 |
| 6.72 | diastereomer B | (S or R)-2-(3-cyclopropyl-1,4-dimethyl-1H-pyrazolo[3,4-b]pyridin-6-yloxy)-N-((S)-5-methoxy-2,3-dihydro-1H-inden-1-yl)propanamide | 3.189 (H) | |
| 6.73 | diastereomer B | (S or R)-2-(3-cyclopropyl-1,4-dimethyl-1H-pyrazolo[3,4-b]pyridin-6-yloxy)-N-((S)-1-(4-methoxyphenyl)ethyl)propanamide | 3.035 (H) | 409.2 |
| 6.74 | 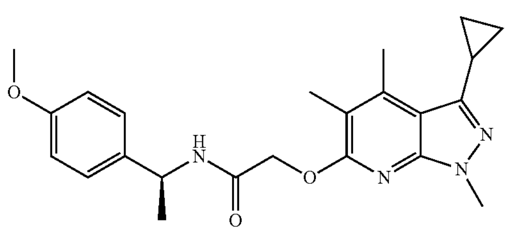 [SMILES: COc1ccc([C@H](C)NC(=O)COc2nc3c(c(C4CC4)nn3C)c(C)c2C)cc1] | (S)-2-(3-cyclopropyl-1,4,5-trimethyl-1H-pyrazolo[3,4-b]pyridin-6-yloxy)-N-(1-(4-methoxyphenyl)ethyl)acetamide | 2.597 (K) | 409.2 |
| 6.75 | 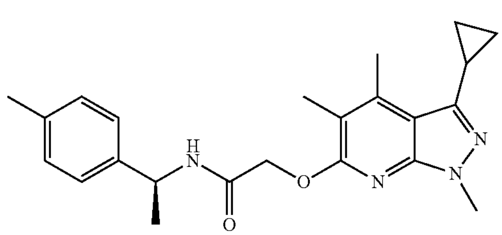 [SMILES: Cc1ccc([C@H](C)NC(=O)COc2nc3c(c(C4CC4)nn3C)c(C)c2C)cc1] | (S)-2-(3-cyclopropyl-1,4,5-trimethyl-1H-pyrazolo[3,4-b]pyridin-6-yloxy)-N-(1-p-tolylethyl)acetamide | 2.100 (M) | 393.2 |

TABLE 4-continued

Compounds Number 6.7 to 6.80

| Number | Structure | IUPAC Name | LCMS Rt [min] (method) | [M + H]+ |
|---|---|---|---|---|
| 6.76 | 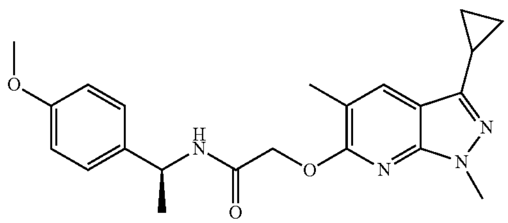 [SMILES: COc1ccc([C@H](C)NC(=O)COc2nc3c(cc2C)c(C2CC2)nn3C)cc1] | (S)-2-(3-cyclopropyl-1,5-dimethyl-1H-pyrazolo[3,4-b]pyridin-6-yloxy)-N-(1-(4-methoxyphenyl)ethyl)acetamide | 2.960 (H) | 395.2 |
| 6.77 | 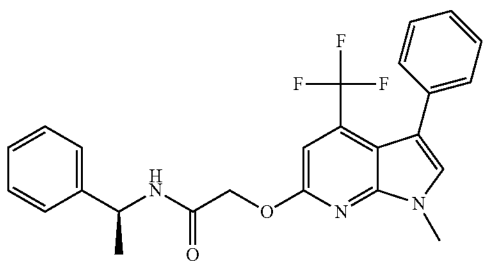 [SMILES: C[C@H](NC(=O)COc1cc(C(F)(F)F)c2c(-c3ccccc3)cn(C)c2n1)c1ccccc1] | (S)-2-(1-methyl-3-phenyl-4-(trifluoromethyl)-1H-pyrrolo[2,3-b]pyridin-6-yloxy)-N-(1-phenylethyl)acetamide | 2.07 (E) | 454.1 |
| 6.78 | 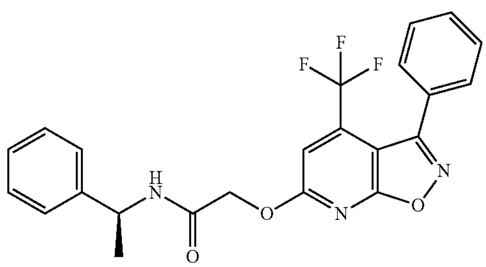 [SMILES: C[C@H](NC(=O)COc1cc(C(F)(F)F)c2c(-c3ccccc3)noc2n1)c1ccccc1] | (S)-2-(3-phenyl-4-(trifluoromethyl)isoxazolo[5,4-b]pyridin-6-yloxy)-N-(1-phenylethyl)acetamide | 0.51 (C) | 441.8 |
| 6.79 | 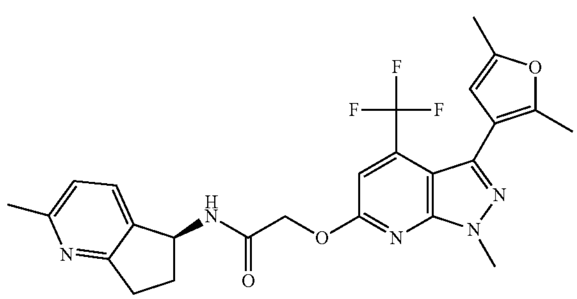 | (S)-2-(3-(2,5-dimethylfuran-3-yl)-1-methyl-4-(trifluoromethyl)-1H-pyrazolo[3,4-b]pyridin-6-yloxy)-N-(2-methyl-6,7-dihydro-5H-cyclopenta[b]pyridin-5-yl)acetamide | 3.049 (L) | 500.2 |
| 6.80 | 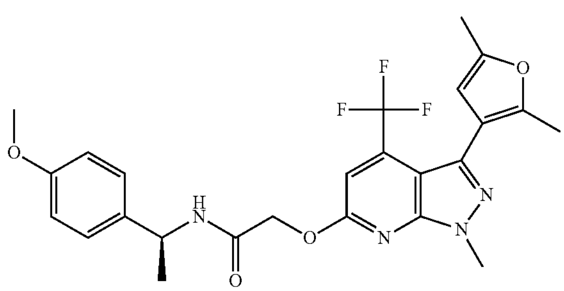 [SMILES: COc1ccc([C@H](C)NC(=O)COc2cc(C(F)(F)F)c3c(-c4cc(C)oc4C)nn(C)c3n2)cc1] | (S)-2-(3-(2,5-dimethylfuran-3-yl)-1-methyl-4-(trifluoromethyl)-1H-pyrazolo[3,4-b]pyridin-6-yloxy)-N-(1-(4-methoxyphenyl)ethyl)acetamide | 2.507 (M) | 503.2 |

METHOD G

Example 7.1

2-(3-cyclopropyl-1,4-dimethyl-1H-pyrazolo[3,4-b]pyridin-6-yloxy)-N-(5,6-dimethoxy-2,3-dihydro-1H-inden-1-yl)acetamide

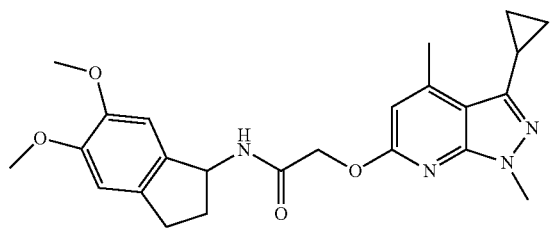 [SMILES: COc1cc2c(cc1OC)C(NC(=O)COc1cc(C)c3c(C4CC4)nn(C)c3n1)CC2]

A stock solution in DMF was prepared, containing HATU (160 mg, 0.421 mmol), NEt$_3$ (0.160 ml, 1.15 mmol), and (3-cyclopropyl-1,4-dimethyl-1H-pyrazolo[3,4-b]pyridin-6-yloxy)-acetic acid (100 mg, 0.383 mmol) per 1 ml DMF. The flask was flushed with argon and the mixture was stirred for 20 min at rt.

This stock solution (1.16 ml) was added to 5,6-dimethoxy-indan-1-ylamine (0.383 mmol) and the reaction was stirred for 17 h at 70° C. The reaction was diluted with water (1 ml) and THF (1 ml) and filtered. The filtrate was purified by a preparative HPLC system using Waters ZQ MS detection under the following conditions: Waters X Bridge C18-ODB column [150×30 mm, 5 μm particle size]; the gradient was composed of eluent A (water containing 0.79 g/L ammonium carbonate) and eluent B (acetonitrile): 0-1.5 min (isocratic elution with 90% A:10% B) at 50 ml/min; 1.5-11.5 min (linear gradient from 90% A:10% B to 20% A:80% B) at 50 ml/min; 11.5-12.5 min (linear gradient from 20% A:80% B to 0% A:100% B) at 50 ml/min; 12.5-13.5 min (isocratic elution with 0% A:100% B) at 50 ml/min; The product was collected by MS detection. The solvent was removed by freeze drying to give the title compound as a colorless powder (53 mg, 32%). [1H-NMR (DMSO-d$_6$, 600 MHz) δ 8.41 (d, 1H), 6.83 (s, 1H), 6.59 (s, 1H), 6.48 (s, 1H), 5.27 (d, 1H), 5.26 (d, 1H), 3.72 (s, 3H), 3.70 (s, 3H), 3.43 (s, 3H), 2.88-2.83 (m, 1H), 2.73-2.68 (m, 1H), 2.65 (s, 3H), 2.38-2.33 (m, 1H), 2.28-2.23 (m, 1H), 1.86-1.80 (m, 1H), 0.92-0.85 (m, 4H); LCMS Rt$_N$=1.09 min; [M+H]$^+$=436.8]

TABLE 5

Compounds Number 7.2 to 7.33

| Number | Structure | IUPAC Name | LCMS Rt [min] (method) | [M + H]$^+$ |
|---|---|---|---|---|
| 7.2 | 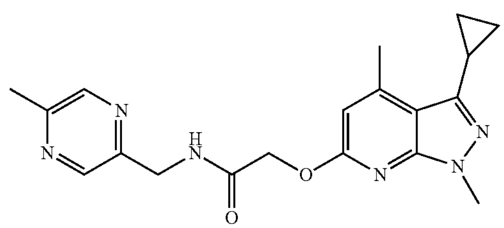 [SMILES: Cc1cnc(CNC(=O)COc2cc(C)c3c(C4CC4)nn(C)c3n2)cn1] | 2-(3-cyclopropyl-1,4-dimethyl-1H-pyrazolo[3,4-b]pyridin-6-yloxy)-N-((5-methylpyrazin-2-yl)methyl)acetamide | 0.94 (N) | 366.8 |
| 7.3 | 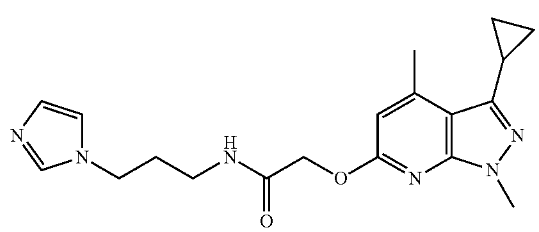 [SMILES: Cc1cc(OCC(=O)NCCCn2ccnc2)nc2c1c(C1CC1)nn2C] | N-(3-(1H-imidazol-1-yl)propyl)-2-(3-cyclopropyl-1,4-dimethyl-1H-pyrazolo[3,4-b]pyridin-6-yloxy)acetamide | 0.79 (N) | 368.8 |
| 7.4 | 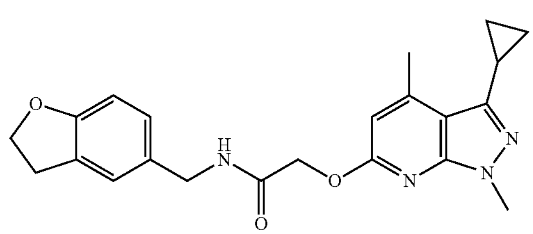 [SMILES: Cc1cc(OCC(=O)NCc2ccc3c(c2)CCO3)nc2c1c(C1CC1)nn2C] | 2-(3-cyclopropyl-1H-dimethyl-1H-pyrazolo[3,4-b]pyridin-6-yloxy)-N-((2,3-dihydrobenzofuran-5-yl)methyl)acetamide | 1.08 (N) | 392.8 |

TABLE 5-continued

Compounds Number 7.2 to 7.33

| Number | Structure | IUPAC Name | LCMS Rt [min] (method) | [M + H]+ |
|---|---|---|---|---|
| 7.5 | 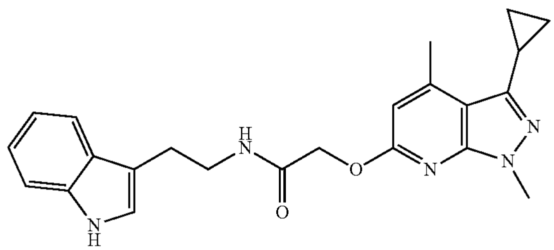 [SMILES: Cc1cc(OCC(=O)NCCc2c[nH]c3ccccc23)nc2c1c(C1CC1)nn2C] | N-(2-(1H-indol-3-yl)ethyl)-2-(3-cyclopropyl-1H-dimethyl-1H-pyrazolo[3,4-b]pyridin-6-yloxy)acetamide | 1.11 (N) | 403.8 |
| 7.6 | 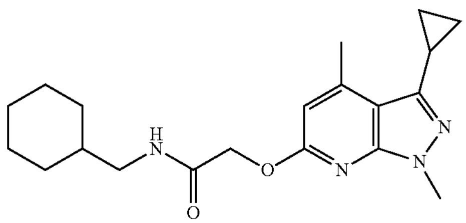 [SMILES: Cc1cc(OCC(=O)NCC2CCCCC2)nc2c1c(C1CC1)nn2C] | N-(cyclohexylmethyl)-2-(3-cyclopropyl-1,4-dimethyl-1H-pyrazolo[3,4-b]pyridin-6-yloxy)acetamide | 1.18 (N) | 356.9 |
| 7.7 | 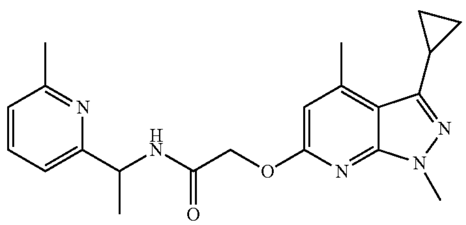 [SMILES: Cc1cccc(C(C)NC(=O)COc2cc(C)c3c(C4CC4)nn(C)c3n2)n1] | 2-(3-cyclopropyl-1,4-dimethyl-1H-pyrazolo[3,4-b]pyridin-6-yloxy)-N-(1-(6-methylpyridin-2-yl)ethyl)acetamide | 0.85 (N) | 379.8 |
| 7.8 | 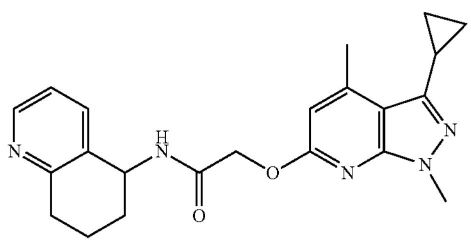 [SMILES: Cc1cc(OCC(=O)NC2CCCc3ncccc32)nc2c1c(C1CC1)nn2C] | 2-(3-cyclopropyl-1H-dimethyl-1H-pyrazolo[3,4-b]pyridin-6-yloxy)-N-(5,6,7,8-tetrahydroquinolin-5-yl)acetamide | 0.83 (N) | 391.8 |
| 7.9 | 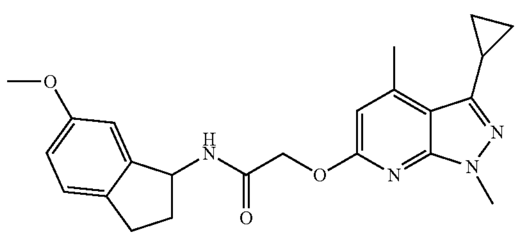 [SMILES: COc1ccc2c(c1)C(NC(=O)COc1cc(C)c3c(C4CC4)nn(C)c3n1)CC2] | 2-(3-cyclopropyl-1,4-dimethyl-1H-pyrazolo[3,4-b]pyridin-6-yloxy)-N-(6-methoxy-2,3-dihydro-1H-inden-1-yl)acetamide | 1.16 (N) | 406.8 |
| 7.10 | 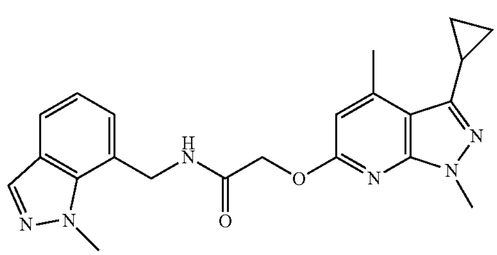 [SMILES: Cc1cc(OCC(=O)NCc2cccc3cnn(C)c23)nc2c1c(C1CC1)nn2C] | 2-(3-cyclopropyl-1,4-dimethyl-1H-pyrazolo[3,4-b]pyridin-6-yloxy)-N-((1-methyl-1H-indazol-7-yl)methyl)acetamide | 1.04 (N) | 404.8 |

TABLE 5-continued

Compounds Number 7.2 to 7.33

| Number | Structure | IUPAC Name | LCMS Rt [min] (method) | [M + H]+ |
|---|---|---|---|---|
| 7.11 | 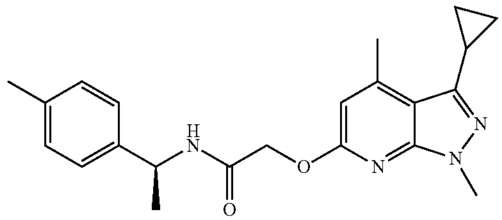 [SMILES: Cc1ccc([C@H](C)NC(=O)COc2cc(C)c3c(C4CC4)nn(C)c3n2)cc1] | (S)-2-(3-cyclopropyl-1,4-dimethyl-1H-pyrazolo[3,4-b]pyridin-6-yloxy)-N-(1-p-tolylethyl)acetamide | 1.17 (N) | 378.8 |
| 7.12 | 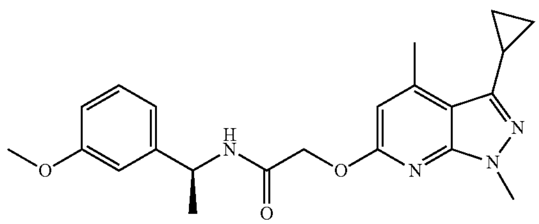 [SMILES: COc1cccc([C@H](C)NC(=O)COc2cc(C)c3c(C4CC4)nn(C)c3n2)c1] | (S)-2-(3-cyclopropyl-1,4-dimethyl-1H-pyrazolo[3,4-b]pyridin-6-yloxy)-N-(1-(3-methoxyphenyl)ethyl)acetamide | 1.12 (N) | 394.8 |
| 7.13 | 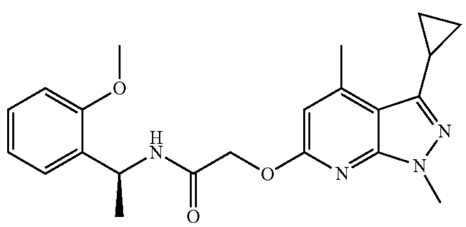 [SMILES: COc1ccccc1[C@H](C)NC(=O)COc1cc(C)c2c(C3CC3)nn(C)c2n1] | (S)-2-(3-cyclopropyl-1,4-dimethyl-1H-pyrazolo[3,4-b]pyridin-6-yloxy)-N-(1-(2-methoxyphenyl)ethyl)acetamide | 1.16 (N) | 394.8 |
| 7.14 | 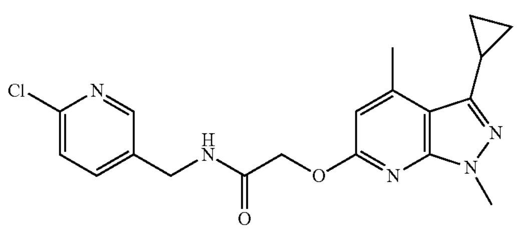 [SMILES: Cc1cc(OCC(=O)NCc2ccc(Cl)nc2)nc2c1c(C1CC1)nn2C] | N-((6-chloropyridin-3-yl)methyl)-2-(3-cyclopropyl-1,4-dimethyl-1H-pyrazolo[3,4-b]pyridin-6-yloxy)acetamide | 1.03 (N) | 385.7/ 387.9 |
| 7.15 | 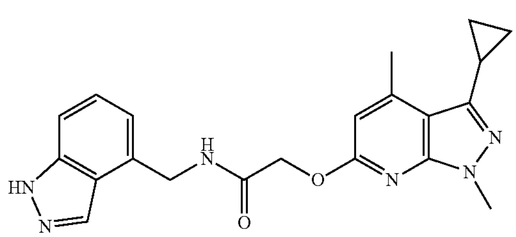 [SMILES: Cc1cc(OCC(=O)NCc2cccc3[nH]ncc23)nc2c1c(C1CC1)nn2C] | N-((1H-indazol-4-yl)methyl)-2-(3-cyclopropyl-1,4-dimethyl-1H-pyrazolo[3,4-b]pyridin-6-yloxy)acetamide | 0.97 (N) | 390.8 |
| 7.16 | 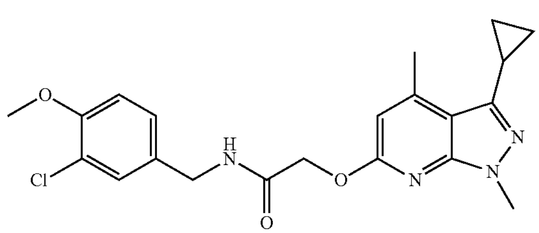 [SMILES: COc1ccc(CNC(=O)COc2cc(C)c3c(C4CC4)nn(C)c3n2)cc1Cl] | N-(3-chloro-4-methoxybenzyl)-2-(3-cyclopropyl-1,4-dimethyl-1H-pyrazolo[3,4-b]pyridin-6-yloxy)acetamide | 1.12 (N) | 414.7 |

TABLE 5-continued

Compounds Number 7.2 to 7.33

| Number | Structure | IUPAC Name | LCMS Rt [min] (method) | [M + H]+ |
|---|---|---|---|---|
| 7.17 | 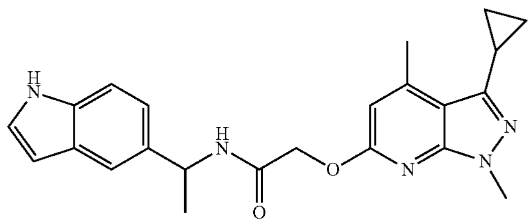 | N-(1-(1H-indol-5-yl)ethyl)-2-(3-cyclopropyl-1,4-dimethyl-1H-pyrazolo[3,4-b]pyridin-6-yloxy)acetamide | 1.09 (N) | 403.8 |
| 7.18 | 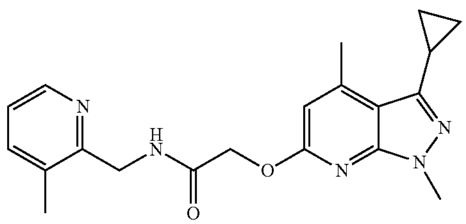 [SMILES: Cc1cccnc1CNC(=O)COc1cc(C)c2c(C3CC3)nn(C)c2n1] | 2-(3-cyclopropyl-1,4-dimethyl-1H-pyrazolo[3,4-b]pyridin-6-yloxy)-N-((3-methylpyridin-2-yl)methyl)acetamide | 0.84 (N) | 365.8 |
| 7.19 | 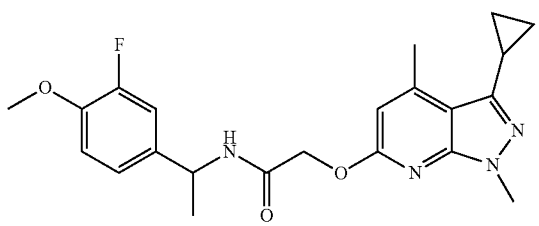 [SMILES: COc1ccc(C(C)NC(=O)COc2cc(C)c3c(C4CC4)nn(C)c3n2)cc1F] | 2-(3-cyclopropyl-1,4-dimethyl-1H-pyrazolo[3,4-b]pyridin-6-yloxy)-N-(1-(3-fluoro-4-methoxy-phenyl)ethyl)acetamide | 1.12 (N) | 412.8 |
| 7.20 | 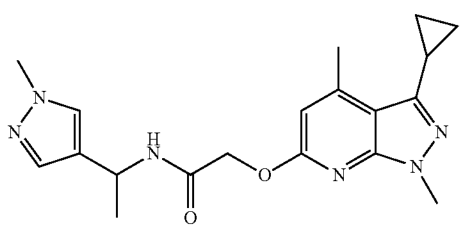 [SMILES: Cc1cc(OCC(=O)NC(C)c2cnn(C)c2)nc2c1c(C1CC1)nn2C] | 2-(3-cyclopropyl-1,4-dimethyl-1H-pyrazolo[3,4-b]pyridin-6-yloxy)-N-(1-(1-methyl-1H-pyrazol-4-yl)ethyl)acetamide | 0.95 (N) | 368.8 |
| 7.21 | 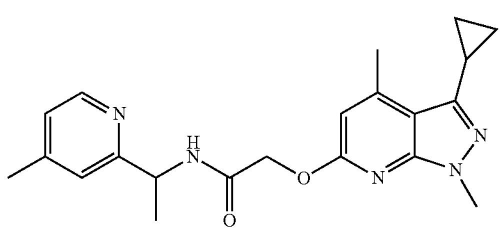 [SMILES: Cc1ccnc(C(C)NC(=O)COc2cc(C)c3c(C4CC4)nn(C)c3n2)c1] | 2-(3-cyclopropyl-1,4-dimethyl-1H-pyrazolo[3,4-b]pyridin-6-yloxy)-N-(1-(4-methylpyridin-2-yl)ethyl)acetamide | 0.84 (N) | 379.8 |
| 7.22 | 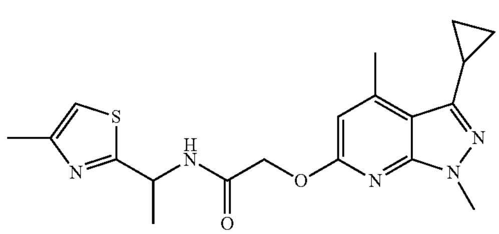 [SMILES: Cc1csc(C(C)NC(=O)COc2cc(C)c3c(C4CC4)nn(C)c3n2)n1] | 2-(3-cyclopropyl-1,4-dimethyl-1H-pyrazolo[3,4-b]pyridin-6-yloxy)-N-(1-(4-methylthiazol-2-yl)ethyl)acetamide | 1.03 (N) | 385.8 |

TABLE 5-continued

Compounds Number 7.2 to 7.33

| Number | Structure | IUPAC Name | LCMS Rt [min] (method) | [M + H]+ |
|---|---|---|---|---|
| 7.23 | 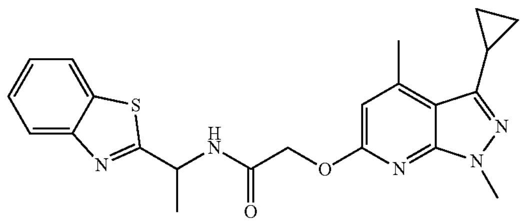 [SMILES: Cc1cc(OCC(=O)NC(C)c2nc3ccccc3s2)nc2c1c(C1CC1)nn2C] | N-(1-(benzo[d]thiazol-2-yl)ethyl)-2-(3-cyclopropyl-1,4-dimethyl-1H-pyrazolo[3,4-b]pyridin-6-yloxy)acetamide | 1.13 (N) | 421.8 |
| 7.24 | 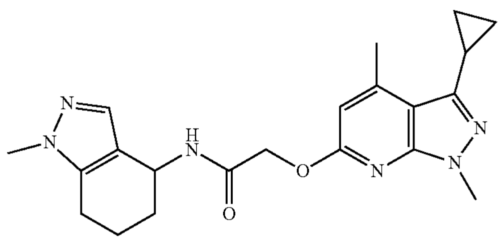 [SMILES: Cc1cc(OCC(=O)NC2CCCc3c2cnn3C)nc2c1c(C1CC1)nn2C] | 2-(3-cyclopropyl-1,4-dimethyl-1H-pyrazolo[3,4-b]pyridin-6-yloxy)-N-(1-methyl-4,5,6,7-tetrahydro-1H-indazol-4-yl)acetamide | 0.97 (N) | 394.8 |
| 7.25 | 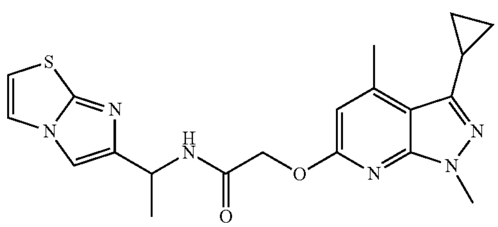 [SMILES: Cc1cc(OCC(=O)NC(C)c2cn3ccsc3n2)nc2c1c(C1CC1)nn2C] | 2-(3-cyclopropyl-1,4-dimethyl-1H-pyrazolo[3,4-b]pyridin-6-yloxy)-N-(1-(imidazo[2,1-b]thiazol-6-yl)ethyl)acetamide | 0.86 (N) | 410.7 |
| 7.26 | 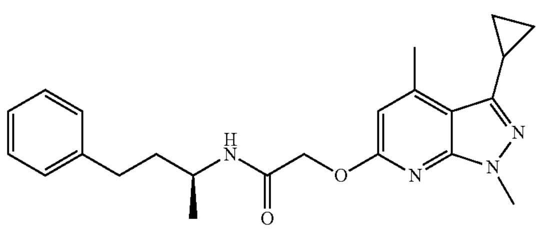 [SMILES: Cc1cc(OCC(=O)N[C@@H](C)CCc2ccccc2)nc2c1c(C1CC1)nn2C] | (S)-2-(3-cyclopropyl-1,4-dimethyl-1H-pyrazolo[3,4-b]pyridin-6-yloxy)-N-(4-phenylbutan-2-yl)acetamide | 1.20 (N) | 392.8 |
| 7.27 | 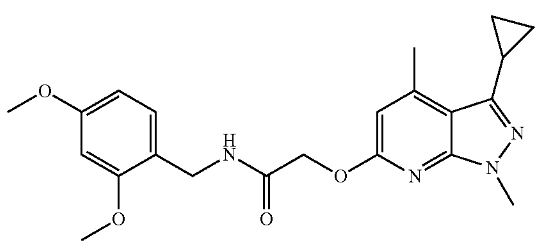 [SMILES: COc1ccc(CNC(=O)COc2cc(C)c3c(C4CC4)nn(C)c3n2)c(OC)c1] | 2-(3-cyclopropyl-1,4-dimethyl-1H-pyrazolo[3,4-b]pyridin-6-yloxy)-N-(2,4-dimethoxybenzyl)acetamide | 1.11 (N) | 410.8 |
| 7.28 | 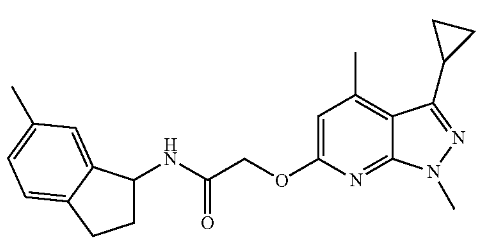 [SMILES: Cc1ccc2c(c1)C(NC(=O)COc1cc(C)c3c(C4CC4)nn(C)c3n1)CC2] | 2-(3-cyclopropyl-1,4-dimethyl-1H-pyrazolo[3,4-b]pyridin-6-yloxy)-N-(6-methyl-2,3-dihydro-1H-inden-1-yl)acetamide | 1.21 (N) | 390.8 |

TABLE 5-continued

Compounds Number 7.2 to 7.33

| Number | Structure | IUPAC Name | LCMS Rt [min] (method) | [M + H]+ |
|---|---|---|---|---|
| 7.29 | 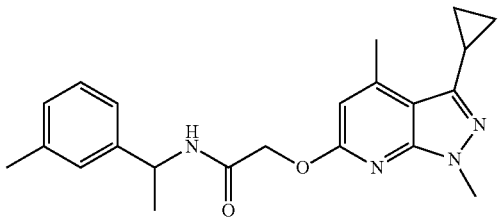 [SMILES: Cc1cccc(C(C)NC(=O)COc2cc(C)c3c(C4CC4)nn(C)c3n2)c1] | 2-(3-cyclopropyl-1,4-dimethyl-1H-pyrazolo[3,4-b]pyridin-6-yloxy)-N-(1-m-tolylethyl)acetamide | 1.17 (N) | 378.8 |
| 7.30 | 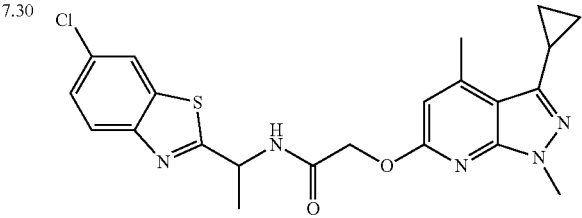 | N-(1-(6-chlorobenzo[d]thiazol-2-yl)ethyl)-2-(3-cyclopropyl-1,4-dimethyl-1H-pyrazolo[3,4-b]pyridin-6-yloxy)acetamide | 1.21 (N) | 455.6/ 457.7 |
| 7.31 | 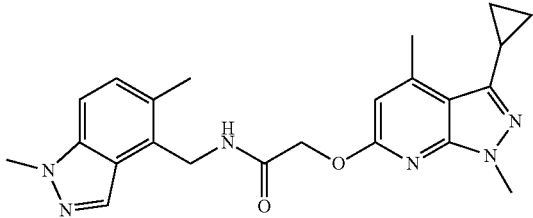 [SMILES: Cc1ccc2c(cnn2C)c1CNC(=O)COc1cc(C)c2c(C3CC3)nn(C)c2n1] | 2-(3-cyclopropyl-1,4-dimethyl-1H-pyrazolo[3,4-b]pyridin-6-yloxy)-N-((1,5-dimethyl-1H-indazol-4-yl)methyl)acetamide | 1.05 (N) | 418.8 |
| 7.32 | 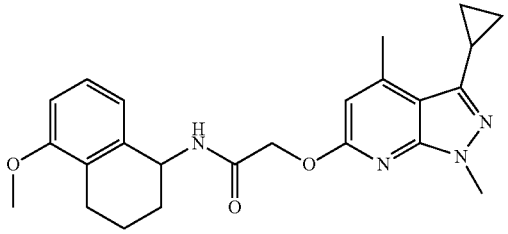 [SMILES: COc1cccc2c1CCCC2NC(=O)COc1cc(C)c2c(C3CC3)nn(C)c2n1] | 2-(3-cyclopropyl-1,4-dimethyl-1H-pyrazolo[3,4-b]pyridin-6-yloxy)-N-(5-methoxy-1,2,3,4-tetrahydronaphthalen-1-yl)acetamide | 1.21 (N) | 420.8 |
| 7.33 | 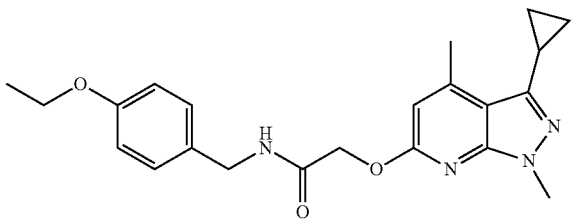 [SMILES: CCOc1ccc(CNC(=O)COc2cc(C)c3c(C4CC4)nn(C)c3n2)cc1] | 2-(3-cyclopropyl-1,4-dimethyl-1H-pyrazolo[3,4-b]pyridin-6-yloxy)-N-(4-ethoxybenzyl)acetamide | 1.14 (N) | 394.8 |

METHOD H

Example 8.1

2-(3-cyclopropyl-1,4-dimethyl-1H-pyrazolo[3,4-b]pyridin-6-yloxy)-N-(1-(1-methyl-1H-pyrrolo[2,3-b]pyridin-5-yl)ethyl)acetamide

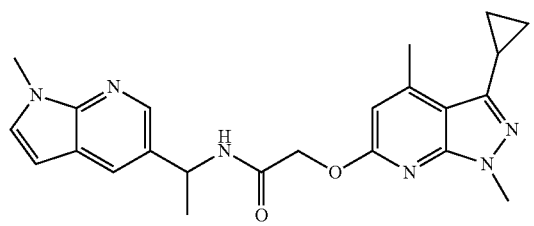 [SMILES: Cc1cc(OCC(=O)NC(C)c2cnc3c(ccn3C)c2)nc2c1c(C1CC1)nn2C]

N-(1-(1H-pyrrolo[2,3-b]pyridin-5-yl)ethyl)-2-(3-cyclopropyl-1,4-dimethyl-1H-pyrazolo[3,4-b]pyridin-6-yloxy)acetamide (example 6.57, 25 mg, 0.062 mmol) was dissolved in DMF (1 ml) and methyliodide (4.25 µl, 0.068 mmol) was added, followed by NaH (60% in mineral oil, 2.7 mg, 0.068 mmol). After stirring for 1 h at rt the reaction was diluted with EtOAc (1 ml) and water (2 ml) and extracted with EtOAc. The combined organic layers were washed with brine, dried over sodium sulfate, and the solvents were evaporated under reduced pressure. The crude product was purified on preparative TLC (DCM/MeOH 95/5) to give the product as colorless solid (15 mg, 58%). [1H-NMR (DMSO-$d_6$, 600 MHz) δ 8.58 (d, 1H), 8.23 (s, 1H), 7.83 (s, 1H), 7.48 (d, 1H), 6.47 (s, 1H), 6.30 (d, 1H, 5.13-5.09 (m, 1H), 4.81 (d, 1H), 4.76 (d, 1H), 3.78 (s, 3H), 3.63 (s, 3H), 2.65 (s, 3H), 2.27-2.22 (m, 1H), 3.06 (d, 3H), 0.93-0.84 (m, 4H); LCMS $Rt_L$=2.901 min; [M+H]$^+$=419.2]

Building Blocks

Building Block A1: [3-(3,5-Dimethoxy-phenyl)-1,4-dimethyl-1H-pyrazolo[3,4-b]pyridin-6-yloxy]-acetic acid

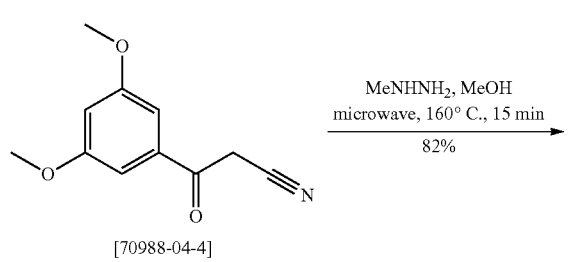

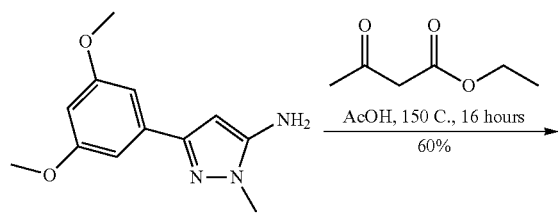

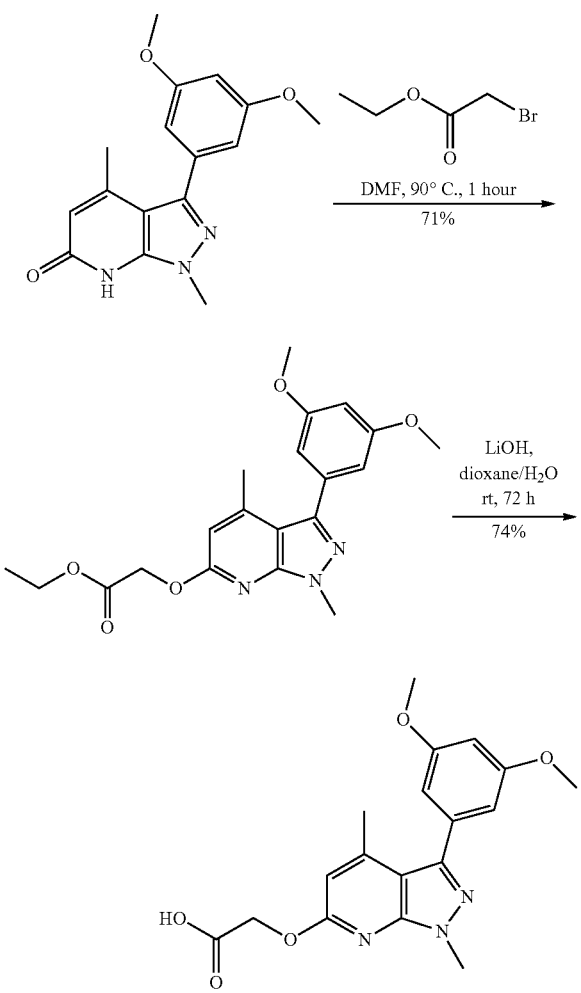

a) 5-(3,5-Dimethoxy-phenyl)-2-methyl-2H-pyrazol-3-ylamine

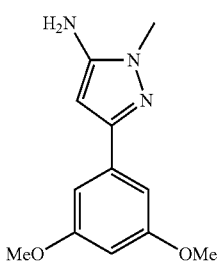 [SMILES: COc1cc(OC)cc(-c2cc(N)n(C)n2)c1]

A solution of 3-(3,5-dimethoxyphenyl)-3-oxopropanenitrile (1.4 g, 6.82 mmol) and methyl hydrazine (0.54 ml, 10.23 mmol) in methanol (5 ml) was irradiated using a microwave at 160° C. for 0.25 h. The solution was evaporated under reduced pressure and the resulting crude product was purified by column chromatography (eluent 10% MeOH in $CH_2Cl_2$) to yield 1.3 g (82%) of the title compound. [1H-NMR (DMSO-$d_6$, 360 MHz) δ 6.82 (d, 2H), 6.38 (t, 1H), 5.69 (2, 1H), 5.25 (s, 2H), 3.77 (s, 6H), 3.58 (s, 3H); UPLC-MS Rt$_f$=0.69 min; [M+H]$^+$=234.1]

b) 3-(3,5-dimethoxyphenyl)-1,4-dimethyl-1H-pyrazolo[3,4-b]pyridin-6(7H)-one

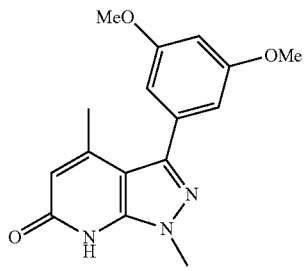 [SMILES: COc1cc(OC)cc(-c2nn(C)c3[nH]c(=O)cc(C)c23)c1]

A solution of 3-(3,5-dimethoxyphenyl)-1-methyl-1H-pyrazol-5-amine (1.3 g, 5.57 mmol) and 3-oxo-butyric acid ethyl ester (1.09 g, 8.36 mmol) in acetic acid (5 ml) was stirred at 150° C. for 18 h. The solution was evaporated under reduced pressure and the resulting crude product was purified by column chromatography (eluent 10% MeOH in CH$_2$Cl$_2$) to yield 1.0 g (60%) of the title compound. [$^1$H-NMR (DMSO-d$_6$, 360 MHz): δ 6.68 (d, 2H), 6.56 (s, 1H), 6.18 (s, 1H), 3.90 (s, 3H), 3.78 (s, 6H), 2.24 (s, 3H); UPLC-MS Rt$_f$=0.79 min; [M+H]$^+$=300.1]

c) Ethyl 2-((3-(3,5-dimethoxyphenyl)-1,4-dimethyl-1H-pyrazolo[3,4-b]pyridin-6-yl)oxy)acetate

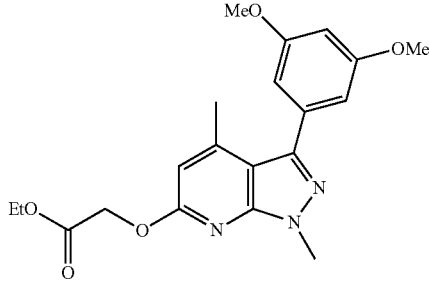 [SMILES: COc1cc(OC)cc(-c2nn(C)c3nc(OCC(=O)O)cc(C)c23)c1]

To a stirred solution of 3-(3,5-dimethoxyphenyl)-1,4-dimethyl-1H-pyrazolo[3,4-b]pyridin-6(7H)-one (1.0 g, 3.34 mmol) in DMF (5 ml) were added DIPEA (1.17 ml, 6.68 mmol) and ethyl 2-bromoacetate (0.56 ml, 5.01 mmol). After stirring at 90° C. for 1 h the mixture was cooled to rt, water was added and extracted three times with CH$_2$Cl$_2$. The organic phases were dried over Na2SO4, filtered and concentrated under reduced pressure. The resulting crude product was purified by column chromatography (eluent 50% hexane in EtOAc) to yield 910 mg (71%) of the title compound. [$^1$H-NMR (DMSO-d$_6$, 600 MHz): δ 6.71 (d, 2H), 6.61 (s, 1H), 6.57 (br s, 1H), 4.98 (s, 2H), 4.18 (q, 2H), 3.91 (s, 3H), 3.78 (s, 6H), 2.37 (s, 3H), 1.21 (t, 3H); UPLC-MS Rt$_f$=1.21 min; [M+H]$^+$=386.1]

d) [3-(3,5-Dimethoxy-phenyl)-1,4-dimethyl-1H-pyrazolo[3,4-b]pyridin-6-yloxy]-acetic acid

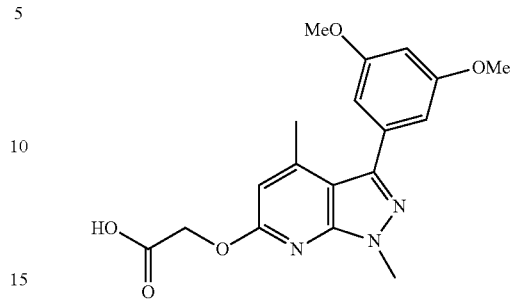

To a solution of ethyl 2-((3-(3,5-dimethoxyphenyl)-1,4-dimethyl-1H-pyrazolo[3,4-b]pyridin-6-yl)oxy)acetate (910 mg, 2.36 mmol) in dioxane (10 ml) and water (10 ml) was added LiOH (113 mg, 4.72 mmol) and the reaction mixture stirred at rt for 72 h. Then, water was added and the mixture extracted with CH2Cl2. The aqueous phase was then adjusted to pH ~2 with aqueous 2M HCl. The resulting precipitate was then filtered off, washed with H2O and dried under vacuum to furnish 620 mg (74%) of the title compound. [$^1$H-NMR (DMSO-d$_6$, 600 MHz): δ 6.70 (br d, 2H), 6.55 (br s, 1H), 6.44 (s, 1H), 4.49 (s, 2H), 3.91 (s, 3H), 3.78 (s, 6H), 2.50 (s, 3H); UPLC-MS Rt$_f$=0.93 min; [M+H]$^+$=358.1]

Building Block A2: (3-Cyclopropyl-4-difluoromethyl-1-methyl-1H-pyrazolo[3,4-b]pyridin-6-yloxy)-acetic acid

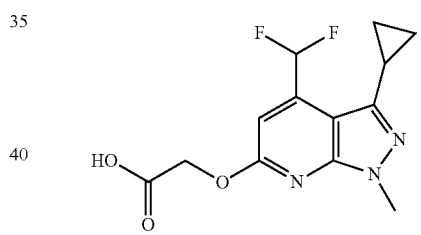

(3-Cyclopropyl-4-difluoromethyl-1-methyl-1H-pyrazolo[3,4-b]pyridin-6-yloxy)-acetic acid was obtained in analogy to building block A1, using 3-cyclopropyl-3-oxo-propionitrile and ethyl 4,4-difluoro-3-oxobutanoate. [$^1$H-NMR (DMSO-d$_6$, 400 MHz) δ 12.99 (br s, 1H), 7.44 (t, 1H), 6.90 (s, 1H), 4.95 (s, 2H), 3.81 (s, 3H), 2.24-2.16 (m, 1H), 0.95-0.83 (m, 4H); LCMS Rt$_f$=1.205 min; [M+H]$^+$=298.2]

Building Block A3: (3-Cyclopropyl-1-methyl-4-trifluoromethyl-1H-pyrazolo[3,4-b]pyridin-6-yloxy)-acetic acid

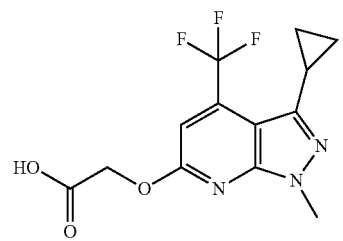 [SMILES: Cn1nc(C2CC2)c2c(C(F)(F)F)cc(OCC(=O)O)nc21]

(3-Cyclopropyl-1-methyl-4-trifluoromethyl-1H-pyrazolo[3,4-b]pyridin-6-yloxy)-acetic acid was obtained in analogy to building block A1, using 3-cyclopropyl-3-oxo-propionitrile and ethyl 4,4,4-trifluoro-3-oxobutanoate. [¹H-NMR (DMSO-d$_6$, 400 MHz) δ 13.11 (br s, 1H), 7.09 (s, 1H), 4.96 (s, 2H), 3.83 (s, 3H), 2.12-2.05 (m, 1H), 0.95-0.83 (m, 4H); LCMS Rt$_f$=1.376 min; [M+H]$^+$=316.2]

Building Block A4: (3-Cyclopropyl-4-isopropyl-1-methyl-1H-pyrazolo[3,4-b]pyridin-6-yloxy)-acetic acid

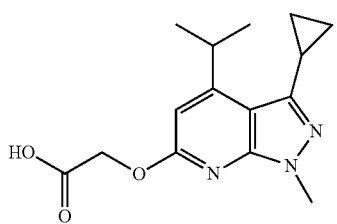 [SMILES: CC(C)c1cc(OCC(=O)O)nc2c1c(C1CC1)nn2C]

(3-Cyclopropyl-4-isopropyl-1-methyl-1H-pyrazolo[3,4-b]pyridin-6-yloxy)-acetic acid was obtained in analogy to building block A1, using 3-cyclopropyl-3-oxo-propionitrile and 4-methyl-3-oxo-pentanoic acid ethyl ester. [¹H-NMR (DMSO-d$_6$, 400 MHz) δ 12.85 (br s, 1H), 6.50 (s, 1H), 4.86 (s, 2H), 3.75 (s, 3H), 3.74-3.67 (m, 1H), 3.29 (s, 3H), 2.24-2.16 (m, 1H), 1.31 (d, 6H), 0.92-0.85 (m, 4H); LCMS Rt$_f$=1.439 min; [M+H]$^+$=290.0]

Building Block A5: (4-Difluoromethyl-1-methyl-3-phenyl-1H-pyrazolo[3,4-b]pyridin-6-yloxy)-acetic acid

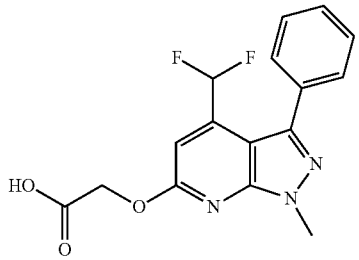 [SMILES: Cn1nc(-c2ccccc2)c2c(C(F)F)cc(OCC(=O)O)nc21]

(4-Difluoromethyl-1-methyl-3-phenyl-1H-pyrazolo[3,4-b]pyridin-6-yloxy)-acetic acid was obtained in analogy to building block A1, using 3-oxo-3-phenyl-propionitrile and ethyl 4,4-difluoro-3-oxobutanoate. [¹H-NMR (DMSO-d$_6$, 400 MHz) δ 13.03 (br s, 1H), 7.59-7.54 (m, 2H), 7.50-7.42 (m, 3H), 7.19 (t, 1H), 6.95 (s, 1H), 5.00 (s, 2H), 3.98 (s, 3H); LCMS Rt$_f$=1.312 min; [M+H]$^+$=334.1]

Building Block A6: (3-Isopropyl-1,4-dimethyl-1H-pyrazolo[3,4-b]pyridin-6-yloxy)-acetic acid

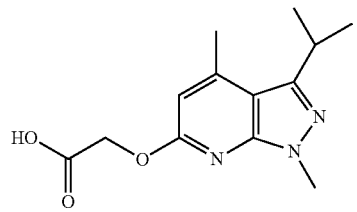 [SMILES: Cc1cc(OCC(=O)O)nc2c1c(C(C)C)nn2C]

(3-Isopropyl-1,4-dimethyl-1H-pyrazolo[3,4-b]pyridin-6-yloxy)-acetic acid was obtained in analogy to building block A1, using 4-methyl-3-oxo-pentanenitrile and ethyl acetoacetate. [¹H-NMR (DMSO-d$_6$, 400 MHz) δ 12.66 (br s, 1H), 6.45 (s, 1H), 4.86 (s, 2H), 3.79 (s, 3H), 3.38-3.30 (m, 1H), 2.57 (s, 3H), 1.29 (d, 6H); LCMS Rt$_f$=1.204 min; [M+H]$^+$=364.1]

Building Block A7: (3-Cyclopropyl-1,4-dimethyl-1H-pyrazolo[3,4-b]pyridin-6-yloxy)-acetic acid

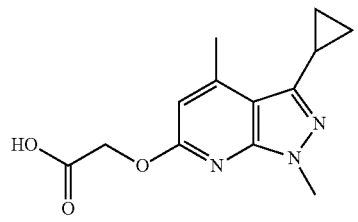 [SMILES: Cc1cc(OCC(=O)O)nc2c1c(C1CC1)nn2C]

(3-Cyclopropyl-1,4-dimethyl-1H-pyrazolo[3,4-b]pyridin-6-yloxy)-acetic acid was obtained in analogy to building block A1, using 3-cyclopropyl-3-oxo-propionitrile and ethyl acetoacetate. [¹H-NMR (DMSO-d$_6$, 600 MHz) δ 12.93 (br s, 1H), 6.48 (s, 1H), 4.87 (s, 2H), 3.76 (s, 3H), 2.67 (s, 3H), 2.28-2.24 (m, 1H), 0.94-0.86 (m, 4H); LCMS Rt$_H$=1.505 min; [M+H]$^+$=262.2]

Building Block A8: (3-Cyclopropyl-1,4,5-trimethyl-1H-pyrazolo[3,4-b]pyridin-6-yloxy)-acetic acid

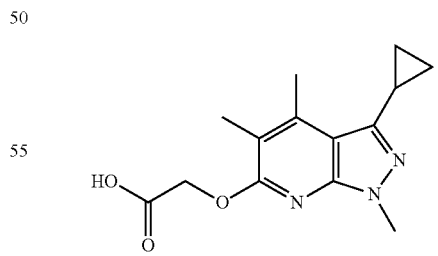

(3-Cyclopropyl-1,4,5-trimethyl-1H-pyrazolo[3,4-b]pyridin-6-yloxy)-acetic acid was obtained in analogy to building block A1, using 5-cyclopropyl-2-methyl-2H-pyrazol-3-ylamine and 2-methyl-3-oxo-butyric acid ethyl ester. [¹H-NMR (DMSO-d$_6$, 600 MHz) δ 12.86 (s, 1H), 4.90 (s, 2H), 3.74 (s, 3H), 2.65 (s, 3H), 2.27-2.23 (m, 1H), 2.18 (s, 3H), 0.91-0.84 (m, 4H); LCMS Rt$_H$=2.287 min; [M+H]$^+$=276.2]

Building Block A9: (3-Cyclopropyl-1,5-dimethyl-1H-pyrazolo[3,4-b]pyridin-6-yloxy)-acetic acid

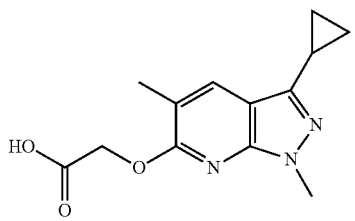 [SMILES: Cc1cc2c(C3CC3)nn(C)c2nc1OCC(=O)O]

(3-Cyclopropyl-1,5-dimethyl-1H-pyrazolo[3,4-b]pyridin-6-yloxy)-acetic acid was obtained in analogy to building block A1, using 5-cyclopropyl-2-methyl-2H-pyrazol-3-ylamine and 2-methyl-3-oxo-propionic acid ethyl ester. [$^1$H-NMR (DMSO-d$_6$, 600 MHz) δ 12.91 (s, 1H), 7.94 (s, 1H), 4.93 (s, 2H), 3.77 (s, 3H), 2.24 (s, 3H), 2.19-2.15 (m, 1H), 0.97-0.89 (m, 4H); LCMS Rt$_H$=1.630 min; [M+H]$^+$=262.0]

Building Block A10: [4-Difluoromethyl-3-(2,5-dimethyl-furan-3-yl)-1-methyl-1H-pyrazolo[3,4-b]pyridin-6-yloxy]-acetic acid

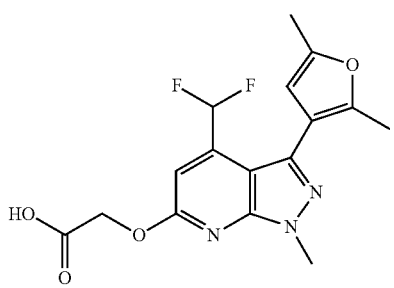 [SMILES: Cc1cc(-c2nn(C)c3nc(OCC(=O)O)cc(C(F)F)c23)c(C)o1]

[4-Difluoromethyl-3-(2,5-dimethyl-furan-3-yl)-1-methyl-1H-pyrazolo[3,4-b]pyridin-6-yloxy]-acetic acid was obtained in analogy to building block A1, using 3-(2,5-dimethyl-furan-3-yl)-3-oxo-propionitrile [175276-62-7] and 4,4-difluoro-3-oxo-butyric acid ethyl ester. [$^1$H-NMR (DMSO-d$_6$, 600 MHz) δ 13.07 (s, 1H), 7.16 (t, 1H), 6.94 (s, 1H), 6.27 (s, 1H), 5.01 (s, 2H), 3.96 (s, 3H), 2.29 (s, 3H), 2.22 (s, 3H); LCMS Rt$_H$=2.696 min; [M+H]$^+$=352.2]

Building Block A11: [3-(2,5-Dimethyl-furan-3-yl)-1-methyl-4-trifluoromethyl-1H-pyrazolo[3,4-b]pyridin-6-yloxy]-acetic acid

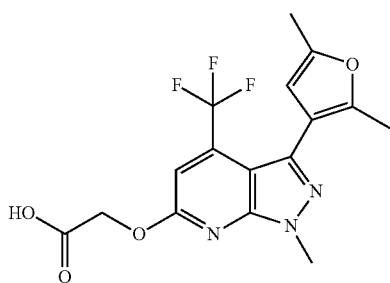 [SMILES: Cc1cc(-c2nn(C)c3nc(OCC(=O)O)cc(C(F)(F)F)c23)c(C)o1]

[3-(2,5-Dimethyl-furan-3-yl)-1-methyl-4-trifluoromethyl-1H-pyrazolo[3,4-b]pyridin-6-yloxy]-acetic acid was obtained in analogy to building block A1, using 3-(2,5-dimethyl-furan-3-yl)-3-oxo-propionitrile [175276-62-7] and 4,4,4-trifluoro-3-oxo-butyric acid ethyl ester. [$^1$H-NMR (DMSO-d$_6$, 600 MHz) δ 13.16 (s, 1H), 7.16 (s, 1H), 6.07 (s, 1H), 5.03 (s, 2H), 3.97 (s, 3H), 2.26 (s, 3H), 2.10 (s, 3H); LCMS Rt$_H$=2.912 min; [M+H]$^+$=370.0]

Building Block A12: [3-(2,5-Dimethyl-furan-3-yl)-1,4-dimethyl-1H-pyrazolo[3,4-b]pyridin-6-yloxy]-acetic acid

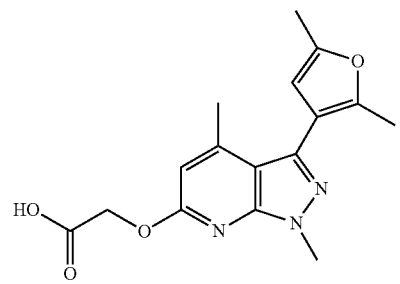 [SMILES: Cc1cc(-c2nn(C)c3nc(OCC(=O)O)cc(C)c23)c(C)o1]

[3-(2,5-Dimethyl-furan-3-yl)-1,4-dimethyl-1H-pyrazolo[3,4-b]pyridin-6-yloxy]-acetic acid was obtained in analogy to building block A1, using 3-(2,5-dimethyl-furan-3-yl)-3-oxo-propionitrile [175276-62-7] and 3-oxo-butyric acid ethyl ester. [$^1$H-NMR (DMSO-d$_6$, 400 MHz) δ 6.51 (s, 1H), 6.22 (s, 1H), 4.89 (s, 2H), 3.87 (s, 3H), 2.26 (s, 3H), 2.21 (s, 3H); LCMS Rt$_J$=0.95 min; [M+H]$^+$=316.2]

Building Block A13: [1,4-Dimethyl-3-(2-methyl-furan-3-yl)-1H-pyrazolo[3,4-b]pyridin-6-yloxy]-acetic acid

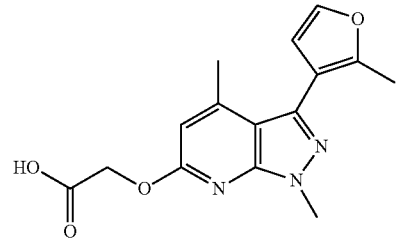 [SMILES: Cc1occc1-c1nn(C)c2nc(OCC(=O)O)cc(C)c12]

[1,4-Dimethyl-3-(2-methyl-furan-3-yl)-1H-pyrazolo[3,4-b]pyridin-6-yloxy]-acetic acid was obtained in analogy to building block A1, using 3-(2-methyl-furan-3-yl)-3-oxo-propionitrile [158386-97-1] and 3-oxo-butyric acid ethyl ester. [$^1$H-NMR (DMSO-d$_6$, 400 MHz) δ 7.62 (s, 1H), 6.64 (s, 1H), 6.50 (s, 1H), 4.90 (s, 2H), 3.88 (s, 3H), 2.26 (s, 3H), 2.27 (s, 3H); LCMS Rt$_J$=0.87 min; [M+H]$^+$=302.1]

Building Block A14: (3-Cyclopropyl-1-methyl-1H-pyrazolo[3,4-b]pyridin-6-yloxy)-acetic acid

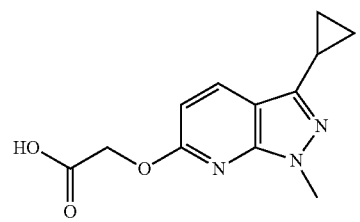 [SMILES: Cn1nc(C2CC2)c2ccc(OCC(=O)O)nc21]

(3-Cyclopropyl-1-methyl-1H-pyrazolo[3,4-b]pyridin-6-yloxy)-acetic acid was obtained in analogy to building block A1, using 5-cyclopropyl-2-methyl-2H-pyrazol-3-ylamine [118430-74-3] and 3,3-dimethoxy-propionic acid methyl ester. [$^1$H-NMR (DMSO-d$_6$, 400 MHz) δ 8.08 (d, 1H), 6.61 (d, 1H), 4.86 (s, 2H), 3.76 (s, 3H), 2.23-2.16 (m, 1H), 0.97-0.87 (m, 4H); LCMS Rt$_f$=0.76 min; [M+H]$^+$=248.0]

Building Block A15: [3-(2-Methoxy-phenyl)-1-methyl-1H-pyrazolo[3,4-b]pyridin-6-yloxy]-acetic acid

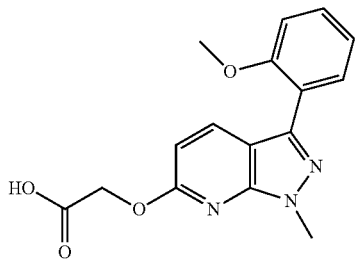 [SMILES: COc1ccccc1-c1nn(C)c2nc(OCC(=O)O)ccc12]

[3-(2-Methoxy-phenyl)-1-methyl-1H-pyrazolo[3,4-b]pyridin-6-yloxy]-acetic acid was obtained in analogy to building block A1, using 5-(2-methoxy-phenyl)-2-methyl-2H-pyrazol-3-ylamine [957313-52-9] and 3,3-dimethoxy-propionic acid methyl ester. [$^1$H-NMR (DMSO-d$_6$, 400 MHz) δ 8.01 (d, 1H), 7.56 (d, 1H), 7.41 (t, 1H), 7.16 (d, 1H), 7.03 (t, 1H), 6.71 (d, 1H), 4.93 (s, 2H), 3.93 (s, 3H), 3.80 (s, 3H); LCMS Rt$_f$=0.88 min; [M+H]$^+$=314.3]

Building Block A16: (3-tert-Butyl-1-methyl-1H-pyrazolo[3,4-b]pyridin-6-yloxy)-acetic acid

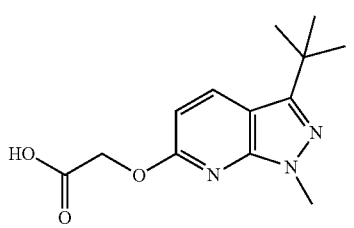 [SMILES: Cn1nc(C(C)(C)C)c2ccc(OCC(=O)O)nc21]

(3-tert-Butyl-1-methyl-1H-pyrazolo[3,4-b]pyridin-6-yloxy)-acetic acid was obtained in analogy to building block A1, using 5-tert-butyl-2-methyl-2H-pyrazol-3-ylamine [118430-73-2] and 3,3-dimethoxy-propionic acid methyl ester. [$^1$H-NMR (DMSO-d$_6$, 400 MHz) δ 8.23 (d, 1H), 6.62 (d, 1H), 4.88 (s, 2H), 3.80 (s, 3H), 2.48 (s, 9H); LCMS Rt$_f$=0.91 min; [M+H]$^+$=264.3]

Building Block A17: (1-Methyl-3-o-tolyl-1H-pyrazolo[3,4-b]pyridin-6-yloxy)-acetic acid

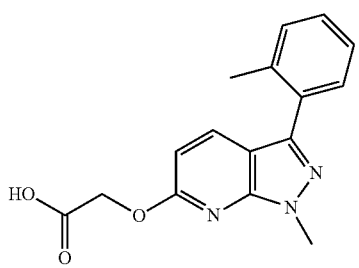 [SMILES: Cc1ccccc1-c1nn(C)c2nc(OCC(=O)O)ccc12]

(1-Methyl-3-o-tolyl-1H-pyrazolo[3,4-b]pyridin-6-yloxy)-acetic acid was obtained in analogy to building block A1, using 3-oxo-3-o-tolyl-propionitrile [35276-81-4] and 3,3-dimethoxy-propionic acid methyl ester. [$^1$H-NMR (DMSO-d$_6$, 400 MHz) δ 12.94 (br s, 1H), 7.98 (d, 1H), 7.45-7.27 (m, 4H), 6.73 (d, 1H), 4.93 (s, 2H), 3.94 (s, 3H), 2.35 (s, 3H); LCMS Rt$_f$=0.95 min; [M+H]$^+$=298.3]

Building Block A18: [3-(4-Methoxy-pyridin-2-yl)-1,4-dimethyl-1H-pyrazolo[3,4-b]pyridin-6-yloxy]-acetic acid

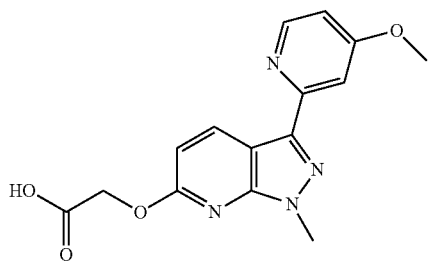 [SMILES: COc1ccnc(-c2nn(C)c3nc(OCC(=O)O)ccc23)c1]

[3-(4-Methoxy-pyridin-2-yl)-1,4-dimethyl-1H-pyrazolo[3,4-b]pyridin-6-yloxy]-acetic acid was obtained in analogy to building block A1, using 3-(4-methoxy-pyridin-2-yl)-3-oxo-propionitrile and 3-oxo-butyric acid ethyl ester. [$^1$H-NMR (DMSO-d$_6$, 360 MHz) δ 8.51 (d, 1H), 7.43 (d, 1H), 7.00 (d, 1H), 6.47 (s, 1H), 4.49 (s, 2H), 3.97 (s, 3H), 3.92 (s, 3H), 2.52 (s, 3H); LCMS Rt$_f$=0.64 min; [M+H]$^+$=329.0]

Building Block A19: (3-Phenyl-4-trifluoromethyl-isoxazolo[5,4-b]pyridin-6-yloxy)-acetic acid

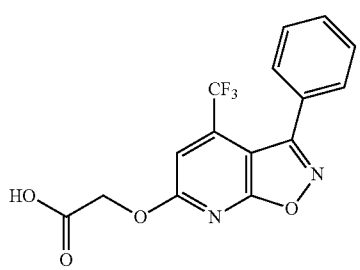 [SMILES: O=C(O)COc1cc(C(F)(F)F)c2c(-c3ccccc3)noc2n1]

(3-Phenyl-4-trifluoromethyl-isoxazolo[5,4-b]pyridin-6-yloxy)-acetic acid was obtained in analogy to the corresponding building block described in example 1.1, using 3-phenyl-isoxazol-5-ylamine [4369-55-5] and 4,4,4-trifluoro-3-oxo-butyric acid ethyl ester. [$^1$H-NMR (CDCl$_3$, 300 MHz) δ 7.60-7.45 (m, 5H), 7.21 (s, 1H), 5.16 (s, 2H); LCMS Rt$_E$=1.87 min; [M−H−CH$_2$COO]$^-$=279.0]

Building Block A20: (1-Methyl-3-phenyl-4-trifluoromethyl-1H-pyrrolo[2,3-b]pyridin-6-yloxy)-acetic acid

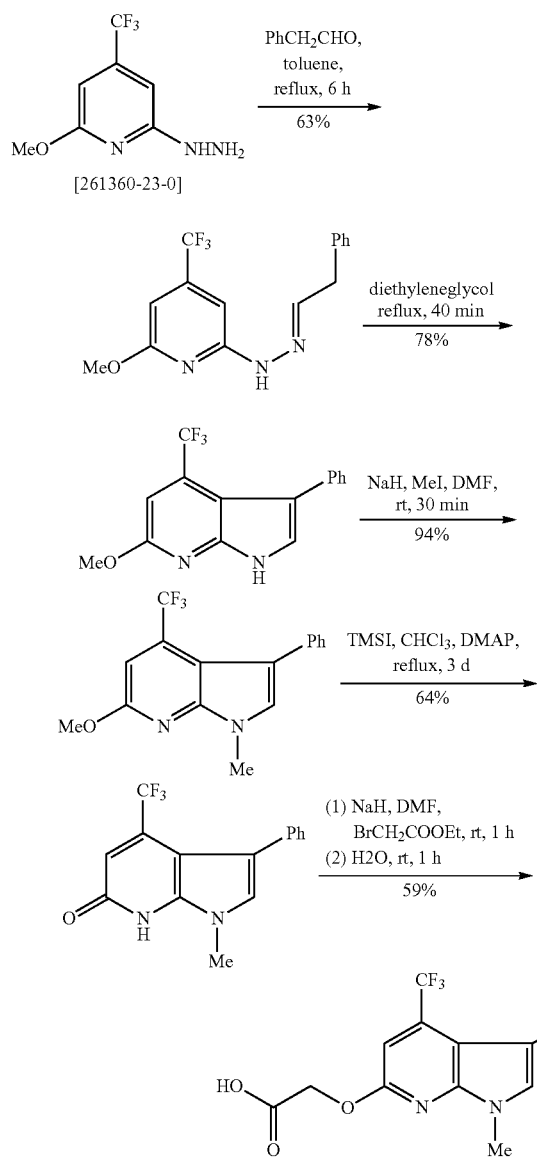

a) 2-methoxy-6-(2-(2-phenylethylidene)hydrazinyl)-4-(trifluoromethyl)pyridine

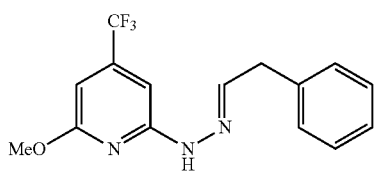 [SMILES: COc1cc(C(F)(F)F)cc(N/N=C/Cc2ccccc2)n1]

A mixture of 2-hydrazinyl-6-methoxy-4-(trifluoromethyl) pyridine [261360-23-0] (0.11 g, 0.55 mmol) and 2-phenylacetaldehyde (0.57 g, 0.66 mmol) in toluene (5 ml) was heated at reflux for 6 h using a Dean-Stark apparatus. The reaction mixture was concentrated under reduced pressure. The crude product was purified by flash column chromatography (5% EtOAc in hexane) to yield the title compound (0.11 g, 63%). [LCMS $Rt_D$=3.75 min; $[M+H]^+$=310.1]

b) 6-methoxy-3-phenyl-4-(trifluoromethyl)-1H-pyrrolo[2,3-b]pyridine

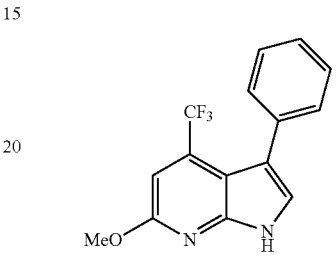

A solution of 2-methoxy-6-(2-(2-phenylethylidene)hydrazinyl)-4-(trifluoromethyl)pyridine (0.11 g, 0.34 mmol) in diethylene glycol (4 ml) was heated at reflux for 40 min. The reaction mixture was concentrated under reduced pressure. The residue was partitioned between water and EtOAc. The organic layer was washed with water and brine, filtered and dried over anhydrous sodium sulfate. The organic layer was concentrated under reduced pressure to yield the title compound (77 mg, 78%). [LCMS $Rt_D$=0.58 min; $[M+H]^+$=292.9]

c) 6-Methoxy-1-methyl-3-phenyl-4-trifluoromethyl-1H-pyrrolo[2,3-b]pyridine

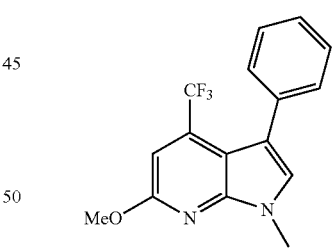

NaH (15 mg, 0.38 mmol) was added to a stirred solution of 6-methoxy-3-phenyl-4-(trifluoromethyl)-1H-pyrrolo[2,3-b] pyridine (73 mg, 0.25 mmol) in DMF (3 ml) and the resulting mixture was stirred for 30 min. Then methyl iodide (0.06 ml, 0.99 mmol) was added and the mixture was stirred for additional 1 h. To the mixture saturated aqueous NH$_4$Cl solution was added and the solution was extracted with EtOAc. The organic layer was washed with water and brine, filtered and dried over anhydrous sodium sulfate. The organic layer was concentrated under reduced pressure. The crude product was purified by flash column chromatography (2% EtOAc in hexane) to yield the title compound (72 mg, 94%). [LCMS $Rt_C$=0.93 min; $[M+H]^+$=307.0]

d) 1-methyl-3-phenyl-4-(trifluoromethyl)-1H-pyrrolo[2,3-b]pyridin-6(7H)-one

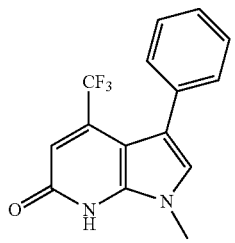 [SMILES: Cn1cc(-c2ccccc2)c2c(C(F)(F)F)cc(=O)[nH]c21]

A mixture of 6-Methoxy-1-methyl-3-phenyl-4-trifluoromethyl-1H-pyrrolo[2,3-b]pyridine (70 mg, 0.23 mmol), trimethylsilyl iodide (686 mg, 3.43 mmol) and DMAP (3 mg, 0.01 mmol) in chloroform (3 ml) was heated at reflux for 3 days. The reaction mixture was concentrated under reduced pressure. To the mixture water was added and the solution was extracted with EtOAc. The organic layer was washed with water, saturated aqueous sodium bisulfite solution and brine, filtered and dried over anhydrous sodium sulfate. The organic layer was concentrated under reduced pressure. The crude product was purified by flash column chromatography (20% EtOAc in hexane) to yield the title compound (43 mg, 64%). [LCMS $Rt_C$=0.45 min; $[M+H]^+$=292.8]

e) 2-(1-methyl-3-phenyl-4-(trifluoromethyl)-1H-pyrrolo[2,3-b]pyridin-6-yloxy)acetic acid

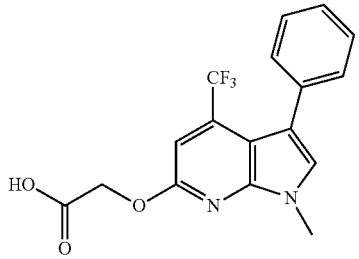 [SMILES: Cn1cc(-c2ccccc2)c2c(C(F)(F)F)cc(OCC(=O)O)nc21]

NaH (23 mg, 0.56 mmol) was added to a stirred solution of 1-methyl-3-phenyl-4-(trifluoromethyl)-1H-pyrrolo[2,3-b]pyridin-6(7H)-one (41 mg, 0.14 mmol) in DMF (4 ml) and the resulting mixture was stirred for 30 min. Then ethyl bromoacetate (47 mg, 6.50 mmol) was added and the mixture was stirred for additional 1 h. To the mixture water (0.5 ml) was added and stirred for 2 h. The reaction mixture was concentrated. 1N aqueous HCL was added to the mixture and the solution was extracted with diethyl ether. The organic layer was washed with water and brine, filtered and dried over anhydrous sodium sulfate. The organic layer was concentrated under reduced pressure. The crude product was purified by flash column chromatography (80% EtOAc in hexane) to yield the title compound (29 mg, 59%) [$^1$H-NMR (CDCl$_3$, 300 MHz) δ 7.45-7.30 (m, 5H), 7.05 (s, 1H), 7.00 (s, 1H), 5.03 (s, 2H), 3.81 (s, 3H); LCMS $Rt_E$=1.94 min; $[M+H]^+$=351.0]

Building Block B1: 3-Methyl-5H-cyclopenta[b]pyridin-7(6H)-one

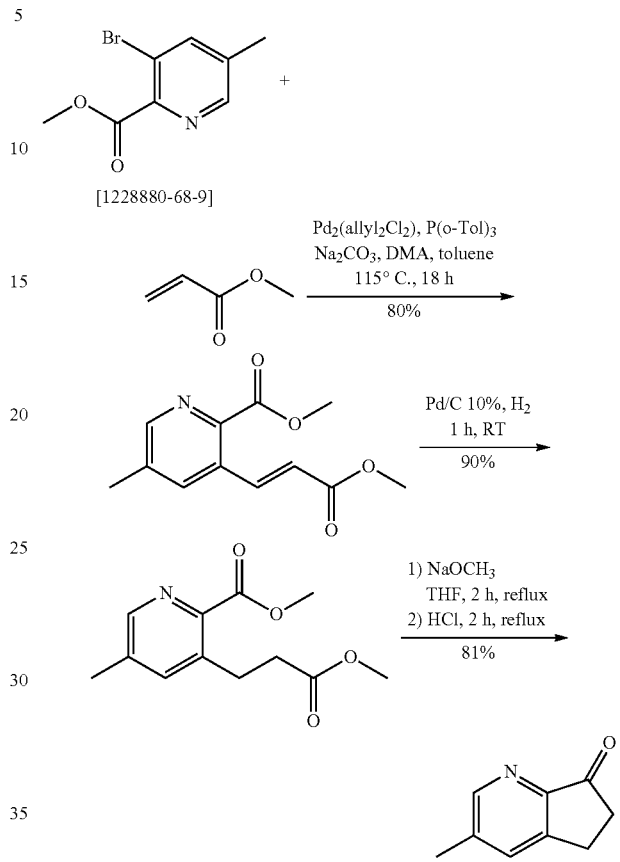

a) 3-(2-Methoxycarbonyl-vinyl)-5-methyl-pyridine-2-carboxylic acid methyl ester

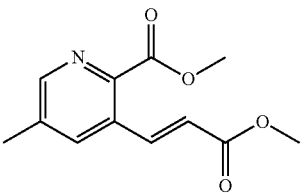

3-Bromo-5-methyl-pyridine-2-carboxylic acid methyl ester (1.6 g, 6.945 mmol), methylacrylate (1.50 g, 17.39 mmol), allylpalladium(II) chloride dimer (0.127 g, 0.348 mmol), tri-o-tolylphosphine (0.212 g, 0.695 mmol), water free sodium carbonate (2.211 g, 20.9 mmol), and N,N.dimethylacetamide (4.56 ml) were added to toluene (15 ml) and the reaction mixture was stirred for 18 h at 115° C. in a microwave apparatus. The mixture was diluted with EtOAc, washed with brine, dried over sodium sulfate, and the solvents were evaporated under reduced pressure. The residue was purified by chromatography on silica (Flashmaster, hex to hex/EtOAc 2/3 over 40 min, 20 min hex/EtOAc 2/3) to give the product as off-white solid (1.31 g, 80%). [$^1$H-NMR (DMSO-d$_6$, 600 MHz) δ 8.51 (s, 1H), 8.20 (s, 1H), 8.10 (d, 1H), 6.69 (d, 1H), 3.88 (s, 3H), 3.74 (s, 3H), 2.39 (s, 3H); LCMS Rt$_L$=2.753 min; [M+H]$^+$=236.0]

b) 3-(2-Methoxycarbonyl-ethyl)-5-methyl-pyridine-2-carboxylic acid methyl ester

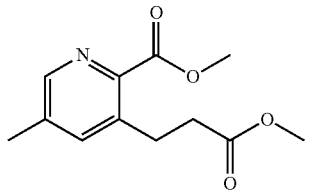

3-(2-Methoxycarbonyl-vinyl)-5-methyl-pyridine-2-carboxylic acid methyl ester (2.58 g, 10.97 mmol) was dissolved in MeOH (100 ml) and hydrogenated at rt with Pd/C (10%, Engelhard 4505, 1.20 g) and 1.0 bar H$_2$ for 1 h. The reaction was filtered and the solvent was evaporated under reduced pressure. The residue was purified by chromatography on silica (hex to hex/EtOAc 2/3 in 40 min) to give the product as colorless oil (2.33 g, 90%). [$^1$H-NMR (DMSO-d$_6$, 600 MHz) δ 8.34 (s, 1H), 7.65 (s, 1H), 3.84 (s, 3H), 3.58 (s, 3H), 3.03 (t, 2H), 2.63 (t, 2H), 2.33 (s, 3H); LCMS Rt$_f$=2.786 min; [M+H]$^+$=238.0.0]

c) 3-Methyl-5H-cyclopenta[b]pyridin-7(6H)-one

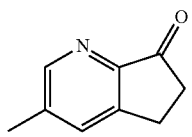

3-(2-Methoxycarbonyl-ethyl)-5-methyl-pyridine-2-carboxylic acid methyl ester (2.33 g, 9.82 mmol) was dissolved in THF (70 ml). NaOMe (0.796 g, 14.7 mmol) was added and the reaction was heated at reflux temperature for 2 h. The solvents were evaporated under reduced pressure. The residue was taken into 4.5 N aqueous hydrochloric acid (24 ml) and the mixture was heated at reflux temperature for 2 h. After cooling to it solid potassium carbonate was added carefully in portions until pH >8. The mixture was extracted with DCM, the combined organic layers were washed with aq Na$_2$CO$_3$ and aq ammonium chloride solution, dried over sodium sulfate, and the solvent was evaporated at reduced pressure. The residue was purified by chromatography on silica (Flashmaster, hes/EtOAc 1/1 to EtOAc over 15 min, EtOAc to EtOAc/MeOH 9/1 over 10 min) to obtain the product as off-white solid (1.7 g, 81%). [$^1$H-NMR (DMSO-d$_6$, 600 MHz) δ 8.57 (s, 1H), 7.87 (s, 1H), 3.06 (t, 2H), 2.65 (t, 2H), 2.42 (s, 3H); LCMS Rt$_f$=2.460 min; [M+H]$^+$=148.0]

Building Block B2: 5-Ethoxy-indan-1-one

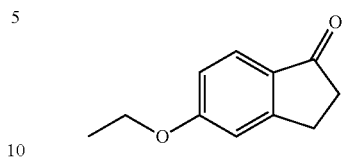

5-Hydroxy-1-indanone (2.5 g, 16.0 mmol) was dissolved in acetone (60 ml) and potassium carbonate (waterfree, 5.15 g, 36.9 mmol) and ethyl iodide (2.88 ml, 35.3 mmol) were added. The reaction was stirred at it under an atmosphere of nitrogene for 6 days. The mixture was filtered, the filtrate collected and the solvent evaporated at reduced pressure. Chromatography on silica (flashmaster, hex to hex/EtOAc 2/3 in 20 min, 15 min hex/EtOAc 2/3) gave the product as off-white solid (2.8 g, 99%). [$^1$H-NMR (DMSO-d$_6$, 600 MHz) δ 7.54 (d, 1H), 7.07 (s, 1H), 6.94 (d, 1H), 4.13 (q, 2H), 3.05-3.03 (m, 2H), 2.58-2.56 (m, 2H), 1.35 (t, 3H); LCMS Rt$_f$=0.88 min; [M+H]$^+$=177.2]

Building Block C1: 1-[5-(2,2-Dimethyl-propyl)-isoxazol-3-yl]-ethylamine

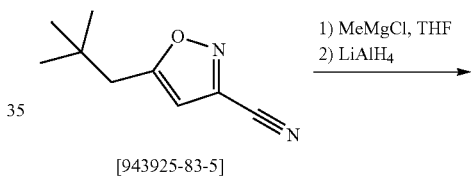

[943925-83-5]

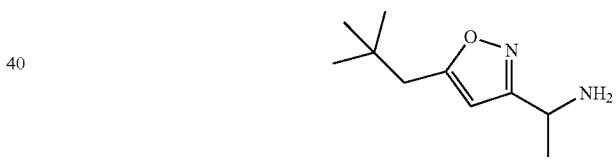

The solution of 5-(2,2-dimethyl-propyl)-isoxazole-3-carbonitrile ([943925-83-5] 16 g, 97.5 mmol) in THF (160 ml) was cooled in an ice bath and under an atmosphere of nitrogen methylmagnesium chloride (3 M solution in THF, 51 ml, 127 mmol) was added slowly so that the reaction temperature did not rise above 10° C. The reaction was stirred for 1 h at rt. LiAlH$_4$ (1 M solution in THF, 110 ml, 110 mmol) was added over 10 min keeping the reaction temperature below 40° C. The reaction was heated at reflux temperature for a few minutes and then stirred at rt for 1 h. The reaction was quenched be the slow addition of water (5 ml) keeping the temperature below 50° C., then cooled with an ice bath and aqueous NaOH (4 M, 5 ml) was added. The reaction mixture was diluted with diethylether (200 ml) and extracted with 1 N aqueous hydrochloric acid. The aqueous layers were combined, basified with concentrated aqueous ammonia and extracted with diethylether. The organic layers were dried over sodium sulfate and the solvent was evaporated under reduced pressure to give the title compound as yellow oil (13.8 g, 77%). [$^1$H-NMR (DMSO-d$_6$, 600 MHz) δ 6.21 (s, 1H), 3.95 (q, 1H), 2.49-2.47 (m, 2H), 1.89 (br s, 2H), 1.25 (d, 3H), 0.90 (s, 9H)

Building Block C2: (S)-3-methyl-6,7-dihydro-5H-cyclopenta[c]pyridin-7-amine hydrochloride

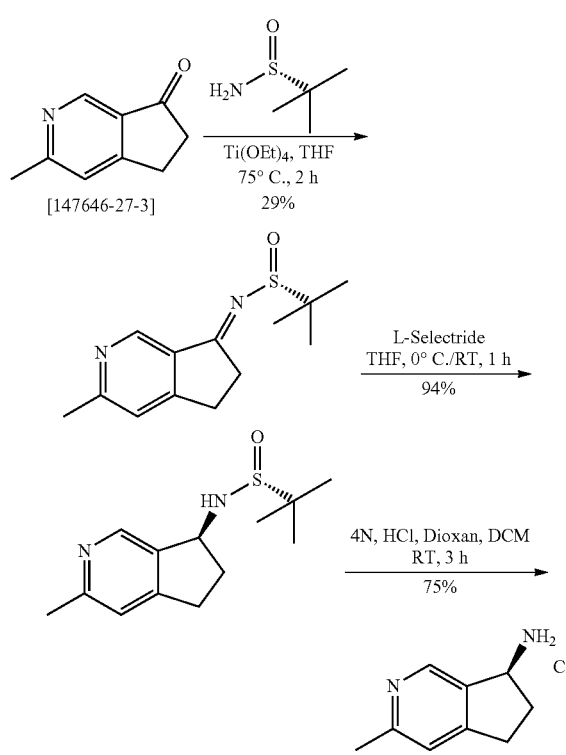

a) [S(R)]-2-methyl-N-(3-methyl-5H-cyclopenta[c]pyridin-7(6H)-ylidene)propane-2-sulfinamide

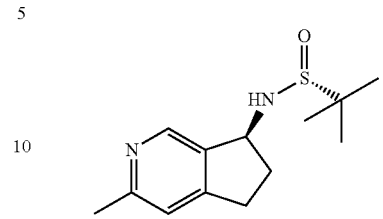

To the solution of 3-methyl-5,6-dihydro-[2]pyridin-7-one (210 mg, 1.43 mmol) in THF (2.5 ml) was added titan (IV)-ethoxid (0.60 ml, 2.85 mmol), followed by a solution of (R)-(+)-2-methyl-2-propansulfinamid (173 mg, 1.43 mmol) in THF (2.5 ml). The reaction was stirred at 75° C. (bath temperature) for 2 h. After cooling to rt the reaction was diluted with EtOAc, washed with water and brine, and dried over sodium sulfate. The solvents were evaporated under reduced pressure and the residue was purified by chromatography on silica (Flashmaster, hex/EtOAC 1/1 to EtOAc over 10 min, EtOAc to EtOAc/MeOH 9/1 over 20 min, 20 min EtOAc/MeOH 9/1) to give the product as greenish solid (105 mg, 29%). [$^1$H-NMR (DMSO-d$_6$, 600 MHz) δ 8.78 (s, 1H), 7.41 (s, 1H), 3.34-3.26 (m, 1H), 3.12-3.06 (m, 2H), 3.02-2.98 (m, 1H), 2.54 (s, 3H), 2.49 (s, 9H); LCMS Rt$_f$=2.494 min; [M+H]$^+$=251.0]

b) [S(R)]-2-methyl-N—((S)-3-methyl-6,7-dihydro-5H-cyclopenta[c]pyridin-7-yl)propane-2-sulfinamide

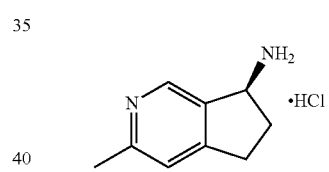

The solution of [S(R)]-2-methyl-N-(3-methyl-5H-cyclopenta[c]pyridin-7(6H)-ylidene)propane-2-sulfinamide (105 mg, 0.42 mmol) in THF (2.5 ml) was cooled in an ice bath and L-selectride (1.26 ml 1 M solution in THF, 1.26 mmol) was added. The reaction was stirred at rt for 1 h and then cooled again in an ice bath before careful addition of MeOH/DCM to destroy the excess of L-selectride. The solvents were evaporated at reduced pressure and the residue purified by chromatography on silica (Flashmaster hex/EtOAC 1/1 to EtOAc over 15 min, EtOAc to EtOAc/MeOH 9/1 over 25 min, 10 min EtOAc/MeOH 9/1) to give the product as brown oil. [1H-NMR (DMSO-d$_6$, 600 MHz) δ 8.30 (s, 1H), 7.13 (s, 1H), 5.67 (d, 1H), 4.77-4.73 (m, 1H), 2.91-2.86 (m, 1H), 2.75-2.70 (m, 1H), 2.43-2.38 (m, 1H), 2.42 (s, 3H), 1.99-1.93 (m, 1H), 1.14 (s, 9H); LCMS Rt$_f$=2.431 min; [M+H]$^+$=253.2]

c) (S)-3-methyl-6,7-dihydro-5H-cyclopenta[c]pyridin-7-amine hydrochloride

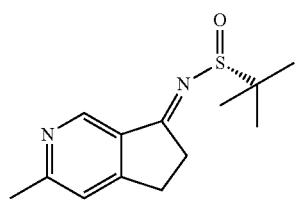 [SMILES: Cc1cc2c(cn1)/C(=N/[S@](=O)C(C)(C)C)CC2]

The solution of [S(R)]-2-methyl-N—((S)-3-methyl-6,7-dihydro-5H-cyclopenta[c]pyridin-7-yl)propane-2-sulfinamide (100 mg, 0.396 mmol) in DCM (0.7 ml) was added slowly to 4 N hydrochloric acid in Dioxan (0.30 ml, 1.2 mmol). The reaction was stirred 3 h at rt before addition of diethylether. The precipitate was filtered off and dried under vacuum to give the title compound as off-white solid (55 mg, 75%). [1H-NMR (DMSO-d$_6$, 600 MHz) δ 8.98 (s, 1H), 8.85 (br s, 3H), 7.81 (s, 1H), 4.91 (br s, 1H), 3.33-3.28 (m, 1H), 3.11-3.06 (m, 1H), 2.70 (s, 3H), 2.58.2.49 (m, 1H), 2.18-2.12 (m, 1H); MS [M+H]$^+$=149.1]

Building Block C3: (S)-2-methyl-6,7-dihydro-5H-cyclopenta[b]pyridin-5-amine hydrochloride

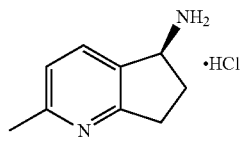

The title compound was obtained in analogues manner as described for building block C2, starting from 2-methyl-6,7- dihydro-5H-cyclopenta[b]pyridin-5-one [173064-91-0]. [1H-NMR (DMSO-d$_6$, 600 MHz) δ 8.78 (br s, 3H), 8.39 (br s, 1H), 7.58 (br s, 1H), 4.82 (br s, 1H), 3.36-3.28 (m, 1H), 3.14-3.07 (m, 1H), 2.66 (s, 3H), 2.65.2.56 (m, 1H), 2.18-2.12 (m, 1H); MS [M+H]$^+$=149.1]

Building Block C4: 2-methyl-6,7-dihydro-5H-cyclopenta[b]pyridin-5-amine hydrochloride

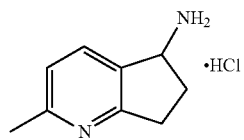

To the solution of 2-methyl-6,7-dihydro-5H-cyclopenta[b]pyridin-5-one ([173064-91-0], 0.275 g, 1.87 mmol) in MeOH (15 ml) was added ammonium acetate (7.2 g, 93 mmol) and the mixture was stirred at rt of 30 min. Sodium cyanoborohydride (0.176 g, 2.80 mmol) was added in portions and the reaction was heated at reflux temperature over night. Most of the solvent was evaporated under reduced pressure and the residue taken in to into EtOAc and 2N aqueous sodium hydroxide. The aqueous layer was separated and dioxane (50 ml) was added, followed by di-tert-butyl dicarbonate (2.04 g, 9.34 mmol). The mixture was stirred at rt for 3 h. The organic layer was separated and most of the solvent evaporated under reduced pressure and the residue was taken in EtOAc. The solution was washed with brine, dried over sodium sulfate and the solvent was evaporated under reduced pressure. The intermediate was purified by chromatography on silica (Flashmaster, hex/EtOAc 1/1 to EtOAc over 15 min, EtOAc to EtOAc/MeOH 9/1 over 15 min). The obtained colorless solid was dissolved in 4 N HCl in dioxane and the reaction was stirred at rt for 2 h. The residue obtained by evaporation of the solvent was redissolved in DCM and the solvent was evaporated again to give the title compound as white solid. [1H-NMR (DMSO-d$_6$, 600 MHz) δ 8.71 (br s, 3H), 8.32 (br s, 1H), 7.54 (br s, 1H), 4.82 (br s, 1H), 3.33-3.25 (m, 1H), 3.12-3.05 (m, 1H), 2.64 (s, 3H), 2.62.2.52 (m, 1H), 2.16-2.11 (m, 1H); MS [M+H]$^+$=149.0]

Building Block C5: 1-(1-methyl-1H-indol-5-yl)ethanamine

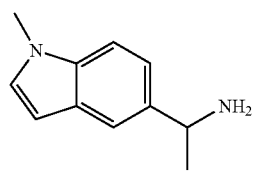

To the solution of 1-(1-methyl-1H-indol-5-yl)ethanone ([61640-20-8], 1.22 g, 7.04 mmol) in MeOH (70 ml) was added ammonium acetate (27.1 g, 352 mmol) and the mixture was stirred at rt of 30 min. Sodium cyanoborohydride (0.664 g, 10.6 mmol) was added in portions and the reaction was heated at reflux temperature over night. A part of the solvent was evaporated under reduced pressure and the residue taken into EtOAc and 2N aqueous sodium hydroxide. The organic layer was washed with 2N sodium hydroxide and brine, dried over sodium sulfate, and the solvent was evaporated under reduced pressure. The yellow oil was purified by chromatography on silica (Flashmaster, DCM to DCM/MeOH/aqNH3 90/10/0.5 over 20 min) to give the product as dark yellow oil (1.08 g, 73%) which decomposes under acidic conditions. (DMSO-d$_6$, 600 MHz) δ 7.49 (s, 1H), 7.33 (d, 1H), 7.26 (d, 1H), 7.17 (d, 1H), 6.34 (d, 1H), 4.07 (q, 1H), 3.75 (s, 3H), 2.13 (br s, 2H), 1.28 (d, 3H); LCMS Rt$_L$=2.138 min; [M+H-Me]$^+$=158.0]

Building Block C6: (S)-3-methyl-6,7-dihydro-5H-cyclopenta[b]pyridin-7-amine

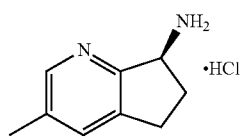

The title compound was obtained in analogues manner as described for building block C2, starting from 3-methyl-5H-cyclopenta[b]pyridin-7(6H)-one [building block B1]. [1H-NMR (DMSO-d$_6$, 600 MHz) δ 8.58 (br s, 3H), 8.38 (s, 1H), 7.67 (s, 1H), 4.65 (br s, 1H), 3.04-3.00 (m, 1H), 2.91-2.86 (m, 1H), 2.57-2.48 (m, 1H), 2.34 (s, 3H), 2.05-1.99 (m, 1H); LCMS Rt$_L$=2.271 min; [M+H]$^+$=149.2]

Building Block C7: 1-(1H-Pyrrolo[2,3-b]pyridin-5-yl)-ethylamine hydrochloride

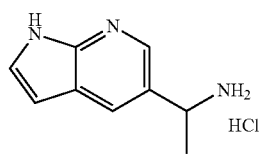

The title compound was obtained in analogues manner as described for building block C4, starting from 1-(1H-pyrrolo[2,3-b]pyridin-5-yl)-ethanone [944937-14-8]. [1H-NMR (DMSO-d$_6$, 600 MHz) δ 12.31 (s, 1H), 8.69 (br s, 3H), 8.48 (s, 1H), 8.41 (s, 1H), 7.64 (s, 1H) 6.63 (s, 1H), 4.62-4.58 (m, 1H), 1.63 (d, 3H); LCMS Rt$_L$=2.088 min; [M+H]$^+$=162.0]

Building Block C8: 1-(1-Methyl-1H-benzoimidazol-5-yl)-ethylamine hydrochloride

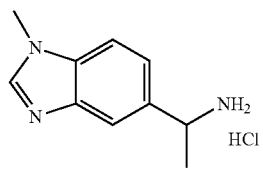

The title compound was obtained in analogues manner as described for building block C4, starting from 1-(1-methyl-1H-benzo[d]imidazol-5-yl)ethanone [265107-91-3]. [1H-NMR (DMSO-d$_6$, 600 MHz) δ 9.51 (s, 1H), 8.76 (br s, 3H), 8.06 (s, 1H), 8.99 (d, 1H), 7.77 (d, 1H) 4.66-4.62 (m, 1H), 4.05 (s, 3H), 1.58 (d, 3H); LCMS $Rt_F$=1-470 min; [M+H]$^F$=176.0]

Building Block C9: (S)-1-Cyclopentyl-ethylamine hydrochloride

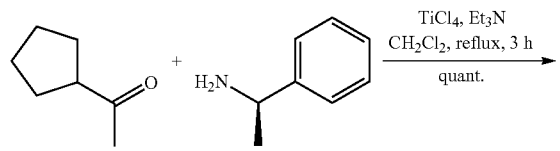

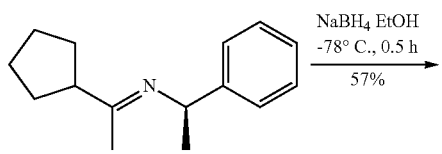

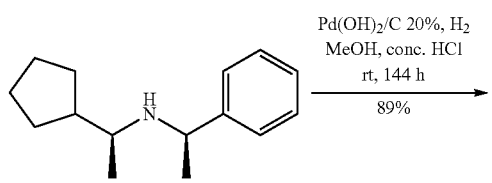

a) [1-Cyclopentyl-ethylidene]-((R)-1-phenyl-ethyl)-amine

(R)-1-Phenylethanamine (1.36 ml, 1.2 mmol) and triethylamine (7.46 ml, 53.5 mmol) were dissolved in DCM (30 ml) and cooled to 0° C. Titanium tetrachloride (0.49 ml, 4.46 mmol) was added, followed by the solution of 1-cyclopentyl-ethanone (1 g, 8.92 mmol) in DCM (5 ml). The reaction mixture was stirred 3 h at reflux temperature. After cooling to rt diethylether was added (130 ml) and the reaction mixture was filtered. The filtrate was collected and the solvents were evaporated at reduced pressure to give the product as yellow, viscous oil (2.04 g, crude quantitative). [1H-NMR (DMSO-$d_6$, 600 MHz) δ 7.35 (d, 2H), 7.28 (t, 2H), 7.17 (t, 1H), 4.61 (q, 1H), 2.67-2.62 (m, 1H), 1.81 (s, 3H), 1.71-1.50 (m, 8H), 1.27 (d, 3H); LCMS $Rt_L$=2.706 min; [M+H]$^+$=216.2]

b) ((S)-1-Cyclopentyl-ethyl)-((R)-1-phenyl-ethyl)amine

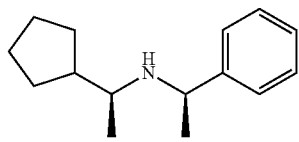

Crude [1-cyclopentyl-ethylidene](R)-1-phenyl-ethyl)-amine (2.0 g, 9.29 mmol) was dissolved in EtOH (25 ml) and cooled to −78° C. Sodium borohydride (1.76 g, 46.4 mmol) was added in portions and the reaction was stirred for another 30 min at −78° C. The mixture was let to warm to −20° C. and 6 N hydrochloric acid (20 ml) was carefully added. The reaction was poured on ice water and extracted with EtOAc. The organic layer was washed with 0.5 N aqueous sodium hydroxide and brine, dried over sodium sulfate, and the solvents were evaporated at reduced pressure. Chromatography on silica (Flashmaster hex to hex/EtOAc 7/3 in 40 min) gave the product as colorless oil (1.14 g, 57%). [1H-NMR (DMSO-$d_6$, 600 MHz) δ 7.33 (d, 2H), 7.28 (t, 2H), 7.18 (t, 1H), 3.80 (br s, 1H), 2.37 (br s, 1H), 1.83-1.77 (m, 1H), 1.69-1.65 (m, 1H), 1.60-1.43 (m, 6H), 1.22-1.17 (m, 2H), 1.19 (d, 3H), 0.82 (d, 3H); LCMS $Rt_L$=2.745 min; [M+H]$^+$=218.2]

c) (S)-1-Cyclopentyl-ethylamine hydrochloride

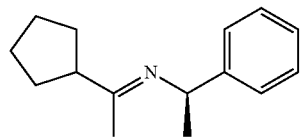 [SMILES: C/C(=N\[C@H](C)c1ccccc1)C1CCCC1]

((S)-1-Cyclopentyl-ethyl)-((R)-1-phenyl-ethyl)-amine (1.12 g, 5.15 mmol) was dissolved in MeOH (20 ml) and concentrated hydrcholoric acid (0.56 ml). The mixture was hydrogenated with Pd(OH)$_2$/C20% (wet 50%, FLUKA) (0.21 g, 0.299 mmol) at 0.1 bar hydrogen for 6 days. Over the 6 days additional catalyst was added in several portions (0.87 g). The reaction was filtered and the solvent was evaporated at reduced pressure. The residue was dissolved in DCM (5 ml) and 1N HCl in diethylether was added. The solvents were again evaporated under reduced pressure to give the title compound as white solid (0.685 g, 89%). [1H-NMR (DMSO-$d_6$, 600 MHz) δ 7.95 (br s, 3H), 3.01-2.94 (m, 1H), 1.95-1.84 (m, 1H), 1.78-1.46 (m, 6H), 1.29-1.13 (m, 2H), 1.17 (d, 3H); LCMS $Rt_L$=2.450 min (no UV signal, time of MS signal reported); [M+H]$^+$=114.2]

Building Block C10: (S)-5-Ethoxy-indan-1-ylamine hydrochloride

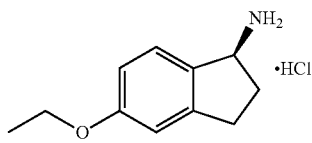

The title compound was obtained in analogues manner as described for building block C2, starting from 5-ethoxy-indan-1-one [building block B2]. [1H-NMR (DMSO-$d_6$, 600 MHz) δ 8.30 (br s, 3H), 7.47 (d, 1H), 6.88 (s, 1H), 6.84 (d, 1H), 4.62-4.60 (m, 1H), 4.02 (q, 2H), 3.07-3.02 (m, 1H), 2.85-2.80 (m, 1H), 2.47-2.41 (m, 1H), 2.01-1.97 (m, 1H), 1.32 (t, 3H); LCMS $Rt_f$=2.591 min; [M+H]$^+$=161.0]

Radioligand Binding Assay I

For crude cell membrane preparations, cells (CHO, Chinese hamster ovary or HEK, human embryonic kidney) expressing human orexin 1 or human orexin 2 receptors, were washed with HEPES (10 mM, pH 7.5), scraped off the culture plates with the same buffer, and centrifuged at 4° C. for 5 min at 2500×g. The cell pellet was either stored at −80° C. or used directly. Before the experiments, cell membranes were resuspended in binding assay buffer (10 mM HEPES, 0.5% (w/v) bovine serum albumin, pH 7.5) by homogenisation with a Polytron homogeniser at 50 Hz for 20 s. Cell membranes were also used as made available by commercial providers.

In initial saturation experiments (to calculate Bmax), cell homogenates (150 μl) were incubated with 25-300 pM of the radioligand ([$^{125}$I]orexin A, 50 μl), 8 concentrations in triplicates in the presence or absence Orexin A (1 μM, 50 μl) to define non specific binding. Bound radioactivity was measured, and data were analysed with the program XLFIT or Graphpad Prism. Protein concentration was determined according to the Bradford/BioRad Protein Assay Kit.

In competition experiments, cell homogenates (150 μl) were incubated in assay buffer (10 mM HEPES, pH 7.5, 0.5% (w/v) bovine serum albumin, 5 mM $MgCl_2$, 1 mM $CaCl_2$, and tween 0.05%) for 1 h at room temperature with about 100 pM of the radioligand ([$^{125}$I]orexin A, 2100 Ci/mmole, 50 μl), and with various concentrations of compounds of the invention (50 μl) in triplicates; non-specific binding was determined in the presence of Orexin A (1 μM). Reactions were terminated by vacuum filtration, 3 washes of ice cold wash buffer (Tris-HCl pH 7.4/10 mM, with NaCl 154 mM). Competition data is expressed in Table 2 as Kd [μM].

Radioligand Binding Assay II

For crude cell membrane preparations, cells (CHO, Chinese hamster ovary or HEK, human embryonic kidney) expressing human orexin 1 or human orexin 2 receptors, were washed with HEPES (10 mM, pH 7.5), scraped off the culture plates with the same buffer, and centrifuged at 4° C. for 5 min at 2500×g. The cell pellet was either stored at −80° C. or used directly. Before the experiments, cell membranes were resuspended in binding assay buffer (10 mM HEPES, 0.5% (w/v) bovine serum albumin, pH 7.5) by homogenisation with a Polytron homogeniser at 50 Hz for 20 s. Cell membranes were also used as made available by commercial providers.

In initial saturation experiments (to calculate Kd and Bmax), cell homogenates (150 μl) were incubated with 0.1 to 15 nM of the radioligand ([$^3$H]-SB649868, 50 μl), 8 concentrations in triplicates in the presence or absence of almorexant (10 μM, 50 μl) to define non specific binding. Bound radioactivity was measured, and data were analysed with the program XLFIT or Graphpad Prism. Protein concentration was determined according to the Bradford/BioRad Protein Assay Kit.

In competition experiments, cell homogenates (150 μl) were incubated in assay buffer (10 mM HEPES, pH 7.5, 0.5% (w/v) bovine serum albumin, 5 mM $MgCl_2$, 1 mM $CaCl_2$, and tween 0.05%) for 1 h at room temperature with about 1 nM of the radioligand ([$^3$H]-SB649868, 66 Ci/mmole, 50 μl), and with various concentrations of compounds of the invention (50 μl) in triplicates; non-specific binding was determined in the presence of almorexant (10 μM). Reactions were terminated by vacuum filtration, 3 washes of ice cold wash buffer (Tris-HCl pH 7.4/10 mM, with NaCl 154 mM). Competition data is expressed in Table 2 as Kd [μM].

Calcium Accumulation in Cells (FLIPR):

Cells expressing human orexin 1 or human orexin 2 receptors, were seeded at 8,000 cells/well in 384 well black-walled clear bottom, poly-D-lysine coated plates. After 24 h, the medium was removed and cells were washed once with phosphate buffered saline and serum-deprived overnight in assay buffer (130 mM NaCl, 5.4 mM KCl, 1.8 mM $CaCl_2$, 0.8 mM $MgSO_4$, 0.9 mM $NaH_2PO_4$, 25 mM glucose, 20 mM HEPES, pH 7.4) containing bovine serum albumin (1% w/v).

On the day of the experiment, the cells seeded in black plates were treated with assay buffer containing the $Ca^{2+}$ sensitive fluorescent dye Fluo4-AM (2 μM), and probenecid (0.1 mM). After 1 h plates were washed twice with, and resuspended in, assay buffer containing probenecid (0.1 mM) using a multi plate washer. The plates were placed into a FLIPR II (Fluorometric Imaging Plate Reader, Molecular Devices, Sunnyvale, Calif., USA) and baseline fluorescence (fluorescence light units, FLU) was measured (5 measurements, 2 S each; laser excitation 488 nm at 0.6-1 W, CCD camera exposure 0.4 s) before addition of buffer alone (basal) or containing test compounds (either compound of formula (I) or (I') alone, agonist alone or agonist in the presence of various concentrations of compounds of formula (I) or (I')). Fluorescence measurements were then continued every 1 S for 120 S followed by every 4 S for 240 S.

The measurements were typically made in two sequences:

In the first round, compounds of formula (I) or (I') were tested alone, to detect possible agonist activity. Compounds of formula I or I' were tested usually in a concentration range from $10^{-9}$ M to $10^{-5}$ M.

In the second round, performed one hour later (to allow for equilibration), Orexin A was tested either in the absence (calibration curves, Orexin A agonist controls) or in the presence of compounds of formula (I) or (I') to determine antagonism.

Inhibition data is expressed in Table 2 as $K_d$ [μM], converted by the Cheng and Prusoff correction ($Kd=IC_{50}/1+(L/EC_{50})$), where $IC_{50}$ is the 50% inhibition value determined in concentration response inhibition curves, $EC_{50}$ is the half maximal activation concentration determined for orexin A in concentration response curves and L is the concentration of orexin A used in inhibition experiments performed in with a submaximal concentration of orexin A in the presence of up to 8 increasing concentrations of compound of formula I'.

Inhibition data is also expressed in Table 2 as % inhibition value measured at a concentration of 10 μM of compound of formula I'.

TABLE 6

Biological Activity of Compounds of formula (I')

| Example | FLIPR hOx1R Ki [μM] | FLIPR hOx2R Ki [μM] | binding I hOx1R Kd [μM] | binding I hOx2R Kd [μM] | binding II hOx1R Kd [μM] | binding II hOx2R Kd [μM] |
|---|---|---|---|---|---|---|
| 1.1 | 0.156 | 0.030 | 0.185 | 0.079 | n.d. | n.d. |
| 1.2 | 0.200 | 0.043 | 0.161 | 0.181 | n.d. | n.d. |
| 1.3 | 0.211 | 0.069 | 0.348 | 0.128 | n.d. | n.d. |
| 1.4 | 0.014 | 0.002 | 0.008 | 0.004 | 0.007 | 0.003 |
| 1.5 | 0.870 | 0.036 | 1.151 | 0.076 | n.d. | n.d. |
| 1.6 | 0.005 | 0.002 | 0.003 | 0.008 | n.d. | n.d. |
| 1.7 | 1.016 | 0.337 | n.d. | n.d. | n.d. | n.d. |
| 1.8 | 39 [a] | 1.617 | n.d. | n.d. | n.d. | n.d. |
| 1.9 | 32 [a] | 2.500 | n.d. | n.d. | n.d. | n.d. |
| 1.10 | 0.650 | 0.324 | n.d. | n.d. | n.d. | n.d. |
| 1.11 | 2.014 | 0.251 | n.d. | n.d. | n.d. | n.d. |
| 1.12 | 2.500 | 1.380 | n.d. | n.d. | n.d. | n.d. |
| 1.13 | 0.181 | 0.233 | 0.045 | 0.143 | n.d. | n.d. |
| 1.14 | 0.422 | 33 [a] | n.d. | n.d. | n.d. | n.d. |
| 1.15 | 44 [a] | 39 [a] | n.d. | n.d. | n.d. | n.d. |
| 1.16 | 0.456 | 0.049 | 0.116 | 0.028 | n.d. | n.d. |
| 1.17 | 0.175 | 0.108 | 0.064 | 0.121 | n.d. | n.d. |
| 1.18 | 0.048 | 0.026 | 0.036 | 0.063 | n.d. | n.d. |
| 1.19 | 0.108 | 0.187 | 0.101 | 0.855 | n.d. | n.d. |
| 1.20 | 0.378 | 0.076 | 0.299 | 0.187 | n.d. | n.d. |
| 1.21 | 38 [a] | 29 [a] | n.d. | n.d. | n.d. | n.d. |
| 1.22 | 0.107 | 0.050 | 0.088 | 0.094 | n.d. | n.d. |
| 1.23 | 0.128 | 0.136 | 0.131 | 0.278 | n.d. | n.d. |
| 1.24 | 0.054 | 0.087 | 0.048 | 0.153 | n.d. | n.d. |
| 1.25 | 54 [a] | 52 [a] | n.d. | n.d. | n.d. | n.d. |
| 1.26 | 0.218 | 0.183 | n.d. | n.d. | n.d. | n.d. |
| 1.27 | 33 [a] | 35 [a] | n.d. | n.d. | n.d. | n.d. |
| 1.28 | 0.941 | 0.411 | n.d. | n.d. | n.d. | n.d. |
| 1.29 | 2.667 | 44 [a] | n.d. | n.d. | n.d. | n.d. |
| 1.30 | 0.970 | 0.582 | n.d. | n.d. | n.d. | n.d. |
| 1.31 | 2.109 | 40 [a] | n.d. | n.d. | n.d. | n.d. |
| 1.32 | 0.851 | 0.115 | 2.602 | 1.379 | n.d. | n.d. |
| 1.33 | 1.648 | 0.427 | n.d. | n.d. | n.d. | n.d. |
| 1.34 | 0.869 | 0.323 | n.d. | n.d. | n.d. | n.d. |
| 1.35 | 22 [a] | 22 [a] | n.d. | n.d. | n.d. | n.d. |
| 1.36 | 3.361 | 30 [a] | n.d. | n.d. | n.d. | n.d. |
| 1.37 | 1.952 | 0.298 | n.d. | n.d. | n.d. | n.d. |
| 1.38 | 0.004 | 0.003 | 0.006 | 0.016 | n.d. | n.d. |
| 1.39 | 0.222 | 0.353 | 0.330 | 1.127 | n.d. | n.d. |
| 1.40 | 37 [a] | 2.903 | n.d. | n.d. | n.d. | n.d. |
| 1.41 | 0.800 | 0.083 | 1.240 | 0.410 | n.d. | n.d. |
| 1.42 | 1.589 | 0.890 | n.d. | n.d. | n.d. | n.d. |
| 1.43 | 24 [a] | 2.057 | n.d. | n.d. | n.d. | n.d. |
| 1.44 | 0.274 | 0.158 | n.d. | n.d. | n.d. | n.d. |
| 1.45 | 0.029 | 0.002 | 0.032 | 0.007 | n.d. | n.d. |
| 1.46 | 0.020 | 0.026 | 0.042 | 0.101 | n.d. | n.d. |
| 1.47 | 0.441 | 0.561 | n.d. | n.d. | n.d. | n.d. |
| 1.48 | 0.178 | 0.075 | 0.490 | 0.212 | n.d. | n.d. |
| 1.49 | 0.015 | 0.243 | 0.006 | 0.715 | n.d. | n.d. |
| 1.50 | 0.730 | 0.168 | n.d. | n.d. | n.d. | n.d. |
| 1.51 | 0.471 | 0.364 | n.d. | n.d. | n.d. | n.d. |
| 1.52 | 1.166 | 0.868 | n.d. | n.d. | n.d. | n.d. |
| 1.53 | 14 [a] | 36 [a] | n.d. | n.d. | n.d. | n.d. |
| 1.54 | 25 [a] | 42 [a] | n.d. | n.d. | n.d. | n.d. |
| 1.55 | 23 [a] | 0.767 | n.d. | n.d. | n.d. | n.d. |
| 1.56 | 0.378 | 0.165 | n.d. | n.d. | n.d. | n.d. |
| 1.57 | 0.066 | 0.106 | 0.114 | 0.477 | n.d. | n.d. |
| 1.58 | 0.077 | 0.201 | 0.170 | 0.436 | n.d. | n.d. |
| 1.59 | 2.287 | 0.949 | n.d. | n.d. | n.d. | n.d. |
| 1.60 | 0.236 | 0.036 | 0.418 | 0.144 | n.d. | n.d. |
| 1.61 | 0.117 | 0.033 | 0.204 | 0.089 | n.d. | n.d. |
| 1.62 | <10 [a] | 36 [a] | n.d. | n.d. | n.d. | n.d. |
| 1.63 | 27 [a] | 34 [a] | n.d. | n.d. | n.d. | n.d. |
| 1.64 | 26 [a] | 39 [a] | n.d. | n.d. | n.d. | n.d. |
| 1.65 | 26 [a] | 30 [a] | n.d. | n.d. | n.d. | n.d. |
| 1.66 | 23 [a] | 41 [a] | n.d. | n.d. | n.d. | n.d. |
| 1.67 | 0.027 | 0.002 | 0.046 | 0.020 | n.d. | n.d. |
| 1.68 | <10 [a] | 16 [a] | n.d. | n.d. | n.d. | n.d. |
| 1.69 | 1.006 | 0.938 | n.d. | n.d. | n.d. | n.d. |
| 1.70 | 0.008 | 0.010 | 0.026 | 0.050 | n.d. | n.d. |
| 1.71 | 0.145 | 0.088 | 0.105 | 0.063 | n.d. | n.d. |
| 1.72 | 2.118 | 1.228 | n.d. | n.d. | n.d. | n.d. |
| 1.73 | 0.226 | 0.091 | 0.225 | 0.162 | n.d. | n.d. |
| 1.74 | <10 [a] | <10 [a] | n.d. | n.d. | n.d. | n.d. |

TABLE 6-continued

Biological Activity of Compounds of formula (I')

| Example | FLIPR hOx1R Ki [μM] | FLIPR hOx2R Ki [μM] | binding I hOx1R Kd [μM] | binding I hOx2R Kd [μM] | binding II hOx1R Kd [μM] | binding II hOx2R Kd [μM] |
|---|---|---|---|---|---|---|
| 1.75 | 27 [a] | 0.809 | n.d. | n.d. | n.d. | n.d. |
| 1.76 | 0.395 | 0.606 | n.d. | n.d. | n.d. | n.d. |
| 1.77 | 0.074 | 0.021 | 0.161 | 0.087 | n.d. | n.d. |
| 2.1 | 0.492 | 0.865 | n.d. | n.d. | n.d. | n.d. |
| 3.1 | 0.357 | 1.135 | n.d. | n.d. | n.d. | n.d. |
| 4.1 | 0.133 | 0.035 | n.d. | n.d. | 0.027 | 0.022 |
| 4.2 | 0.067 | 0.032 | n.d. | n.d. | 0.010 | 0.017 |
| 4.3 | 2.679 | 2.224 | n.d. | n.d. | n.d. | n.d. |
| 4.4 | 0.799 | 0.725 | n.d. | n.d. | n.d. | n.d. |
| 4.5 | 0.670 | 0.923 | n.d. | n.d. | n.d. | n.d. |
| 4.6 | 0.247 | 0.089 | n.d. | n.d. | 0.076 | 0.082 |
| 4.7 | 0.004 | 0.009 | n.d. | n.d. | 0.011 | 0.013 |
| 4.8 | 0.052 | 0.015 | n.d. | n.d. | 0.020 | 0.022 |
| 4.9 | 0.012 | 0.005 | n.d. | n.d. | 0.014 | 0.019 |
| 4.10 | 0.005 | 0.005 | n.d. | n.d. | 0.005 | 0.006 |
| 4.11 | 4.333 | 1.633 | n.d. | n.d. | n.d. | n.d. |
| 4.12 | 0.240 | 0.202 | n.d. | n.d. | n.d. | n.d. |
| 4.13 | 1.160 | 0.626 | n.d. | n.d. | n.d. | n.d. |
| 5.1 | 0.010 | 0.010 | n.d. | n.d. | 0.004 | 0.003 |
| 5.2 | 0.006 | 0.001 | n.d. | n.d. | 0.003 | 0.003 |
| 5.3 | 0.010 | 0.039 | n.d. | n.d. | 0.007 | 0.019 |
| 5.4 | 0.179 | 0.011 | n.d. | n.d. | 0.046 | 0.026 |
| 5.5 | 0.021 | 0.028 | n.d. | n.d. | 0.015 | 0.037 |
| 5.6 | 0.006 | 0.005 | n.d. | n.d. | 0.004 | 0.003 |
| 5.7 | 0.046 | 0.056 | n.d. | n.d. | 0.010 | 0.021 |
| 6.1 | 0.120 | 0.185 | n.d. | n.d. | n.d. | n.d. |
| 6.2 | 0.284 | 0.050 | n.d. | n.d. | 0.061 | 0.075 |
| 6.3 | 0.192 | 0.017 | n.d. | n.d. | 0.101 | 0.039 |
| 6.4 | 1.762 | 1.474 | n.d. | n.d. | n.d. | n.d. |
| 6.5 | 0.152 | 0.012 | n.d. | n.d. | 0.067 | 0.024 |
| 6.6 | 0.606 | 0.047 | n.d. | n.d. | 1.011 | 0.138 |
| 6.7 | 0.068 | 0.021 | n.d. | n.d. | 0.036 | 0.027 |
| 6.8 | 0.014 | 0.005 | n.d. | n.d. | 0.022 | 0.019 |
| 6.9 | 0.778 | 0.527 | n.d. | n.d. | n.d. | n.d. |
| 6.10 | 0.516 | 0.184 | n.d. | n.d. | n.d. | n.d. |
| 6.11 | 0.691 | 0.208 | n.d. | n.d. | n.d. | n.d. |
| 6.12 | 0.680 | 0.165 | n.d. | n.d. | n.d. | n.d. |
| 6.13 | 0.052 | 0.006 | n.d. | n.d. | 0.044 | 0.014 |
| 6.14 | 0.523 | 0.072 | n.d. | n.d. | 0.428 | 0.141 |
| 6.15 | 0.160 | 0.012 | n.d. | n.d. | 0.146 | 0.037 |
| 6.16 | 1.593 | 0.188 | n.d. | n.d. | n.d. | n.d. |
| 6.17 | 0.019 | 0.002 | n.d. | n.d. | 0.011 | 0.007 |
| 6.18 | 0.535 | 0.098 | n.d. | n.d. | n.d. | n.d. |
| 6.19 | 41 [a] | 0.800 | n.d. | n.d. | n.d. | n.d. |
| 6.20 | 0.063 | 0.059 | n.d. | n.d. | 0.022 | 0.090 |
| 6.21 | 0.029 | 0.007 | n.d. | n.d. | 0.037 | 0.030 |
| 6.22 | 0.175 | 0.037 | n.d. | n.d. | 0.056 | 0.042 |
| 6.23 | 1.099 | 0.237 | n.d. | n.d. | n.d. | n.d. |
| 6.24 | 0.133 | 0.105 | n.d. | n.d. | 0.045 | 0.150 |
| 6.25 | 0.545 | 0.065 | n.d. | n.d. | 0.242 | 0.164 |
| 6.26 | 0.164 | 0.032 | n.d. | n.d. | 0.119 | 0.076 |
| 6.27 | 0.415 | 0.105 | n.d. | n.d. | n.d. | n.d. |
| 6.28 | 39 [a] | 1.216 | n.d. | n.d. | n.d. | n.d. |
| 6.29 | 36 [a] | 34 [a] | n.d. | n.d. | n.d. | n.d. |
| 6.30 | 0.010 | 0.062 | n.d. | n.d. | 0.019 | 0.168 |
| 6.31 | 0.018 | 0.047 | n.d. | n.d. | 0.040 | 0.221 |
| 6.32 | 0.845 | 0.950 | n.d. | n.d. | n.d. | n.d. |
| 6.33 | 0.011 | 0.170 | n.d. | n.d. | 0.014 | 0.126 |
| 6.34 | 0.103 | 0.113 | n.d. | n.d. | 0.070 | 0.188 |
| 6.35 | 0.256 | 0.126 | n.d. | n.d. | n.d. | n.d. |
| 6.36 | 0.029 | 0.323 | n.d. | n.d. | 0.019 | 0.498 |
| 6.37 | 0.007 | 0.010 | n.d. | n.d. | 0.006 | 0.017 |
| 6.38 | 0.091 | 0.064 | n.d. | n.d. | 0.123 | 0.271 |
| 6.39 | 0.015 | 0.046 | n.d. | n.d. | 0.020 | 0.065 |
| 6.40 | 21 [a] | 0.589 | n.d. | n.d. | n.d. | n.d. |
| 6.41 | 0.495 | 0.029 | n.d. | n.d. | 0.908 | 0.225 |
| 6.42 | 0.083 | 0.010 | n.d. | n.d. | 0.063 | 0.014 |
| 6.43 | 0.234 | 0.003 | n.d. | n.d. | 0.206 | 0.018 |
| 6.44 | 0.223 | 0.014 | n.d. | n.d. | 0.067 | 0.028 |
| 6.45 | 20 [a] | 19 [a] | n.d. | n.d. | n.d. | n.d. |
| 6.46 | 16 [a] | 26 [a] | n.d. | n.d. | n.d. | n.d. |
| 6.47 | 1.486 | 0.747 | n.d. | n.d. | n.d. | n.d. |
| 6.48 | <10 [a] | <10 [a] | n.d. | n.d. | n.d. | n.d. |
| 6.49 | 21 | 0.611 | n.d. | n.d. | n.d. | n.d. |

TABLE 6-continued

Biological Activity of Compounds of formula (I')

| Example | FLIPR hOx1R Ki [μM] | FLIPR hOx2R Ki [μM] | binding I hOx1R Kd [μM] | binding I hOx2R Kd [μM] | binding II hOx1R Kd [μM] | binding II hOx2R Kd [μM] |
|---|---|---|---|---|---|---|
| 6.50 | 10 [a] | 42 [a] | n.d. | n.d. | n.d. | n.d. |
| 6.51 | 26 [a] | 0.575 | n.d. | n.d. | n.d. | n.d. |
| 6.52 | <10 [a] | <10 [a] | n.d. | n.d. | n.d. | n.d. |
| 6.53 | 17 [a] | 38 [a] | n.d. | n.d. | n.d. | n.d. |
| 6.54 | 44 [a] | 29 [a] | n.d. | n.d. | n.d. | n.d. |
| 6.55 | 53 [a] | 0.525 | n.d. | n.d. | n.d. | n.d. |
| 6.56 | <10 [a] | <10 [a] | n.d. | n.d. | n.d. | n.d. |
| 6.57 | 0.658 | 0.077 | n.d. | n.d. | 0.358 | 0.170 |
| 6.58 | 1.005 | 0.382 | n.d. | n.d. | n.d. | n.d. |
| 6.59 | 0.127 | 0.063 | n.d. | n.d. | 0.070 | 0.162 |
| 6.60 | 11 [a] | 1.175 | n.d. | n.d. | n.d. | n.d. |
| 6.61 | 0.227 | 0.093 | n.d. | n.d. | 0.157 | 0.159 |
| 6.62 | 0.626 | 0.160 | n.d. | n.d. | n.d. | n.d. |
| 6.63 | 0.109 | 0.022 | n.d. | n.d. | 0.054 | 0.042 |
| 6.64 | 0.783 | 0.093 | n.d. | n.d. | n.d. | n.d. |
| 6.65 | <10 [a] | 0.825 | n.d. | n.d. | n.d. | n.d. |
| 6.66 | 3.892 | 1.304 | n.d. | n.d. | n.d. | n.d. |
| 6.67 | 29 [a] | 40 [a] | n.d. | n.d. | n.d. | n.d. |
| 6.68 | 0.071 | 0.151 | n.d. | n.d. | 0.052 | 0.317 |
| 6.69 | 0.126 | 31 [a] | n.d. | n.d. | n.d. | n.d. |
| 6.70 | 1.062 | 1.070 | n.d. | n.d. | n.d. | n.d. |
| 6.71 | 0.348 | 0.055 | n.d. | n.d. | 0.589 | 0.095 |
| 6.72 | 46 [a] | 48 [a] | n.d. | n.d. | n.d. | n.d. |
| 6.73 | 43 [a] | 29 [a] | n.d. | n.d. | n.d. | n.d. |
| 6.74 | 23 [a] | 38 [a] | n.d. | n.d. | n.d. | n.d. |
| 6.75 | 1.754 | 0.567 | n.d. | n.d. | n.d. | n.d. |
| 6.76 | 23 [a] | 34 [a] | n.d. | n.d. | n.d. | n.d. |
| 6.77 | 0.148 | 0.059 | 0.501 | 0.240 | n.d. | n.d. |
| 6.78 | 43 [a] | 1.833 | n.d. | n.d. | n.d. | n.d. |
| 6.79 | 0.023 | 0.007 | n.d. | n.d. | 0.034 | 0.090 |
| 6.80 | 0.006 | 0.007 | n.d. | n.d. | 0.012 | 0.032 |
| 7.1 | 0.140 | 0.052 | n.d. | n.d. | 0.055 | 0.065 |
| 7.2 | <10 [a] | 15 [a] | n.d. | n.d. | n.d. | n.d. |
| 7.3 | <10 [a] | 16 [a] | n.d. | n.d. | n.d. | n.d. |
| 7.4 | <10 [a] | 26 [a] | n.d. | n.d. | n.d. | n.d. |
| 7.5 | <10 [a] | 0.479 | n.d. | n.d. | n.d. | n.d. |
| 7.6 | 18 [a] | <10 [a] | n.d. | n.d. | n.d. | n.d. |
| 7.7 | 32 [a] | 21 [a] | n.d. | n.d. | n.d. | n.d. |
| 7.8 | 26 [a] | 20 [a] | n.d. | n.d. | n.d. | n.d. |
| 7.9 | 0.877 | 0.742 | n.d. | n.d. | n.d. | n.d. |
| 7.10 | 34 [a] | 40 [a] | n.d. | n.d. | n.d. | n.d. |
| 7.11 | 0.050 | 0.024 | n.d. | n.d. | 0.018 | 0.017 |
| 7.12 | 0.736 | 43 [a] | n.d. | n.d. | n.d. | n.d. |
| 7.13 | 1.543 | 0.450 | n.d. | n.d. | n.d. | n.d. |
| 7.14 | 31 [a] | 20 [a] | n.d. | n.d. | n.d. | n.d. |
| 7.15 | 26 [a] | 18 [a] | n.d. | n.d. | n.d. | n.d. |
| 7.16 | 3.630 | 1.034 | n.d. | n.d. | n.d. | n.d. |
| 7.17 | 0.414 | 0.094 | n.d. | n.d. | n.d. | n.d. |
| 7.18 | <10 [a] | 11 [a] | n.d. | n.d. | n.d. | n.d. |
| 7.19 | 2.619 | 0.674 | n.d. | n.d. | n.d. | n.d. |
| 7.20 | 34 [a] | 31 [a] | n.d. | n.d. | n.d. | n.d. |
| 7.21 | <10 [a] | 22 [a] | n.d. | n.d. | n.d. | n.d. |
| 7.22 | 40 [a] | 32 [a] | n.d. | n.d. | n.d. | n.d. |
| 7.23 | 0.564 | 0.150 | n.d. | n.d. | n.d. | n.d. |
| 7.24 | 28 [a] | 25 [a] | n.d. | n.d. | n.d. | n.d. |
| 7.25 | 1.562 | 0.584 | n.d. | n.d. | n.d. | n.d. |
| 7.26 | 1.643 | 0.184 | n.d. | n.d. | n.d. | n.d. |
| 7.27 | 48 [a] | 0.472 | n.d. | n.d. | n.d. | n.d. |
| 7.28 | 34 [a] | 37 [a] | n.d. | n.d. | n.d. | n.d. |
| 7.29 | 1.800 | 0.900 | n.d. | n.d. | n.d. | n.d. |
| 7.30 | 0.938 | 26 [a] | n.d. | n.d. | n.d. | n.d. |
| 7.31 | 0.857 | 0.833 | n.d. | n.d. | n.d. | n.d. |
| 7.32 | 0.138 | 0.301 | n.d. | n.d. | n.d. | n.d. |
| 7.33 | 3.171 | 24 [a] | n.d. | n.d. | n.d. | n.d. |
| 8.1 | 0.092 | 0.165 | n.d. | n.d. | n.d. | n.d. | n.d. = not determined

[a] % inhibition value measured at a concentration of 10 μM of compound of formula I'.

The following are further embodiments of the invention:

EMBODIMENT 1

A compound of the formula I'

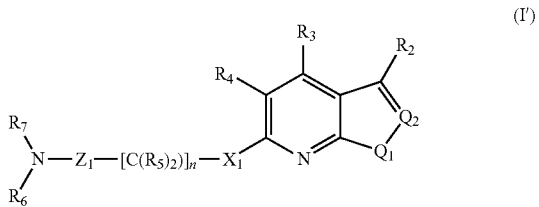

(I')

wherein
$Q_1$ is —$N(R_1)$—;
wherein $R_1$ is hydrogen; $C_{1-6}$alkyl; $C_{1-6}$halogenalkyl; $C_{2-6}$alkenyl; $C_{2-6}$halogenalkenyl; $C_{2-6}$alkynyl; $C_{2-6}$halogenalkynyl; a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_8$, and wherein a substituent on a nitrogen in a heterocyclic ring system may not be halogen;
and
$R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_9$, and wherein a substituent on a nitrogen in a heterocyclic ring system may not be halogen; or $R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{10}$, and wherein a substituent on a nitrogen in a heterocyclic ring system may not be halogen;
or
wherein $R_1$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{11}$, and wherein a substituent on a nitrogen in a heterocyclic ring system may not be halogen;
and
$R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{12}$, and wherein a substituent on a nitrogen in a heterocyclic ring system may not be halogen;

each $R_8$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_8$ at the same ring atom together are oxo;
each $R_9$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_9$ at the same ring atom together are oxo;
each $R_{12}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{12}$ at the same ring atom together are oxo;
each $R_{10}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{10}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{13}$, and wherein a substituent on a nitrogen in a heterocyclic ring system may not be halogen; and wherein each $R_{13}$ independently is halogen or $C_{1-6}$alkyl, or two $R_{13}$ at the same ring atom together are oxo;
each $R_{11}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{11}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{14}$, and wherein a substituent on a nitrogen in a heterocyclic ring system may not be halogen; and wherein each $R_{14}$ independently is halogen or $C_{1-6}$alkyl, or two $R_{14}$ at the same ring atom together are oxo;
or
$Q_1$ is —O— and
$R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{9a}$, and wherein a substituent on a nitrogen in a heterocyclic ring system may not be halogen; or $R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{10a}$, and wherein a substituent on a nitrogen in a heterocyclic ring system may not be halogen;

each $R_{9a}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{9a}$ at the same ring atom together are oxo;

each $R_{10a}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{10a}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{13a}$, and wherein a substituent on a nitrogen in a heterocyclic ring system may not be halogen; and wherein each $R_{13a}$ independently is halogen or $C_{1-6}$alkyl, or two $R_{13a}$ at the same ring atom together are oxo;

$Q_2$ is =N— or =C($R_{1a}$)—;
wherein $R_{1a}$ is hydrogen; $C_{1-6}$alkyl; $C_{1-6}$halogenalkyl; $C_{2-6}$alkenyl; $C_{2-6}$halogenalkenyl; $C_{2-6}$alkynyl; $C_{2-6}$halogenalkynyl;

$R_3$ and $R_4$ are each independently selected from hydrogen, halogen, hydroxyl, $C_{1-6}$alkyl, $C_{1-6}$halogenalkyl, $C_{1-6}$alkoxy, $C_{1-6}$halogenalkoxy, $C_{2-6}$alkenyl, $C_{2-6}$halogenalkenyl, $C_{2-6}$alkinyl, $C_{2-6}$halogenalkinyl, $C_{3-7}$cycloalkyl, $C_{3-7}$cycloalkyl($C_{1-4}$alkyl);

$X_1$ is —O—, —N($R_{15}$)—;
$R_{15}$ is hydrogen or $C_{1-6}$alkyl;
n is 1, 2 or 3;
each $R_5$ independently is selected from hydrogen, halogen, hydroxyl, $C_{1-6}$alkyl, $C_{1-6}$halogenalkyl, $C_{1-6}$alkoxy, $C_{1-6}$halogenalkoxy, $C_{3-7}$cycloalkyl, $C_{3-7}$cycloalkyl($C_{1-4}$alkyl); or two $R_5$ at the same carbon atom together with said carbon atom form $C_{3-7}$cycloalkyl; or two $R_5$ at adjacent carbon atoms together with said carbon atoms form $C_{3-7}$cycloalkyl; or two $R_5$ at carbon atoms separated by one further carbon atom together with said carbon atoms form $C_{4-7}$cycloalkyl;

$Z_1$ is —C(O)—, —S(O)— or —S(O)$_2$—;
$R_6$ is $C_{1-6}$alkyl, $C_{1-6}$halogenalkyl, $C_{2-6}$alkenyl, $C_{2-6}$halogenalkenyl, $C_{2-6}$alkynyl, $C_{2-6}$halogenalkynyl, $C_{3-7}$cycloalkyl, $C_{3-7}$cycloalkyl($C_{1-4}$alkyl) or a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system is attached to the nitrogen atom via a $C_{1-4}$alkylene group, and wherein the ring system may be substituted once or more than once by $R_{16}$, and wherein a substituent on a nitrogen in a heterocyclic ring system may not be halogen;

each $R_{16}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

or two $R_{16}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{17}$, and wherein a substituent on a nitrogen in a heterocyclic ring system may not be halogen; and wherein each $R_{17}$ independently is halogen or $C_{1-6}$alkyl, or two $R_{17}$ at the same ring atom together are oxo;

or
$R_6$ is a group A

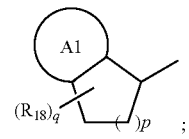

A wherein
p is 1 or 2;
q is 0, 1, 2, 3 or 4;
each $R_{18}$ independently is halogen or $C_{1-6}$alkyl;
A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by $R_{19}$, and wherein a substituent on a nitrogen in a heterocyclic ring system may not be halogen;
each $R_{19}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;
and $R_7$ is hydrogen, $C_{1-6}$alkyl, $C_{1-6}$halogenalkyl, $C_{2-6}$alkenyl, $C_{2-6}$halogenalkenyl, $C_{2-6}$alkinyl, $C_{2-6}$halogenalkinyl, $C_{3-7}$cycloalkyl, $C_{3-7}$cycloalkyl($C_{1-4}$alkyl);
in free form or in salt form
for use as a medicament.

EMBODIMENT 2

A compound of formula I'

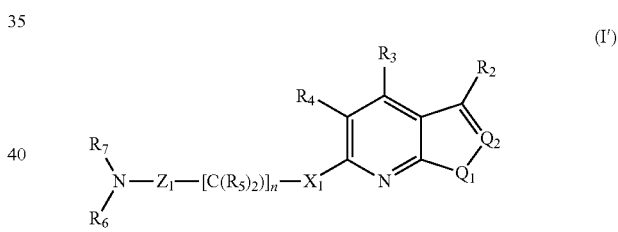

(I')

wherein
$Q_1$ is —N($R_1$)—;
wherein $R_1$ is hydrogen; $C_{1-6}$alkyl; $C_{1-6}$halogenalkyl; $C_{2-6}$alkenyl; $C_{2-6}$halogenalkenyl; $C_{2-6}$alkynyl; $C_{2-6}$halogenalkynyl; a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_8$, and wherein a substituent on a nitrogen in a heterocyclic ring system may not be halogen;
and
$R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_9$, and wherein a substituent on a nitrogen in a heterocyclic ring system may not be halogen; or $R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{10}$, and wherein a substituent on a nitrogen in a heterocyclic ring system may not be halogen;

or wherein $R_1$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{11}$, and wherein a substituent on a nitrogen in a heterocyclic ring system may not be halogen;

and $R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{12}$, and wherein a substituent on a nitrogen in a heterocyclic ring system may not be halogen;

each $R_8$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_8$ at the same ring atom together are oxo;

each $R_9$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_9$ at the same ring atom together are oxo;

each $R_{12}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{12}$ at the same ring atom together are oxo;

each $R_{10}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{10}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{13}$, and wherein a substituent on a nitrogen in a heterocyclic ring system may not be halogen; and wherein each $R_{13}$ independently is halogen or $C_{1-6}$alkyl, or two $R_{13}$ at the same ring atom together are oxo;

each $R_{11}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{11}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{14}$, and wherein a substituent on a nitrogen in a heterocyclic ring system may not be halogen; and wherein each $R_{14}$ independently is halogen or $C_{1-6}$alkyl, or two $R_{14}$ at the same ring atom together are oxo;

or $Q_1$ is —O— and $R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{9a}$, and wherein a substituent on a nitrogen in a heterocyclic ring system may not be halogen; or $R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{10a}$, and wherein a substituent on a nitrogen in a heterocyclic ring system may not be halogen;

each $R_{9a}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{9a}$ at the same ring atom together are oxo;

each $R_{10a}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{10a}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{13a}$, and wherein a substituent on a nitrogen in a heterocyclic ring system may not be halogen; and wherein each $R_{13a}$ independently is halogen or $C_{1-6}$alkyl, or two $R_{13a}$ at the same ring atom together are oxo;

$Q_2$ is =N— or =C($R_{1a}$)—;

wherein $R_{1a}$ is hydrogen; $C_{1-6}$alkyl; $C_{1-6}$halogenalkyl; $C_{2-6}$alkenyl; $C_{2-6}$halogenalkenyl; $C_{2-6}$alkynyl; $C_{2-6}$halogenalkynyl;

$R_3$ and $R_4$ are each independently selected from hydrogen, halogen, hydroxyl, $C_{1-6}$alkyl, $C_{1-6}$halogenalkyl, $C_{1-6}$alkoxy, $C_{1-6}$halogenalkoxy, $C_{2-6}$alkenyl, $C_{2-6}$halogenalkenyl, $C_{2-6}$alkinyl, $C_{2-6}$halogenalkinyl, $C_{3-7}$cycloalkyl, $C_{3-7}$cycloalkyl($C_{1-4}$alkyl);

$X_1$ is —O—, —N($R_{15}$)—;

$R_{15}$ is hydrogen or $C_{1-6}$alkyl;

n is 1, 2 or 3;

each $R_5$ independently is selected from hydrogen, halogen, hydroxyl, $C_{1-6}$alkyl, $C_{1-6}$halogenalkyl, $C_{1-6}$alkoxy, $C_{1-6}$halogenalkoxy, $C_{3-7}$cycloalkyl, $C_{3-7}$cycloalkyl($C_{1-4}$alkyl); or two $R_5$ at the same carbon atom together with said carbon atom form $C_{3-7}$cycloalkyl; or two $R_5$ at adjacent carbon atoms together with said carbon atoms form $C_{3-7}$cycloalkyl; or two $R_5$ at carbon atoms separated by one further carbon atom together with said carbon atoms form $C_{4-7}$cycloalkyl;

$Z_1$ is —C(O)—, —S(O)— or —S(O)$_2$—;

$R_6$ is $C_{1-6}$alkyl, $C_{1-6}$halogenalkyl, $C_{2-6}$alkenyl, $C_{2-6}$halogenalkenyl, $C_{2-6}$alkynyl, $C_{2-6}$halogenalkynyl, $C_{3-7}$cycloalkyl, $C_{3-7}$cycloalkyl($C_{1-4}$alkyl) or a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system is attached to the nitrogen atom via a $C_{1-4}$alkylene group, and wherein the ring system may be substituted once or more than once by $R_{16}$, and wherein a substituent on a nitrogen in a heterocyclic ring system may not be halogen;

each $R_{16}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

or two $R_{16}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{17}$, and wherein a substituent on a nitrogen in a heterocyclic ring system may not be halogen; and wherein each $R_{17}$ independently is halogen or $C_{1-6}$alkyl, or two $R_{17}$ at the same ring atom together are oxo;

or $R_6$ is a group A

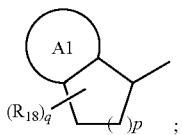

wherein
p is 1 or 2;
q is 0, 1, 2, 3 or 4;
each $R_{18}$ independently is halogen or $C_{1-6}$alkyl;
A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by $R_{19}$, and wherein a substituent on a nitrogen in a heterocyclic ring system may not be halogen;
each $R_{19}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;
and $R_7$ is hydrogen, $C_{1-6}$alkyl, $C_{1-6}$halogenalkyl, $C_{2-6}$alkenyl, $C_{2-6}$halogenalkenyl, $C_{2-6}$alkinyl, $C_{2-6}$halogenalkinyl, $C_{3-7}$cycloalkyl, $C_{3-7}$cycloalkyl($C_{1-4}$alkyl);
and provided that the compounds
N-(2-methoxybenzyl)-2-(1-methyl-3-phenyl-4-(trifluoromethyl)-1H-pyrazolo[3,4-b]pyridin-6-yloxy)acetamide;
2-(1-methyl-3-phenyl-4-(trifluoromethyl)-1H-pyrazolo[3,4-b]pyridin-6-yloxy)-N-(2-methylbenzyl)acetamide;
N-(2-ethoxybenzyl)-2-(1-methyl-3-phenyl-4-(trifluoromethyl)-1H-pyrazolo[3,4-b]pyridin-6-yloxy)acetamide;
N-(3-fluorobenzyl)-2-(1-methyl-3-phenyl-4-(trifluoromethyl)-1H-pyrazolo[3,4-b]pyridin-6-yloxy)acetamide;
2-(1-methyl-3-phenyl-4-(trifluoromethyl)-1H-pyrazolo[3,4-b]pyridin-6-yloxy)-N-(4-phenylbutan-2-yl)acetamide;
N-cyclohexyl-2-(1-methyl-3-phenyl-4-(trifluoromethyl)-1H-pyrazolo[3,4-b]pyridin-6-yloxy)acetamide;
N-(4-fluorobenzyl)-2-(1-methyl-3-phenyl-4-(trifluoromethyl)-1H-pyrazolo[3,4-b]pyridin-6-yloxy)acetamide;
2-(1-methyl-3-phenyl-4-(trifluoromethyl)-1H-pyrazolo[3,4-b]pyridin-6-yloxy)-N-(1-phenylethyl)acetamide;
N-(benzo[d][1,3]dioxol-5-ylmethyl)-2-(1-methyl-3-phenyl-4-(trifluoromethyl)-1H-pyrazolo[3,4-b]pyridin-6-yloxy)acetamide;
N-cyclopentyl-2-(1-methyl-3-phenyl-4-(trifluoromethyl)-1H-pyrazolo[3,4-b]pyridin-6-yloxy)acetamide;
N-(4-chlorobenzyl)-2-(1-methyl-3-phenyl-4-(trifluoromethyl)-1H-pyrazolo[3,4-b]pyridin-6-yloxy)acetamide;
N-(2-chlorobenzyl)-2-(1-methyl-3-phenyl-4-(trifluoromethyl)-1H-pyrazolo[3,4-b]pyridin-6-yloxy)acetamide; and
N-benzyl-2-(1-methyl-3-phenyl-4-(trifluoromethyl)-1H-pyrazolo[3,4-b]pyridin-6-yloxy)acetamide
are excluded;
in free form or in salt form.

EMBODIMENT 3

A compound of the formula I

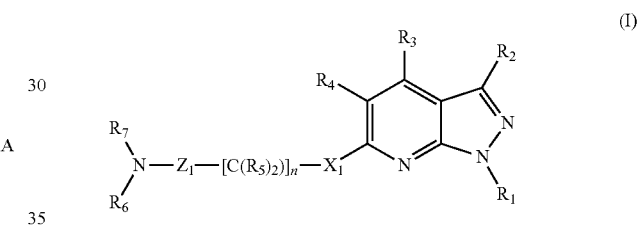

wherein
$R_1$ is hydrogen; $C_{1-6}$alkyl; $C_{1-6}$halogenalkyl; $C_{2-6}$alkenyl; $C_{2-6}$halogenalkenyl; $C_{2-6}$alkynyl; $C_{2-6}$halogenalkynyl; or $R_1$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the nitrogen atom of the 1H-pyrazolo[3,4b]pyridine or via a $C_{1-4}$alkylene group, and wherein the ring system may be substituted once or more than once by $R_8$, and wherein a substituent on a nitrogen in a heterocyclic ring system may not be halogen; and
$R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a $C_{1-4}$alkylene group, and wherein the ring system may be substituted once or more than once by $R_9$, and wherein a substituent on a nitrogen in a heterocyclic ring system may not be halogen; or $R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a $C_{1-4}$alkylene group, and wherein the ring system may be substituted once or more than once by $R_{10}$, and wherein a substituent on a nitrogen in a heterocyclic ring system may not be halogen; or $R_1$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the nitrogen atom of the 1H-pyrazolo[3,4b]pyridine or via a $C_{1-4}$alkylene group, and wherein the ring system may be substituted once or more than once by $R_{11}$, and wherein a substituent on a nitrogen in a heterocyclic ring system may not be halogen;

and $R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a $C_{1-4}$alkylene group, and wherein the ring system may be substituted once or more than once by $R_{12}$, and wherein a substituent on a nitrogen in a heterocyclic ring system may not be halogen;

each $R_8$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_8$ at the same ring atom together are oxo;

each $R_9$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_9$ at the same ring atom together are oxo;

each $R_{12}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{12}$ at the same ring atom together are oxo;

each $R_{10}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{10}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{13}$, and wherein a substituent on a nitrogen in a heterocyclic ring system may not be halogen; and wherein each $R_{13}$ independently is halogen or $C_{1-6}$alkyl, or two $R_{13}$ at the same ring atom together are oxo;

each $R_{11}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{11}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{14}$, and wherein a substituent on a nitrogen in a heterocyclic ring system may not be halogen; and wherein each $R_{14}$ independently is halogen or $C_{1-6}$alkyl, or two $R_{14}$ at the same ring atom together are oxo;

$R_3$ and $R_4$ are each independently selected from hydrogen, halogen, hydroxyl, $C_{1-6}$alkyl, $C_{1-6}$halogenalkyl, $C_{1-6}$alkoxy, $C_{1-6}$halogenalkoxy, $C_{2-6}$alkenyl, $C_{2-6}$halogenalkenyl, $C_{2-6}$alkynyl, $C_{2-6}$halogenalkynyl, $C_{3-7}$cycloalkyl, $C_{3-7}$cycloalkyl($C_{1-4}$alkyl);

$X_1$ is —O—, —N($R_{15}$)—;

$R_{15}$ is hydrogen or $C_{1-6}$alkyl;

n is 1, 2 or 3;

each $R_5$ independently is selected from hydrogen, halogen, hydroxyl, $C_{1-6}$alkyl, $C_{1-6}$halogenalkyl, $C_{1-6}$alkoxy, $C_{1-6}$halogenalkoxy, $C_{3-7}$cycloalkyl, $C_{3-7}$cycloalkyl($C_{1-4}$alkyl); or two $R_5$ at the same carbon atom together with said carbon atom form $C_{3-7}$cycloalkyl; or two $R_5$ at adjacent carbon atoms together with said carbon atoms form $C_{3-7}$cycloalkyl; or two $R_5$ at carbon atoms separated by one further carbon atom together with said carbon atoms form $C_{4-7}$cycloalkyl;

$Z_1$ is —C(O)—, —S(O)— or —S(O)$_2$—;

$R_6$ is $C_{1-6}$alkyl, $C_{1-6}$halogenalkyl, $C_{2-6}$alkenyl, $C_{2-6}$halogenalkenyl, $C_{2-6}$alkynyl, $C_{2-6}$halogenalkynyl, $C_{3-7}$cycloalkyl, $C_{3-7}$cycloalkyl($C_{1-4}$alkyl) or a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system is attached to the nitrogen atom via a $C_{1-4}$alkylene group, and wherein the ring system may be substituted once or more than once by $R_{16}$, and wherein a substituent on a nitrogen in a heterocyclic ring system may not be halogen;

each $R_{16}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

or two $R_{16}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{17}$, and wherein a substituent on a nitrogen in a heterocyclic ring system may not be halogen; and wherein each $R_{17}$ independently is halogen or $C_{1-6}$alkyl, or two $R_{17}$ at the same ring atom together are oxo; or $R_6$ is a group A

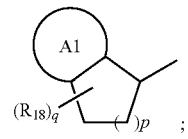

A wherein p is 1 or 2;

q is 0, 1, 2, 3 or 4;

each $R_{18}$ independently is halogen or $C_{1-6}$alkyl;

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by $R_{19}$, and wherein a substituent on a nitrogen in a heterocyclic ring system may not be halogen;

each $R_{19}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

and $R_7$ is hydrogen, $C_{1-6}$alkyl, $C_{1-6}$halogenalkyl, $C_{2-6}$alkenyl, $C_{2-6}$halogenalkenyl, $C_{2-6}$alkynyl, $C_{2-6}$halogenalkynyl, $C_{3-7}$cycloalkyl, $C_{3-7}$cycloalkyl($C_{1-4}$alkyl);

in free form or in salt form
for use as a medicament.

EMBODIMENT 4

A compound of the formula I

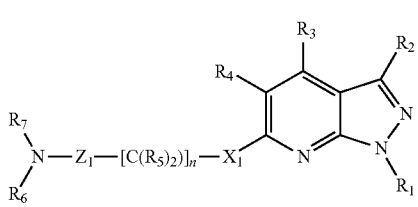

(I)

wherein $R_1$ is hydrogen; $C_{1-6}$alkyl; $C_{1-6}$halogenalkyl; $C_{2-6}$alkenyl; $C_{2-6}$halogenalkenyl; $C_{2-6}$alkynyl; $C_{2-6}$halogenalkynyl; or $R_1$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the nitrogen atom of the 1H-pyrazolo[3,4b]pyridine or via a $C_{1-4}$alkylene group, and wherein the ring system may be substituted once or more than once by $R_8$, and wherein a substituent on a nitrogen in a heterocyclic ring system may not be halogen; and $R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a $C_{1-4}$alkylene group, and wherein the ring system may be substituted once or more than once by $R_9$, and wherein a substituent on a nitrogen in a heterocyclic ring system may not be halogen; or $R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a $C_{1-4}$alkylene group, and wherein the ring system may be substituted once or more than once by $R_{10}$, and wherein a substituent on a nitrogen in a heterocyclic ring system may not be halogen;

or $R_1$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the nitrogen atom of the 1H-pyrazolo[3,4b]pyridine or via a $C_{1-4}$alkylene group, and wherein the ring system may be substituted once or more than once by $R_{11}$, and wherein a substituent on a nitrogen in a heterocyclic ring system may not be halogen;

and $R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a $C_{1-4}$alkylene group, and wherein the ring system may be substituted once or more than once by $R_{12}$, and wherein a substituent on a nitrogen in a heterocyclic ring system may not be halogen;

each $R_8$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_8$ at the same ring atom together are oxo;

each $R_9$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_9$ at the same ring atom together are oxo;

each $R_{12}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{12}$ at the same ring atom together are oxo;

each $R_{10}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{10}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{13}$, and wherein a substituent on a nitrogen in a heterocyclic ring system may not be halogen; and wherein each $R_{13}$ independently is halogen or $C_{1-6}$alkyl, or two $R_{13}$ at the same ring atom together are oxo;

each $R_{11}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{11}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{14}$, and wherein a substituent on a nitrogen in a heterocyclic ring system may not be halogen; and wherein each $R_{14}$ independently is halogen or $C_{1-6}$alkyl, or two $R_{14}$ at the same ring atom together are oxo;

$R_3$ and $R_4$ are each independently selected from hydrogen, halogen, hydroxyl, $C_{1-6}$alkyl, $C_{1-6}$halogenalkyl, $C_{1-6}$alkoxy, $C_{1-6}$halogenalkoxy, $C_{2-6}$alkenyl, $C_{2-6}$halogenalkenyl, $C_{2-6}$alkynyl, $C_{2-6}$halogenalkynyl, $C_{3-7}$cycloalkyl, $C_{3-7}$cycloalkyl($C_{1-4}$alkyl);

$X_1$ is —O—, —N($R_{15}$)—;

$R_{15}$ is hydrogen or $C_{1-6}$alkyl;

n is 1, 2 or 3;

each $R_5$ independently is selected from hydrogen, halogen, hydroxyl, $C_{1-6}$alkyl, $C_{1-6}$halogenalkyl, $C_{1-6}$alkoxy, $C_{1-6}$halogenalkoxy, $C_{3-7}$cycloalkyl, $C_{3-7}$cycloalkyl($C_{1-4}$alkyl); or two $R_5$ at the same carbon atom together with said carbon atom form $C_{3-7}$cycloalkyl; or two $R_5$ at adjacent carbon atoms together with said carbon atoms form $C_{3-7}$cycloalkyl; or two $R_5$ at carbon atoms separated by one further carbon atom together with said carbon atoms form $C_{4-7}$cycloalkyl;

$Z_1$ is —C(O)—, —S(O)— or —S(O)$_2$—;

$R_6$ is $C_{1-6}$alkyl, $C_{1-6}$halogenalkyl, $C_{2-6}$alkenyl, $C_{2-6}$halogenalkenyl, $C_{2-6}$alkynyl, $C_{2-6}$halogenalkynyl, $C_{3-7}$cycloalkyl, $C_{3-7}$cycloalkyl($C_{1-4}$alkyl) or a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system is attached to the nitrogen atom via a $C_{1-4}$alkylene group, and wherein the ring system may be substituted once or more than once by $R_{16}$, and wherein a substituent on a nitrogen in a heterocyclic ring system may not be halogen;

each $R_{16}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

or two $R_{16}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{17}$, and wherein a substituent on a nitrogen in a heterocyclic ring system may not be halogen; and wherein each $R_{17}$ independently is halogen or $C_{1-6}$alkyl, or two $R_{17}$ at the same ring atom together are oxo;

or $R_6$ is a group A

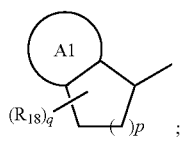

wherein p is 1 or 2;

q is 0, 1, 2, 3 or 4;

each $R_{18}$ independently is halogen or $C_{1-6}$alkyl;

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by $R_{19}$, and wherein a substituent on a nitrogen in a heterocyclic ring system may not be halogen;

each $R_{19}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

and $R_7$ is hydrogen, $C_{1-6}$alkyl, $C_{1-6}$halogenalkyl, $C_{2-6}$alkenyl, $C_{2-6}$halogenalkenyl, $C_{2-6}$alkynyl, $C_{2-6}$halogenalkynyl, $C_{3-7}$cycloalkyl, $C_{3-7}$cycloalkyl($C_{1-4}$alkyl);

and provided that the compounds

N-(2-methoxybenzyl)-2-(1-methyl-3-phenyl-4-(trifluoromethyl)-1H-pyrazolo[3,4-b]pyridin-6-yloxy)acetamide;

2-(1-methyl-3-phenyl-4-(trifluoromethyl)-1H-pyrazolo[3,4-b]pyridin-6-yloxy)-N-(2-methylbenzyl)acetamide;

N-(2-ethoxybenzyl)-2-(1-methyl-3-phenyl-4-(trifluoromethyl)-1H-pyrazolo[3,4-b]pyridin-6-yloxy)acetamide;

N-(3-fluorobenzyl)-2-(1-methyl-3-phenyl-4-(trifluoromethyl)-1H-pyrazolo[3,4-b]pyridin-6-yloxy)acetamide;

2-(1-methyl-3-phenyl-4-(trifluoromethyl)-1H-pyrazolo[3,4-b]pyridin-6-yloxy)-N-(4-phenylbutan-2-yl)acetamide;

N-cyclohexyl-2-(1-methyl-3-phenyl-4-(trifluoromethyl)-1H-pyrazolo[3,4-b]pyridin-6-yloxy)acetamide;

N-(4-fluorobenzyl)-2-(1-methyl-3-phenyl-4-(trifluoromethyl)-1H-pyrazolo[3,4-b]pyridin-6-yloxy)acetamide;

2-(1-methyl-3-phenyl-4-(trifluoromethyl)-1H-pyrazolo[3,4-b]pyridin-6-yloxy)-N-(1-phenylethyl)acetamide;

N-(benzo[d][1,3]dioxol-5-ylmethyl)-2-(1-methyl-3-phenyl-4-(trifluoromethyl)-1H-pyrazolo[3,4-b]pyridin-6-yloxy)acetamide;

N-cyclopentyl-2-(1-methyl-3-phenyl-4-(trifluoromethyl)-1H-pyrazolo[3,4-b]pyridin-6-yloxy)acetamide;

N-(4-chlorobenzyl)-2-(1-methyl-3-phenyl-4-(trifluoromethyl)-1H-pyrazolo[3,4-b]pyridin-6-yloxy)acetamide;

N-(2-chlorobenzyl)-2-(1-methyl-3-phenyl-4-(trifluoromethyl)-1H-pyrazolo[3,4-b]pyridin-6-yloxy)acetamide; and N-benzyl-2-(1-methyl-3-phenyl-4-(trifluoromethyl)-1H-pyrazolo[3,4-b]pyridin-6-yloxy)acetamide are excluded;

in free form or in salt form.

EMBODIMENT 5

A compound of formula I' according to embodiment 2, wherein $Q_1$ is —N($R_1$)— and $Q_2$ is =N—; or $Q_1$ is —N($R_1$)— and $Q_2$ is =C($R_{1a}$)—; or $Q_1$ is —O— and $Q_2$ is =N—.

EMBODIMENT 6

A compound of formula I' according to embodiment 2 or 5, wherein $R_1$ is hydrogen, $C_{1-6}$alkyl, $C_{1-6}$halogenalkyl, $C_{2-6}$alkenyl, $C_{2-6}$halogenalkenyl, $C_{2-6}$alkynyl or $C_{2-6}$halogenalkynyl.

EMBODIMENT 7

A compound of formula I' according to embodiment 2 or 5 or 6, wherein $X_1$ is —O—; n is 1; each $R_5$ is hydrogen; and $Z_1$ is —C(O)—.

EMBODIMENT 8

A compound of formula I' according to any of embodiments 2 or 5 to 7, wherein $R_3$ is $C_{1-6}$alkyl or $C_{1-6}$halogenalkyl; and $R_4$ is hydrogen.

EMBODIMENT 9

A compound of formula I' according to claim 2, wherein said compound is a compound of formula I'-2

(I'-2)

wherein $Q_1$ is —N($R_1$)— or —O—;

$Q_2$ is =N— or =C($R_{1a}$)—;

especially $Q_1$ is —N($R_1$)— and $Q_2$ is =N—; or $Q_1$ is —N($R_1$)— and $Q_2$ is =C($R_{1a}$)—; or $Q_1$ is —O— and $Q_2$ is =N—;

$R_1$ is hydrogen, $C_{1-6}$alkyl, $C_{1-6}$halogenalkyl, $C_{2-6}$alkenyl, $C_{2-6}$halogenalkenyl, $C_{2-6}$alkynyl or $C_{2-6}$halogenalkynyl; especially $R_1$ is hydrogen or $C_{1-6}$alkyl; further especially methyl; further especially hydrogen;

$R1_a$ is hydrogen, $C_{1-6}$alkyl, $C_{1-6}$halogenalkyl, $C_{2-6}$alkenyl, $C_{2-6}$halogenalkenyl, $C_{2-6}$alkynyl or $C_{2-6}$halogenalkynyl; especially $R_1$ is hydrogen or $C_{1-6}$alkyl; further especially methyl; further especially hydrogen;

$R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{10}$, and wherein a substituent on a nitrogen in a heterocyclic ring system may not be halogen; each $R_{10}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

$R_3$ is selected from $C_{1-6}$alkyl and $C_{1-6}$halogenalkyl; especially $R_3$ is methyl or trifluoromethyl;

n is 1;

$R_{6a}$ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by $R_{16}$, and wherein a substituent on a nitrogen in a heterocyclic ring system may not be halogen; each $R_{16}$ independently is especially halogen, $C_{1-6}$alkyl, especially $C_{1-4}$alkyl, $C_{1-6}$alkoxy or $C_{1-6}$halogenalkyl; and $R_{6b}$ is $C_{1-3}$alkyl, especially $R_{6b}$ is methyl.

EMBODIMENT 10

A compound of formula I' according to embodiment 2, wherein said compound is a compound of formula I'-4

(I'-4)

wherein $Q_1$ is —N($R_1$)— or —O—;

$Q_2$ is =N— or =C($R_{1a}$)—;

especially $Q_1$ is —N($R_1$)— and $Q_2$ is =N—; or $Q_1$ is —N($R_1$)— and $Q_2$ is =C($R_{1a}$)—; or $Q_1$ is —O— and $Q_2$ is =N—;

$R_1$ is hydrogen, $C_{1-6}$alkyl, $C_{1-6}$halogenalkyl, $C_{2-6}$alkenyl, $C_{2-6}$halogenalkenyl, $C_{2-6}$alkynyl or $C_{2-6}$halogenalkynyl; especially $R_1$ is hydrogen or $C_{1-6}$alkyl; further especially methyl; further especially hydrogen;

$R1_a$ is hydrogen, $C_{1-6}$alkyl, $C_{1-6}$halogenalkyl, $C_{2-6}$alkenyl, $C_{2-6}$halogenalkenyl, $C_{2-6}$alkynyl or $C_{2-6}$halogenalkynyl; especially $R_1$ is hydrogen or $C_{1-6}$alkyl; further especially methyl; further especially hydrogen;

$R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{10}$, and wherein a substituent on a nitrogen in a heterocyclic ring system may not be halogen; each $R_{10}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

$R_3$ is selected from $C_{1-6}$alkyl and $C_{1-6}$halogenalkyl; especially $R_3$ is methyl or trifluoromethyl;

n is 1,

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by $R_{19}$, and wherein a substituent on a nitrogen in a heterocyclic ring system may not be halogen; and each $R_{19}$ independently is halogen, $C_{1-6}$alkyl, $C_{1-6}$alkoxy or $C_{1-6}$halogenalkyl.

EMBODIMENT 11

A compound of formula I according to embodiment 4. wherein said compound is a compound of formula I-2

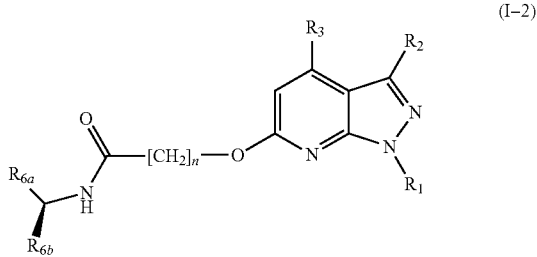

wherein $R_1$ is hydrogen, $C_{1-6}$alkyl, $C_{1-6}$halogenalkyl, $C_{2-6}$alkenyl, $C_{2-6}$halogenalkenyl, $C_{2-6}$alkynyl or $C_{2-6}$halogenalkynyl; especially $R_1$ is hydrogen or $C_{1-6}$alkyl; further especially methyl; further especially hydrogen;

$R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a $C_{1-4}$alkylene group, and wherein the ring system may be substituted once or more than once by $R_{10}$, and wherein a substituent on a nitrogen in a heterocyclic ring system may not be halogen; each $R_{10}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

$R_3$ is selected from $C_{1-6}$alkyl and $C_{1-6}$halogenalkyl; especially $R_3$ is methyl or trifluoromethyl;

n is 1;

$R_{6a}$ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_{16}$, and wherein a substituent on a nitrogen in a heterocyclic ring system may not be halogen; each $R_{16}$ independently is especially halogen, $C_{1-6}$alkyl or $C_{1-6}$halogenalkyl; and $R_{6b}$ is $C_{1-3}$alkyl, especially $R_{6b}$ is methyl.

EMBODIMENT 12

A compound of formula I according to claim 4, wherein said compound is a compound of formula I-4

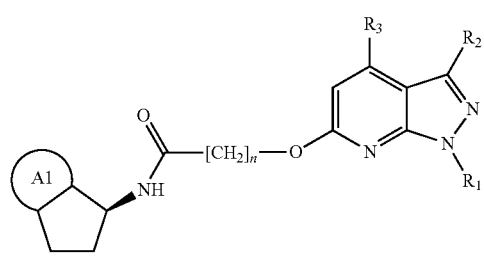

wherein $R_1$ is hydrogen, $C_{1-6}$alkyl, $C_{1-6}$halogenalkyl, $C_{2-6}$alkenyl, $C_{2-6}$halogenalkenyl, $C_{2-6}$alkynyl or $C_{2-6}$halogenalkynyl; especially $R_1$ is hydrogen or $C_{1-6}$alkyl; further especially methyl; further especially hydrogen;

$R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a $C_{1-4}$alkylene group, and wherein the ring system may be substituted once or more than once by $R_{10}$, and wherein a substituent on a nitrogen in a heterocyclic ring system may not be halogen; each $R_{10}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

$R_3$ is selected from $C_{1-6}$alkyl and $C_{1-6}$halogenalkyl; especially $R_3$ is methyl or trifluoromethyl;

n is 1;

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by $R_{19}$, and wherein a substituent on a nitrogen in a heterocyclic ring system may not be halogen; and each $R_{19}$ independently is halogen, $C_{1-6}$alkyl or $C_{1-6}$halogenalkyl.

EMBODIMENT 13

A compound according to any of the preceding embodiment in free form or in pharmaceutically acceptable form which is selected from the group consisting of 2-(3-(2-fluorophenyl)-1-methyl-4-(trifluoromethyl)-1H-pyrazolo[3,4-b]pyridin-6-yloxy)-N-(1-phenylethyl)acetamide;

2-(3-phenyl-4-(trifluoromethyl)-1H-pyrazolo[3,4-b]pyridin-6-yloxy)-N-(1-phenylethyl)acetamide;

N-(2,3-dihydro-1H-inden-1-yl)-2-(1-methyl-3-phenyl-4-(trifluoromethyl)-1H-pyrazolo[3,4-b]pyridin-6-yloxy)acetamide;

N-(1-(4-methoxyphenyl)ethyl)-2-(1-methyl-3-phenyl-4-(trifluoromethyl)-1H-pyrazolo[3,4-b]pyridin-6-yloxy)acetamide;

2-(1-methyl-3-phenyl-4-(trifluoromethyl)-1H-pyrazolo[3,4-b]pyridin-6-yloxy)-N-(2-phenylpropyl)acetamide;

N-(1-(3,5-dimethyl-1H-pyrazol-4-yl)ethyl)-2-(1-methyl-3-phenyl-4-(trifluoromethyl)-1H-pyrazolo[3,4-b]pyridin-6-yloxy)acetamide;

N-(2-ethoxybenzyl)-2-(1-methyl-3-phenyl-4-(trifluoromethyl)-1H-pyrazolo[3,4-b]pyridin-6-yloxy)acetamide;

2-(1,4-dimethyl-3-phenyl-1H-pyrazolo[3,4-b]pyridin-6-yloxy)-N-(1-phenylethyl)acetamide;

N-(2-chlorobenzyl)-2-(1,4-dimethyl-3-phenyl-1H-pyrazolo[3,4-b]pyridin-6-yloxy)acetamide;

N-(benzo[d][1,3]dioxol-5-ylmethyl)-2-(1,4-dimethyl-3-phenyl-1H-pyrazolo[3,4-b]pyridin-6-yloxy)acetamide;

2-(1,4-dimethyl-3-phenyl-1H-pyrazolo[3,4-b]pyridin-6-yloxy)-N-(4-phenylbutan-2-yl)acetamide;

2-(3-(3-methoxyphenyl)-1-methyl-4-(trifluoromethyl)-1H-pyrazolo[3,4-b]pyridin-6-yloxy)-N-(1-phenylethyl)acetamide;

2-(3-(4-methoxyphenyl)-1-methyl-4-(trifluoromethyl)-1H-pyrazolo[3,4-b]pyridin-6-yloxy)-N-(1-phenylethyl)acetamide;

2-(1-methyl-3-(pyridin-2-yl)-4-(trifluoromethyl)-1H-pyrazolo[3,4-b]pyridin-6-yloxy)-N-(1-phenylethyl)acetamide;

2-(3-(3-fluorophenyl)-1-methyl-4-(trifluoromethyl)-1H-pyrazolo[3,4-b]pyridin-6-yloxy)-N-(1-phenylethyl)acetamide;
2-(3-(4-fluorophenyl)-1-methyl-4-(trifluoromethyl)-1H-pyrazolo[3,4-b]pyridin-6-yloxy)-N-(1-phenylethyl)acetamide;
2-(1-methyl-3-m-tolyl-4-(trifluoromethyl)-1H-pyrazolo[3,4-b]pyridin-6-yloxy)-N-(1-phenylethyl)acetamide;
2-(1-methyl-3-(pyridin-4-yl)-4-(trifluoromethyl)-1H-pyrazolo[3,4-b]pyridin-6-yloxy)-N-(1-phenylethyl)acetamide;
2-(1-methyl-3-o-tolyl-4-(trifluoromethyl)-1H-pyrazolo[3,4-b]pyridin-6-yloxy)-N-(1-phenylethyl)acetamide;
2-(1-methyl-3-phenyl-4-(trifluoromethyl)-1H-pyrazolo[3,4-b]pyridin-6-yloxy)-N-(1-(5-methylfuran-2-yl)ethyl)acetamide;
2-(1-methyl-3-phenyl-4-(trifluoromethyl)-1H-pyrazolo[3,4-b]pyridin-6-yloxy)-N-(1-(pyridin-2-yl)ethyl)acetamide;
2-(1-methyl-3-phenyl-4-(trifluoromethyl)-1H-pyrazolo[3,4-b]pyridin-6-yloxy)-N-(1-(pyridin-3-yl)ethyl)acetamide;
2-(1-methyl-3-phenyl-4-(trifluoromethyl)-1H-pyrazolo[3,4-b]pyridin-6-yloxy)-N-(1-(pyridin-4-yl)ethyl)acetamide;
2-(1-methyl-3-phenyl-4-(trifluoromethyl)-1H-pyrazolo[3,4-b]pyridin-6-yloxy)-N-(4-methylbenzyl)acetamide;
N-(3-methoxybenzyl)-2-(1-methyl-3-phenyl-4-(trifluoromethyl)-1H-pyrazolo[3,4-b]pyridin-6-yloxy)acetamide;
2-(1-methyl-3-(pyridin-3-yl)-4-(trifluoromethyl)-1H-pyrazolo[3,4-b]pyridin-6-yloxy)-N-(1-phenylethyl)acetamide;
N-(1-(4-ethyl-4H-1,2,4-triazol-3-yl)ethyl)-2-(1-methyl-3-phenyl-4-(trifluoromethyl)-1H-pyrazolo[3,4-b]pyridin-6-yloxy)acetamide;
N-(1-(3-isopropyl-1,2,4-oxadiazol-5-yl)ethyl)-2-(1-methyl-3-phenyl-4-(trifluoromethyl)-1H-pyrazolo[3,4-b]pyridin-6-yloxy)acetamide;
2-(3-tert-butyl-1-methyl-4-(trifluoromethyl)-1H-pyrazolo[3,4-b]pyridin-6-yloxy)-N-(1-phenylethyl)acetamide;
N-(1-(1-ethyl-1H-pyrazol-5-yl)ethyl)-2-(1-methyl-3-phenyl-4-(trifluoromethyl)-1H-pyrazolo[3,4-b]pyridin-6-yloxy)acetamide;
N-(1-(2,5-dimethylthiazol-4-yl)ethyl)-2-(1-methyl-3-phenyl-4-(trifluoromethyl)-1H-pyrazolo[3,4-b]pyridin-6-yloxy)acetamide;
N-(4-methoxybenzyl)-2-(1-methyl-3-phenyl-4-(trifluoromethyl)-1H-pyrazolo[3,4-b]pyridin-6-yloxy)acetamide;
N-(2-fluorobenzyl)-2-(1-methyl-3-phenyl-4-(trifluoromethyl)-1H-pyrazolo[3,4-b]pyridin-6-yloxy)acetamide;
N-(3-chlorobenzyl)-2-(1-methyl-3-phenyl-4-(trifluoromethyl)-1H-pyrazolo[3,4-b]pyridin-6-yloxy)acetamide;
N-(1-(2-methoxyphenyl)ethyl)-2-(1-methyl-3-phenyl-4-(trifluoromethyl)-1H-pyrazolo[3,4-b]pyridin-6-yloxy)acetamide;
N-(1-(4-methoxyphenyl)ethyl)-2-(1-methyl-3-phenyl-4-(trifluoromethyl)-1H-pyrazolo[3,4-b]pyridin-6-yloxy)acetamide;
N-(1-(3-methoxyphenyl)ethyl)-2-(1-methyl-3-phenyl-4-(trifluoromethyl)-1H-pyrazolo[3,4-b]pyridin-6-yloxy)acetamide;
2-(4-cyclopropyl-1-methyl-3-phenyl-1H-pyrazolo[3,4-b]pyridin-6-yloxy)-N-(1-phenylethyl)acetamide;
2-(1-methyl-3-p-tolyl-4-(trifluoromethyl)-1H-pyrazolo[3,4-b]pyridin-6-yloxy)-N-(1-phenylethyl)acetamide;
2-(3-(2-methoxyphenyl)-1-methyl-4-(trifluoromethyl)-1H-pyrazolo[3,4-b]pyridin-6-yloxy)-N-(1-phenylethyl)acetamide;
2-(3-cyclopropyl-1-methyl-4-(trifluoromethyl)-1H-pyrazolo[3,4-b]pyridin-6-yloxy)-N-(1-phenylethyl)acetamide;
2-(3-cyclohexyl-1-methyl-4-(trifluoromethyl)-1H-pyrazolo[3,4-b]pyridin-6-yloxy)-N-(1-phenylethyl)acetamide;
2-(3-cyclopentyl-1-methyl-4-(trifluoromethyl)-1H-pyrazolo[3,4-b]pyridin-6-yloxy)-N-(1-phenylethyl)acetamide;
N-cyclopropyl-2-(1-methyl-3-phenyl-4-(trifluoromethyl)-1H-pyrazolo[3,4-b]pyridin-6-yloxy)acetamide;
N-cyclobutyl-2-(1-methyl-3-phenyl-4-(trifluoromethyl)-1H-pyrazolo[3,4-b]pyridin-6-yloxy)acetamide;
2-(1-methyl-3-phenyl-4-(trifluoromethyl)-1H-pyrazolo[3,4-b]pyridin-6-yloxy)-N-propylacetamide;
2-(1-methyl-3-phenyl-4-(trifluoromethyl)-1H-pyrazolo[3,4-b]pyridin-6-yloxy)-N-(1,2,3,4-tetrahydronaphthalen-1-yl)acetamide;
2-(3-(3-chlorophenyl)-1-methyl-4-(trifluoromethyl)-1H-pyrazolo[3,4-b]pyridin-6-yloxy)-N-(1-phenylethyl)acetamide;
2-(3-(3-bromophenyl)-1-methyl-4-(trifluoromethyl)-1H-pyrazolo[3,4-b]pyridin-6-yloxy)-N-(1-phenylethyl)acetamide;
N-(1-(4-methoxyphenyl)ethyl)-2-(1-methyl-3-phenyl-4-(trifluoromethyl)-1H-pyrazolo[3,4-b]pyridin-6-yloxy)acetamide;
N-(2,3-dihydro-1H-inden-1-yl)-2-(3-(2-fluorophenyl)-1-methyl-4-(trifluoromethyl)-1H-pyrazolo[3,4-b]pyridin-6-yloxy)acetamide;
N-(2,3-dihydro-1H-inden-1-yl)-2-(3-(3-fluorophenyl)-1-methyl-4-(trifluoromethyl)-1H-pyrazolo[3,4-b]pyridin-6-yloxy)acetamide;
2-(1-methyl-3-phenyl-1H-pyrazolo[3,4-b]pyridin-6-yloxy)-N-(1-phenylethyl)acetamide;
2-(1-methyl-3-phenyl-4-(trifluoromethyl)-1H-pyrazolo[3,4-b]pyridin-6-ylamino)-N-(1-phenylethyl)acetamide;
2-(1,4-dimethyl-3-phenyl-1H-pyrazolo[3,4-b]pyridin-6-yloxy)-N-(1-(pyridin-4-yl)ethyl)acetamide;
2-(1,4-dimethyl-3-phenyl-1H-pyrazolo[3,4-b]pyridin-6-yloxy)-N-(1-(pyridin-3-yl)ethyl)acetamide;
2-(1,4-dimethyl-3-phenyl-1H-pyrazolo[3,4-b]pyridin-6-yloxy)-N-(1-(pyridin-2-yl)ethyl)acetamide;
2-(1-methyl-3-phenyl-4-(trifluoromethyl)-1H-pyrazolo[3,4-b]pyridin-6-yloxy)-N-(3-methylbenzyl)acetamide;
N-(1-(6-methoxypyridin-3-yl)ethyl)-2-(1-methyl-3-phenyl-4-(trifluoromethyl)-1H-pyrazolo[3,4-b]pyridin-6-yloxy)acetamide;
N-isopentyl-2-(1-methyl-3-phenyl-4-(trifluoromethyl)-1H-pyrazolo[3,4-b]pyridin-6-yloxy)acetamide;
2-(3-cyclopropyl-1,4-dimethyl-1H-pyrazolo[3,4-b]pyridin-6-yloxy)-N-(1-phenylethyl)acetamide;
2-(1-methyl-3-phenyl-4-(trifluoromethyl)-1H-pyrazolo[3,4-b]pyridin-6-yloxy)-N-(1-(1,3,5-trimethyl-1H-pyrazol-4-yl)ethyl)acetamide;
2-(3-cyclopropyl-1,4-dimethyl-1H-pyrazolo[3,4-b]pyridin-6-yloxy)-N-(1-(4-methoxyphenyl)ethyl)acetamide;
2-(3-cyclopropyl-1,4-dimethyl-1H-pyrazolo[3,4-b]pyridin-6-yloxy)-N-(1-(1,3,5-trimethyl-1H-pyrazol-4-yl)ethyl)acetamide;
2-(1-methyl-3-phenyl-4-(trifluoromethyl)-1H-pyrazolo[3,4-b]pyridin-6-yloxy)-N-(1-phenylethyl)propanamide;
2-(3-cyclopropyl-1,4-dimethyl-1H-pyrazolo[3,4-b]pyridin-6-yloxy)-N-(2,3-dihydro-1H-inden-1-yl)acetamide;
2-(3-cyclopropyl-1,4-dimethyl-1H-pyrazolo[3,4-b]pyridin-6-yloxy)-N-(1-(3,5-dimethyl-1H-pyrazol-4-yl)ethyl)acetamide;
2-(1-methyl-3-phenyl-4-(trifluoromethyl)-1H-pyrazolo[3,4-b]pyridin-6-yloxy)-N-(1-(6-methylpyridin-3-yl)ethyl)acetamide;
2-(3-(3-fluoropyridin-2-yl)-1,4-dimethyl-1H-pyrazolo[3,4-b]pyridin-6-yloxy)-N-(1-p-tolylethyl)acetamide;

2-(1,4-dimethyl-3-(1-methyl-1H-pyrazol-5-yl)-1H-pyrazolo[3,4-b]pyridin-6-yloxy)-N-(1-p-tolylethyl)acetamide;
2-(3-(1,2-dimethyl-1H-imidazol-5-yl)-1,4-dimethyl-1H-pyrazolo[3,4-b]pyridin-6-yloxy)-N-(1-p-tolylethyl)acetamide;
2-(3-(1,3-dimethyl-1H-pyrazol-5-yl)-1,4-dimethyl-1H-pyrazolo[3,4-b]pyridin-6-yloxy)-N-(1-p-tolylethyl)acetamide;
2-(1,4-dimethyl-3-(1-methyl-1H-pyrazol-4-yl)-1H-pyrazolo[3,4-b]pyridin-6-yloxy)-N-(1-p-tolylethyl)acetamide;
2-(1,4-dimethyl-3-(pyrimidin-2-yl)-1H-pyrazolo[3,4-b]pyridin-6-yloxy)-N-(1-p-tolylethyl)acetamide;
2-(1,4-dimethyl-3-(pyrazin-2-yl)-1H-pyrazolo[3,4-b]pyridin-6-yloxy)-N-(1-p-tolylethyl)acetamide;
2-(1,4-dimethyl-3-(5-methylpyridin-2-yl)-1H-pyrazolo[3,4-b]pyridin-6-yloxy)-N-(1-p-tolylethyl)acetamide;
2-(1,4-dimethyl-3-(thiazol-4-yl)-1H-pyrazolo[3,4-b]pyridin-6-yloxy)-N-(1-p-tolylethyl)acetamide;
2-(1,4-dimethyl-3-(1-methyl-1H-imidazol-5-yl)-1H-pyrazolo[3,4-b]pyridin-6-yloxy)-N-(1-p-tolylethyl)acetamide;
2-(3-(6-methoxypyrazin-2-yl)-1,4-dimethyl-1H-pyrazolo[3,4-b]pyridin-6-yloxy)-N-(1-p-tolylethyl)acetamide;
2-(1,4-dimethyl-3-(1-methyl-1H-imidazol-4-yl)-1H-pyrazolo[3,4-b]pyridin-6-yloxy)-N-(1-p-tolylethyl)acetamide;
2-(1,4-dimethyl-3-(oxazol-2-yl)-1H-pyrazolo[3,4-b]pyridin-6-yloxy)-N-(1-p-tolylethyl)acetamide;
2-(1,4-dimethyl-3-(4-methylthiazol-2-yl)-1H-pyrazolo[3,4-b]pyridin-6-yloxy)-N-(1-p-tolylethyl)acetamide;
2-(1,4-dimethyl-3-(thiazol-2-yl)-1H-pyrazolo[3,4-b]pyridin-6-yloxy)-N-(1-p-tolylethyl)acetamide;
2-(3-(4-methoxypyrimidin-2-yl)-1,4-dimethyl-1H-pyrazolo[3,4-b]pyridin-6-yloxy)-N-(1-p-tolylethyl)acetamide;
2-(1,4-dimethyl-3-(thiazol-5-yl)-1H-pyrazolo[3,4-b]pyridin-6-yloxy)-N-(1-p-tolylethyl)acetamide;
2-(3-(2-methoxythiazol-4-yl)-1,4-dimethyl-1H-pyrazolo[3,4-b]pyridin-6-yloxy)-N-(1-p-tolylethyl)acetamide;
2-(1,4-dimethyl-3-(5-methylthiazol-2-yl)-1H-pyrazolo[3,4-b]pyridin-6-yloxy)-N-(1-p-tolylethyl)acetamide;
2-(1,4-dimethyl-3-(6-methylpyridin-2-yl)-1H-pyrazolo[3,4-b]pyridin-6-yloxy)-N-(1-p-tolylethyl)acetamide;
2-(3-(3,5-dimethoxyphenyl)-1,4-dimethyl-1H-pyrazolo[3,4-b]pyridin-6-yloxy)-N-(1-p-tolylethyl)acetamide;
2-(3-cyclopropyl-4-(difluoromethyl)-1-methyl-1H-pyrazolo[3,4-b]pyridin-6-yloxy)-N-(2-methyl-6,7-dihydro-5H-cyclopenta[b]pyridin-5-yl)acetamide;
2-(3-cyclopropyl-1,4-dimethyl-1H-pyrazolo[3,4-b]pyridin-6-yloxy)-N-(5-methoxy-2,3-dihydro-1H-inden-1-yl)acetamide;
2-(3-cyclopropyl-1,4-dimethyl-1H-pyrazolo[3,4-b]pyridin-6-yloxy)-N-(2-p-tolylpropan-2-yl)acetamide;
2-(3-cyclopropyl-4-(difluoromethyl)-1-methyl-1H-pyrazolo[3,4-b]pyridin-6-yloxy)-N-(1-(4-methoxyphenyl)ethyl)acetamide;
2-(3-cyclopropyl-4-(difluoromethyl)-1-methyl-1H-pyrazolo[3,4-b]pyridin-6-yloxy)-N-(1-p-tolylethyl)acetamide;
2-(3-cyclopropyl-4-(difluoromethyl)-1-methyl-1H-pyrazolo[3,4-b]pyridin-6-yloxy)-N-(1-(1,3,5-trimethyl-1H-pyrazol-4-yl)ethyl)acetamide;
2-(3-cyclopropyl-4-(difluoromethyl)-1-methyl-1H-pyrazolo[3,4-b]pyridin-6-yloxy)-N-(1-(6-methoxypyridin-3-yl)ethyl)acetamide;
2-(3-cyclopropyl-4-isopropyl-1-methyl-1H-pyrazolo[3,4-b]pyridin-6-yloxy)-N-(1-p-tolylethyl)acetamide;
2-(3-cyclopropyl-1-methyl-4-(trifluoromethyl)-1H-pyrazolo[3,4-b]pyridin-6-yloxy)-N-(1-(1,3,5-trimethyl-1H-pyrazol-4-yl)ethyl)acetamide;
2-(3-cyclopropyl-1-methyl-4-(trifluoromethyl)-1H-pyrazolo[3,4-b]pyridin-6-yloxy)-N-(1-p-tolylethyl)acetamide;
2-(3-cyclopropyl-1-methyl-4-(trifluoromethyl)-1H-pyrazolo[3,4-b]pyridin-6-yloxy)-N-(1-(6-methoxypyridin-3-yl)ethyl)acetamide;
2-(3-cyclopropyl-1-methyl-4-(trifluoromethyl)-1H-pyrazolo[3,4-b]pyridin-6-yloxy)-N-(1-(4-methoxyphenyl)ethyl)acetamide;
2-(3-cyclopropyl-1-methyl-4-(trifluoromethyl)-1H-pyrazolo[3,4-b]pyridin-6-yloxy)-N-(1-(6-methylpyridin-3-yl)ethyl)acetamide;
2-(4-(difluoromethyl)-1-methyl-3-phenyl-1H-pyrazolo[3,4-b]pyridin-6-yloxy)-N-(1-(4-methoxyphenyl)ethyl)acetamide;
2-(4-(difluoromethyl)-1-methyl-3-phenyl-1H-pyrazolo[3,4-b]pyridin-6-yloxy)-N-(1-(6-methylpyridin-3-yl)ethyl)acetamide;
2-(3-cyclopropyl-4-(difluoromethyl)-1-methyl-1H-pyrazolo[3,4-b]pyridin-6-yloxy)-N-(1-(6-methylpyridin-3-yl)ethyl)acetamide;
2-(4-(difluoromethyl)-1-methyl-3-phenyl-1H-pyrazolo[3,4-b]pyridin-6-yloxy)-N-(1-(1,3,5-trimethyl-1H-pyrazol-4-yl)ethyl)acetamide;
2-(4-(difluoromethyl)-1-methyl-3-phenyl-1H-pyrazolo[3,4-b]pyridin-6-yloxy)-N-(1-p-tolylethyl)acetamide;
2-(4-(difluoromethyl)-1-methyl-3-phenyl-1H-pyrazolo[3,4-b]pyridin-6-yloxy)-N-(1-(6-methoxypyridin-3-yl)ethyl)acetamide;
2-(3-cyclopropyl-1-methyl-1H-pyrazolo[3,4-b]pyridin-6-yloxy)-N-(1-p-tolylethyl)acetamide;
2-(3-(2-methoxyphenyl)-1-methyl-1H-pyrazolo[3,4-b]pyridin-6-yloxy)-N-(1-p-tolylethyl)acetamide;
2-(3-tert-butyl-1-methyl-1H-pyrazolo[3,4-b]pyridin-6-yloxy)-N41-p-tolylethyl)acetamide;
2-(3-isopropyl-1,4-dimethyl-1H-pyrazolo[3,4-b]pyridin-6-yloxy)-N41-p-tolylethyl)acetamide;
2-(3-isopropyl-1,4-dimethyl-1H-pyrazolo[3,4-b]pyridin-6-yloxy)-N-(1-(4-methoxyphenyl)ethyl)acetamide;
2-(3-isopropyl-1,4-dimethyl-1H-pyrazolo[3,4-b]pyridin-6-yloxy)-N-(1-(6-methoxypyridin-3-yl)ethyl)acetamide;
2-(3-isopropyl-1,4-dimethyl-1H-pyrazolo[3,4-b]pyridin-6-yloxy)-N-(1-(1,3,5-trimethyl-1H-pyrazol-4-yl)ethyl)acetamide;
2-(3-(2,5-dimethylfuran-3-yl)-1,4-dimethyl-1H-pyrazolo[3,4-b]pyridin-6-yloxy)-N41-p-tolylethyl)acetamide;
2-(3-(2,5-dimethylfuran-3-yl)-1,4-dimethyl-1H-pyrazolo[3,4-b]pyridin-6-yloxy)-N-(1-(4-methoxyphenyl)ethyl)acetamide;
2-(3-(2,5-dimethylfuran-3-yl)-1,4-dimethyl-1H-pyrazolo[3,4-b]pyridin-6-yloxy)-N-(1-(6-methoxypyridin-3-yl)ethyl)acetamide;
2-(3-(2,5-dimethylfuran-3-yl)-1,4-dimethyl-1H-pyrazolo[3,4-b]pyridin-6-yloxy)-N-(1-(1,3,5-trimethyl-1H-pyrazol-4-yl)ethyl)acetamide;
2-(1,4-dimethyl-3-(2-methylfuran-3-yl)-1H-pyrazolo[3,4-b]pyridin-6-yloxy)-N-(1-(4-methoxyphenyl)ethyl)acetamide;
2-(1-methyl-3-o-tolyl-1H-pyrazolo[3,4-b]pyridin-6-yloxy)-N-(1-p-tolylethyl)acetamide;
2-(3-(3,5-dimethoxyphenyl)-1,4-dimethyl-1H-pyrazolo[3,4-b]pyridin-6-yloxy)-N-(1-(4-methoxyphenyl)ethyl)acetamide;
2-(3-(4-methoxypyridin-2-yl)-1,4-dimethyl-1H-pyrazolo[3,4-b]pyridin-6-yloxy)-N-(1-p-tolylethyl)acetamide;

2-(3-cyclopropyl-1,4-dimethyl-1H-pyrazolo[3,4-b]pyridin-6-yloxy)-N-(5-fluoro-2,3-dihydro-1H-inden-1-yl)acetamide;

2-(3-cyclopropyl-4-(difluoromethyl)-1-methyl-1H-pyrazolo[3,4-b]pyridin-6-yloxy)-N-(5-methoxy-2,3-dihydro-1H-inden-1-yl)acetamide;

2-(3-cyclopropyl-1-methyl-4-(trifluoromethyl)-1H-pyrazolo[3,4-b]pyridin-6-yloxy)-N-(5-methoxy-2,3-dihydro-1H-inden-1-yl)acetamide;

2-(3-cyclopropyl-1,4-dimethyl-1H-pyrazolo[3,4-b]pyridin-6-yloxy)-N-(5-methyl-2,3-dihydro-1H-inden-1-yl)acetamide;

2-(3-cyclopropyl-1,4-dimethyl-1H-pyrazolo[3,4-b]pyridin-6-yloxy)-N-isobutylacetamide;

N-cyclopentyl-2-(3-cyclopropyl-1,4-dimethyl-1H-pyrazolo[3,4-b]pyridin-6-yloxy)acetamide;

2-(3-cyclopropyl-1,4-dimethyl-1H-pyrazolo[3,4-b]pyridin-6-yloxy)-N-(1-(6-methoxypyridin-3-yl)ethyl)acetamide;

2-(3-cyclopropyl-1,4-dimethyl-1H-pyrazolo[3,4-b]pyridin-6-yloxy)-N-(1-(5-neopentylisoxazol-3-yl)ethyl)acetamide;

2-(3-cyclopropyl-1,4-dimethyl-1H-pyrazolo[3,4-b]pyridin-6-yloxy)-N-phenethylacetamide;

2-(3-cyclopropyl-1,4-dimethyl-1H-pyrazolo[3,4-b]pyridin-6-yloxy)-N-(3-phenylpropyl)acetamide;

2-(3-cyclopropyl-1,4-dimethyl-1H-pyrazolo[3,4-b]pyridin-6-yloxy)-N-(1-(4-methoxyphenyl)ethyl)-N-methylacetamide;

2-(3-cyclopropyl-1,4-dimethyl-1H-pyrazolo[3,4-b]pyridin-6-yloxy)-N-methylacetamide;

2-(3-cyclopropyl-1,4-dimethyl-1H-pyrazolo[3,4-b]pyridin-6-yloxy)-N-(1-cyclopropylethyl)acetamide;

2-(3-cyclopropyl-1,4-dimethyl-1H-pyrazolo[3,4-b]pyridin-6-yloxy)-N-(1-(1-ethyl-1H-pyrazol-3-yl)ethyl)acetamide;

2-(3-cyclopropyl-1,4-dimethyl-1H-pyrazolo[3,4-b]pyridin-6-yloxy)-N-(1-(6-methylpyridin-3-yl)ethyl)acetamide;

N-(1-cyclopentylethyl)-2-(3-cyclopropyl-1,4-dimethyl-1H-pyrazolo[3,4-b]pyridin-6-yloxy)acetamide;

N-(1-(1H-pyrrolo[2,3-b]pyridin-5-yl)ethyl)-2-(3-cyclopropyl-1,4-dimethyl-1H-pyrazolo[3,4-b]pyridin-6-yloxy)acetamide;

2-(3-cyclopropyl-1,4-dimethyl-1H-pyrazolo[3,4-b]pyridin-6-yloxy)-N-(1-(1-methyl-1H-benzo[d]imidazol-5-yl)ethyl)acetamide;

2-(3-cyclopropyl-1,4-dimethyl-1H-pyrazolo[3,4-b]pyridin-6-yloxy)-N-(1-(1-methyl-1H-indol-5-yl)ethyl)acetamide;

2-(3-cyclopropyl-1,5-dimethyl-1H-pyrazolo[3,4-b]pyridin-6-yloxy)-N-(1-p-tolylethyl)acetamide;

2-(3-cyclopropyl-1,4-dimethyl-1H-pyrazolo[3,4-b]pyridin-6-yloxy)-N-(2-(4-methoxyphenyl)propan-2-yl)acetamide;

2-(3-cyclopropyl-1,4-dimethyl-1H-pyrazolo[3,4-b]pyridin-6-yloxy)-N-(2-methyl-6,7-dihydro-5H-cyclopenta[b]pyridin-5-yl)acetamide;

2-(3-cyclopropyl-1,4-dimethyl-1H-pyrazolo[3,4-b]pyridin-6-yloxy)-N-(3-methyl-6,7-dihydro-5H-cyclopenta[c]pyridin-7-yl)acetamide;

2-(3-cyclopropyl-1,4-dimethyl-1H-pyrazolo[3,4-b]pyridin-6-yloxy)-N-(4-methylbenzyl)acetamide;

2-(3-cyclopropyl-1,4-dimethyl-1H-pyrazolo[3,4-b]pyridin-6-yloxy)-N-(4-methoxybenzyl)acetamide;

2-(3-cyclopropyl-1,4-dimethyl-1H-pyrazolo[3,4-b]pyridin-6-yloxy)-N-(5-ethoxy-2,3-dihydro-1H-inden-1-yl)acetamide;

2-(3-cyclopropyl-1,4-dimethyl-1H-pyrazolo[3,4-b]pyridin-6-yloxy)-N-(5-isopropoxy-2,3-dihydro-1H-inden-1-yl)acetamide;

2-(3-cyclopropyl-1,4-dimethyl-1H-pyrazolo[3,4-b]pyridin-6-yloxy)-N-(5-methoxy-2,3-dihydro-1H-inden-1-yl)propanamide;

2-(3-cyclopropyl-1,4-dimethyl-1H-pyrazolo[3,4-b]pyridin-6-yloxy)-N-(1-(4-methoxyphenyl)ethyl)propanamide;

2-(3-cyclopropyl-1,4,5-trimethyl-1H-pyrazolo[3,4-b]pyridin-6-yloxy)-N-(1-(4-methoxyphenyl)ethyl)acetamide;

2-(3-cyclopropyl-1,4,5-trimethyl-1H-pyrazolo[3,4-b]pyridin-6-yloxy)-N-(1-p-tolylethyl)acetamide;

2-(3-cyclopropyl-1,5-dimethyl-1H-pyrazolo[3,4-b]pyridin-6-yloxy)-N-(1-(4-methoxyphenyl)ethyl)acetamide;

2-(1-methyl-3-phenyl-4-(trifluoromethyl)-1H-pyrrolo[2,3-b]pyridin-6-yloxy)-N-(1-phenylethyl)acetamide;

2-(3-phenyl-4-(trifluoromethyl)isoxazolo[5,4-b]pyridin-6-yloxy)-N-(1-phenylethyl)acetamide;

2-(3-(2,5-dimethylfuran-3-yl)-1-methyl-4-(trifluoromethyl)-1H-pyrazolo[3,4-b]pyridin-6-yloxy)-N-(2-methyl-6,7-dihydro-5H-cyclopenta[b]pyridin-5-yl)acetamide;

2-(3-(2,5-dimethylfuran-3-yl)-1-methyl-4-(trifluoromethyl)-1H-pyrazolo[3,4-b]pyridin-6-yloxy)-N-(1-(4-methoxyphenyl)ethyl)acetamide;

2-(4-(difluoromethyl)-3-(2,5-dimethylfuran-3-yl)-1-methyl-1H-pyrazolo[3,4-b]pyridin-6-yloxy)-N-(2-methyl-6,7-dihydro-5H-cyclopenta[b]pyridin-5-yl)acetamide;

2-(4-(difluoromethyl)-3-(2,5-dimethylfuran-3-yl)-1-methyl-1H-pyrazolo[3,4-b]pyridin-6-yloxy)-N-(1-(4-methoxyphenyl)ethyl)acetamide;

2-(3-cyclopropyl-1,4-dimethyl-1H-pyrazolo[3,4-b]pyridin-6-yloxy)-N-(5,6-dimethoxy-2,3-dihydro-1H-inden-1-yl)acetamide;

2-(3-cyclopropyl-1,4-dimethyl-1H-pyrazolo[3,4-b]pyridin-6-yloxy)-N-((5-methylpyrazin-2-yl)methyl)acetamide;

N-(3-(1H-imidazol-1-yl)propyl)-2-(3-cyclopropyl-1,4-dimethyl-1H-pyrazolo[3,4-b]pyridin-6-yloxy)acetamide;

2-(3-cyclopropyl-1,4-dimethyl-1H-pyrazolo[3,4-b]pyridin-6-yloxy)-N-((2,3-dihydrobenzofuran-5-yl)methyl)acetamide;

N-(2-(1H-indol-3-yl)ethyl)-2-(3-cyclopropyl-1,4-dimethyl-1H-pyrazolo[3,4-b]pyridin-6-yloxy)acetamide;

N-(cyclohexylmethyl)-2-(3-cyclopropyl-1,4-dimethyl-1H-pyrazolo[3,4-b]pyridin-6-yloxy)acetamide;

2-(3-cyclopropyl-1,4-dimethyl-1H-pyrazolo[3,4-b]pyridin-6-yloxy)-N-(1-(6-methylpyridin-2-yl)ethyl)acetamide;

2-(3-cyclopropyl-1,4-dimethyl-1H-pyrazolo[3,4-b]pyridin-6-yloxy)-N-(5,6,7,8-tetrahydroquinolin-5-yl)acetamide;

2-(3-cyclopropyl-1,4-dimethyl-1H-pyrazolo[3,4-b]pyridin-6-yloxy)-N-(6-methoxy-2,3-dihydro-1H-inden-1-yl)acetamide;

2-(3-cyclopropyl-1,4-dimethyl-1H-pyrazolo[3,4-b]pyridin-6-yloxy)-N-(1-p-tolylethyl)acetamide;

2-(3-cyclopropyl-1,4-dimethyl-1H-pyrazolo[3,4-b]pyridin-6-yloxy)-N-(1-(3-methoxyphenyl)ethyl)acetamide;

2-(3-cyclopropyl-1,4-dimethyl-1H-pyrazolo[3,4-b]pyridin-6-yloxy)-N-(1-(2-methoxyphenyl)ethyl)acetamide;

N-((6-chloropyridin-3-yl)methyl)-2-(3-cyclopropyl-1,4-dimethyl-1H-pyrazolo[3,4-b]pyridin-6-yloxy)acetamide;

N-(3-chloro-4-methoxybenzyl)-2-(3-cyclopropyl-1,4-dimethyl-1H-pyrazolo[3,4-b]pyridin-6-yloxy)acetamide;

N-(1-(1H-indol-5-yl)ethyl)-2-(3-cyclopropyl-1,4-dimethyl-1H-pyrazolo[3,4-b]pyridin-6-yloxy)acetamide;

2-(3-cyclopropyl-1,4-dimethyl-1H-pyrazolo[3,4-b]pyridin-6-yloxy)-N-((3-methylpyridin-2-yl)methyl)acetamide;

2-(3-cyclopropyl-1,4-dimethyl-1H-pyrazolo[3,4-b]pyridin-6-yloxy)-N-(1-(3-fluoro-4-methoxyphenyl)ethyl)acetamide;

2-(3-cyclopropyl-1,4-dimethyl-1H-pyrazolo[3,4-b]pyridin-6-yloxy)-N-(1-(1-methyl-1H-pyrazol-4-yl)ethyl)acetamide;
2-(3-cyclopropyl-1,4-dimethyl-1H-pyrazolo[3,4-b]pyridin-6-yloxy)-N-(1-(4-methylpyridin-2-yl)ethyl)acetamide;
2-(3-cyclopropyl-1,4-dimethyl-1H-pyrazolo[3,4-b]pyridin-6-yloxy)-N-(1-(4-methylthiazol-2-yl)ethyl)acetamide;
N-(1-(benzo[d]thiazol-2-yl)ethyl)-2-(3-cyclopropyl-1,4-dimethyl-1H-pyrazolo[3,4-b]pyridin-6-yloxy)acetamide;
2-(3-cyclopropyl-1,4-dimethyl-1H-pyrazolo[3,4-b]pyridin-6-yloxy)-N-(1-methyl-4,5,6,7-tetrahydro-1H-indazol-4-yl)acetamide;
2-(3-cyclopropyl-1,4-dimethyl-1H-pyrazolo[3,4-b]pyridin-6-yloxy)-N-(1-(imidazo[2,1-b]thiazol-6-yl)ethyl)acetamide;
2-(3-cyclopropyl-1,4-dimethyl-1H-pyrazolo[3,4-b]pyridin-6-yloxy)-N-(4-phenylbutan-2-yl)acetamide;
2-(3-cyclopropyl-1,4-dimethyl-1H-pyrazolo[3,4-b]pyridin-6-yloxy)-N-(2,4-dimethoxybenzyl)acetamide;
2-(3-cyclopropyl-1,4-dimethyl-1H-pyrazolo[3,4-b]pyridin-6-yloxy)-N-(1-m-tolylethyl)acetamide;
2-(3-cyclopropyl-1,4-dimethyl-1H-pyrazolo[3,4-b]pyridin-6-yloxy)-N-((1,5-dimethyl-1H-indazol-4-yl)methyl)acetamide;
2-(3-cyclopropyl-1,4-dimethyl-1H-pyrazolo[3,4-b]pyridin-6-yloxy)-N-(5-methoxy-1,2,3,4-tetrahydronaphthalen-1-yl)acetamide;
2-(3-cyclopropyl-1,4-dimethyl-1H-pyrazolo[3,4-b]pyridin-6-yloxy)-N-(4-ethoxybenzyl)acetamide;
2-(3-cyclopropyl-1,4-dimethyl-1H-pyrazolo[3,4-b]pyridin-6-yloxy)-N-((1-methyl-1H-indazol-7-yl)methyl)acetamide;
N-((1H-indazol-4-yl)methyl)-2-(3-cyclopropyl-1,4-dimethyl-1H-pyrazolo[3,4-b]pyridin-6-yloxy)acetamide;
2-(3-cyclopropyl-1,4-dimethyl-1H-pyrazolo[3,4-b]pyridin-6-yloxy)-N-(6-methyl-2,3-dihydro-1H-inden-1-yl)acetamide;
N-(1-(6-chlorobenzo[d]thiazol-2-yl)ethyl)-2-(3-cyclopropyl-1,4-dimethyl-1H-pyrazolo[3,4-b]pyridin-6-yloxy)acetamide;
2-(3-cyclopropyl-1,4-dimethyl-1H-pyrazolo[3,4-b]pyridin-6-yloxy)-N-(1-(1-methyl-1H-pyrrolo[2,3-b]pyridin-5-yl)ethyl)acetamide;
2-(3-cyclopropyl-1,4-dimethyl-1H-pyrazolo[3,4-b]pyridin-6-yloxy)-N-(-5-methoxy-2,3-dihydro-1H-inden-1-yl)propanamide; and
2-(3-cyclopropyl-1,4-dimethyl-1H-pyrazolo[3,4-b]pyridin-6-yloxy)-N-(-1-(4-methoxyphenyl)ethyl)propanamide.

EMBODIMENT 14

A pharmaceutical composition comprising a therapeutically effective amount of a compound according to any one of embodiments 1 to 13 and one or more pharmaceutically acceptable carriers.

EMBODIMENT 15

A combination comprising a therapeutically effective amount of the compound according to any one of embodiments 1 to 13 and one or more therapeutically active agents.

EMBODIMENT 16

A method of treating a disorder or a disease in a subject mediated by orexin receptors, wherein the method comprises administering to the subject a therapeutically effective amount of the compound according to any one of embodiments 1 to 13.

EMBODIMENT 17

A compound according to any one of embodiments 1 to 13, for use in the treatment of a disorder or disease in a subject mediated by orexin receptors, wherein said disorder or disease is selected from sleep disorders, eating disorders, substance-related disorders and Alzheimer's disease.

The invention claimed is:
1. A compound of formula I'

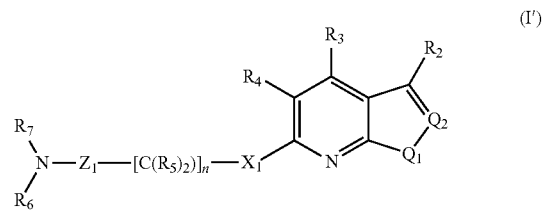

wherein
$Q_1$ is $-N(R_1)-$;
wherein $R_1$ is hydrogen; $C_{1-6}$alkyl; $C_{1-6}$halogenalkyl; $C_{2-6}$alkenyl; $C_{2-6}$halogenalkenyl; $C_{2-6}$alkynyl; $C_{2-6}$halogenalkynyl; a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_8$, and wherein a substituent on a nitrogen in a heterocyclic ring system may not be halogen;
and
$R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_9$, and wherein a substituent on a nitrogen in a heterocyclic ring system may not be halogen; or $R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{10}$, and wherein a substituent on a nitrogen in a heterocyclic ring system may not be halogen;
or
wherein $R_1$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{11}$, and wherein a substituent on a nitrogen in a heterocyclic ring system may not be halogen;

and $R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{12}$, and wherein a substituent on a nitrogen in a heterocyclic ring system may not be halogen;

each $R_8$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_8$ at the same ring atom together are oxo;

each $R_9$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_9$ at the same ring atom together are oxo;

each $R_{12}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{12}$ at the same ring atom together are oxo;

each $R_{10}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{10}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{13}$, and wherein a substituent on a nitrogen in a heterocyclic ring system may not be halogen; and wherein each $R_{13}$ independently is halogen or $C_{1-6}$alkyl, or two $R_{13}$ at the same ring atom together are oxo;

each $R_{11}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{11}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{14}$, and wherein a substituent on a nitrogen in a heterocyclic ring system may not be halogen; and wherein each $R_{14}$ independently is halogen or $C_{1-6}$alkyl, or two $R_{14}$ at the same ring atom together are oxo;

or $Q_1$ is —O— and $R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{9a}$, and wherein a substituent on a nitrogen in a heterocyclic ring system may not be halogen; or $R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{10a}$, and wherein a substituent on a nitrogen in a heterocyclic ring system may not be halogen;

each $R_{9a}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{9a}$ at the same ring atom together are oxo;

each $R_{10a}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{10a}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{13a}$, and wherein a substituent on a nitrogen in a heterocyclic ring system may not be halogen; and wherein each $R_{13a}$ independently is halogen or $C_{1-6}$alkyl, or two $R_{13a}$ at the same ring atom together are oxo;

$Q_2$ is =N— or =C($R_{1a}$)—;

wherein $R_{1a}$ is hydrogen; $C_{1-6}$alkyl; $C_{1-6}$halogenalkyl; $C_{2-6}$alkenyl; $C_{2-6}$halogenalkenyl; $C_{2-6}$alkynyl; $C_{2-6}$halogenalkynyl;

$R_3$ and $R_4$ are each independently selected from hydrogen, halogen, hydroxyl, $C_{1-6}$alkyl, $C_{1-6}$halogenalkyl, $C_{1-6}$alkoxy, $C_{1-6}$halogenalkoxy, $C_{2-6}$alkenyl, $C_{2-6}$halogenalkenyl, $C_{2-6}$alkinyl, $C_{2-6}$halogenalkinyl, $C_{3-7}$cycloalkyl, $C_{3-7}$cycloalkyl($C_{1-4}$alkyl);

$X_1$ is —O—, —N($R_{15}$)—;

$R_{15}$ is hydrogen or $C_{1-6}$alkyl;

n is 1, 2 or 3;

each $R_5$ independently is selected from hydrogen, halogen, hydroxyl, $C_{1-6}$alkyl, $C_{1-6}$halogenalkyl, $C_{1-6}$alkoxy, $C_{1-6}$halogenalkoxy, $C_{3-7}$cycloalkyl, $C_{3-7}$cycloalkyl($C_{1-4}$alkyl); or two $R_5$ at the same carbon atom together with said carbon atom form $C_{3-7}$cycloalkyl; or two $R_5$ at adjacent carbon atoms together with said carbon atoms form $C_{3-7}$cycloalkyl; or two $R_5$ at carbon atoms separated by one further carbon atom together with said carbon atoms form $C_{4-7}$cycloalkyl;

$Z_1$ is —C(O)—, —S(O)— or —S(O)$_2$—;

$R_6$ is $C_{1-6}$alkyl, $C_{1-6}$halogenalkyl, $C_{2-6}$alkenyl, $C_{2-6}$halogenalkenyl, $C_{2-6}$alkynyl, $C_{2-6}$halogenalkynyl, $C_{3-7}$cycloalkyl, $C_{3-7}$cycloalkyl($C_{1-4}$alkyl) or a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system is attached to the nitrogen atom via a $C_{1-4}$alkylene group, and wherein the ring system may be substituted once or more than once by $R_{16}$, and wherein a substituent on a nitrogen in a heterocyclic ring system may not be halogen;

each $R_{16}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

or two $R_{16}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{17}$, and wherein a substituent on a nitrogen in a heterocyclic ring system may not be halogen; and wherein each $R_{17}$ independently is halogen or $C_{1-6}$alkyl, or two $R_{17}$ at the same ring atom together are oxo;

or $R_6$ is a group A

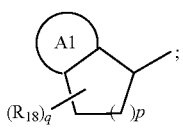

A wherein p is 1 or 2;

q is 0, 1, 2, 3 or 4;

each $R_{18}$ independently is halogen or $C_{1-6}$alkyl;

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by $R_{19}$, and wherein a substituent on a nitrogen in a heterocyclic ring system may not be halogen;

each $R_{19}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

and $R_7$ is hydrogen, $C_{1-6}$alkyl, $C_{1-6}$halogenalkyl, $C_{2-6}$alkenyl, $C_{2-6}$halogenalkenyl, $C_{2-6}$alkinyl, $C_{2-6}$halogenalkinyl, $C_{3-7}$cycloalkyl, $C_{3-7}$cycloalkyl($C_{1-4}$alkyl);

in free form or in salt form.

2. The compound of claim 1 of formula (I')

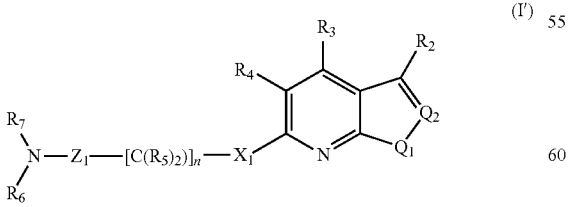

(I')

wherein $Q_1$ is —N($R_1$)—;

wherein $R_1$ is hydrogen; $C_{1-6}$alkyl; $C_{1-6}$halogenalkyl; $C_{2-6}$alkenyl; $C_{2-6}$halogenalkenyl; $C_{2-6}$alkynyl; $C_{2-6}$halogenalkynyl; a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_8$, and wherein a substituent on a nitrogen in a heterocyclic ring system may not be halogen;

and $R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_9$, and wherein a substituent on a nitrogen in a heterocyclic ring system may not be halogen; or $R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{10}$, and wherein a substituent on a nitrogen in a heterocyclic ring system may not be halogen;

or wherein $R_1$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{11}$, and wherein a substituent on a nitrogen in a heterocyclic ring system may not be halogen;

and $R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{12}$, and wherein a substituent on a nitrogen in a heterocyclic ring system may not be halogen;

each $R_8$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_8$ at the same ring atom together are oxo;

each $R_9$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_9$ at the same ring atom together are oxo;

each $R_{12}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{12}$ at the same ring atom together are oxo;

each $R_{10}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{10}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{13}$, and wherein a substituent on a nitrogen in a heterocyclic ring system may not be halogen; and wherein each $R_{13}$ independently is halogen or $C_{1-6}$alkyl, or two $R_{13}$ at the same ring atom together are oxo;

each $R_{11}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{11}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{14}$, and wherein a substituent on a nitrogen in a heterocyclic ring system may not be halogen; and wherein each $R_{14}$ independently is halogen or $C_{1-6}$alkyl, or two $R_{14}$ at the same ring atom together are oxo;

or $Q_1$ is —O— and $R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{9a}$, and wherein a substituent on a nitrogen in a heterocyclic ring system may not be halogen; or $R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{10a}$, and wherein a substituent on a nitrogen in a heterocyclic ring system may not be halogen;

each $R_{9a}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{9a}$ at the same ring atom together are oxo;

each $R_{10a}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{10a}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{13a}$, and wherein a substituent on a nitrogen in a heterocyclic ring system may not be halogen; and wherein each $R_{13a}$ independently is halogen or $C_{1-6}$alkyl, or two $R_{13a}$ at the same ring atom together are oxo;

$Q_2$ is =N— or =C($R_{1a}$)—;

wherein $R_{1a}$ is hydrogen; $C_{1-6}$alkyl; $C_{1-6}$halogenalkyl; $C_{2-6}$alkenyl; $C_{2-6}$halogenalkenyl; $C_{2-6}$alkynyl; $C_{2-6}$halogenalkynyl;

$R_3$ and $R_4$ are each independently selected from hydrogen, halogen, hydroxyl, $C_{1-6}$alkyl, $C_{1-6}$halogenalkyl, $C_{1-6}$alkoxy, $C_{1-6}$halogenalkoxy, $C_{2-6}$alkenyl, $C_{2-6}$halogenalkenyl, $C_{2-6}$alkinyl, $C_{2-6}$halogenalkinyl, $C_{3-7}$cycloalkyl, $C_{3-7}$cycloalkyl($C_{1-4}$alkyl);

$X_1$ is —O—, —N($R_{15}$)—;

$R_{15}$ is hydrogen or $C_{1-6}$alkyl;

n is 1, 2 or 3;

each $R_5$ independently is selected from hydrogen, halogen, hydroxyl, $C_{1-6}$alkyl, $C_{1-6}$halogenalkyl, $C_{1-6}$alkoxy, $C_{1-6}$halogenalkoxy, $C_{3-7}$cycloalkyl, $C_{3-7}$cycloalkyl($C_{1-4}$ alkyl); or two $R_5$ at the same carbon atom together with said carbon atom form $C_{3-7}$cycloalkyl; or two $R_5$ at adjacent carbon atoms together with said carbon atoms form $C_{3-7}$cycloalkyl; or two $R_5$ at carbon atoms separated by one further carbon atom together with said carbon atoms form $C_{4-7}$cycloalkyl;

$Z_1$ is —C(O)—, —S(O)— or —S(O)$_2$—;

$R_6$ is $C_{1-6}$alkyl, $C_{1-6}$halogenalkyl, $C_{2-6}$alkenyl, $C_{2-6}$halogenalkenyl, $C_{2-6}$alkynyl, $C_{2-6}$halogenalkynyl, $C_{3-7}$cycloalkyl, $C_{3-7}$cycloalkyl($C_{1-4}$alkyl) or a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system is attached to the nitrogen atom via a $C_{1-4}$alkylene group, and wherein the ring system may be substituted once or more than once by $R_{16}$, and wherein a substituent on a nitrogen in a heterocyclic ring system may not be halogen;

each $R_{16}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

or two $R_{16}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{17}$, and wherein a substituent on a nitrogen in a heterocyclic ring system may not be halogen; and wherein each $R_{17}$ independently is halogen or $C_{1-6}$alkyl, or two $R_{17}$ at the same ring atom together are oxo;

or

R$_6$ is a group A

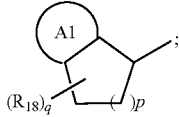

wherein p is 1 or 2;

q is 0, 1, 2, 3 or 4;

each R$_{18}$ independently is halogen or C$_{1-6}$alkyl;

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by R$_{19}$, and wherein a substituent on a nitrogen in a heterocyclic ring system may not be halogen;

each R$_{19}$ independently is halogen, C$_{1-6}$alkyl, C$_{1-6}$halogenalkyl, C$_{3-7}$cycloalkyl, C$_{3-7}$cycloalkyl(C$_{1-4}$alkyl), C$_{1-6}$alkoxy, or C$_{1-6}$halogenalkoxy;

and R$_7$ is hydrogen, C$_{1-6}$alkyl, C$_{1-6}$halogenalkyl, C$_{2-6}$alkenyl, C$_{2-6}$halogenalkenyl, C$_{2-6}$alkinyl, C$_{2-6}$halogenalkinyl, C$_{3-7}$cycloalkyl, C$_{3-7}$cycloalkyl(C$_{1-4}$alkyl);

and provided that the compounds

N-(2-methoxybenzyl)-2-(1-methyl-3-phenyl-4-(trifluoromethyl)-1H-pyrazolo[3,4-b]pyridin-6-yloxy)acetamide;

2-(1-methyl-3-phenyl-4-(trifluoromethyl)-1H-pyrazolo[3,4-b]pyridin-6-yloxy)-N-(2-methylbenzyl)acetamide;

N-(2-ethoxybenzyl)-2-(1-methyl-3-phenyl-4-(trifluoromethyl)-1H-pyrazolo[3,4-b]pyridin-6-yloxy)acetamide;

N-(3-fluorobenzyl)-2-(1-methyl-3-phenyl-4-(trifluoromethyl)-1H-pyrazolo[3,4-b]pyridin-6-yloxy)acetamide;

2-(1-methyl-3-phenyl-4-(trifluoromethyl)-1H-pyrazolo[3,4-b]pyridin-6-yloxy)-N-(4-phenylbutan-2-yl)acetamide;

N-cyclohexyl-2-(1-methyl-3-phenyl-4-(trifluoromethyl)-1H-pyrazolo[3,4-b]pyridin-6-yloxy)acetamide;

N-(4-fluorobenzyl)-2-(1-methyl-3-phenyl-4-(trifluoromethyl)-1H-pyrazolo[3,4-b]pyridin-6-yloxy)acetamide;

2-(1-methyl-3-phenyl-4-(trifluoromethyl)-1H-pyrazolo[3,4-b]pyridin-6-yloxy)-N-(1-phenylethyl)acetamide;

N-(benzo[d][1,3]dioxol-5-ylmethyl)-2-(1-methyl-3-phenyl-4-(trifluoromethyl)-1H-pyrazolo[3,4-b]pyridin-6-yloxy)acetamide;

N-cyclopentyl-2-(1-methyl-3-phenyl-4-(trifluoromethyl)-1H-pyrazolo[3,4-b]pyridin-6-yloxy)acetamide;

N-(4-chlorobenzyl)-2-(1-methyl-3-phenyl-4-(trifluoromethyl)-1H-pyrazolo[3,4-b]pyridin-6-yloxy)acetamide;

N-(2-chlorobenzyl)-2-(1-methyl-3-phenyl-4-(trifluoromethyl)-1H-pyrazolo[3,4-b]pyridin-6-yloxy)acetamide; and N-benzyl-2-(1-methyl-3-phenyl-4-(trifluoromethyl)-1H-pyrazolo[3,4-b]pyridin-6-yloxy)acetamide are excluded;

in free form or in salt form.

3. The compound of claim 1 of formula I

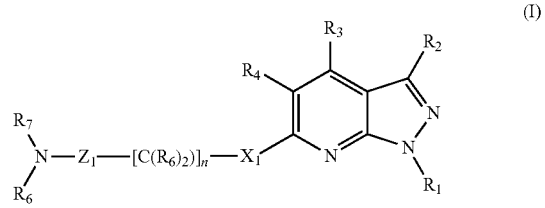

wherein

R$_1$ is hydrogen; C$_{1-6}$alkyl; C$_{1-6}$halogenalkyl; C$_{2-6}$alkenyl; C$_{2-6}$halogenalkenyl; C$_{2-6}$alkynyl; C$_{2-6}$halogenalkynyl; or R$_1$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the nitrogen atom of the 1H-pyrazolo[3,4b]pyridine or via a C$_{1-4}$alkylene group, and wherein the ring system may be substituted once or more than once by R$_8$, and wherein a substituent on a nitrogen in a heterocyclic ring system may not be halogen;

and

R$_2$ is C$_{2-6}$alkyl; C$_{2-6}$halogenalkyl; C$_{2-6}$alkenyl; C$_{2-6}$halogenalkenyl; C$_{2-6}$alkynyl; C$_{2-6}$halogenalkynyl; or R$_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a C$_{1-4}$alkylene group, and wherein the ring system may be substituted once or more than once by R$_9$, and wherein a substituent on a nitrogen in a heterocyclic ring system may not be halogen; or R$_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a C$_{1-4}$alkylene group, and wherein the ring system may be substituted once or more than once by R$_{10}$, and wherein a substituent on a nitrogen in a heterocyclic ring system may not be halogen;

or

R$_1$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the nitrogen atom of the 1H-pyrazolo[3,4b]pyridine or via a C$_{1-4}$alkylene group, and wherein the ring system may be substituted once or more than once by R$_{11}$, and wherein a substituent on a nitrogen in a heterocyclic ring system may not be halogen;

and

R$_2$ is C$_{2-6}$alkyl; C$_{2-6}$halogenalkyl; C$_{2-6}$alkenyl; C$_{2-6}$halogenalkenyl; C$_{2-6}$alkynyl; C$_{2-6}$halogenalkynyl; or R$_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a $C_{1-4}$alkylene group, and wherein the ring system may be substituted once or more than once by $R_{12}$, and wherein a substituent on a nitrogen in a heterocyclic ring system may not be halogen;

each $R_8$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_8$ at the same ring atom together are oxo;

each $R_9$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_9$ at the same ring atom together are oxo;

each $R_{12}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{12}$ at the same ring atom together are oxo;

each $R_{10}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{10}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{13}$, and wherein a substituent on a nitrogen in a heterocyclic ring system may not be halogen; and wherein each $R_{13}$ independently is halogen or $C_{1-6}$alkyl, or two $R_{13}$ at the same ring atom together are oxo;

each $R_{11}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{11}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{14}$, and wherein a substituent on a nitrogen in a heterocyclic ring system may not be halogen; and wherein each $R_{14}$ independently is halogen or $C_{1-6}$alkyl, or two $R_{14}$ at the same ring atom together are oxo;

$R_3$ and $R_4$ are each independently selected from hydrogen, halogen, hydroxyl, $C_{1-6}$alkyl, $C_{1-6}$halogenalkyl, $C_{1-6}$alkoxy, $C_{1-6}$halogenalkoxy, $C_{2-6}$alkenyl, $C_{2-6}$halogenalkenyl, $C_{2-6}$alkynyl, $C_{2-6}$halogenalkynyl, $C_{3-7}$cycloalkyl, $C_{3-7}$cycloalkyl($C_{1-4}$alkyl);

$X_1$ is —O—, —N($R_{15}$)—;

$R_{15}$ is hydrogen or $C_{1-6}$alkyl;

n is 1, 2 or 3;

each $R_5$ independently is selected from hydrogen, halogen, hydroxyl, $C_{1-6}$alkyl, $C_{1-6}$halogenalkyl, $C_{1-6}$alkoxy, $C_{1-6}$halogenalkoxy, $C_{3-7}$cycloalkyl, $C_{3-7}$cycloalkyl($C_{1-4}$alkyl); or two $R_5$ at the same carbon atom together with said carbon atom form $C_{3-7}$cycloalkyl; or two $R_5$ at adjacent carbon atoms together with said carbon atoms form $C_{3-7}$cycloalkyl; or two $R_5$ at carbon atoms separated by one further carbon atom together with said carbon atoms form $C_{4-7}$cycloalkyl;

$Z_1$ is —C(O)—, —S(O)— or —S(O)$_2$—;

$R_6$ is $C_{1-6}$alkyl, $C_{1-6}$halogenalkyl, $C_{2-6}$alkenyl, $C_{2-6}$halogenalkenyl, $C_{2-6}$alkynyl, $C_{2-6}$halogenalkynyl, $C_{3-7}$cycloalkyl, $C_{3-7}$cycloalkyl($C_{1-4}$alkyl) or a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system is attached to the nitrogen atom via a $C_{1-4}$alkylene group, and wherein the ring system may be substituted once or more than once by $R_{16}$, and wherein a substituent on a nitrogen in a heterocyclic ring system may not be halogen;

each $R_{16}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

or two $R_{16}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{17}$, and wherein a substituent on a nitrogen in a heterocyclic ring system may not be halogen; and wherein each $R_{17}$ independently is halogen or $C_{1-6}$alkyl, or two $R_{17}$ at the same ring atom together are oxo;

or $R_6$ is a group A

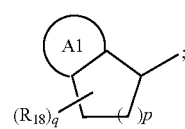

wherein p is 1 or 2;

q is 0, 1, 2, 3 or 4;

each $R_{18}$ independently is halogen or $C_{1-6}$alkyl;

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by $R_{19}$, and wherein a substituent on a nitrogen in a heterocyclic ring system may not be halogen;

each $R_{19}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

and $R_7$ is hydrogen, $C_{1-6}$alkyl, $C_{1-6}$halogenalkyl, $C_{2-6}$alkenyl, $C_{2-6}$halogenalkenyl, $C_{2-6}$alkynyl, $C_{2-6}$halogenalkynyl, $C_{3-7}$cycloalkyl, $C_{3-7}$cycloalkyl($C_{1-4}$alkyl);

in free form or in salt form for use as a medicament.

4. A compound of claim 1 of formula I

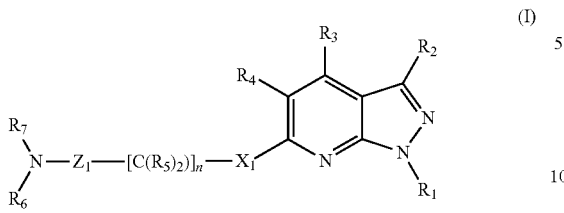

wherein $R_1$ is hydrogen; $C_{1-6}$alkyl; $C_{1-6}$halogenalkyl; $C_{2-6}$alkenyl; $C_{2-6}$halogenalkenyl; $C_{2-6}$alkynyl; $C_{2-6}$halogenalkynyl; or $R_1$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the nitrogen atom of the 1H-pyrazolo[3,4b]pyridine or via a $C_{1-4}$alkylene group, and wherein the ring system may be substituted once or more than once by $R_8$, and wherein a substituent on a nitrogen in a heterocyclic ring system may not be halogen; and $R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a $C_{1-4}$alkylene group, and wherein the ring system may be substituted once or more than once by $R_9$, and wherein a substituent on a nitrogen in a heterocyclic ring system may not be halogen; or $R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a $C_{1-4}$alkylene group, and wherein the ring system may be substituted once or more than once by $R_{10}$, and wherein a substituent on a nitrogen in a heterocyclic ring system may not be halogen;

or $R_1$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the nitrogen atom of the 1H-pyrazolo[3,4b]pyridine or via a $C_{1-4}$alkylene group, and wherein the ring system may be substituted once or more than once by $R_{11}$, and wherein a substituent on a nitrogen in a heterocyclic ring system may not be halogen;

and $R_2$ is $C_{2-6}$alkyl; $C_{2-6}$halogenalkyl; $C_{2-6}$alkenyl; $C_{2-6}$halogenalkenyl; $C_{2-6}$alkynyl; $C_{2-6}$halogenalkynyl; or $R_2$ is a three- to eight-membered monocyclic or bicyclic saturated or unsaturated non-aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a $C_{1-4}$alkylene group, and wherein the ring system may be substituted once or more than once by $R_{12}$, and wherein a substituent on a nitrogen in a heterocyclic ring system may not be halogen;

each $R_8$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_8$ at the same ring atom together are oxo;

each $R_9$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_9$ at the same ring atom together are oxo;

each $R_{12}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{12}$ at the same ring atom together are oxo;

each $R_{10}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{10}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{13}$, and wherein a substituent on a nitrogen in a heterocyclic ring system may not be halogen; and wherein each $R_{13}$ independently is halogen or $C_{1-6}$alkyl, or two $R_{13}$ at the same ring atom together are oxo;

each $R_{11}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy; or two $R_{11}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{14}$, and wherein a substituent on a nitrogen in a heterocyclic ring system may not be halogen; and wherein each $R_{14}$ independently is halogen or $C_{1-6}$alkyl, or two $R_{14}$ at the same ring atom together are oxo;

$R_3$ and $R_4$ are each independently selected from hydrogen, halogen, hydroxyl, $C_{1-6}$alkyl, $C_{1-6}$halogenalkyl, $C_{1-6}$alkoxy, $C_{1-6}$halogenalkoxy, $C_{2-6}$alkenyl, $C_{2-6}$halogenalkenyl, $C_{2-6}$alkynyl, $C_{2-6}$halogenalkynyl, $C_{3-7}$cycloalkyl, $C_{3-7}$cycloalkyl($C_{1-4}$alkyl);

$X_1$ is —O—, —N($R_{15}$)—;

$R_{15}$ is hydrogen or $C_{1-6}$alkyl;

n is 1, 2 or 3;

each $R_5$ independently is selected from hydrogen, halogen, hydroxyl, $C_{1-6}$alkyl, $C_{1-6}$halogenalkyl, $C_{1-6}$alkoxy, $C_{1-6}$halogenalkoxy, $C_{3-7}$cycloalkyl, $C_{3-7}$cycloalkyl($C_{1-4}$alkyl); or two $R_5$ at the same carbon atom together with said carbon atom form $C_{3-7}$cycloalkyl; or two $R_5$ at adjacent carbon atoms together with said carbon atoms form $C_{3-7}$cycloalkyl; or two $R_5$ at carbon atoms separated by one further carbon atom together with said carbon atoms form $C_{4-7}$cycloalkyl;

$Z_1$ is —C(O)—, —S(O)— or —S(O)$_2$—;

$R_6$ is $C_{1-6}$alkyl, $C_{1-6}$halogenalkyl, $C_{2-6}$alkenyl, $C_{2-6}$halogenalkenyl, $C_{2-6}$alkynyl, $C_{2-6}$halogenalkynyl, $C_{3-7}$cycloalkyl, $C_{3-7}$cycloalkyl($C_{1-4}$alkyl) or a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system is attached to the nitrogen atom via a $C_{1-4}$alkylene group, and wherein the ring system may be substituted once or more than once by $R_{16}$, and wherein a substituent on a nitrogen in a heterocyclic ring system may not be halogen;

each $R_{16}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

or two $R_{16}$ at adjacent ring atoms form together with said ring atoms a fused five- to seven-membered unsaturated non-aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may in turn be substituted once or more than once by $R_{17}$, and wherein a substituent on a nitrogen in a heterocyclic ring system may not be halogen; and wherein each $R_{17}$ independently is halogen or $C_{1-6}$alkyl, or two $R_{17}$ at the same ring atom together are oxo;

or $R_6$ is a group A

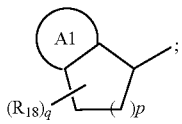

wherein p is 1 or 2;

q is 0, 1, 2, 3 or 4;

each $R_{18}$ independently is halogen or $C_{1-6}$alkyl;

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by $R_{19}$, and wherein a substituent on a nitrogen in a heterocyclic ring system may not be halogen;

each $R_{19}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

and $R_7$ is hydrogen, $C_{1-6}$alkyl, $C_{1-6}$halogenalkyl, $C_{2-6}$alkenyl, $C_{2-6}$halogenalkenyl, $C_{2-6}$alkynyl, $C_{2-6}$halogenalkynyl, $C_{3-7}$cycloalkyl, $C_{3-7}$cycloalkyl($C_{1-4}$alkyl);

and provided that the compounds

N-(2-methoxybenzyl)-2-(1-methyl-3-phenyl-4-(trifluoromethyl)-1H-pyrazolo[3,4-b]pyridin-6-yloxy)acetamide;

2-(1-methyl-3-phenyl-4-(trifluoromethyl)-1H-pyrazolo[3,4-b]pyridin-6-yloxy)-N-(2-methylbenzyl)acetamide;

N-(2-ethoxybenzyl)-2-(1-methyl-3-phenyl-4-(trifluoromethyl)-1H-pyrazolo[3,4-b]pyridin-6-yloxy)acetamide;

N-(3-fluorobenzyl)-2-(1-methyl-3-phenyl-4-(trifluoromethyl)-1H-pyrazolo[3,4-b]pyridin-6-yloxy)acetamide;

2-(1-methyl-3-phenyl-4-(trifluoromethyl)-1H-pyrazolo[3,4-b]pyridin-6-yloxy)-N-(4-phenylbutan-2-yl)acetamide;

N-cyclohexyl-2-(1-methyl-3-phenyl-4-(trifluoromethyl)-1H-pyrazolo[3,4-b]pyridin-6-yloxy)acetamide;

N-(4-fluorobenzyl)-2-(1-methyl-3-phenyl-4-(trifluoromethyl)-1H-pyrazolo[3,4-b]pyridin-6-yloxy)acetamide;

2-(1-methyl-3-phenyl-4-(trifluoromethyl)-1H-pyrazolo[3,4-b]pyridin-6-yloxy)-N-(1-phenylethyl)acetamide;

N-(benzo[d][1,3]dioxol-5-ylmethyl)-2-(1-methyl-3-phenyl-4-(trifluoromethyl)-1H-pyrazolo[3,4-b]pyridin-6-yloxy)acetamide;

N-cyclopentyl-2-(1-methyl-3-phenyl-4-(trifluoromethyl)-1H-pyrazolo[3,4-b]pyridin-6-yloxy)acetamide;

N-(4-chlorobenzyl)-2-(1-methyl-3-phenyl-4-(trifluoromethyl)-1H-pyrazolo[3,4-b]pyridin-6-yloxy)acetamide;

N-(2-chlorobenzyl)-2-(1-methyl-3-phenyl-4-(trifluoromethyl)-1H-pyrazolo[3,4-b]pyridin-6-yloxy)acetamide; and N-benzyl-2-(1-methyl-3-phenyl-4-(trifluoromethyl)-1H-pyrazolo[3,4-b]pyridin-6-yloxy)acetamide are excluded;

in free form or in salt form.

5. The compound of claim 2, wherein $Q_1$ is —N($R_1$)— and $Q_2$ is =N—; or $Q_1$ is —N($R_1$)— and $Q_2$ is =C($R_{1a}$)—; or $Q_1$ is —O— and $Q_2$ is =N—.

6. The compound of claim 2, wherein $R_1$ is hydrogen, $C_{1-6}$alkyl, $Cl_{1-6}$halogenalkyl, $C_{2-6}$alkenyl, $C_{2-6}$halogenalkenyl, $C_{2-6}$alkynyl or $C_{2-6}$halogenalkynyl.

7. The compound of claim 2, wherein $X_1$ is —O—; n is 1; each $R_5$ is hydrogen; and $Z_1$ is —C(O)—.

8. The compound of claim 2, wherein $R_3$ is $C_{1-6}$alkyl or $C_{1-6}$halogenalkyl; and $R_4$ is hydrogen.

9. The compound of claim 2, wherein said compound is a compound of formula I'-2

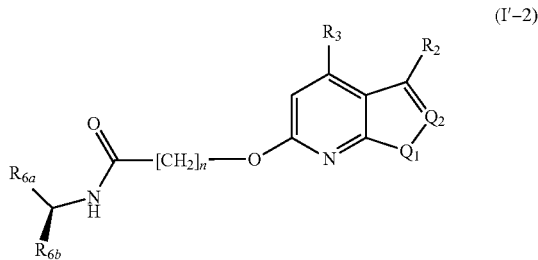

wherein $Q_1$ is —N($R_1$)— and $Q_2$ is =N—; or $Q_1$ is —N($R_1$)— and $Q_2$ is =C($R_{1a}$)—; or $Q_1$ is —O— and $Q_2$ is =N—;

$R_1$ is hydrogen, $C_{1-6}$alkyl, $C_{1-6}$halogenalkyl, $C_{2-6}$alkenyl, $C_{2-6}$halogenalkenyl, $C_{2-6}$alkynyl or $C_{2-6}$halogenalkynyl;

$R1_a$ is hydrogen, $C_{1-6}$alkyl, $C_{1-6}$halogenalkyl, $C_{2-6}$alkenyl, $C_{2-6}$halogenalkenyl, $C_{2-6}$alkynyl or $C_{2-6}$halogenalkynyl;

$R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{10}$, and wherein a substituent on a nitrogen in a heterocyclic ring system may not be halogen; each $R_{10}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

$R_3$ is selected from $C_{1-6}$alkyl and $C_{1-6}$halogenalkyl;

n is 1;

$R_{6a}$ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by $R_{16}$, and wherein a substituent on a nitrogen in a heterocyclic ring system may not be halogen; each $R_{16}$ independently is halogen, $C_{1-6}$alkyl, especially $C_{1-4}$-alkyl, $C_{1-6}$alkoxy or $C_{1-6}$halogenalkyl; and $R_{6b}$ is $C_{1-3}$alkyl.

10. The compound of claim 2, wherein said compound is a compound of formula I'-4

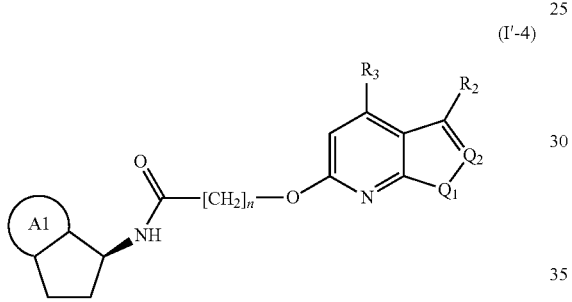

(I'-4)

wherein $Q_1$ is —N($R_1$)— and $Q_2$ is =N—; or $Q_1$ is —N($R_1$)— and $Q_2$ is =C($R_{1a}$)—; or $Q_1$ is —O— and $Q_2$ is =N—;

$R_1$ is hydrogen, $C_{1-6}$alkyl, $C_{1-6}$halogenalkyl, $C_{2-6}$alkenyl, $C_{2-6}$halogenalkenyl, $C_{2-6}$alkynyl or $C_{2-6}$halogenalkynyl;

$R1_a$ is hydrogen, $C_{1-6}$alkyl, $C_{1-6}$halogenalkyl, $C_{2-6}$alkenyl, $C_{2-6}$halogenalkenyl, $C_{2-6}$alkynyl or $C_{2-6}$halogenalkynyl;

$R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly or via a $C_{1-4}$alkylene group, and wherein the ring system may be substituted once or more than once by $R_{10}$, and wherein a substituent on a nitrogen in a heterocyclic ring system may not be halogen; each $R_{10}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

$R_3$ is selected from $C_{1-6}$alkyl and $C_{1-6}$halogenalkyl;

n is 1;

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by $R_{19}$, and wherein a substituent on a nitrogen in a heterocyclic ring system may not be halogen; and each $R_{19}$ independently is halogen, $C_{1-6}$alkyl, $C_{1-6}$alkoxy or $C_{1-6}$halogenalkyl.

11. The compound of claim 4, wherein said compound is a compound of formula I-2

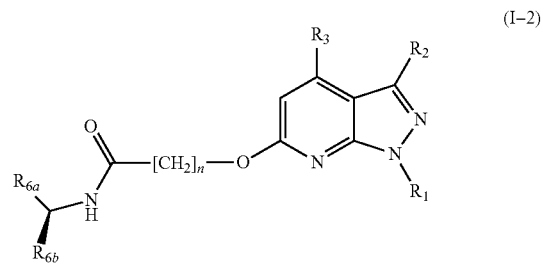

(I-2)

wherein $R_1$ is hydrogen, $C_{1-6}$alkyl, $C_{1-6}$halogenalkyl, $C_{2-6}$alkenyl, $C_{2-6}$halogenalkenyl, $C_{2-6}$alkynyl or $C_{2-6}$halogenalkynyl;

$R_2$ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a $C_{1-4}$alkylene group, and wherein the ring system may be substituted once or more than once by $R_{10}$, and wherein a substituent on a nitrogen in a heterocyclic ring system may not be halogen; each $R_{10}$ independently is halogen, $C_{1-6}$alkyl, $C_{1-6}$halogenalkyl, $C_{3-7}$cycloalkyl, $C_{3-7}$cycloalkyl($C_{1-4}$alkyl), $C_{1-6}$alkoxy, or $C_{1-6}$halogenalkoxy;

$R_3$ is selected from $C_{1-6}$alkyl and $C_{1-6}$halogenalkyl;

n is 1;

$R_{6a}$ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_{16}$, and wherein a substituent on a nitrogen in a heterocyclic ring system may not be halogen; each $R_{16}$ independently is halogen, $C_{1-6}$alkyl or $C_{1-6}$halogenalkyl; and $R_{6b}$ is $C_{1-3}$alkyl.

12. The compound of claim 4, wherein said compound is a compound of formula I-4

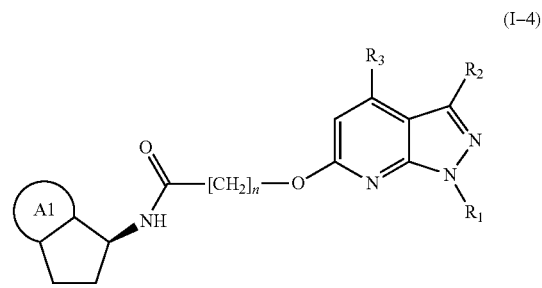

(I-4)

wherein
R₁ is hydrogen, C$_{1-6}$alkyl, C$_{1-6}$halogenalkyl, C$_{2-6}$alkenyl, C$_{2-6}$halogenalkenyl, C$_{2-6}$alkynyl or C$_{2-6}$halogenalkynyl;

R₂ is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be attached directly to the carbon atom of the 1H-pyrazolo[3,4b]pyridine or via a C$_{1-4}$alkylene group, and wherein the ring system may be substituted once or more than once by R$_{10}$, and wherein a substituent on a nitrogen in a heterocyclic ring system may not be halogen; each R$_{10}$ independently is halogen, C$_{1-6}$alkyl, C$_{1-6}$halogenalkyl, C$_{3-7}$cycloalkyl, C$_{3-7}$cycloalkyl(C$_{1-4}$alkyl), C$_{1-6}$alkoxy, or C$_{1-6}$halogenalkoxy;

R₃ is selected from C$_{1-6}$alkyl and C$_{1-6}$halogenalkyl;
n is 1;

A1 is a five- to six-membered monocyclic aromatic ring system which may contain from 1 to 4 hetero atoms selected from nitrogen, oxygen and sulfur, wherein the ring system may contain not more than 2 oxygen atoms and not more than 2 sulfur atoms, wherein the ring system may be substituted once or more than once by R$_{19}$, and wherein a substituent on a nitrogen in a heterocyclic ring system may not be halogen; and each R$_{19}$ independently is halogen, C$_{1-6}$alkyl or C$_{1-6}$halogenalkyl.

13. The compound of claim 1 in free form or in pharmaceutically acceptable form which is selected from the group consisting of
2-(3-(2-fluorophenyl)-1-methyl-4-(trifluoromethyl)-1H-pyrazolo[3,4-b]pyridin-6-yloxy)-N-(1-phenylethyl)acetamide;
2-(3-phenyl-4-(trifluoromethyl)-1H-pyrazolo[3,4-b]pyridin-6-yloxy)-N-(1-phenylethyl)acetamide;
N-(2,3-dihydro-1H-inden-1-yl)-2-(1-methyl-3-phenyl-4-(trifluoromethyl)-1H-pyrazolo[3,4-b]pyridin-6-yloxy)acetamide;
N-(1-(4-methoxyphenyl)ethyl)-2-(1-methyl-3-phenyl-4-(trifluoromethyl)-1H-pyrazolo[3,4-b]pyridin-6-yloxy)acetamide;
2-(1-methyl-3-phenyl-4-(trifluoromethyl)-1H-pyrazolo[3,4-b]pyridin-6-yloxy)-N-(2-phenylpropyl)acetamide;
N-(1-(3,5-dimethyl-1H-pyrazol-4-yl)ethyl)-2-(1-methyl-3-phenyl-4-(trifluoromethyl)-1H-pyrazolo[3,4-b]pyridin-6-yloxy)acetamide;
N-(2-ethoxybenzyl)-2-(1-methyl-3-phenyl-4-(trifluoromethyl)-1H-pyrazolo[3,4-b]pyridin-6-yloxy)acetamide;
2-(1,4-dimethyl-3-phenyl-1H-pyrazolo[3,4-b]pyridin-6-yloxy)-N-(1-phenylethyl)acetamide;
N-(2-chlorobenzyl)-2-(1,4-dimethyl-3-phenyl-1H-pyrazolo[3,4-b]pyridin-6-yloxy)acetamide;
N-(benzo[d][1,3]dioxol-5-ylmethyl)-2-(1,4-dimethyl-3-phenyl-1H-pyrazolo[3,4-b]pyridin-6-yloxy)acetamide;
2-(1,4-dimethyl-3-phenyl-1H-pyrazolo[3,4-b]pyridin-6-yloxy)-N-(4-phenylbutan-2-yl)acetamide;
2-(3-(3-methoxyphenyl)-1-methyl-4-(trifluoromethyl)-1H-pyrazolo[3,4-b]pyridin-6-yloxy)-N-(1-phenylethyl)acetamide;
2-(3-(4-methoxyphenyl)-1-methyl-4-(trifluoromethyl)-1H-pyrazolo[3,4-b]pyridin-6-yloxy)-N-(1-phenylethyl)acetamide;
2-(1-methyl-3-(pyridin-2-yl)-4-(trifluoromethyl)-1H-pyrazolo[3,4-b]pyridin-6-yloxy)-N-(1-phenylethyl)acetamide;
2-(3-(3-fluorophenyl)-1-methyl-4-(trifluoromethyl)-1H-pyrazolo[3,4-b]pyridin-6-yloxy)-N-(1-phenylethyl)acetamide;
2-(3-(4-fluorophenyl)-1-methyl-4-(trifluoromethyl)-1H-pyrazolo[3,4-b]pyridin-6-yloxy)-N-(1-phenylethyl)acetamide;
2-(1-methyl-3-m-tolyl-4-(trifluoromethyl)-1H-pyrazolo[3,4-b]pyridin-6-yloxy)-N-(1-phenylethyl)acetamide;
2-(1-methyl-3-(pyridin-4-yl)-4-(trifluoromethyl)-1H-pyrazolo[3,4-b]pyridin-6-yloxy)-N-(1-phenylethyl)acetamide;
2-(1-methyl-3-o-tolyl-4-(trifluoromethyl)-1H-pyrazolo[3,4-b]pyridin-6-yloxy)-N-(1-phenylethyl)acetamide;
2-(1-methyl-3-phenyl-4-(trifluoromethyl)-1H-pyrazolo[3,4-b]pyridin-6-yloxy)-N-(1-(5-methylfuran-2-yl)ethyl)acetamide;
2-(1-methyl-3-phenyl-4-(trifluoromethyl)-1H-pyrazolo[3,4-b]pyridin-6-yloxy)-N-(1-(pyridin-2-yl)ethyl)acetamide;
2-(1-methyl-3-phenyl-4-(trifluoromethyl)-1H-pyrazolo[3,4-b]pyridin-6-yloxy)-N-(1-(pyridin-3-yl)ethyl)acetamide;
2-(1-methyl-3-phenyl-4-(trifluoromethyl)-1H-pyrazolo[3,4-b]pyridin-6-yloxy)-N-(1-(pyridin-4-yl)ethyl)acetamide;
2-(1-methyl-3-phenyl-4-(trifluoromethyl)-1H-pyrazolo[3,4-b]pyridin-6-yloxy)-N-(4-methylbenzyl)acetamide;
N-(3-methoxybenzyl)-2-(1-methyl-3-phenyl-4-(trifluoromethyl)-1H-pyrazolo[3,4-b]pyridin-6-yloxy)acetamide;
2-(1-methyl-3-(pyridin-3-yl)-4-(trifluoromethyl)-1H-pyrazolo[3,4-b]pyridin-6-yloxy)-N-(1-phenylethyl)acetamide;
N-(1-(4-ethyl-4H-1,2,4-triazol-3-yl)ethyl)-2-(1-methyl-3-phenyl-4-(trifluoromethyl)-1H-pyrazolo[3,4-b]pyridin-6-yloxy)acetamide;
N-(1-(3-isopropyl-1,2,4-oxadiazol-5-yl)ethyl)-2-(1-methyl-3-phenyl-4-(trifluoromethyl)-1H-pyrazolo[3,4-b]pyridin-6-yloxy)acetamide;
2-(3-tert-butyl-1-methyl-4-(trifluoromethyl)-1H-pyrazolo[3,4-b]pyridin-6-yloxy)-N-(1-phenylethyl)acetamide;
N-(1-(1-ethyl-1H-pyrazol-5-yl)ethyl)-2-(1-methyl-3-phenyl-4-(trifluoromethyl)-1H-pyrazolo[3,4-b]pyridin-6-yloxy)acetamide;
N-(1-(2,5-dimethylthiazol-4-yl)ethyl)-2-(1-methyl-3-phenyl-4-(trifluoromethyl)-1H-pyrazolo[3,4-b]pyridin-6-yloxy)acetamide;
N-(4-methoxybenzyl)-2-(1-methyl-3-phenyl-4-(trifluoromethyl)-1H-pyrazolo[3,4-b]pyridin-6-yloxy)acetamide;
N-(2-fluorobenzyl)-2-(1-methyl-3-phenyl-4-(trifluoromethyl)-1H-pyrazolo[3,4-b]pyridin-6-yloxy)acetamide;
N-(3-chlorobenzyl)-2-(1-methyl-3-phenyl-4-(trifluoromethyl)-1H-pyrazolo[3,4-b]pyridin-6-yloxy)acetamide;
N-(1-(2-methoxyphenyl)ethyl)-2-(1-methyl-3-phenyl-4-(trifluoromethyl)-1H-pyrazolo[3,4-b]pyridin-6-yloxy)acetamide;
N-(1-(4-methoxyphenyl)ethyl)-2-(1-methyl-3-phenyl-4-(trifluoromethyl)-1H-pyrazolo[3,4-b]pyridin-6-yloxy)acetamide;
N-(1-(3-methoxyphenyl)ethyl)-2-(1-methyl-3-phenyl-4-(trifluoromethyl)-1H-pyrazolo[3,4-b]pyridin-6-yloxy)acetamide;
2-(4-cyclopropyl-1-methyl-3-phenyl-1H-pyrazolo[3,4-b]pyridin-6-yloxy)-N-(1-phenylethyl)acetamide;

2-(1-methyl-3-p-tolyl-4-(trifluoromethyl)-1H-pyrazolo[3,4-b]pyridin-6-yloxy)-N-(1-phenylethyl)acetamide;
2-(3-(2-methoxyphenyl)-1-methyl-4-(trifluoromethyl)-1H-pyrazolo[3,4-b]pyridin-6-yloxy)-N-(1-phenylethyl)acetamide;
2-(3-cyclopropyl-1-methyl-4-(trifluoromethyl)-1H-pyrazolo[3,4-b]pyridin-6-yloxy)-N-(1-phenylethyl)acetamide;
2-(3-cyclohexyl-1-methyl-4-(trifluoromethyl)-1H-pyrazolo[3,4-b]pyridin-6-yloxy)-N-(1-phenylethyl)acetamide;
2-(3-cyclopentyl-1-methyl-4-(trifluoromethyl)-1H-pyrazolo[3,4-b]pyridin-6-yloxy)-N-(1-phenylethyl)acetamide;
N-cyclopropyl-2-(1-methyl-3-phenyl-4-(trifluoromethyl)-1H-pyrazolo[3,4-b]pyridin-6-yloxy)acetamide;
N-cyclobutyl-2-(1-methyl-3-phenyl-4-(trifluoromethyl)-1H-pyrazolo[3,4-b]pyridin-6-yloxy)acetamide;
2-(1-methyl-3-phenyl-4-(trifluoromethyl)-1H-pyrazolo[3,4-b]pyridin-6-yloxy)-N-propylacetamide;
2-(1-methyl-3-phenyl-4-(trifluoromethyl)-1H-pyrazolo[3,4-b]pyridin-6-yloxy)-N-(1,2,3,4-tetrahydronaphthalen-1-yl)acetamide;
2-(3-(3-chlorophenyl)-1-methyl-4-(trifluoromethyl)-1H-pyrazolo[3,4-b]pyridin-6-yloxy)-N-(1-phenylethyl)acetamide;
2-(3-(3-bromophenyl)-1-methyl-4-(trifluoromethyl)-1H-pyrazolo[3,4-b]pyridin-6-yloxy)-N-(1-phenylethyl)acetamide;
N-(1-(4-methoxyphenyl)ethyl)-2-(1-methyl-3-phenyl-(trifluoromethyl)-1H-pyrazolo[3,4-b]pyridin-6-yloxy)acetamide;
N-(2,3-dihydro-1H-inden-1-yl)-2-(3-(2-fluorophenyl)-1-methyl-4-(trifluoromethyl)-1H-pyrazolo[3,4-b]pyridin-6-yloxy)acetamide;
N-(2,3-dihydro-1H-inden-1-yl)-2-(3-(3-fluorophenyl)-1-methyl-4-(trifluoromethyl)-1H-pyrazolo[3,4-b]pyridin-6-yloxy)acetamide;
2-(1-methyl-3-phenyl-1H-pyrazolo[3,4-b]pyridin-6-yloxy)-N-(1-phenylethyl)acetamide;
2-(1-methyl-3-phenyl-4-(trifluoromethyl)-1H-pyrazolo[3,4-b]pyridin-6-ylamino)-N-(1-phenylethyl)acetamide
2-(1,4-dimethyl-3-phenyl-1H-pyrazolo[3,4-b]pyridin-6-yloxy)-N-(1-(pyridin-4-yl)ethyl)acetamide;
2-(1,4-dimethyl-3-phenyl-1H-pyrazolo[3,4-b]pyridin-6-yloxy)-N-(1-(pyridin-3-yl)ethyl)acetamide;
2-(1,4-dimethyl-3-phenyl-1H-pyrazolo[3,4-b]pyridin-6-yloxy)-N-(1-(pyridin-2-yl)ethyl)acetamide;
2-(1-methyl-3-phenyl-4-(trifluoromethyl)-1H-pyrazolo[3,4-b]pyridin-6-yloxy)-N-(3-methylbenzyl)acetamide;
N-(1-(6-methoxypyridin-3-yl)ethyl)-2-(1-methyl-3-phenyl-4-(trifluoromethyl)-1H-pyrazolo[3,4-b]pyridin-6-yloxy)acetamide;
N-isopentyl-2-(1-methyl-3-phenyl-4-(trifluoromethyl)-1H-pyrazolo[3,4-b]pyridin-6-yloxy)acetamide;
2-(3-cyclopropyl-1,4-dimethyl-1H-pyrazolo[3,4-b]pyridin-6-yloxy)-N-(1-phenylethyl)acetamide;
2-(1-methyl-3-phenyl-4-(trifluoromethyl)-1H-pyrazolo[3,4-b]pyridin-6-yloxy)-N-(1-(1,3,5-trimethyl-1H-pyrazol-4-yl)ethyl)acetamide;
2-(3-cyclopropyl-1,4-dimethyl-1H-pyrazolo[3,4-b]pyridin-6-yloxy)-N-(1-(4-methoxyphenyl)ethyl)acetamide;
2-(3-cyclopropyl-1,4-dimethyl-1H-pyrazolo[3,4-b]pyridin-6-yloxy)-N-(1-(1,3,5-trimethyl-1H-pyrazol-4-yl)ethyl)acetamide;
2-(1-methyl-3-phenyl-4-(trifluoromethyl)-1H-pyrazolo[3,4-b]pyridin-6-yloxy)-N-(1-phenylethyl)propanamide;
2-(3-cyclopropyl-1,4-dimethyl-1H-pyrazolo[3,4-b]pyridin-6-yloxy)-N-(2,3-dihydro-1H-inden-1-yl)acetamide;
2-(3-cyclopropyl-1,4-dimethyl-1H-pyrazolo[3,4-b]pyridin-6-yloxy)-N-(1-(3,5-dimethyl-1H-pyrazol-4-yl)ethyl)acetamide;
2-(1-methyl-3-phenyl-4-(trifluoromethyl)-1H-pyrazolo[3,4-b]pyridin-6-yloxy)-N-(1-(6-methylpyridin-3-yl)ethyl)acetamide;
2-(3-(3-fluoropyridin-2-yl)-1,4-dimethyl-1H-pyrazolo[3,4-b]pyridin-6-yloxy)-N-(1-p-tolylethyl)acetamide;
2-(1,4-dimethyl-3-(1-methyl-1H-pyrazol-5-yl)-1H-pyrazolo[3,4-b]pyridin-6-yloxy)-N-(1-p-tolylethyl)acetamide;
2-(3-(1,2-dimethyl-1H-imidazol-5-yl)-1,4-dimethyl-1H-pyrazolo[3,4-b]pyridin-6-yloxy)-N-(1-p-tolylethyl)acetamide;
2-(3-(1,3-dimethyl-1H-pyrazol-5-yl)-1,4-dimethyl-1H-pyrazolo[3,4-b]pyridin-6-yloxy)-N-(1-p-tolylethyl)acetamide;
2-(1,4-dimethyl-3-(1-methyl-1H-pyrazol-4-yl)-1H-pyrazolo[3,4-b]pyridin-6-yloxy)-N-(1-p-tolylethyl)acetamide;
2-(1,4-dimethyl-3-(pyrimidin-2-yl)-1H-pyrazolo[3,4-b]pyridin-6-yloxy)-N-(1-p-tolylethyl)acetamide;
2-(1,4-dimethyl-3-(pyrazin-2-yl)-1H-pyrazolo[3,4-b]pyridin-6-yloxy)-N-(1-p-tolylethyl)acetamide;
2-(1,4-dimethyl-3-(5-methylpyridin-2-yl)-1H-pyrazolo[3,4-b]pyridin-6-yloxy)-N-(1-p-tolylethyl)acetamide;
2-(1,4-dimethyl-3-(thiazol-4-yl)-1H-pyrazolo[3,4-b]pyridin-6-yloxy)-N-(1-p-tolylethyl)acetamide;
2-(1,4-dimethyl-3-(1-methyl-1H-imidazol-5-yl)-1H-pyrazolo[3,4-b]pyridin-6-yloxy)-N-(1-p-tolylethyl)acetamide;
2-(3-(6-methoxypyrazin-2-yl)-1,4-dimethyl-1H-pyrazolo[3,4-b]pyridin-6-yloxy)-N-(1-p-tolylethyl)acetamide;
2-(1,4-dimethyl-3-(1-methyl-1H-imidazol-4-yl)-1H-pyrazolo[3,4-b]pyridin-6-yloxy)-N-(1-p-tolylethyl)acetamide;
2-(1,4-dimethyl-3-(oxazol-2-yl)-1H-pyrazolo[3,4-b]pyridin-6-yloxy)-N-(1-p-tolylethyl)acetamide;
2-(1,4-dimethyl-3-(4-methylthiazol-2-yl)-1H-pyrazolo[3,4-b]pyridin-6-yloxy)-N-(1-p-tolylethyl)acetamide;
2-(1,4-dimethyl-3-(thiazol-2-yl)-1H-pyrazolo[3,4-b]pyridin-6-yloxy)-N-(1-p-tolylethyl)acetamide;
2-(3-(4-methoxypyrimidin-2-yl)-1,4-dimethyl-1H-pyrazolo[3,4-b]pyridin-6-yloxy)-N-(1-p-tolylethyl)acetamide;
2-(1,4-dimethyl-3-(thiazol-5-yl)-1H-pyrazolo[3,4-b]pyridin-6-yloxy)-N-(1-p-tolylethyl)acetamide;
2-(3-(2-methoxythiazol-4-yl)-1,4-dimethyl-1H-pyrazolo[3,4-b]pyridin-6-yloxy)-N-(1-p-tolylethyl)acetamide;
2-(1,4-dimethyl-3-(5-methylthiazol-2-yl)-1H-pyrazolo[3,4-b]pyridin-6-yloxy)-N-(1-p-tolylethyl)acetamide;
2-(1,4-dimethyl-3-(6-methylpyridin-2-yl)-1H-pyrazolo[3,4-b]pyridin-6-yloxy)-N-(1-p-tolylethyl)acetamide;
2-(3-(3,5-dimethoxyphenyl)-1,4-dimethyl-1H-pyrazolo[3,4-b]pyridin-6-yloxy)-N-(1-p-tolylethyl)acetamide;
2-(3-cyclopropyl-4-(difluoromethyl)-1-methyl-1H-pyrazolo[3,4-b]pyridin-6-yloxy)-N-(2-methyl-6,7-dihydro-5H-cyclopenta[b]pyridin-5-yl)acetamide;
2-(3-cyclopropyl-1,4-dimethyl-1H-pyrazolo[3,4-b]pyridin-6-yloxy)-N-(5-methoxy-2,3-dihydro-1H-inden-1-yl)acetamide;

2-(3-cyclopropyl-1,4-dimethyl-1H-pyrazolo[3,4-b]pyridin-6-yloxy)-N-(2-p-tolylpropan-2-yl)acetamide;
2-(3-cyclopropyl-4-(difluoromethyl)-1-methyl-1H-pyrazolo[3,4-b]pyridin-6-yloxy)-N-(1-(4-methoxyphenyl)ethyl)acetamide;
2-(3-cyclopropyl-4-(difluoromethyl)-1-methyl-1H-pyrazolo[3,4-b]pyridin-6-yloxy)-N-(1-p-tolylethyl)acetamide;
2-(3-cyclopropyl-4-(difluoromethyl)-1-methyl-1H-pyrazolo[3,4-b]pyridin-6-yloxy)-N-(1-(1,3,5-trimethyl-1H-pyrazol-4-yl)ethyl)acetamide;
2-(3-cyclopropyl-4-(difluoromethyl)-1-methyl-1H-pyrazolo[3,4-b]pyridin-6-yloxy)-N-(1-(6-methoxypyridin-3-yl)ethyl)acetamide;
2-(3-cyclopropyl-4-isopropyl-1-methyl-1H-pyrazolo[3,4-b]pyridin-6-yloxy)-N-(1-p-tolylethyl)acetamide;
2-(3-cyclopropyl-1-methyl-4-(trifluoromethyl)-1H-pyrazolo[3,4-b]pyridin-6-yloxy)-N-(1-(1,3,5-trimethyl-1H-pyrazol-4-yl)ethyl)acetamide;
2-(3-cyclopropyl-1-methyl-4-(trifluoromethyl)-1H-pyrazolo[3,4-b]pyridin-6-yloxy)-N-(1-p-tolylethyl)acetamide;
2-(3-cyclopropyl-1-methyl-4-(trifluoromethyl)-1H-pyrazolo[3,4-b]pyridin-6-yloxy)-N-(1-(6-methoxypyridin-3-yl)ethyl)acetamide;
2-(3-cyclopropyl-1-methyl-4-(trifluoromethyl)-1H-pyrazolo[3,4-b]pyridin-6-yloxy)-N-(1-(4-methoxyphenyl)ethyl)acetamide;
2-(3-cyclopropyl-1-methyl-4-(trifluoromethyl)-1H-pyrazolo[3,4-b]pyridin-6-yloxy)-N-(1-(6-methylpyridin-3-yl)ethyl)acetamide;
2-(4-(difluoromethyl)-1-methyl-3-phenyl-1H-pyrazolo[3,4-b]pyridin-6-yloxy)-N-(1-(4-methoxyphenyl)ethyl)acetamide;
2-(4-(difluoromethyl)-1-methyl-3-phenyl-1H-pyrazolo[3,4-b]pyridin-6-yloxy)-N-(1-(6-methylpyridin-3-yl)ethyl)acetamide;
2-(3-cyclopropyl-4-(difluoromethyl)-1-methyl-1H-pyrazolo[3,4-b]pyridin-6-yloxy)-N-(1-(6-methylpyridin-3-yl)ethyl)acetamide;
2-(4-(difluoromethyl)-1-methyl-3-phenyl-1H-pyrazolo[3,4-b]pyridin-6-yloxy)-N-(1-(1,3,5-trimethyl-1H-pyrazol-4-yl)ethyl)acetamide;
2-(4-(difluoromethyl)-1-methyl-3-phenyl-1H-pyrazolo[3,4-b]pyridin-6-yloxy)-N-(1-p-tolylethyl)acetamide;
2-(4-(difluoromethyl)-1-methyl-3-phenyl-1H-pyrazolo[3,4-b]pyridin-6-yloxy)-N-(1-(6-methoxypyridin-3-yl)ethyl)acetamide;
2-(3-cyclopropyl-1-methyl-1H-pyrazolo[3,4-b]pyridin-6-yloxy)-N-(1-p-tolylethyl)acetamide;
2-(3-(2-methoxyphenyl)-1-methyl-1H-pyrazolo[3,4-b]pyridin-6-yloxy)-N-(1-p-tolylethyl)acetamide;
2-(3-tert-butyl-1-methyl-1H-pyrazolo[3,4-b]pyridin-6-yloxy)-N-(1-p-tolylethyl)acetamide;
2-(3-isopropyl-1,4-dimethyl-1H-pyrazolo[3,4-b]pyridin-6-yloxy)-N-(1-p-tolylethyl)acetamide;
2-(3-isopropyl-1,4-dimethyl-1H-pyrazolo[3,4-b]pyridin-6-yloxy)-N-(1-(4-methoxyphenyl)ethyl)acetamide;
2-(3-isopropyl-1,4-dimethyl-1H-pyrazolo[3,4-b]pyridin-6-yloxy)-N-(1-(6-methoxypyridin-3-yl)ethyl)acetamide;
2-(3-isopropyl-1,4-dimethyl-1H-pyrazolo[3,4-b]pyridin-6-yloxy)-N-(1-(1,3,5-trimethyl-1H-pyrazol-4-yl)ethyl)acetamide;
2-(3-(2,5-dimethylfuran-3-yl)-1,4-dimethyl-1H-pyrazolo[3,4-b]pyridin-6-yloxy)-N-(1-p-tolylethyl)acetamide;
2-(3-(2,5-dimethylfuran-3-yl)-1,4-dimethyl-1H-pyrazolo[3,4-b]pyridin-6-yloxy)-N-(1-(4-methoxyphenyl)ethyl)acetamide;
2-(3-(2,5-dimethylfuran-3-yl)-1,4-dimethyl-1H-pyrazolo[3,4-b]pyridin-6-yloxy)-N-(1-(6-methoxypyridin-3-yl)ethyl)acetamide;
2-(3-(2,5-dimethylfuran-3-yl)-1,4-dimethyl-1H-pyrazolo[3,4-b]pyridin-6-yloxy)-N-(1-(1,3,5-trimethyl-1H-pyrazol-4-yl)ethyl)acetamide;
2-(1,4-dimethyl-3-(2-methylfuran-3-yl)-1H-pyrazolo[3,4-b]pyridin-6-yloxy)-N-(1-(4-methoxyphenyl)ethyl)acetamide;
2-(1-methyl-3-o-tolyl-1H-pyrazolo[3,4-b]pyridin-6-yloxy)-N-(1-p-tolylethyl)acetamide;
2-(3-(3,5-dimethoxyphenyl)-1,4-dimethyl-1H-pyrazolo[3,4-b]pyridin-6-yloxy)-N-(1-(4-methoxyphenyl)ethyl)acetamide;
2-(3-(4-methoxypyridin-2-yl)-1,4-dimethyl-1H-pyrazolo[3,4-b]pyridin-6-yloxy)-N-(1-p-tolylethyl)acetamide;
2-(3-cyclopropyl-1,4-dimethyl-1H-pyrazolo[3,4-b]pyridin-6-yloxy)-N-(5-fluoro-2,3-dihydro-1H-inden-1-yl)acetamide;
2-(3-cyclopropyl-4-(difluoromethyl)-1-methyl-1H-pyrazolo[3,4-b]pyridin-6-yloxy)-N-(5-methoxy-2,3-dihydro-1H-inden-1-yl)acetamide;
2-(3-cyclopropyl-1-methyl-4-(trifluoromethyl)-1H-pyrazolo[3,4-b]pyridin-6-yloxy)-N-(5-methoxy-2,3-dihydro-1H-inden-1-yl)acetamide;
2-(3-cyclopropyl-1,4-dimethyl-1H-pyrazolo[3,4-b]pyridin-6-yloxy)-N-(5-methyl-2,3-dihydro-1H-inden-1-yl)acetamide;
2-(3-cyclopropyl-1,4-dimethyl-1H-pyrazolo[3,4-b]pyridin-6-yloxy)-N-isobutylacetamide;
N-cyclopentyl-2-(3-cyclopropyl-1,4-dimethyl-1H-pyrazolo[3,4-b]pyridin-6-yloxy)acetamide;
2-(3-cyclopropyl-1,4-dimethyl-1H-pyrazolo[3,4-b]pyridin-6-yloxy)-N-(1-(6-methoxypyridin-3-yl)ethyl)acetamide;
2-(3-cyclopropyl-1,4-dimethyl-1H-pyrazolo[3,4-b]pyridin-6-yloxy)-N-(1-(5-neopentylisoxazol-3-yl)ethyl)acetamide;
2-(3-cyclopropyl-1,4-dimethyl-1H-pyrazolo[3,4-b]pyridin-6-yloxy)-N-phenethylacetamide;
2-(3-cyclopropyl-1,4-dimethyl-1H-pyrazolo[3,4-b]pyridin-6-yloxy)-N-(3-phenylpropyl)acetamide;
2-(3-cyclopropyl-1,4-dimethyl-1H-pyrazolo[3,4-b]pyridin-6-yloxy)-N-(1-(4-methoxyphenyl)ethyl)-N-methylacetamide;
2-(3-cyclopropyl-1,4-dimethyl-1H-pyrazolo[3,4-b]pyridin-6-yloxy)-N-methylacetamide;
2-(3-cyclopropyl-1,4-dimethyl-1H-pyrazolo[3,4-b]pyridin-6-yloxy)-N-(1-cyclopropylethyl)acetamide;
2-(3-cyclopropyl-1,4-dimethyl-1H-pyrazolo[3,4-b]pyridin-6-yloxy)-N-(1-(1-ethyl-1H-pyrazol-3-yl)ethyl)acetamide;
2-(3-cyclopropyl-1,4-dimethyl-1H-pyrazolo[3,4-b]pyridin-6-yloxy)-N-(1-(6-methylpyridin-3-yl)ethyl)acetamide;
N-(1-cyclopentylethyl)-2-(3-cyclopropyl-1,4-dimethyl-1H-pyrazolo[3,4-b]pyridin-6-yloxy)acetamide;
N-(1-(1H-pyrrolo[2,3-b]pyridin-5-yl)ethyl)-2-(3-cyclopropyl-1,4-dimethyl-1H-pyrazolo[3,4-b]pyridin-6-yloxy)acetamide;
2-(3-cyclopropyl-1,4-dimethyl-1H-pyrazolo[3,4-b]pyridin-6-yloxy)-N-(1-(1-methyl-1H-benzo[d]imidazol-5-yl)ethyl)acetamide;

2-(3-cyclopropyl-1,4-dimethyl-1H-pyrazolo[3,4-b]pyridin-6-yloxy)-N-(1-(1-methyl-1H-indol-5-yl)ethyl)acetamide;

2-(3-cyclopropyl-1,5-dimethyl-1H-pyrazolo[3,4-b]pyridin-6-yloxy)-N-(1-p-tolylethyl)acetamide;

2-(3-cyclopropyl-1,4-dimethyl-1H-pyrazolo[3,4-b]pyridin-6-yloxy)-N-(2-(4-methoxyphenyl)propan-2-yl)acetamide;

2-(3-cyclopropyl-1,4-dimethyl-1H-pyrazolo[3,4-b]pyridin-6-yloxy)-N-(2-methyl-6,7-dihydro-5H-cyclopenta[b]pyridin-5-yl)acetamide;

2-(3-cyclopropyl-1,4-dimethyl-1H-pyrazolo[3,4-b]pyridin-6-yloxy)-N-(3-methyl-6,7-dihydro-5H-cyclopenta[c]pyridin-7-yl)acetamide;

2-(3-cyclopropyl-1,4-dimethyl-1H-pyrazolo[3,4-b]pyridin-6-yloxy)-N-(4-methylbenzyl)acetamide;

2-(3-cyclopropyl-1,4-dimethyl-1H-pyrazolo[3,4-b]pyridin-6-yloxy)-N-(4-methoxybenzyl)acetamide;

2-(3-cyclopropyl-1,4-dimethyl-1H-pyrazolo[3,4-b]pyridin-6-yloxy)-N-(5-ethoxy-2,3-dihydro-1H-inden-1-yl)acetamide;

2-(3-cyclopropyl-1,4-dimethyl-1H-pyrazolo[3,4-b]pyridin-6-yloxy)-N-(5-isopropoxy-2,3-dihydro-1H-inden-1-yl)acetamide;

2-(3-cyclopropyl-1,4-dimethyl-1H-pyrazolo[3,4-b]pyridin-6-yloxy)-N-(5-methoxy-2,3-dihydro-1H-inden-1-yl)propanamide;

2-(3-cyclopropyl-1,4-dimethyl-1H-pyrazolo[3,4-b]pyridin-6-yloxy)-N-(1-(4-methoxyphenyl)ethyl)propanamide;

2-(3-cyclopropyl-1,4,5-trimethyl-1H-pyrazolo[3,4-b]pyridin-6-yloxy)-N-(1-(4-methoxyphenyl)ethyl)acetamide;

2-(3-cyclopropyl-1,4,5-trimethyl-1H-pyrazolo[3,4-b]pyridin-6-yloxy)-N-(1-p-tolylethyl)acetamide;

2-(3-cyclopropyl-1,5-dimethyl-1H-pyrazolo[3,4-b]pyridin-6-yloxy)-N-(1-(4-methoxyphenyl)ethyl)acetamide;

2-(1-methyl-3-phenyl-4-(trifluoromethyl)-1H-pyrrolo[2,3-b]pyridin-6-yloxy)-N-(1-phenylethyl)acetamide;

2-(3-phenyl-4-(trifluoromethyl)isoxazolo[5,4-b]pyridin-6-yloxy)-N-(1-phenylethyl)acetamide;

2-(3-(2,5-dimethylfuran-3-yl)-1-methyl-4-(trifluoromethyl)-1H-pyrazolo[3,4-b]pyridin-6-yloxy)-N-(2-methyl-6,7-dihydro-5H-cyclopenta[b]pyridin-5-yl)acetamide;

2-(3-(2,5-dimethylfuran-3-yl)-1-methyl-4-(trifluoromethyl)-1H-pyrazolo[3,4-b]pyridin-6-yloxy)-N-(1-(4-methoxyphenyl)ethyl)acetamide;

2-(4-(difluoromethyl)-3-(2,5-dimethylfuran-3-yl)-1-methyl-1H-pyrazolo[3,4-b]pyridin-6-yloxy)-N-(2-methyl-6,7-dihydro-5H-cyclopenta[b]pyridin-5-yl)acetamide;

2-(4-(difluoromethyl)-3-(2,5-dimethylfuran-3-yl)-1-methyl-1H-pyrazolo[3,4-b]pyridin-6-yloxy)-N-(1-(4-methoxyphenyl)ethyl)acetamide;

2-(3-cyclopropyl-1,4-dimethyl-1H-pyrazolo[3,4-b]pyridin-6-yloxy)-N-(5,6-dimethoxy-2,3-dihydro-1H-inden-1-yl)acetamide;

2-(3-cyclopropyl-1,4-dimethyl-1H-pyrazolo[3,4-b]pyridin-6-yloxy)-N-((5-methylpyrazin-2-yl)methyl)acetamide;

N-(3-(1H-imidazol-1-yl)propyl)-2-(3-cyclopropyl-1,4-dimethyl-1H-pyrazolo[3,4-b]pyridin-6-yloxy)acetamide;

2-(3-cyclopropyl-1,4-dimethyl-1H-pyrazolo[3,4-b]pyridin-6-yloxy)-N-((2,3-dihydrobenzofuran-5-yl)methyl)acetamide;

N-(2-(1H-indol-3-yl)ethyl)-2-(3-cyclopropyl-1,4-dimethyl-1H-pyrazolo[3,4-b]pyridin-6-yloxy)acetamide;

N-(cyclohexylmethyl)-2-(3-cyclopropyl-1,4-dimethyl-1H-pyrazolo[3,4-b]pyridin-6-yloxy)acetamide;

2-(3-cyclopropyl-1,4-dimethyl-1H-pyrazolo[3,4-b]pyridin-6-yloxy)-N-(1-(6-methylpyridin-2-yl)ethyl)acetamide;

2-(3-cyclopropyl-1,4-dimethyl-1H-pyrazolo[3,4-b]pyridin-6-yloxy)-N-(5,6,7,8-tetrahydroquinolin-5-yl)acetamide;

2-(3-cyclopropyl-1,4-dimethyl-1H-pyrazolo[3,4-b]pyridin-6-yloxy)-N-(6-methoxy-2,3-dihydro-1H-inden-1-yl)acetamide;

2-(3-cyclopropyl-1,4-dimethyl-1H-pyrazolo[3,4-b]pyridin-6-yloxy)-N-(1-p-tolylethyl)acetamide;

2-(3-cyclopropyl-1,4-dimethyl-1H-pyrazolo[3,4-b]pyridin-6-yloxy)-N-(1-(3-methoxyphenyl)ethyl)acetamide;

2-(3-cyclopropyl-1,4-dimethyl-1H-pyrazolo[3,4-b]pyridin-6-yloxy)-N-(1-(2-methoxyphenyl)ethyl)acetamide;

N-((6-chloropyridin-3-yl)methyl)-2-(3-cyclopropyl-1,4-dimethyl-1H-pyrazolo[3,4-b]pyridin-6-yloxy)acetamide;

N-(3-chloro-4-methoxybenzyl)-2-(3-cyclopropyl-1,4-dimethyl-1H-pyrazolo[3,4-b]pyridin-6-yloxy)acetamide;

N-(1-(1H-indol-5-yl)ethyl)-2-(3-cyclopropyl-1,4-dimethyl-1H-pyrazolo[3,4-b]pyridin-6-yloxy)acetamide;

2-(3-cyclopropyl-1,4-dimethyl-1H-pyrazolo[3,4-b]pyridin-6-yloxy)-N-((3-methylpyridin-2-yl)methyl)acetamide;

2-(3-cyclopropyl-1,4-dimethyl-1H-pyrazolo[3,4-b]pyridin-6-yloxy)-N-(1-(3-fluoro-4-methoxyphenyl)ethyl)acetamide;

2-(3-cyclopropyl-1,4-dimethyl-1H-pyrazolo[3,4-b]pyridin-6-yloxy)-N-(1-(1-methyl-1H-pyrazol-4-yl)ethyl)acetamide;

2-(3-cyclopropyl-1,4-dimethyl-1H-pyrazolo[3,4-b]pyridin-6-yloxy)-N-(1-(4-methylpyridin-2-yl)ethyl)acetamide;

2-(3-cyclopropyl-1,4-dimethyl-1H-pyrazolo[3,4-b]pyridin-6-yloxy)-N-(1-(4-methylthiazol-2-yl)ethyl)acetamide;

N-(1-(benzo[d]thiazol-2-yl)ethyl)-2-(3-cyclopropyl-1,4-dimethyl-1H-pyrazolo[3,4-b]pyridin-6-yloxy)acetamide;

2-(3-cyclopropyl-1,4-dimethyl-1H-pyrazolo[3,4-b]pyridin-6-yloxy)-N-(1-methyl-4,5,6,7-tetrahydro-1H-indazol-4-yl)acetamide;

2-(3-cyclopropyl-1,4-dimethyl-1H-pyrazolo[3,4-b]pyridin-6-yloxy)-N-(1-(imidazo[2,1-b]thiazol-6-yl)ethyl)acetamide;

2-(3-cyclopropyl-1,4-dimethyl-1H-pyrazolo[3,4-b]pyridin-6-yloxy)-N-(4-phenylbutan-2-yl)acetamide;

2-(3-cyclopropyl-1,4-dimethyl-1H-pyrazolo[3,4-b]pyridin-6-yloxy)-N-(2,4-dimethoxybenzyl)acetamide;

2-(3-cyclopropyl-1,4-dimethyl-1H-pyrazolo[3,4-b]pyridin-6-yloxy)-N-(1-m-tolylethyl)acetamide;

2-(3-cyclopropyl-1,4-dimethyl-1H-pyrazolo[3,4-b]pyridin-6-yloxy)-N-((1,5-dimethyl-1H-indazol-4-yl)methyl)acetamide;

2-(3-cyclopropyl-1,4-dimethyl-1H-pyrazolo[3,4-b]pyridin-6-yloxy)-N-(5-methoxy-1,2,3,4-tetrahydronaphthalen-1-yl)acetamide;

2-(3-cyclopropyl-1,4-dimethyl-1H-pyrazolo[3,4-b]pyridin-6-yloxy)-N-(4-ethoxybenzyl)acetamide;

2-(3-cyclopropyl-1,4-dimethyl-1H-pyrazolo[3,4-b]pyridin-6-yloxy)-N-((1-methyl-1H-indazol-7-yl)methyl)acetamide;

N-((1H-indazol-4-yl)methyl)-2-(3-cyclopropyl-1,4-dimethyl-1H-pyrazolo[3,4-b]pyridin-6-yloxy)acetamide;

2-(3-cyclopropyl-1,4-dimethyl-1H-pyrazolo[3,4-b]pyridin-6-yloxy)-N-(6-methyl-2,3-dihydro-1H-inden-1-yl)acetamide;

N-(1-(6-chlorobenzo[d]thiazol-2-yl)ethyl)-2-(3-cyclopropyl-1,4-dimethyl-1H-pyrazolo[3,4-b]pyridin-6-yloxy)acetamide;

2-(3-cyclopropyl-1,4-dimethyl-1H-pyrazolo[3,4-b]pyridin-6-yloxy)-N-(1-(1-methyl-1H-pyrrolo[2,3-b]pyridin-5-yl)ethyl)acetamide;

2-(3-cyclopropyl-1,4-dimethyl-1H-pyrazolo[3,4-b]pyridin-6-yloxy)-N-(-5-methoxy-2,3-dihydro-1H-inden-1-yl)propanamide; and 2-(3-cyclopropyl-1,4-dimethyl-1H-pyrazolo[3,4-b]pyridin-6-yloxy)-N-(-1-(4-methoxyphenyl)ethyl) propanamide.

14. A pharmaceutical composition comprising a therapeutically effective amount of a compound of claim 1 and one or more pharmaceutically acceptable carriers.

15. A combination comprising a therapeutically effective amount of the compound of claim 1 and one or more therapeutically active agents.

16. A compound in free form or in pharmaceutically acceptable form having the structure:

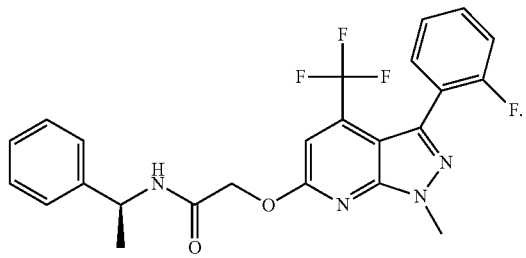 [SMILES: C[C@H](NC(=O)COc1cc(C(F)(F)F)c2c(-c3ccccc3F)nn(C)c2n1)c1ccccc1]

* * * * *